United States Patent
Talley et al.

(10) Patent No.: US 10,266,511 B2
(45) Date of Patent: Apr. 23, 2019

(54) NO-RELEASING NITROOXY-CHROMENE CONJUGATES

(71) Applicant: Euclises Pharmaceuticals, Inc., St. Louis, MO (US)

(72) Inventors: John J. Talley, St. Louis, MO (US); Eduardo J. Martinez, Bryn Mawr, PA (US)

(73) Assignee: EUCLISES PHARMACEUTICALS, INC., St. Louis, MO (US)

( * ) Notice: Subject to any disclaimer, the term of this patent is extended or adjusted under 35 U.S.C. 154(b) by 0 days.

(21) Appl. No.: 15/111,767

(22) PCT Filed: Jan. 14, 2015

(86) PCT No.: PCT/US2015/011454
§ 371 (c)(1),
(2) Date: Jul. 14, 2016

(87) PCT Pub. No.: WO2015/109011
PCT Pub. Date: Jul. 23, 2015

(65) Prior Publication Data
US 2016/0340330 A1 Nov. 24, 2016

Related U.S. Application Data

(60) Provisional application No. 61/927,344, filed on Jan. 14, 2014.

(51) Int. Cl.
| | | |
|---|---|---|
| A61K 31/353 | (2006.01) | |
| C07D 311/58 | (2006.01) | |
| C07D 491/048 | (2006.01) | |
| A61K 31/34 | (2006.01) | |
| A61K 31/352 | (2006.01) | |
| A61K 47/52 | (2017.01) | |

(52) U.S. Cl.
CPC ............ *C07D 311/58* (2013.01); *A61K 31/34* (2013.01); *A61K 31/352* (2013.01); *A61K 31/353* (2013.01); *A61K 47/52* (2017.08); *C07D 491/048* (2013.01)

(58) Field of Classification Search
CPC .......................... A61K 31/353; C07D 311/58
USPC ............................................. 514/457; 549/405
See application file for complete search history.

(56) References Cited

U.S. PATENT DOCUMENTS

| | | | |
|---|---|---|---|
| 2005/0101563 A1 | 5/2005 | Pulaski et al. | 514/54 |
| 2005/0148777 A1 | 7/2005 | Carter et al. | 546/169 |
| 2006/0009431 A1 | 1/2006 | Earl et al. | 514/171 |
| 2008/0287407 A1 | 11/2008 | Garvey et al. | 514/173 |

FOREIGN PATENT DOCUMENTS

| | | | |
|---|---|---|---|
| CN | 103012350 | 4/2013 | ........... C07D 311/58 |
| WO | WO 2004/087687 | 10/2004 | ........... C07D 311/58 |

OTHER PUBLICATIONS

Abubakar, et al. (2014) "An overview of treatment options to combat peste des petits ruminants in endemic situations." *Research Journal for Veterinary Practitioners*, vol. 2(1S):4-7, Special Issue 1(2014) "Epidemiology and Occurrence of PPR in Endemic Situations".

Krysan, et al. (2004) "COX-2-dependent stabilization of surviving in non-small cell lung cancer[1]." *FASEB Journal*, vol. 18(1):206-208.

Tomozawa, S., et al. (2000) "Cyclooxygenase-2 overexpression correlates with tumour recurrence, especially haematogenous metastasis, of colorectal cancer." *British Journal of Cancer* 83(3):324-328.

International Search Report (ISR) dated Apr. 13, 2015 in PCT/US2015/011454 published as WO 2015/109011.

Dong Sung Lim: "The Pentafluorosulfanyl Group in Organic and Bioorganic Chemistry", A Dissertation Submitted to the University at Albany, State University of New York in Partial Fulfillment of the Requirement for the Degree of Doctor of Philosophy, Jan. 1, 2007, pp. vi-vii.

Oleksandr S. Kanishchev et al.: "SF5-Substituted Aromatic Heterocycles", AdvaiKes in Heterocyclic Chemistry, vol. 120, ISSN 0065-2725, http;//dx. doi.org/10,1016/bs.aihch.2016.03.008, Jan. 1, 2016, pp. 1-42.

Yanmei Zhang et al.; "Pentafluorosulfanyl-Substituted Benzopyran Analogues as New Cyclooxygenase-2 Inhibitors with Excellent Pharmacokinetics and Efficacy in Blocking Inflammation", Journal of Medicinal Chemistry, vol. 60, No. 10, May 5, 2017, pp. 4135-4146.

Supplementary European Search Report from corresponding European Patent Application No. 15737116.2 dated Aug. 22, 2017.

*Primary Examiner* — Brenda L Coleman
(74) *Attorney, Agent, or Firm* — Harness, Dickey & Pierce, P.L.C.

(57) ABSTRACT

The present invention provides NO-releasing nitrooxy-alkylenyl-linked-chromene conjugates, having the structure of Formula (1) wherein R1, R2, R3, R4, X, and L are as defined in the detailed description; pharmaceutical compositions comprising at least one compound o Formula (I); and methods useful for healing wounds, preventing and treating cancer and treating actinic keratosis, cystic fibrosis, and acne, using a compound of Formula (1).

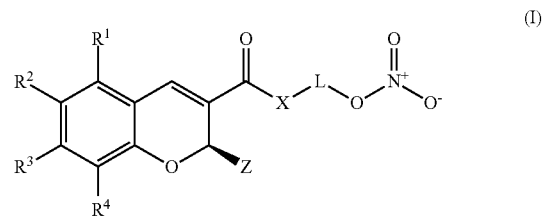

6 Claims, No Drawings

NO-RELEASING NITROOXY-CHROMENE CONJUGATES

CROSS-REFERENCE TO RELATED APPLICATIONS

This application is a national phase application of PCT Application No. PCT/US2015/011454, filed on 14 Jan. 2015, which claims benefit of U.S. Provisional Application No. 61/927,344, filed on 14 Jan. 2014. The entire disclosure of the applications identified in this paragraph are incorporated herein by reference.

FIELD

The present invention generally relates to NO-releasing chromene conjugate compounds, pharmaceutical compositions comprising the compounds, methods useful for treating a subject by administering a therapeutically effective amount of the compounds, and methods for making the compounds. More specifically, the present invention relates to a class of NO-releasing nitrooxy-chromene gastro-protective compounds, pharmaceutical compositions thereof, and methods useful for healing wounds, preventing and treating cancer, and treating actinic keratosis, cystic fibrosis, and acne.

BACKGROUND

Despite decades of effort, cancer remains an especially difficult disease for development of therapeutics. According to the Cancer Prevention Coalition (University of Illinois), cancer rates have increased 24% in the past thirty years even after adjusting for aging of the population. Remarkably, despite significant progress during this period, the overall five-year survival rates have remained virtually static (approximately 50% depending on the cancer). Thus, new drugs are required to develop more effective life-saving cancer therapies.

Celecoxib, a selective COX-2 inhibitor, is one of the world's most successful drugs, alleviating pain and inflammation for millions of patients. In addition, COX-2 overexpression has been found in several types of human cancers, such as colon, breast, lung, prostate, and pancreas, and appears to control many cellular processes. COX-2 plays a role in carcinogenesis, apoptosis, and angiogenesis and, therefore, represents an excellent drug target for the development of novel medicines for prevention and/or treatment of human cancers. Currently, celecoxib is approved for limited use in the reduction of polyps in familial adenomatous polyposis (FAP).

The Adenoma Prevention with Celecoxib (APC) trial demonstrated human efficacy of celecoxib in the prevention of sporadic colorectal adenoma. However, this trial also showed that the elevated dose of celecoxib required for anti-cancer efficacy was accompanied by concomitant increase in adverse cardiovascular (CV) events (*Cancer Prev. Res.* 2, 310-321(2009)).

Development of more potent or selective COX-2 inhibitors does not improve CV safety; this liability is thought to be a mechanism-based effect. This was demonstrated in the VIGOR trial by Vioxx®, an extremely potent and highly selective COX-2 inhibitor withdrawn from the market in 2004 due to CV concerns about increased risk of heart attack and stroke with long term, high dose use. These facts have undermined the development of novel COX-2 inhibitors and slowed research to expand their utility to other disease indications, such as cancer.

Chromene coxibs represent a class of coxibs that could fulfill an unmet medical need in inflammation and cancer. Chromene coxibs have a carboxylate moiety and, uniquely among the coxib class of molecules, do not bind in the hydrophobic binding pocket of the COX-2 active site. Selected chromene derivatives have comparable potency, efficacy, and selectivity to the older diaryl heterocyclic coxibs (e.g., celecoxib, valdecoxib, rofecoxib, and etoricoxib) in the standard rat models of inflammation and pain (*Bioorg. Med. Chem. Lett.* 20(23):7155-7158 (2010); *Bioorg. Med. Chem. Lett.* 20(23):7159-7163 (2010); *Bioorg. Med. Chem. Lett.* 20(23):7164-716 (2010)). One benzopyran derivative was demonstrated to be effective in mitigating acute dental pain (*Clin. Pharmacol. Ther.* 83(6):857-866 (2008)).

Nitric oxide (NO) is an important endogenous signaling molecule and vasodilator. NO is synthesized from L-arginine by the enzyme NO synthase (NOS), which exists in three distinct isoforms, namely, the constitutively expressed endothelial (eNOS) and neuronal (nNOS) forms, and the mainly inducible form (iNOS). Arginine administration has been shown to reduce blood pressure and renal vascular resistance in essential hypertensive patients with normal or insufficient renal function (*Am. J. Hypertens.* 12, 8-15 (1999)). It has also been shown that NO deficiency promotes vascular side-effects of celecoxib and other COX inhibitors (*Blood* 108, 4059-4062 (2006)).

The role of NO in cancer is complex; however, pharmacological evidence using NO-releasing compounds of NSAIDs has shown increased anti-tumor efficacy in cell culture and animal cancer models. The different molecular mechanisms of NO are expected to simultaneously enhance anti-cancer efficacy of celecoxib, and improve CV safety by preventing an increase in blood pressure associated with COX-2 inhibition, while maintaining gastric-sparing properties superior to NSAIDs.

Diverse molecular mechanisms of NO delivery are well known. For example, it is reported that nitric oxide-donating NSAIDs (NO-sulindac, NO-ibuprofen, NO-indomethacin, and NO-aspirin) inhibit the growth of various cultured human cancer cells, providing evidence of a tissue type-independent effect (*J. Pharmacol. Exp. Ther.* 303, 1273-1282 (2002)).

In another example, it is reported that nitric oxide-donating aspirin prevented pancreatic cancer in a hamster tumor model (*Cancer Res.* 66, 4503-4511 (2006)).

Two isoforms of cyclooxygenase (COX) are known to exist, a constitutive form (COX-1) present in nearly all tissues and an inducible form (COX-2) upregulated in response to inflammatory stimuli. The discovery of COX-2 led to the development of selective COX-2 inhibitors as anti-inflammatory drugs (coxibs), which were shown to be largely devoid of the antiplatelet activity and gastrointestinal ulcerogenicity believed to be associated with inhibition of COX-1.

NSAIDs are among the most widely used treatments for pain, fever, and inflammation, and have long been known to reduce the risk of cancer in multiple organ sites. The use of aspirin in treatment and prevention of cancer has widespread support in the medical community; however, the risks of regular aspirin use are also well established and the risk-benefit profile is not sufficient to recommend aspirin treatment for cancer prevention. With the advent of coxibs, research has focused on COX-2 as a target for the treatment and prevention of certain cancers. Compelling data from the APC trial, described above, demonstrated that celecoxib was useful in preventing sporadic colorectal adenoma in patients at high risk for colorectal cancer.

Lung cancer is the leading cause of cancer-related deaths in the US and is responsible for more deaths than breast, prostate, and colon cancers combined. Current research suggests that COX-2 and epidermal growth factor receptor (EGFR) are important mediators in non-small cell lung cancer (NSCLC). One study demonstrates a strong cooperative effect on slowing tumor progression by blocking both the EGFR and COX-2 pathways using gefitinib and celecoxib (Zhang, X, *Clin. Cancer Res.* 11, 6261-6269 (2005)).

In human NSCLC patients, a combination of erlotinib (a tyrosine kinase inhibitor) and celecoxib showed high response rates, and demonstrable clinical benefit (Reckamp, K. L, *Clin. Cancer Res.* 12, 3381-3388 (2006)). NSCLC currently represents one of the preferred indications for COX-2 inhibition cancer therapy (Brown, J. R., *Clin. Cancer Res.* 10, 4266s-4269s (2004); and Gadgeel, S. M., *Cancer* 110, 2775-2784 (2007)).

A key feature of COX-2 biology is its ability alone to cause cancer formation in a number of transgenic mouse models. COX-2 derived PGE2 plays a prominent role in tumor growth and is the most abundant prostanoid in many human malignancies. Metabolism of arachidonic acid by COX-2 leads to the formation of several prostaglandins (PGs) that bind to tumor suppressor p53, preventing p53-mediated apoptosis. COX-2-derived PGE2 promotes epithelial-to-mesenchymal transition and, thus, increases resistance to EGFR tyrosine kinase inhibitors in lung cancer (Krysan, K., *J. Thorac. Oncol.* 3, 107-110 (2008)).

Colorectal cancer (CRC) is the second-leading cause of cancer-related deaths in the US. Colorectal cancer progression and metastasis occurs through aberrant signaling through the prostaglandin-endoperoxide synthase 2 (PTGS2) and epithelial growth factor (EGF) signaling pathways (Wang, D., *Cancers* 3, 3894-3908 (2011)). COX-2 over-expression contributes to PTGS2 signaling and therefore COX-2 inhibitors may provide a successful treatment modality for colorectal neoplasia (Eberhart, C. E., *Gastroenterology* 107, 1183-1188 (1994)).

Nitric oxide exhibits a number of important pharmacological actions including vascular relaxation (vasodilatation) and inhibition of platelet aggregation and adhesion. Inhibition of NO synthesis leads to an increase in systemic blood pressure. NO also prevents atherogenesis by inhibiting vascular smooth muscle cell proliferation, and preventing low-density lipoprotein oxidation and macrophage activation. Vascular NO generation is important in controlling blood pressure, and a growing body of evidence indicates that NO signaling is a key factor in counteracting the onset and development of several CV diseases including hypertension, myocardial infarction, and stroke. NO can be used to counteract CV liabilities associated with COX-2 inhibition.

NO-releasing COX inhibitors were originally created to improve gastrointestinal (GI) tolerability (*Inflammopharmacology* 11(4), 415-22 (2003)). Naproxcinod is a NO-releasing prodrug of the NSAID naproxen. Naproxcinod showed significantly improved GI tolerability compared to naproxen alone in a chronic rat study (*Life Sciences* 62, 235-240 (1998)). In another example, L-arginine, coadministered with the NSAID ibuprofen, showed a protective effect on gastric mucosa against ibuprofen-induced mucosal lesions (*Free Radic. Res.* 38(9), 903-11 (2004)).

NO modulates the activity of transcription factor NF-κB, which represents a potential mechanism for inflammation control, but also regulation of apoptotic mechanisms. NO promotes apoptosis and can reverse tumor cell resistance to chemotherapeutic agents. Studies with NO-releasing NSAIDs have shown that NO contributes to anti-cancer activity in cell culture and enhanced in vivo efficacy in rodent cancer models. For example, it is reported that nitric oxide-naproxen is an effective agent against carcinogenesis in rodent models of colon and urinary bladder cancers (*Cancer Prev. Res.* 2, 951-956 (2009)).

Chromenes useful in the treatment of dermatological disorders, including acne and inflammation, have been reported in US 2005/0014729. The compounds described therein for the aforementioned use include a chromene of the structure:

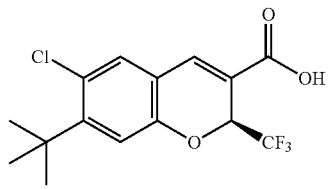 [SMILES: CC(C)(C)c1cc2c(cc1Cl)C=C(C(=O)O)[C@@H](C(F)(F)F)O2]

Nitric oxide-releasing agents non-covalently combined with chromenes useful in the treatment of inflammation and the reduction of adverse cardiovascular and/or ulcerogenic events associated with chronic use of COX-2 inhibitors are reported in US 2005/0113409, including (S)-6-chloro-7-(1,1-dimethylethyl)-2-(trifluoromethyl)-2H-1-benzopyran-3-carboxylic acid of the structure:

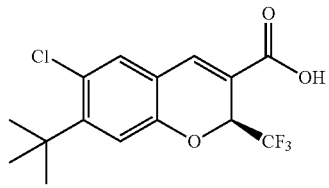 [SMILES: CC(C)(C)c1cc2c(cc1Cl)C=C(C(=O)O)[C@@H](C(F)(F)F)O2]

Nitric oxide-releasing chromene prodrugs useful in the treatment of inflammation and the reduction of adverse cardiovascular and/or ulcerogenic events associated with chronic use of COX-2 inhibitors have been reported in WO 2001/045703, including chromenes substituted with an nitrooxyalkyl of the structure:

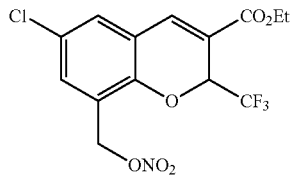

Nitric oxide-releasing chromene prodrugs useful in the treatment of inflammation, cancer, and the reduction of adverse cardiovascular and/or ulcerogenic events associated with chronic use of COX-2 inhibitors are reported in WO 2006/040676, including chromenes substituted with an nitrooxyalkyl of the following structures:

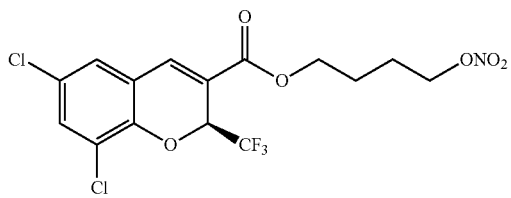

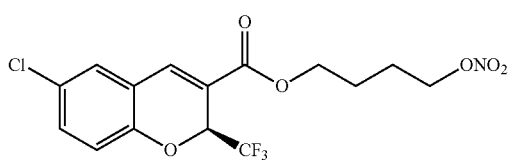

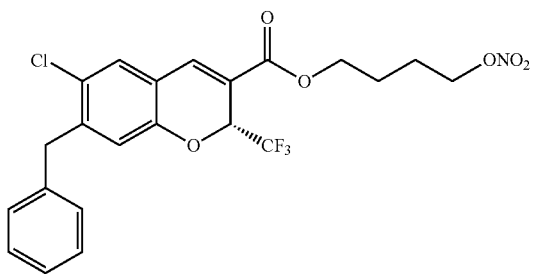

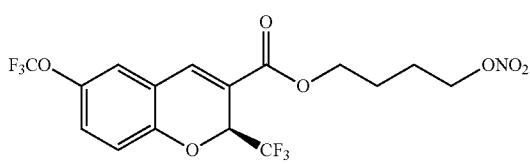

Nitric oxide-releasing prodrugs useful in the treatment of inflammation and the reduction of adverse cardiovascular events associated with high doses of anti-inflammatories are reported in U.S. Pat. No. 7,932,294. The compounds described therein include celecoxib substituted with a nitrooxy-ethylene-disulfide-ethyleneoxy-carbonyl radical to sulfonamide nitrogen, yielding structure (1) below:

(1)

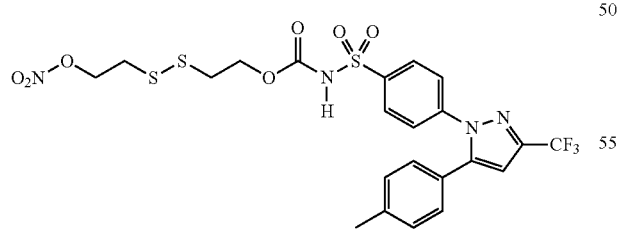

Nitrate prodrugs useful in the treatment of inflammatory, ischemic, degenerative, and proliferative diseases are reported in EP 01336602. The compounds described therein include celecoxib substituted with nitrooxy-alkylenyl-carbonyl or a carboxy(dinitrooxy)ethylene-carbonyl radical to sulfonamide nitrogen yielding, respectively, structures (2*) & (3) below:

(2*)

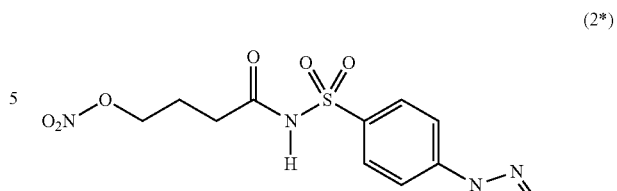

(3)

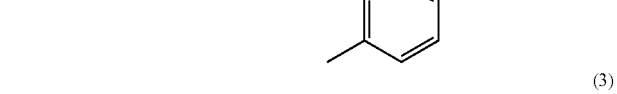

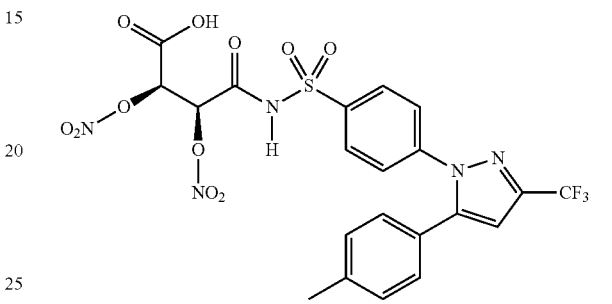

*Note: Structure (2*) above is also reported in U.S. Pat. No. 7,776,902 and WO 2004/000781.

Nitric oxide-releasing compounds useful in the treatment of COX-2 mediated diseases and cancer are reported in WO 2004/037798. The compounds described therein include celecoxib substituted with nitrooxy-alkylenyl-carbonyl or a nitrooxy-butylene-O-carbonyl radical at sulfonamide nitrogen, yielding, respectively, structures (4) & (5) below:

(4)

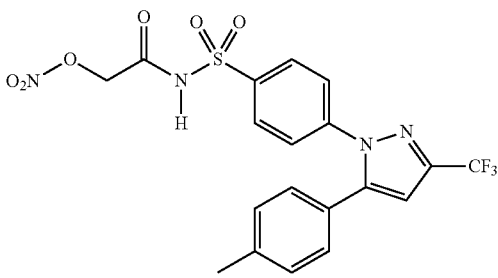

(5)

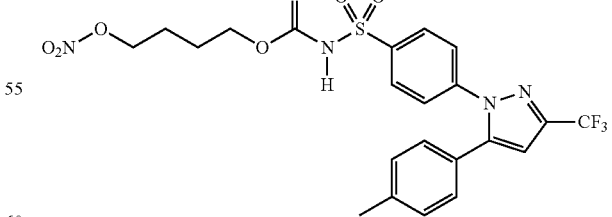

SUMMARY OF THE INVENTION

Chromene-based coxib drugs possess a number of advantages over existing medicines for the treatment of inflammation, pain, and cancer. The molecules of the present invention have the potential to be renal-sparing, safer on the gastrointestinal tract, and will not show coxib-induced hypertension due to their intrinsic and distinct structural, pharmacological and physiochemical properties.

Herein described is a family of NO-releasing chromene conjugates which provides a therapeutic benefit to a subject with a disease indication, such as cancer, actinic keratosis, cystic fibrosis, or acne, or provides a wound healing benefit to a subject. Such NO-releasing chromene conjugates can reduce gastric erosion of cancer therapy, improve CV safety, permit higher dose of cancer-treating compound, enhance cancer-treating efficacy, and/or maintain gastric-sparing properties superior to NSAIDs.

In one embodiment, there is provided a compound of Formula (I):

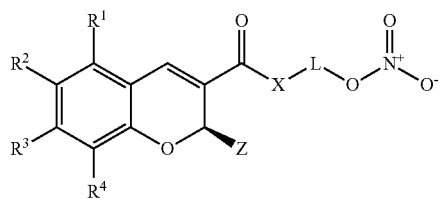

(I)

and pharmaceutically acceptable salts thereof, wherein Z, $R^1$, $R^2$, $R^3$, $R^4$, X and L are as defined in the detailed description.

Compounds of the present invention can exist in tautomeric, geometric or stereoisomeric forms. Ester, metabolite, oxime, prodrug, onium, hydrate, solvate, and N-oxide forms of a compound of Formula (I) are also embraced by the invention. The present invention considers all such compounds, including, but not limited to, cis- and trans-geometric isomers (Z- and E-geometric isomers), R- and S-enantiomers, diastereomers, d-isomers, l-isomers, atropisomers, epimers, conformers, rotamers, mixtures of isomers, and racemates thereof, as falling within the scope of the invention.

DETAILED DESCRIPTION

A. Compounds

One embodiment of the invention is a compound, or a pharmaceutically acceptable salt, or solvate of a compound or salt, of Formula (I):

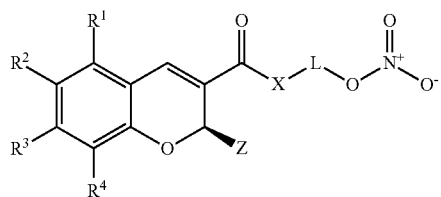

(I)

wherein Z is selected from the group consisting of $CF_3$, $OCF_3$, and $C_2F_5$; each of $R^1$, $R^2$, $R^3$, and $R^4$ is independently selected from the group consisting of H, alkyl, aralkyl, cycloalkyl, cycloalkenyl, halo, haloalkyl, alkoxy, haloalkoxy, alkylthio, haloalkylthio, pentafluorosulfanyl, hydroxyalkyl, trialkylsilyl, alkynyl, and alkenyl; —X— is selected from the group consisting of O,

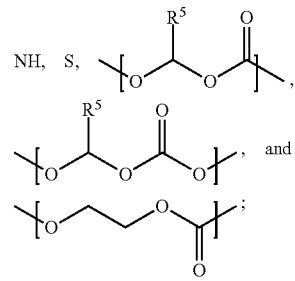

-L- is $C_{1-8}$ alkylenyl, wherein at least one —$CH_2$— radical is optionally replaced with a radical independently selected from the group consisting of $CH(R^6)$ and $C(R^6)_2$, or -L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)$ $CH_2CH_2$, $CH_2CH_2N(R^7)CH_2$, $CH_2N(R^7)CH_2CH_2$, $CH_2OCH_2CH_2$, $CH_2SCH_2CH_2$, $CH_2S$—$SCH_2CH_2$, and

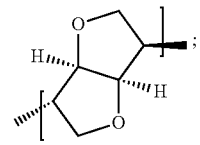

$R^5$ is selected from the group consisting of H, alkyl, cycloalkyl, cycloalkenyl, aryl, aralkyl, and heterocyclyl; $R^6$ is independently selected from the group consisting of alkyl, cycloalkyl, cycloalkenyl, aryl, aralkyl, heterocyclyl, carboxy, carboxyalkylenyl, and nitrooxy $C_{1-3}$ alkylenyl, with the proviso that when —X— is O or NH and -L- is $C_{1-6}$ alkylenyl, at least one —$CH_2$— radical must be replaced with a radical independently selected from the group consisting of $CH(R^6)$ and $C(R^6)_2$; and $R^7$ is selected from the group consisting of H, alkyl, cycloalkyl, cycloalkenyl, aryl, aralkyl, heterocyclyl, carboxy, carboxyalkylenyl, and acyl.

In another family of the compounds of Formula (I), $R^1$ is selected from the group consisting of H, alkyl, and halo; $R^2$ is selected from the group consisting of alkyl, halo, haloalkyl, alkoxy, haloalkoxy, alkylthio, haloalkylthio, and pentafluorosulfanyl; $R^3$ is selected from the group consisting of H, alkyl, cycloalkyl, halo, haloalkyl, hydroxyalkyl, and trialkylsilyl; $R^4$ is selected from the group consisting of H, alkyl, halo, alkynyl, and alkenyl; —X— is selected from the group consisting of O, NH, S,

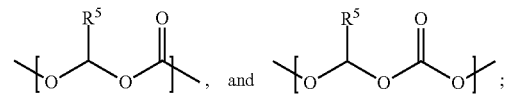

$R^5$ is selected from the group consisting of H, alkyl, and cycloalkyl; and $R^7$ is selected from the group consisting of H, alkyl, cycloalkyl, aryl, aralkyl, heterocyclyl, and acyl.

In another embodiment of the invention is a compound, or a pharmaceutically acceptable salt, or solvate of a compound or salt, of Formula (II):

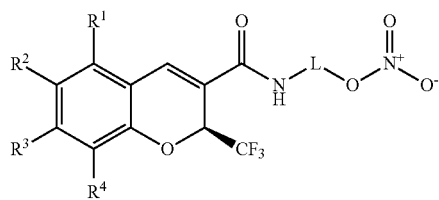

wherein: $R^1$ is selected from the group consisting of H, methyl, Cl, and F; $R^2$ is selected from the group consisting of Cl, Br, methyl, trifluoromethoxy, pentafluorosulfanyl, $OCH_3$, $OCH_2CH_3$, $OCF_2H$, $SCH_3$, $SCH_2CH_3$, $SCF_3$, $SCF_2H$, $CF_3$, and $CF_2CF_3$; $R^3$ is selected from the group consisting of H, methyl, tert-butyl, ethyl, n-propyl, isopropyl, n-butyl, $CH(CH_3)CH_3CH_2$, $CH_2CH(CH_3)_2$, $C(CH_3)_2CH_2OH$, Cl, F, Br, $CF_3$, and $Si(CH_3)_3$; $R^4$ is selected from the group consisting of H, Cl, methyl, ethyl, C≡CH, CH=CH$_2$, and Br; -L- is $C_{1-6}$ alkylenyl, wherein at least one —CH$_2$— radical is optionally replaced with a radical independently selected from the group consisting of CH(R$^6$) and C(R$^6$)$_2$, or -L- is selected from the group consisting of $CH_2CH_2OCH_2CH_2$, $CH_2CH_2SCH_2CH_2$, and $CH_2CH_2N(R^7)CH_2CH_2$; $R^6$ is independently selected from the group consisting of alkyl, cycloalkyl, aryl, aralkyl, heterocyclyl, carboxy, carboxyalkylenyl and nitrooxy $C_{1-3}$ alkylenyl, with the proviso that when -L- is $C_{1-6}$ alkylenyl, at least one —CH$_2$— radical must be replaced with a radical independently selected from the group consisting of CH(R$^6$) and C(R$^6$)$_2$; and $R^7$ is selected from the group consisting of H, alkyl, cycloalkyl, and acyl.

In another family of the compounds of Formula (II), $R^1$ is H or methyl; $R^2$ is selected from the group consisting of Cl, Br, methyl, trifluoromethoxy, and pentafluorosulfanyl; $R^3$ is selected from the group consisting of H, methyl, and tert-butyl; $R^4$ is selected from the group consisting of H, Cl, methyl, and ethyl; and -L- is $CH_2CH_2OCH_2CH_2$. Non-limiting examples include:

| Ex. | Structure | Name |
|---|---|---|
| 2 | 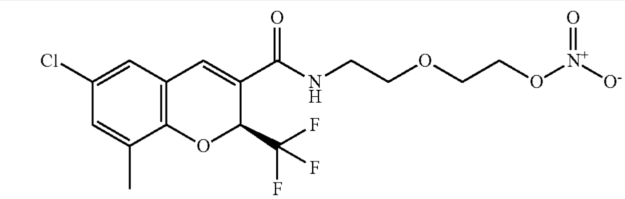 | (S)-2-(2-(6-chloro-8-methyl-2-(trifluoromethyl)-2H-chromene-3-carboxamido)ethoxy)ethyl nitrate |
| 3 | 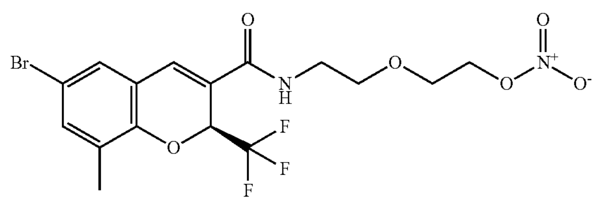 [SMILES: Cc1cc(Cl)cc2c1O[C@H](C(F)(F)F)C(C(=O)NCCOCCO[N+](=O)[O-])=C2] | (S)-2-(2-(6-bromo-8-methyl-2-(trifluoromethyl)-2H-chromene-3-carboxamido)ethoxy)ethyl nitrate |
| 6 | 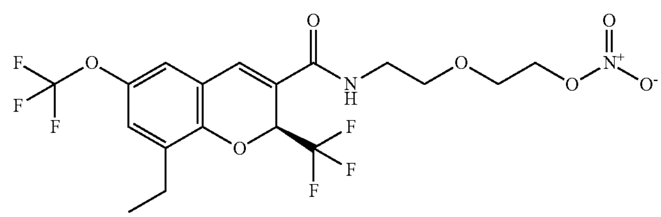 [SMILES: CCc1cc(OC(F)(F)F)cc2c1O[C@H](C(F)(F)F)C(C(=O)NCCOCCO[N+](=O)[O-])=C2] | (S)-2-(2-(8-ethyl-6-(trifluoromethoxy)-2-(trifluoromethyl)-2H-chromene-3-carboxamido)ethoxy)ethyl nitrate |
| 11 | 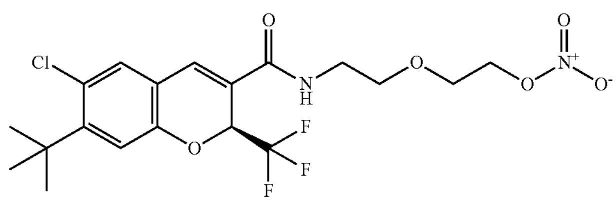 [SMILES: CC(C)(C)c1cc2c(cc1Cl)C=C(C(=O)NCCOCCO[N+](=O)[O-])[C@@H](C(F)(F)F)O2] | (S)-2-(2-(7-(tert-butyl)-6-chloro-2-(trifluoromethyl)-2H-chromene-3-carboxamido)ethoxy)ethyl nitrate |

The present invention is also directed to a subclass of compounds, including pharmaceutically acceptable salts of compounds, wherein compounds have the structure of Formula (III):

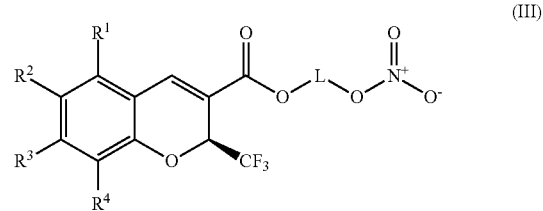

wherein: $R^1$ is selected from the group consisting of H, methyl, Cl, and F; $R^2$ is selected from the group consisting of Cl, Br, methyl, trifluoromethoxy, pentafluorosulfanyl, $OCH_3$, $OCH_2CH_3$, $OCF_2H$, $SCH_3$, $SCH_2CH_3$, $SCF_3$, $SCF_2H$, $CF_3$, and $CF_2CF_3$; $R^3$ is selected from the group consisting of H, methyl, tert-butyl, ethyl, n-propyl, isopropyl, n-butyl, $CH(CH_3)CH_3CH_2$, $CH_2CH(CH_3)_2$, $C(CH_3)_2CH_2OH$, Cl, F, Br, $CF_3$, and $Si(CH_3)_3$; $R^4$ is selected from the group consisting of H, Cl, methyl, ethyl, C≡CH, CH=CH_2, and Br; -L- is $C_{1-6}$ alkylenyl, wherein at least one —$CH_2$— radical is optionally replaced with a radical independently selected from the group consisting of $CH(R^6)$ and $C(R^6)_2$, or -L- is selected from the group consisting of $CH_2CH_2OCH_2CH_2$, $CH_2CH_2SCH_2CH_2$, $CH_2CH_2S—SCH_2CH_2$, $CH_2CH_2N(R^7)CH_2CH_2$, and

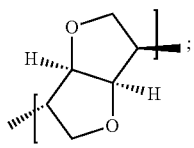

$R^6$ is independently selected from the group consisting of alkyl, cycloalkyl, aryl, aralkyl, heterocyclyl, carboxy, carboxyalkylenyl, and nitrooxy $C_{1-3}$ alkylenyl, with the proviso that when -L- is $C_{1-6}$ alkylenyl, at least one —$CH_2$— radical must be replaced with a radical independently selected from the group consisting of $CH(R^6)$ and $C(R^6)_2$; and $R^7$ is selected from the group consisting of H, alkyl, cycloalkyl, and acyl.

In another family of the compounds of Formula (III), $R^1$ is H or methyl; $R^2$ is selected from the group consisting of Cl, Br, methyl, trifluoromethoxy, and pentafluorosulfanyl; $R^3$ is selected from the group consisting of H, methyl, and tert-butyl; and $R^4$ is selected from the group consisting of H, Cl, methyl, and ethyl.

In another family of the compounds of Formula (III), -L- is $C_{2-3}$ alkylenyl, wherein at least one —$CH_2$— radical is replaced with $CH(R^6)$; and $R^6$ is nitrooxymethyl. Non-limiting examples include:

| Ex. | Structure | Name |
|---|---|---|
| 13 | 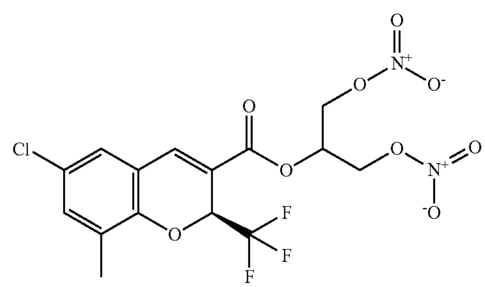 | (S)-1,3-bis(nitrooxy)propan-2-yl 6-chloro-8-methyl-2-(trifluoromethyl)-2H-chromene-3-carboxylate |
| 14 | 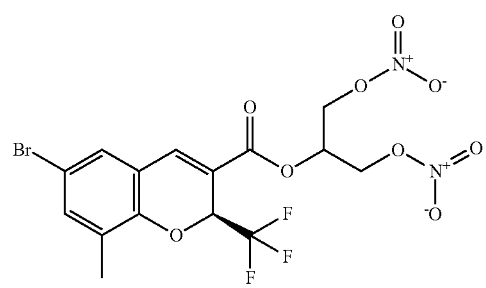 | (S)-1,3-bis(nitrooxy)propan-2-yl 6-bromo-8-methyl-2-(trifluoromethyl)-2H-chromene-3-carboxylate |
| 17 | 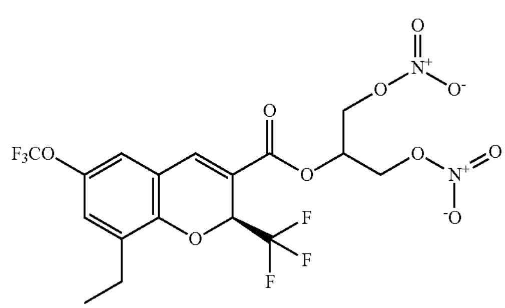 | (S)-1,3-bis(nitrooxy)propan-2-yl 8-ethyl-6-(trifluoromethoxy)-2-(trifluoromethyl)-2H-chromene-3-carboxylate |

| Ex. | Structure | Name |
|---|---|---|
| 20 | 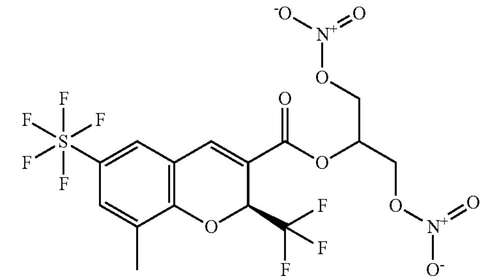 | (S)-1,3-bis(nitrooxy)propan-2-yl 6-(pentafluorosulfanyl)-8-methyl-2-(trifluoromethyl)-2H-chromene-3-carboxylate |
| 21 | 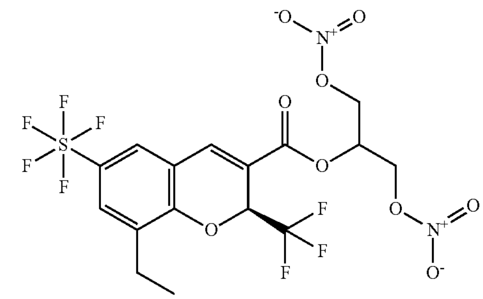 | (S)-1,3-bis(nitrooxy)propan-2-yl 6-(pentafluorosulfanyl)-8-ethyl-2-(trifluoromethyl)-2H-chromene-3-carboxylate |
| 22 | 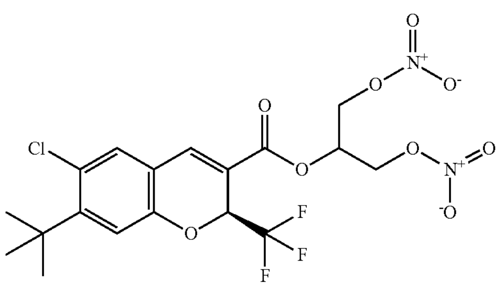 | (S)-1,3-bis(nitrooxy)propan-2-yl 7-(tert-butyl)-6-chloro-2-(trifluoromethyl)-2H-chromene-3-carboxylate |

In another family of the compounds of Formula (III), -L- is

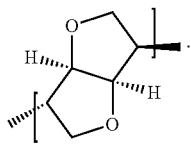

Non-limiting examples include:

| Ex. | Structure | Name |
|---|---|---|
| 24 | 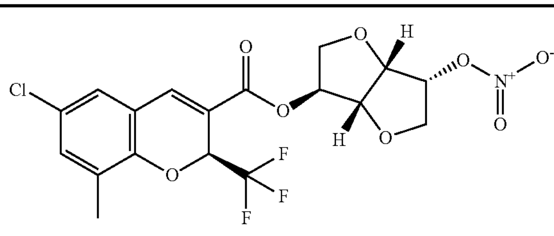 | (S)-(3S,3aR,6R,6aS)-6-(nitrooxy)hexahydrofuro[3,2-b]furan-3-yl 6-chloro-8-methyl-2-(trifluoromethyl)-2H-chromene-3-carboxylate |

-continued

| Ex. | Structure | Name |
|---|---|---|
| 25 | 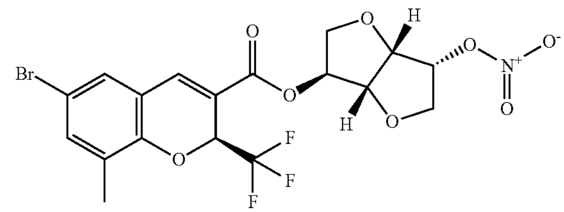 [SMILES: Cc1cc(Cl)cc2c1O[C@H](C(F)(F)F)C(C(=O)O[C@H]1CO[C@H]3[C@@H]1OC[C@H]3O[N+](=O)[O-])=C2] | (S)-(3S,3aR,6R,6aS)-6-(nitrooxy)hexahydrofuro[3,2-b]furan-3-yl 6-bromo-8-methyl-2-(trifluoromethyl)-2H-chromene-3-carboxylate |
| 28 | 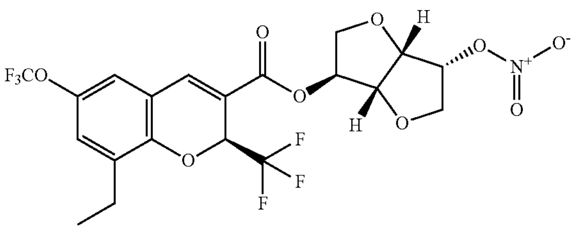 [SMILES: CCc1cc(OC(F)(F)F)cc2c1O[C@H](C(F)(F)F)C(C(=O)O[C@H]1CO[C@H]3[C@@H]1OC[C@H]3O[N+](=O)[O-])=C2] | (S)-(3S,3aR,6R,6aS)-6-(nitrooxy)hexahydrofuro[3,2-b]furan-3-yl 8-ethyl-6-(trifluoromethoxy)-2-(trifluoromethyl)-2H-chromene-3-carboxylate |
| 31 | 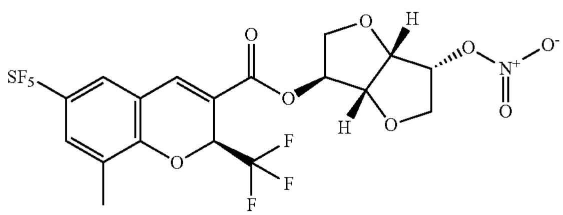 | (S)-(3S,3aR,6R,6aS)-6-(nitrooxy)hexahydrofuro[3,2-b]furan-3-yl 6-(pentafluorosulfanyl)-8-methyl-2-(trifluoromethyl)-2H-chromene-3-carboxylate |
| 32 | 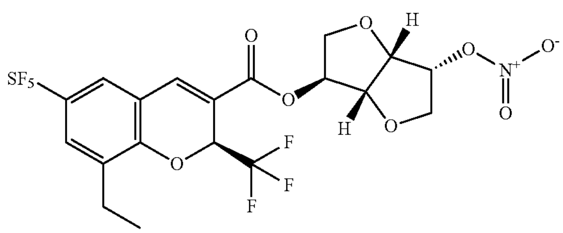 | (S)-(3S,3aR,6R,6aS)-6-(nitrooxy)hexahydrofuro[3,2-b]furan-3-yl 6-(pentafluorosulfanyl)-8-ethyl-2-(trifluoromethyl)-2H-chromene-3-carboxylate |
| 33 | 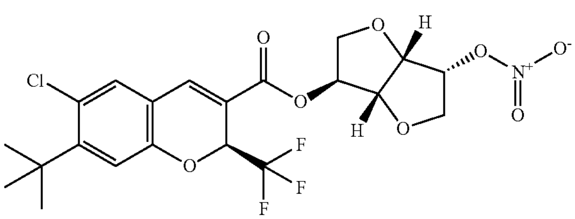 [SMILES: CC(C)(C)c1cc2c(cc1Cl)C=C(C(=O)O[C@H]1CO[C@H]3[C@@H]1OC[C@H]3O[N+](=O)[O-])[C@@H](C(F)(F)F)O2] | (S)-(3S,3aR,6R,6aS)-6-(nitrooxy)hexahydrofuro[3,2-b]furan-3-yl 7-(tert-butyl)-6-chloro-2-(trifluoromethyl)-2H-chromene-3-carboxylate |

In another family of the compounds of Formula (III), -L- is selected from the group consisting of $CH_2CH_2OCH_2CH_2$, $CH_2CH_2SCH_2CH_2$, $CH_2CH_2S-SCH_2CH_2$, and $CH_2CH_2N(R^7)CH_2CH_2$. $R^7$ is methyl or acetyl. Non-limiting examples include:

| Ex. | Structure | Name |
|---|---|---|
| 35 | 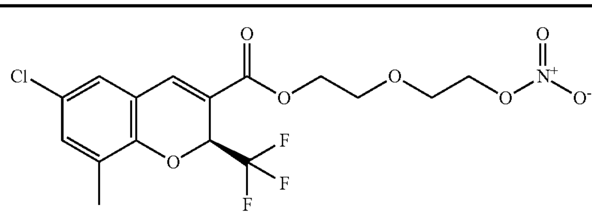 | (S)-2-(2-(nitrooxy)ethoxy)ethyl 6-chloro-8-methyl-2-(trifluoromethyl)-2H-chromene-3-carboxylate |

-continued

| Ex. | Structure | Name |
|---|---|---|
| 36 | 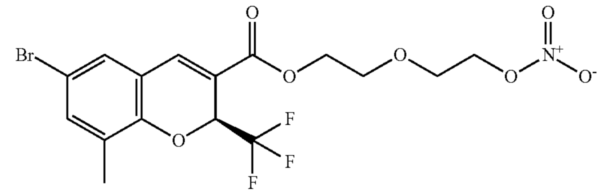 [SMILES: Cc1cc(Cl)cc2c1O[C@H](C(F)(F)F)C(C(=O)OCCOCCO[N+](=O)[O-])=C2] | (S)-2-(2-(nitrooxy)ethoxy)ethyl 6-bromo-8-methyl-2-(trifluoromethyl)-2H-chromene-3-carboxylate |
| 39 | 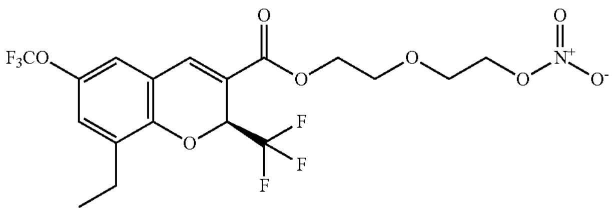 [SMILES: CCc1cc(OC(F)(F)F)cc2c1O[C@H](C(F)(F)F)C(C(=O)OCCOCCO[N+](=O)[O-])=C2] | (S)-2-(2-(nitrooxy)ethoxy)ethyl 8-ethyl-6-(trifluoromethoxy)-2-(trifluoromethyl)-2H-chromene-3-carboxylate |
| 44 | 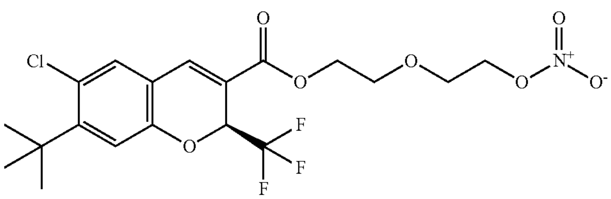 [SMILES: CC(C)(C)c1cc2c(cc1Cl)C=C(C(=O)OCCOCCO[N+](=O)[O-])[C@@H](C(F)(F)F)O2] | (S)-2-(2-(nitrooxy)ethoxy)ethyl 7-(tert-butyl)-6-chloro-2-(trifluoromethyl)-2H-chromene-3-carboxylate |
| 68 | 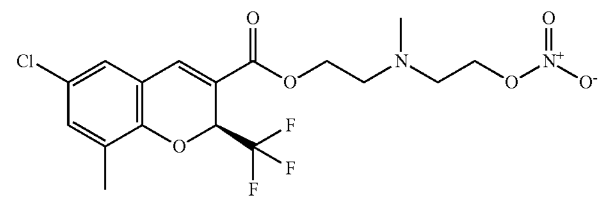 | (S)-2-(methyl(2-(nitrooxy)ethyl)amino)ethyl 6-chloro-8-methyl-2-(trifluoromethyl)-2H-chromene-3-carboxylate |
| 69 | 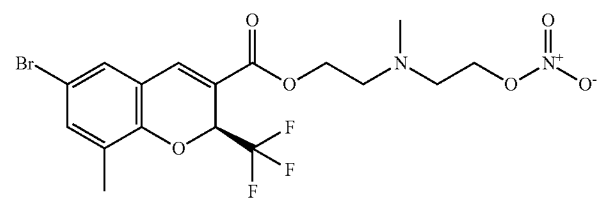 [SMILES: Cc1cc(Cl)cc2c1O[C@H](C(F)(F)F)C(C(=O)OCCN(C)CCO[N+](=O)[O-])=C2] | (S)-2-(methyl(2-(nitrooxy)ethyl)amino)ethyl 6-bromo-8-methyl-2-(trifluoromethyl)-2H-chromene-3-carboxylate |
| 72 | 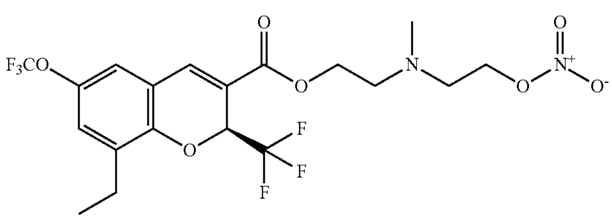 [SMILES: CCc1cc(OC(F)(F)F)cc2c1O[C@H](C(F)(F)F)C(C(=O)OCCN(C)CCO[N+](=O)[O-])=C2] | (S)-2-(methyl(2-(nitrooxy)ethyl)amino)ethyl 8-ethyl-6-(trifluoromethoxy)-2-(trifluoromethyl)-2H-chromene-3-carboxylate |
| 77 | 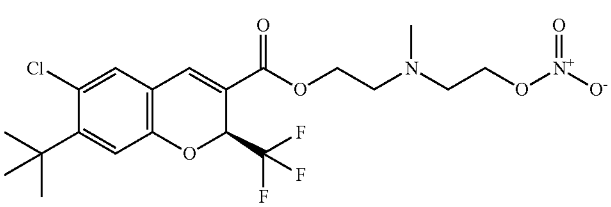 [SMILES: CN(CCOC(=O)C1=Cc2cc(Cl)c(C(C)(C)C)cc2O[C@@H]1C(F)(F)F)CCO[N+](=O)[O-]] | (S)-2-(methyl(2-(nitrooxy)ethyl)amino)ethyl 7-(tert-butyl)-6-chloro-2-(trifluoromethyl)-2H-chromene-3-carboxylate |

The present invention is also directed to a subclass of compounds, including pharmaceutically acceptable salts of compounds, wherein compounds have the structure of Formula (IV):

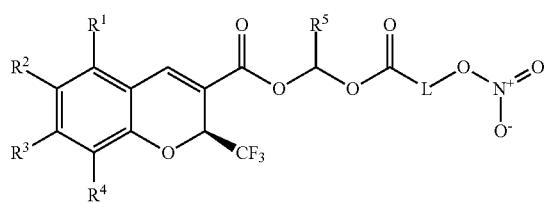

(IV)

wherein R¹ is selected from the group consisting of H, methyl, Cl, and F; R² is selected from the group consisting of Cl, Br, methyl, trifluoromethoxy, pentafluorosulfanyl, $OCH_3$, $OCH_2CH_3$, $OCF_2H$, $SCH_3$, $SCH_2CH_3$, $SCF_3$, $SCF_2H$, $CF_3$, and $CF_2CF_3$; R³ is selected from the group consisting of H, methyl, tert-butyl, ethyl, n-propyl, isopropyl, n-butyl, $CH(CH_3)CH_3CH_2$, $CH_2CH(CH_3)_2$, $C(CH_3)_2CH_2OH$, Cl, F, Br, $CF_3$, and $Si(CH_3)_3$; R⁴ is selected from the group consisting of H, Cl, methyl, ethyl, C≡CH, CH=$CH_2$, and Br; -L- is $C_{1-6}$alkylenyl, wherein at least one —$CH_2$— radical is optionally replaced with a radical independently selected from the group consisting of $CH(R^6)$ and $C(R^6)_2$, or -L- is selected from the group consisting of $CH_2OCH_2CH_2$, $CH_2SCH_2CH_2$, and $CH_2N(R^7)CH_2CH_2$; R⁵ is selected from the group consisting of H, alkyl and cycloalkyl; R⁶ is independently selected from the group consisting of alkyl, cycloalkyl, aryl, aralkyl, heterocyclyl, carboxy, carboxyalkylenyl and nitrooxy $C_{1-3}$ alkylenyl; and R⁷ is selected from the group consisting of H, alkyl, cycloalkyl, and acyl.

In another family of the compounds of Formula (IV), R¹ is H or methyl; R² is selected from the group consisting of Cl, Br, methyl, trifluoromethoxy, and pentafluorosulfanyl; R³ is selected from the group consisting of H, methyl, and tert-butyl; and R⁴ is selected from the group consisting of H, Cl, methyl, and ethyl.

In another family of the compounds of Formula (IV), -L- is $C_{1-3}$alkylenyl, wherein at least one —$CH_2$— radicals must be replaced with a radical independently selected from the group consisting of $CH(R^6)$ and $C(R^6)_2$; R⁵ is H or methyl; and R⁶ is independently selected from H or methyl. Non-limiting examples include:

| Ex. | Structure | Name |
|---|---|---|
| 91 | 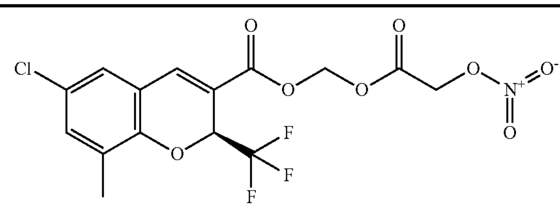 | (S)-(2-(nitrooxy)acetoxy)methyl 6-chloro-8-methyl-2-(trifluoromethyl)-2H-chromene-3-carboxylate |
| 93 | 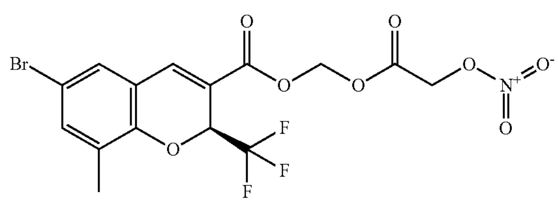 | (S)-(2-(nitrooxy)acetoxy)methyl 6-bromo-8-methyl-2-(trifluoromethyl)-2H-chromene-3-carboxylate |
| 99 | 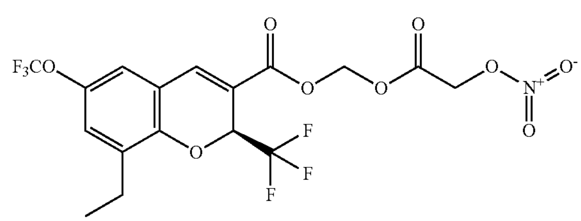 | (S)-(2-(nitrooxy)acetoxy)methyl 8-ethyl-6-(trifluoromethoxy)-2-(trifluoromethyl)-2H-chromene-3-carboxylate |
| 109 | 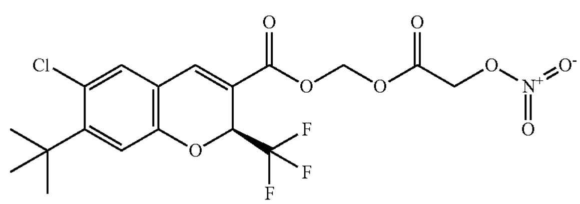 | (S)-(2-(nitrooxy)acetoxy)methyl 7-(tert-butyl)-6-chloro-2-(trifluoromethyl)-2H-chromene-3-carboxylate |
| 113 | 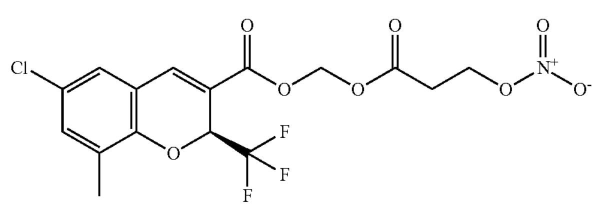 | (S)-((3-(nitrooxy)propanoyl)oxy)methyl 6-chloro-8-methyl-2-(trifluoromethyl)-2H-chromene-3-carboxylate |

-continued

| Ex. | Structure | Name |
|---|---|---|
| 115 | 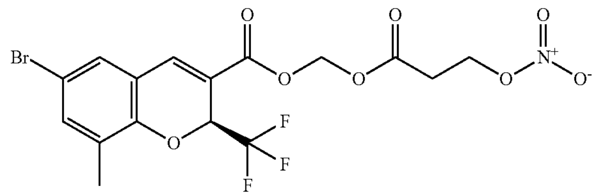 [SMILES: Cc1cc(Cl)cc2c1O[C@H](C(F)(F)F)C(C(=O)OCOC(=O)CCO[N+](=O)[O-])=C2] | (S)-((3-(nitrooxy)propanoyl)oxy)methyl 6-bromo-8-methyl-2-(trifluoromethyl)-2H-chromene-3-carboxylate |
| 121 | 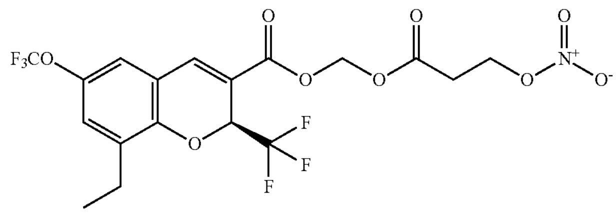 [SMILES: CCc1cc(OC(F)(F)F)cc2c1O[C@H](C(F)(F)F)C(C(=O)OCOC(=O)CCO[N+](=O)[O-])=C2] | (S)-((3-(nitrooxy)propanoyl)oxy)methyl 8-ethyl-6-(trifluoromethoxy)-2-(trifluoromethyl)-2H-chromene-3-carboxylate |
| 131 | 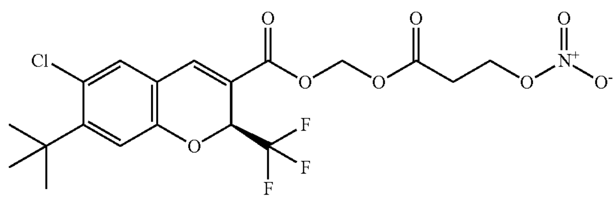 [SMILES: CC(C)(C)c1cc2c(cc1Cl)C=C(C(=O)OCOC(=O)CCO[N+](=O)[O-])[C@@H](C(F)(F)F)O2] | (S)-((3-(nitrooxy)propanoyl)oxy)methyl 7-(tert-butyl)-6-chloro-2-(trifluoromethyl)-2H-chromene-3-carboxylate |
| 135 | 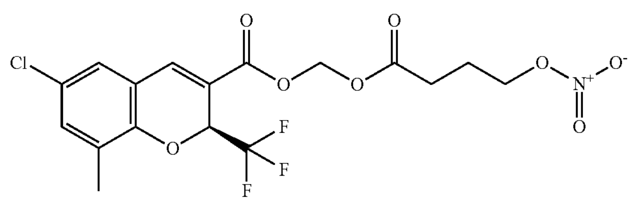 | (S)-((4-(nitrooxy)butanoyl)oxy)methyl 6-chloro-8-methyl-2-(trifluoromethyl)-2H-chromene-3-carboxylate |
| 137 | 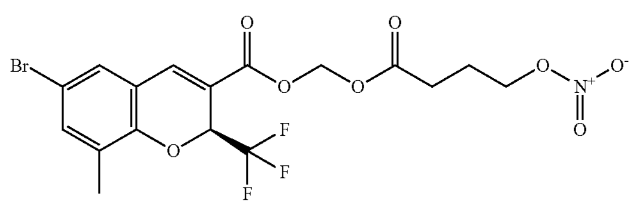 [SMILES: Cc1cc(Cl)cc2c1O[C@H](C(F)(F)F)C(C(=O)OCOC(=O)CCCO[N+](=O)[O-])=C2] | (S)-((4-(nitrooxy)butanoyl)oxy)methyl 6-bromo-8-methyl-2-(trifluoromethyl)-2H-chromene-3-carboxylate |
| 143 | 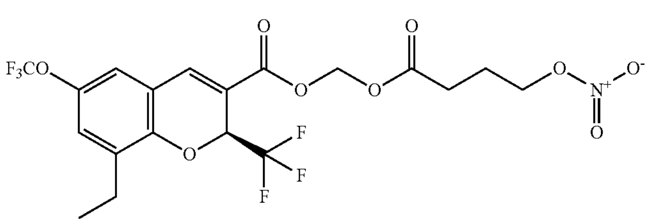 [SMILES: CCc1cc(OC(F)(F)F)cc2c1O[C@H](C(F)(F)F)C(C(=O)OCOC(=O)CCCO[N+](=O)[O-])=C2] | (S)-((4-(nitrooxy)butanoyl)oxy)methyl 8-ethyl-6-(trifluoromethoxy)-2-(trifluoromethyl)-2H-chromene-3-carboxylate |
| 153 | 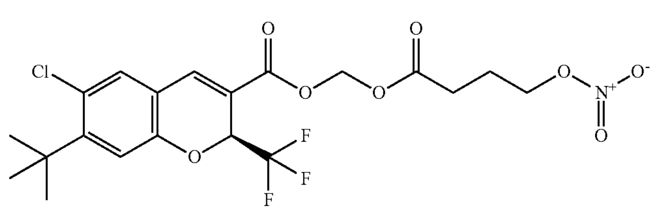 [SMILES: CC(C)(C)c1cc2c(cc1Cl)C=C(C(=O)OCOC(=O)CCCO[N+](=O)[O-])[C@@H](C(F)(F)F)O2] | (S)-((4-(nitrooxy)butanoyl)oxy)methyl 7-(tert-butyl)-6-chloro-2-(trifluoromethyl)-2H-chromene-3-carboxylate |

| Ex. | Structure | Name |
|---|---|---|
| 155 | 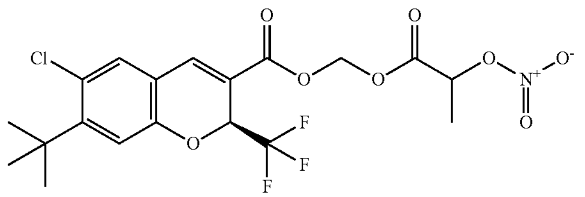 [SMILES: CC(O[N+](=O)[O-])C(=O)OCOC(=O)C1=Cc2cc(Cl)c(C(C)(C)C)cc2O[C@@H]1C(F)(F)F] | (2S)-((2-(nitrooxy)propanoyl)oxy)methyl 7-(tert-butyl)-6-chloro-2-(trifluoromethyl)-2H-chromene-3-carboxylate |
| 157 | 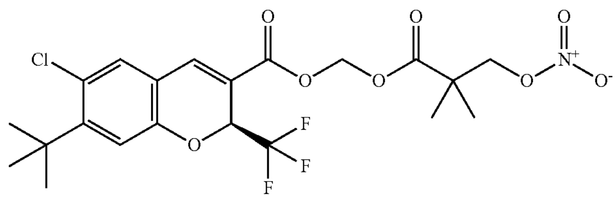 [SMILES: CC(C)(CO[N+](=O)[O-])C(=O)OCOC(=O)C1=Cc2cc(Cl)c(C(C)(C)C)cc2O[C@@H]1C(F)(F)F] | (2S)-((2,2-dimethyl-3-(nitrooxy)propanoyl)oxy)methyl 7-(tert-butyl)-6-chloro-2-(trifluoromethyl)-2H-chromene-3-carboxylate |

In another family of the compounds of Formula (IV), -L- is selected from the group consisting of $CH_2OCH_2CH_2$, $CH_2SCH_2CH_2$, and $CH_2N(R^7)CH_2CH_2$; $R^5$ is H or methyl; and $R^7$ is methyl or acetyl. Non-limiting examples include:

| Ex. | Structure | Name |
|---|---|---|
| 159 | 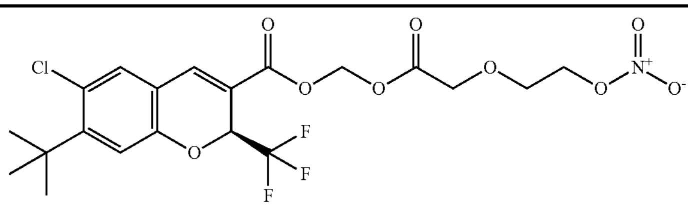 | (S)-(2-(2-(nitrooxy)ethoxy)acetoxy)methyl 7-(tert-butyl)-6-chloro-2-(trifluoromethyl)-2H-chromene-3-carboxylate |
| 162 | 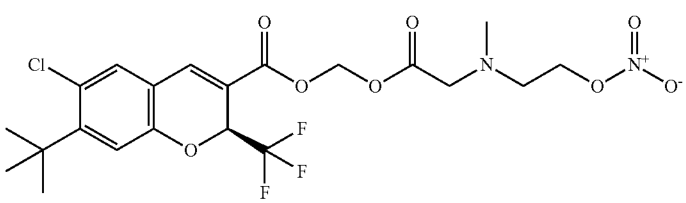 [SMILES: CN(CCO[N+](=O)[O-])CC(=O)OCOC(=O)C1=Cc2cc(Cl)c(C(C)(C)C)cc2O[C@@H]1C(F)(F)F] | (S)-(2-(methyl(2-(nitrooxy)ethyl)amino)acetoxy)methyl 7-(tert-butyl)-6-chloro-2-(trifluoromethyl)-2H-chromene-3-carboxylate |

The present invention is also directed to a subclass of compounds, including pharmaceutically acceptable salts of compounds, wherein compounds have the structure of Formula (V):

(V)

wherein $R^1$ is selected from the group consisting of H, methyl, Cl, and F; $R^2$ is selected from the group consisting of Cl, Br, methyl, trifluoromethoxy, pentafluorosulfanyl, $OCH_3$, $OCH_2CH_3$, $OCF_2H$, $SCH_3$, $SCH_2CH_3$, $SCF_3$, $SCF_2H$, $CF_3$, and $CF_2CF_3$; $R^3$ is selected from the group consisting of H, methyl, tert-butyl, ethyl, n-propyl, isopropyl, n-butyl, $CH(CH_3)CH_3CH_2$, $CH_2CH(CH_3)_2$, $C(CH_3)_2CH_2OH$, Cl, F, Br, $CF_3$, and $Si(CH_3)_3$; $R^4$ is selected from the group consisting of H, Cl, methyl, ethyl, C≡CH, CH=$CH_2$, and Br; -L- is $C_{1-6}$alkylenyl, wherein at least one —$CH_2$— radical is optionally replaced with a radical independently selected from the group consisting of $CH(R^6)$ and $C(R^6)_2$, or -L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)CH_2CH_2$, and

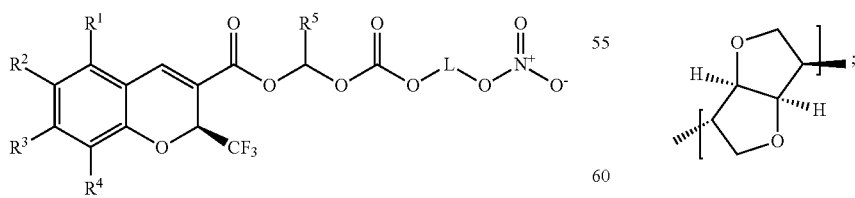

$R^5$ is selected from the group consisting of H, alkyl and cycloalkyl; $R^6$ is independently selected from the group consisting of alkyl, cycloalkyl, aryl, aralkyl, heterocyclyl, carboxy, carboxyalkylenyl and nitrooxy $C_{1-3}$ alkylenyl; and $R^7$ is selected from the group consisting of H, alkyl, cycloalkyl and acyl.

In another family of the compounds of Formula (V), $R^1$ is H or methyl; $R^2$ is selected from the group consisting of Cl, Br, methyl, trifluoromethoxy, and pentafluorosulfanyl; $R^3$ is selected from the group consisting of H, methyl, and tert-butyl; and $R^4$ is selected from the group consisting of H, Cl, methyl, and ethyl.

In another family of the compounds of Formula (V), -L- is $C_{2-4}$alkylenyl, wherein at least one —$CH_2$— radical must be replaced with a radical independently selected from the group consisting of $CH(R^6)$ and $C(R^6)_2$; $R^5$ is H or methyl; and $R^6$ is independently selected from the group consisting of H, methyl, and nitrooxymethyl. Non-limiting examples include:

| Ex. | Structure | Name |
|---|---|---|
| 185 | 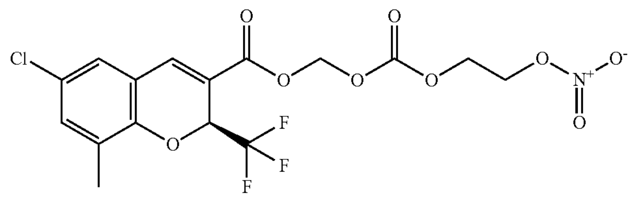 [SMILES: Cc1cc(Cl)cc2c1O[C@H](C(F)(F)F)C(C(=O)OCOC(=O)OCCO[N+](=O)[O-])=C2] | (S)-(((2-(nitrooxy)ethoxy)carbonyl)oxy)methyl 6-chloro-8-methyl-2-(trifluoromethyl)-2H-chromene-3-carboxylate |
| 186 | 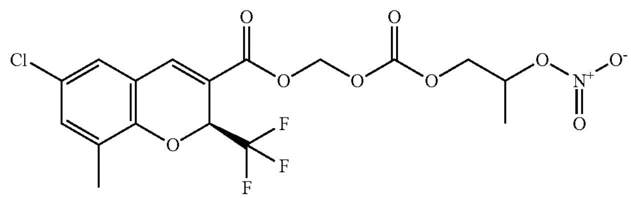 [SMILES: Cc1cc(Cl)cc2c1O[C@H](C(F)(F)F)C(C(=O)OCOC(=O)OCC(C)O[N+](=O)[O-])=C2] | (2S)-(((2-(nitrooxy)propoxy)carbonyl)oxy)methyl 6-chloro-8-methyl-2-(trifluoromethyl)-2H-chromene-3-carboxylate |
| 187 | 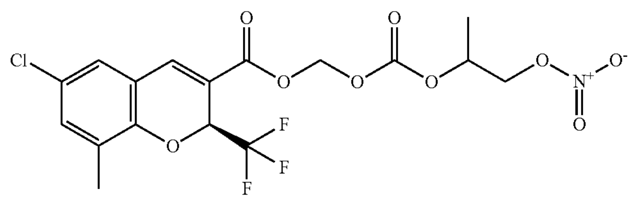 [SMILES: Cc1cc(Cl)cc2c1O[C@H](C(F)(F)F)C(C(=O)OCOC(=O)OC(C)CO[N+](=O)[O-])=C2] | (2S)-((((1-(nitrooxy)propan-2-yl)oxy)carbonyl)oxy)methyl 6-chloro-8-methyl-2-(trifluoromethyl)-2H-chromene-3-carboxylate |
| 188 | 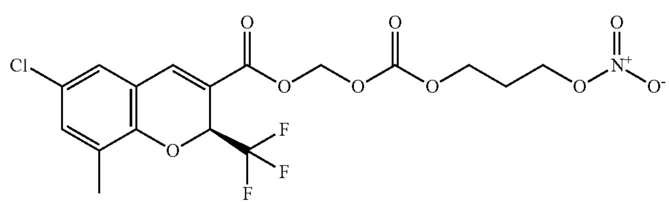 [SMILES: Cc1cc(Cl)cc2c1O[C@H](C(F)(F)F)C(C(=O)OCOC(=O)OCCCO[N+](=O)[O-])=C2] | (S)-(((3-(nitrooxy)propoxy)carbonyl)oxy)methyl 6-chloro-8-methyl-2-(trifluoromethyl)-2H-chromene-3-carboxylate |
| 189 | 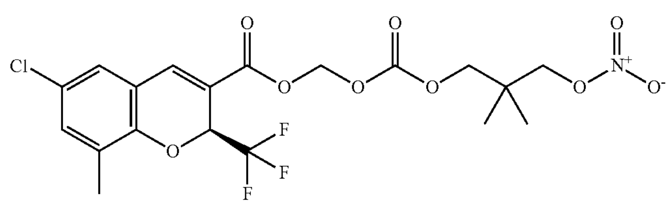 [SMILES: Cc1cc(Cl)cc2c1O[C@H](C(F)(F)F)C(C(=O)OCOC(=O)OCC(C)(C)CO[N+](=O)[O-])=C2] | (S)-(((2,2-dimethyl-3-(nitrooxy)propoxy)carbonyl)oxy)methyl 6-chloro-8-methyl-2-(trifluoromethyl)-2H-chromene-3-carboxylate |
| 190 | 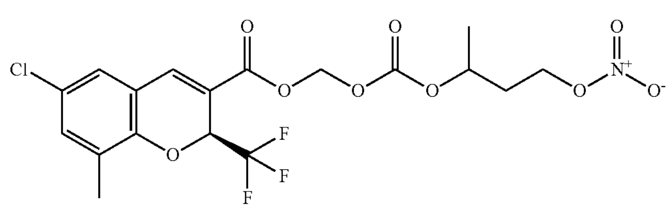 [SMILES: Cc1cc(Cl)cc2c1O[C@H](C(F)(F)F)C(C(=O)OCOC(=O)OC(C)CCO[N+](=O)[O-])=C2] | (2S)-((((4-(nitrooxy)butan-2-yl)oxy)carbonyl)oxy)methyl 6-chloro-8-methyl-2-(trifluoromethyl)-2H-chromene-3-carboxylate |
| 191 | 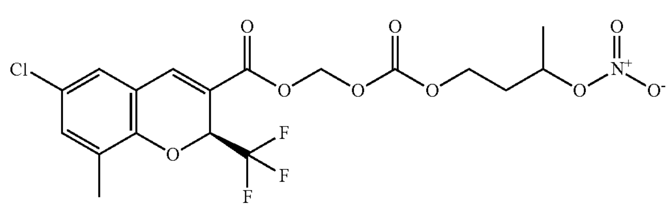 [SMILES: Cc1cc(Cl)cc2c1O[C@H](C(F)(F)F)C(C(=O)OCOC(=O)OCCC(C)O[N+](=O)[O-])=C2] | (2S)-(((3-(nitrooxy)butoxy)carbonyl)oxy)methyl 6-chloro-8-methyl-2-(trifluoromethyl)-2H-chromene-3-carboxylate |

| Ex. | Structure | Name |
| --- | --- | --- |
| 192 | 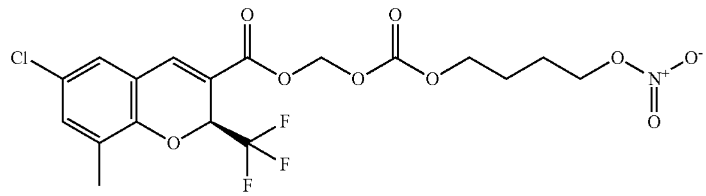 [SMILES: Cc1cc(Cl)cc2c1O[C@H](C(F)(F)F)C(C(=O)OCOC(=O)OCCCCO[N+](=O)[O-])=C2] | (S)-(((4-(nitrooxy)butoxy)carbonyl)oxy) methyl 6-chloro-8-methyl-2-(trifluoromethyl)-2H-chromene-3-carboxylate |
| 207 | 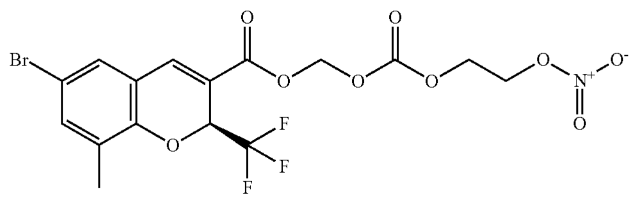 | (S)-(((2-(nitrooxy)ethoxy)carbonyl)oxy) methyl 6-bromo-8-methyl-2-(trifluoromethyl)-2H-chromene-3-carboxylate |
| 208 | 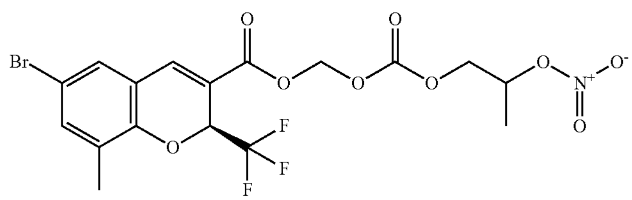 | (2S)-(((2-(nitrooxy)propoxy)carbonyl)oxy)methyl 6-bromo-8-methyl-2-(trifluoromethyl)-2H-chromene-3-carboxylate |
| 209 | 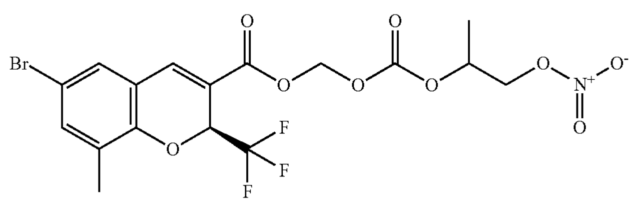 | (2S)-((((1-(nitrooxy)propan-2-yl)oxy)carbonyl)oxy)methyl 6-bromo-8-methyl-2-(trifluoromethyl)-2H-chromene-3-carboxylate |
| 210 | 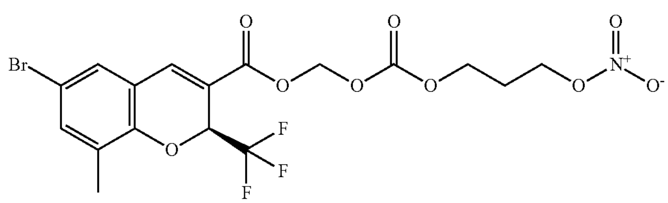 | (S)-(((3-(nitrooxy)propoxy)carbonyl)oxy)methyl 6-bromo-8-methyl-2-(trifluoromethyl)-2H-chromene-3-carboxylate |
| 211 | 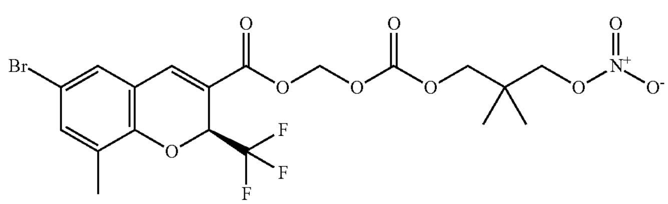 | (S)-(((2,2-dimethyl-3-(nitrooxy)propoxy)carbonyl)oxy)methyl 6-bromo-8-methyl-2-(trifluoromethyl)-2H-chromene-3-carboxylate |
| 212 | 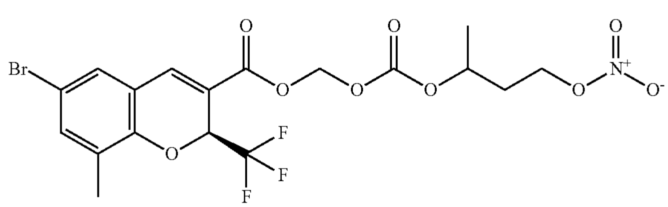 | (2S)-((((4-(nitrooxy)butan-2-yl)oxy)carbonyl)oxy)methyl 6-bromo-8-methyl-2-(trifluoromethyl)-2H-chromene-3-carboxylate |

-continued

| Ex. | Structure | Name |
|---|---|---|
| 213 | 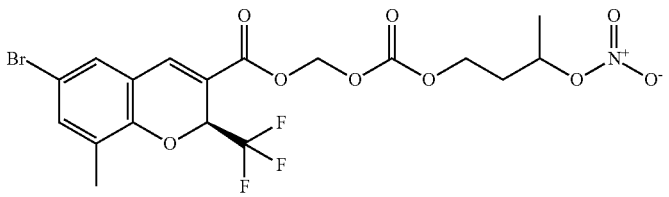 [SMILES: Cc1cc(Br)cc2c1O[C@H](C(F)(F)F)C(C(=O)OCOC(=O)OCCC(C)O[N+](=O)[O-])=C2] | (2S)-(((3-(nitrooxy)butoxy)carbonyl)oxy)methyl 6-bromo-8-methyl-2-(trifluoromethyl)-2H-chromene-3-carboxylate |
| 214 | 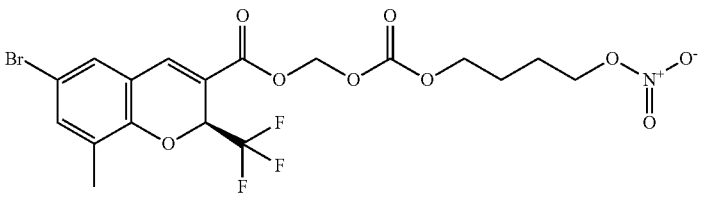 | (S)-(((4-(nitrooxy)butoxy)carbonyl)oxy)methyl 6-bromo-8-methyl-2-(trifluoromethyl)-2H-chromene-3-carboxylate |
| 273 | 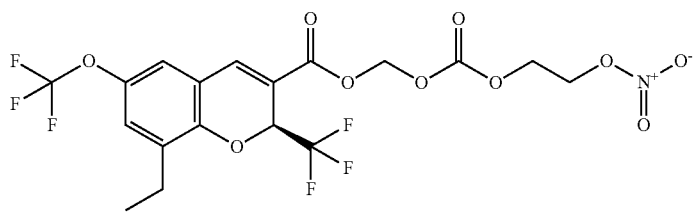 [SMILES: CCc1cc(OC(F)(F)F)cc2c1O[C@H](C(F)(F)F)C(C(=O)OCOC(=O)OCCO[N+](=O)[O-])=C2] | (S)-(((2-(nitrooxy)ethoxy)carbonyl)oxy)methyl 6-trifluoromethoxy-8-ethyl-2-(trifluoromethyl)-2H-chromene-3-carboxylate |
| 274 | 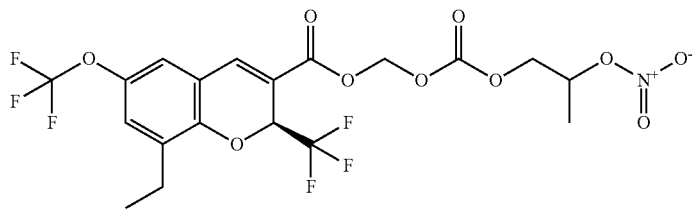 [SMILES: CCc1cc(OC(F)(F)F)cc2c1O[C@H](C(F)(F)F)C(C(=O)OCOC(=O)OCC(C)O[N+](=O)[O-])=C2] | (2S)-(((2-(nitrooxy)propoxy)carbonyl)oxy)methyl 6-trifluoromethoxy-8-ethyl-2-(trifluoromethyl)-2H-chromene-3-carboxylate |
| 275 | 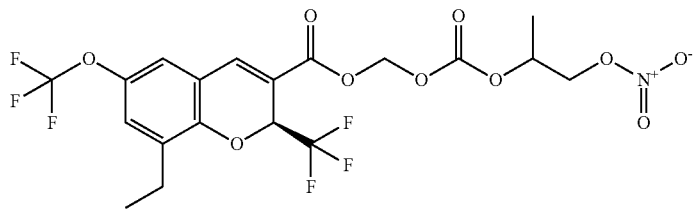 [SMILES: CCc1cc(OC(F)(F)F)cc2c1O[C@H](C(F)(F)F)C(C(=O)OCOC(=O)OC(C)CO[N+](=O)[O-])=C2] | (2S)-((((1-(nitrooxy)propan-2-yl)oxy)carbonyl)oxy)methyl 6-trifluoromethoxy-8-ethyl-2-(trifluoromethyl)-2H-chromene-3-carboxylate |
| 276 | 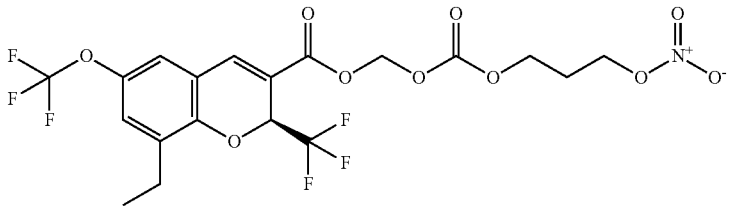 [SMILES: CCc1cc(OC(F)(F)F)cc2c1O[C@H](C(F)(F)F)C(C(=O)OCOC(=O)OCCCO[N+](=O)[O-])=C2] | (S)-(((3-(nitrooxy)propoxy)carbonyl)oxy)methyl 6-trifluoromethoxy-8-ethyl-2-(trifluoromethyl)-2H-chromene-3-carboxylate |
| 277 | 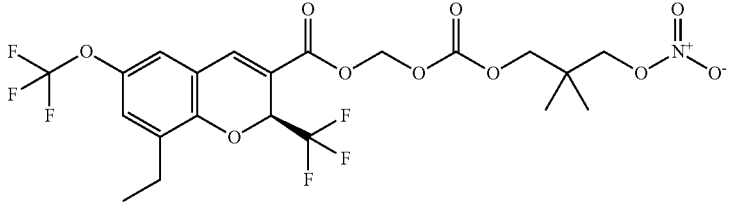 [SMILES: CCc1cc(OC(F)(F)F)cc2c1O[C@H](C(F)(F)F)C(C(=O)OCOC(=O)OCC(C)(C)CO[N+](=O)[O-])=C2] | (S)-(((2,2-dimethyl-3-(nitrooxy)propoxy)carbonyl)oxy)methyl 6-trifluoromethoxy-8-ethyl-2-(trifluoromethyl)-2H-chromene-3-carboxylate |

| Ex. | Structure | Name |
|---|---|---|
| 278 | 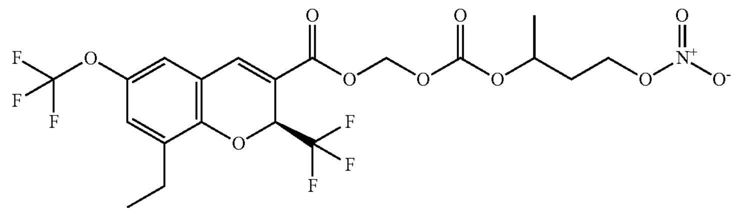 [SMILES: CCc1cc(OC(F)(F)F)cc2c1O[C@H](C(F)(F)F)C(C(=O)OCOC(=O)OC(C)CCO[N+](=O)[O-])=C2] | (2S)-((((4-(nitrooxy)butan-2-yl)oxy)carbonyl)oxy)methyl 6-trifluoromethoxy-8-ethyl-2-(trifluoromethyl)-2H-chromene-3-carboxylate |
| 279 | 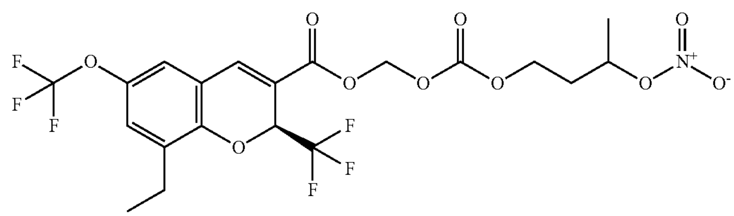 [SMILES: CCc1cc(OC(F)(F)F)cc2c1O[C@H](C(F)(F)F)C(C(=O)OCOC(=O)OCCC(C)O[N+](=O)[O-])=C2] | (2S)-(((3-(nitrooxy)butoxy)carbonyl)oxy)methyl 6-trifluoromethoxy-8-ethyl-2-(trifluoromethyl)-2H-chromene-3-carboxylate |
| 280 | 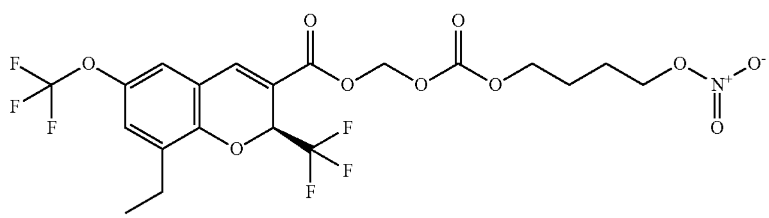 [SMILES: CCc1cc(OC(F)(F)F)cc2c1O[C@H](C(F)(F)F)C(C(=O)OCOC(=O)OCCCCO[N+](=O)[O-])=C2] | (S)-(((4-(nitrooxy)butoxy)carbonyl)oxy) methyl 6-trifluoromethoxy-8-ethyl-2-(trifluoromethyl)-2H-chromene-3-carboxylate |
| 383 | 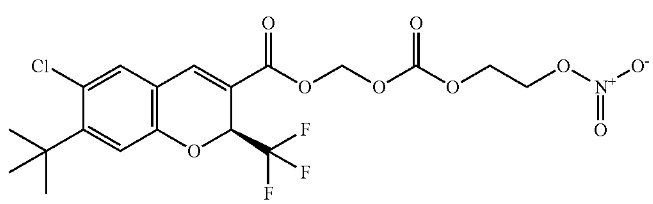 [SMILES: CC(C)(C)c1cc2c(cc1Cl)C=C(C(=O)OCOC(=O)OCCO[N+](=O)[O-])[C@@H](C(F)(F)F)O2] | (S)-(((2-(nitrooxy)ethoxy)carbonyl)oxy) methyl 6-chloro-7-tert-butyl-2-(trifluoromethyl)-2H-chromene-3-carboxylate |
| 384 | 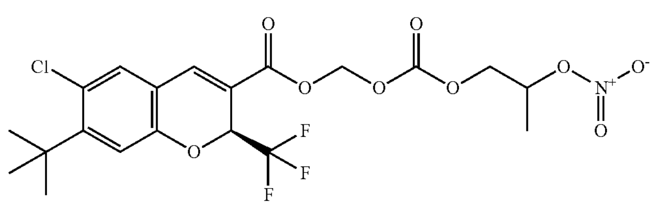 [SMILES: CC(COC(=O)OCOC(=O)C1=Cc2cc(Cl)c(C(C)(C)C)cc2O[C@@H]1C(F)(F)F)O[N+](=O)[O-]] | (2S)-(((2-(nitrooxy)propoxy)carbonyl)oxy)methyl 6-chloro-7-tert-butyl-2-(trifluoromethyl)-2H-chromene-3-carboxylate |
| 385 | 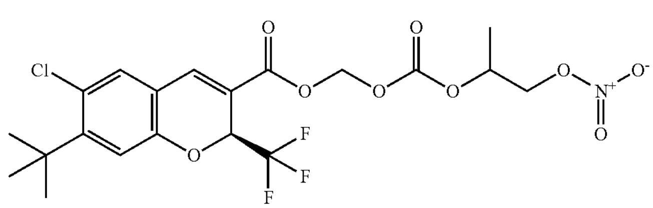 [SMILES: CC(CO[N+](=O)[O-])OC(=O)OCOC(=O)C1=Cc2cc(Cl)c(C(C)(C)C)cc2O[C@@H]1C(F)(F)F] | (2S)-((((1-(nitrooxy)propan-2-yl)oxy)carbonyl)oxy)methy 6-chloro-7-tert-butyl-2-(trifluoromethyl)-2H-chromene-3-carboxylate |
| 386 | 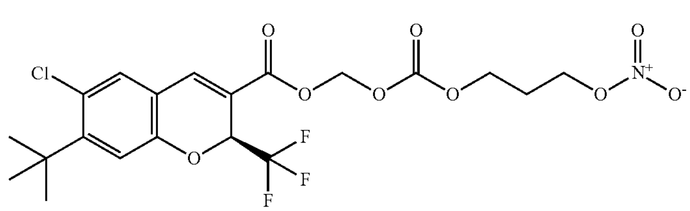 [SMILES: CC(C)(C)c1cc2c(cc1Cl)C=C(C(=O)OCOC(=O)OCCCO[N+](=O)[O-])[C@@H](C(F)(F)F)O2] | (S)-(((3-(nitrooxy)propoxy)carbonyl)oxy)methyl 6-chloro-7-tert-butyl-2-(trifluoromethyl)-2H-chromene-3-carboxylate |

-continued

| Ex. | Structure | Name |
|---|---|---|
| 387 | 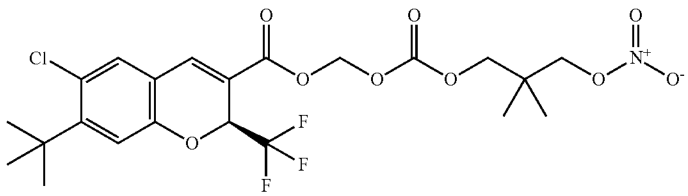 [SMILES: CC(C)(COC(=O)OCOC(=O)C1=Cc2cc(Cl)c(C(C)(C)C)cc2O[C@@H]1C(F)(F)F)CO[N+](=O)[O-]] | (S)-(((2,2-dimethyl-3-(nitrooxy)propoxy)carbonyl)oxy)methyl 6-chloro-7-tert-butyl-2-(trifluoromethyl)-2H-chromene-3-carboxylate |
| 388 | 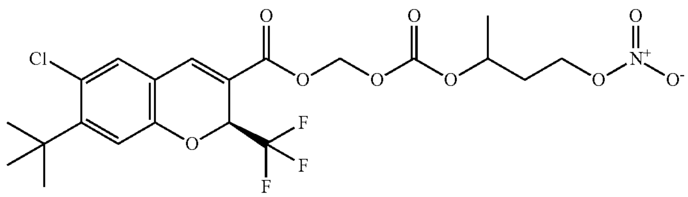 [SMILES: CC(CCO[N+](=O)[O-])OC(=O)OCOC(=O)C1=Cc2cc(Cl)c(C(C)(C)C)cc2O[C@@H]1C(F)(F)F] | (2S)-((((4-(nitrooxy)butan-2-yl)oxy)carbonyl)oxy)methyl 6-chloro-7-tert-butyl-2-(trifluoromethyl)-2H-chromene-3-carboxylate |
| 389 | 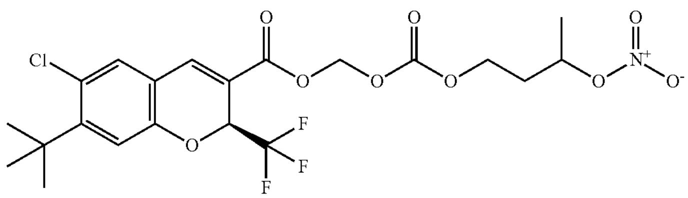 [SMILES: CC(CCOC(=O)OCOC(=O)C1=Cc2cc(Cl)c(C(C)(C)C)cc2O[C@@H]1C(F)(F)F)O[N+](=O)[O-]] | (2S)-(((3-(nitrooxy)butoxy)carbonyl)oxy)methyl 6-chloro-7-tert-butyl-2-(trifluoromethyl)-2H-chromene-3-carboxylate |
| 390 | 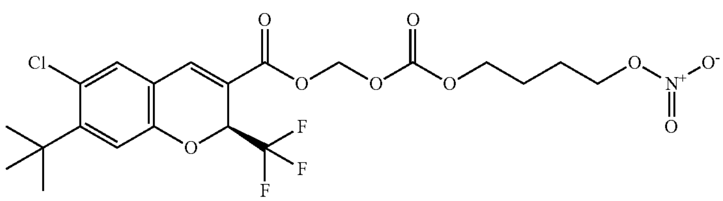 [SMILES: CC(C)(C)c1cc2c(cc1Cl)C=C(C(=O)OCOC(=O)OCCCCO[N+](=O)[O-])[C@@H](C(F)(F)F)O2] | (S)-(((4-(nitrooxy)butoxy)carbonyl)oxy)methyl 6-chloro-7-tert-butyl-2-(trifluoromethyl)-2H-chromene-3-carboxylate |
| 405 | 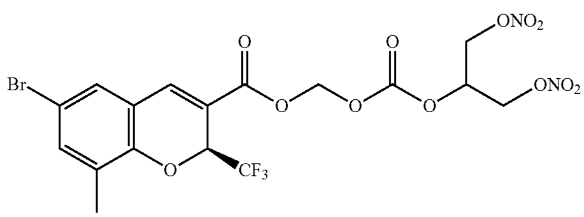 | (S)-((((1,3-bis(nitrooxy)propan-2-yl)oxy)carbonyl)oxy)methyl 6-bromo-8-methyl-2-(trifluoromethyl)-2H-chromene-3-carboxylate |
| 407 | 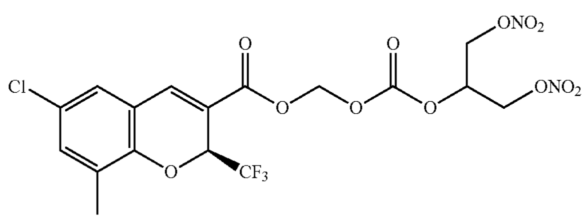 | (S)-((((1,3-bis(nitrooxy)propan-2-yl)oxy)carbonyl)oxy)methyl 6-chloro-8-methyl-2-(trifluoromethyl)-2H-chromene-3-carboxylate |
| 411 | 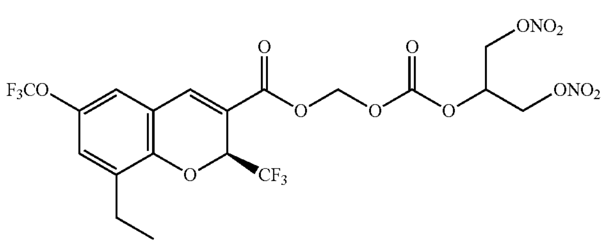 | (S)-((((1,3-bis(nitrooxy)propan-2-yl)oxy)carbonyl)oxy)methyl 8-ethyl-6-(trifluoromethoxy)-2-(trifluoromethyl)-2H-chromene-3-carboxylate |

| Ex. | Structure | Name |
|---|---|---|
| 417 | 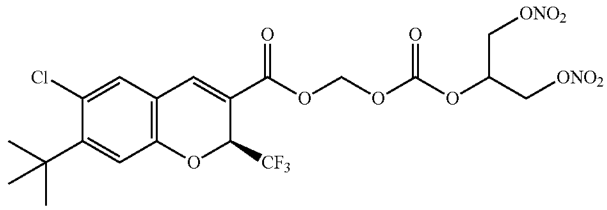 | (S)-((((1,3-bis(nitrooxy)propan-2-yl)oxy)carbonyl)oxy)methyl 7-(tert-butyl)-6-chloro-2-(trifluoromethyl)-2H-chromene-3-carboxylate |
| 418 | 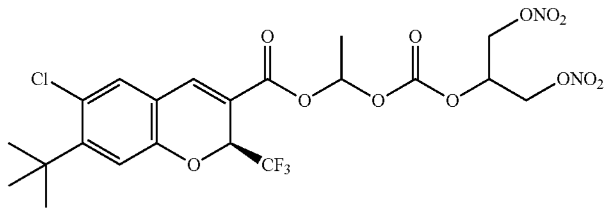 | (2S)-1-((((1,3-bis(nitrooxy)propan-2-yl)oxy)carbonyl)oxy)ethyl 7-(tert-butyl)-6-chloro-2-(trifluoromethyl)-2H-chromene-3-carboxylate |

In another family of the compounds of Formula (V), -L- is $CH_2CH_2OCH_2CH_2$ or $CH_2CH_2N(R^7)CH_2CH_2$; $R^5$ is H or methyl; and $R^7$ is methyl or acetyl. Non-limiting examples include:

| Ex. | Structure | Name |
|---|---|---|
| 193 | 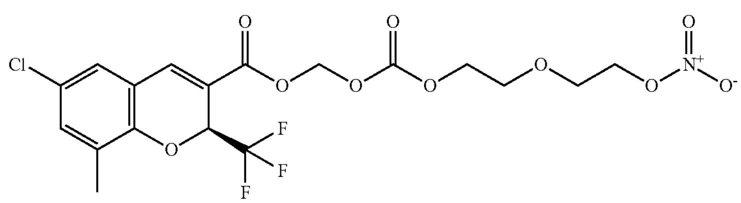 [SMILES: Cc1cc(Cl)cc2c1O[C@H](C(F)(F)F)C(C(=O)OCOC(=O)OCCOCCO[N+](=O)[O-])=C2] | (S)-(((2-(2-(nitrooxy)ethoxy)ethoxy)carbonyl)oxy)methyl 6-chloro-8-methyl-2-(trifluoromethyl)-2H-chromene-3-carboxylate |
| 195 | 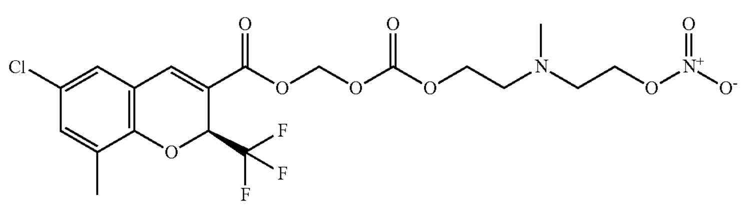 | (S)-(((2-(methyl(2-(nitrooxy)ethyl)amino)ethoxy)carbonyl)oxy)methyl 6-chloro-8-methyl-2-(trifluoromethyl)-2H-chromene-3-carboxylate |
| 215 | 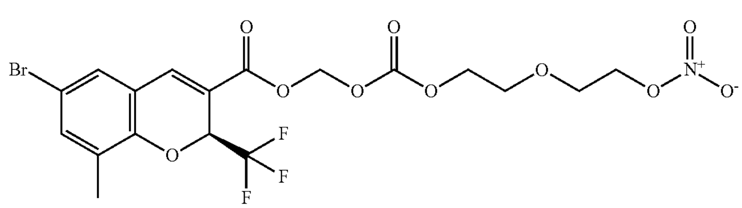 | (S)-(((2-(2-(nitrooxy)ethoxy)ethoxy)carbonyl)oxy)methyl 6-bromo-8-methyl-2-(trifluoromethyl)-2H-chromene-3-carboxylate |
| 217 | 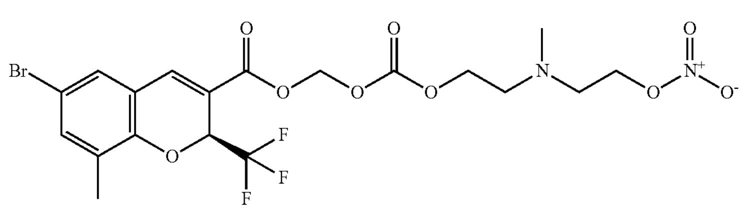 [SMILES: Cc1cc(Cl)cc2c1O[C@H](C(F)(F)F)C(C(=O)OCOC(=O)OCCN(C)CCO[N+](=O)[O-])=C2] | (S)-(((2-(methyl(2-(nitrooxy)ethyl)amino)ethoxy)carbonyl)oxy)methyl 6-bromo-8-methyl-2-(trifluoromethyl)-2H-chromene-3-carboxylate |

-continued

| Ex. | Structure | Name |
|---|---|---|
| 281 | 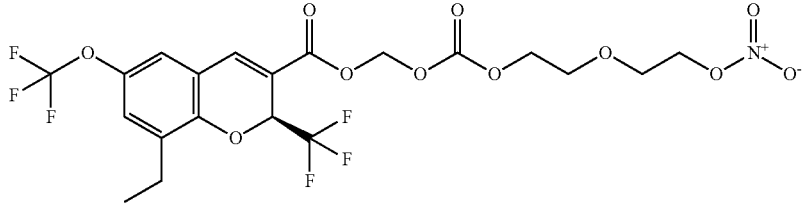 [SMILES: CCc1cc(OC(F)(F)F)cc2c1O[C@H](C(F)(F)F)C(C(=O)OCOC(=O)OCCOCCO[N+](=O)[O-])=C2] | (S)-(((2-(2-(nitrooxy)ethoxy)ethoxy)carbonyl)oxy) methyl 8-ethyl-6-(trifluoromethoxy)-2-(trifluoromethyl)-2H-chromene-3-carboxylate |
| 283 | 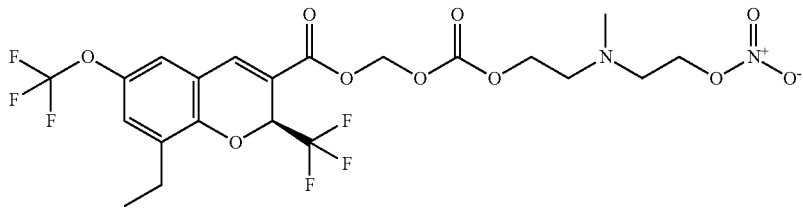 [SMILES: CCc1cc(OC(F)(F)F)cc2c1O[C@H](C(F)(F)F)C(C(=O)OCOC(=O)OCCN(C)CCO[N+](=O)[O-])=C2] | (S)-(((2-(methyl(2-(nitrooxy) ethyl)amino)ethoxy)carbonyl)oxy) methyl 8-ethyl-6-(trifluoromethoxy)-2-(trifluoromethyl)-2H-chromene-3-carboxylate |
| 391 | 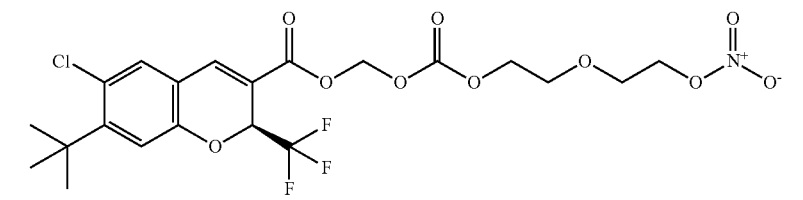 [SMILES: CC(C)(C)c1cc2c(cc1Cl)C=C(C(=O)OCOC(=O)OCCOCCO[N+](=O)[O-])[C@@H](C(F)(F)F)O2] | (S)-(((2-(2-(nitrooxy) ethoxy)ethoxy)carbonyl)oxy)methyl 6-chloro-7-tert-butyl-2-(trifluoromethyl)-2H-chromene-3-carboxylate |
| 393 | 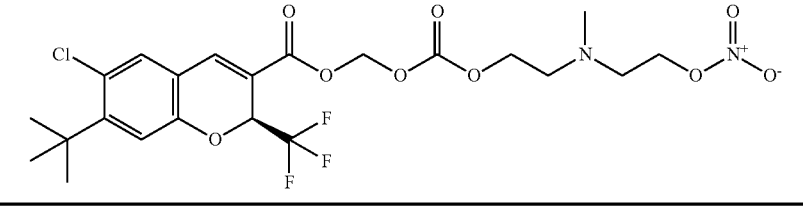 | (S)-(((2-(methyl(2-(nitrooxy) ethyl)amino)ethoxy)carbonyl)oxy) methyl 6-chloro-7-tert-butyl-2-(trifluoromethyl)-2H-chromene-3-carboxylate |

B. Other Embodiments

In another embodiment, there is provided a pharmaceutical composition comprising a compound of the structural formulae herein, and a pharmaceutically-acceptable carrier.

In another embodiment, the pharmaceutical composition further comprises one or more additional pharmaceutically active compounds.

In another embodiment, there is provided a method for treating or preventing a disease condition comprising administering to a subject a therapeutically effective amount of a compound of the structural formulae herein, wherein the condition to be treated or prevented includes, for example, cancer. Further non-limiting examples include non-small cell lung cancer, skin cancer, liver cancer, colorectal cancer (including metastatic colorectal cancer, and FAP), glioblastoma (and other CNS related cancers), squamous cell cancer, bladder cancer, breast cancer, biliary tract cancer, cervical cancer, prostate cancer, small cell lung cancer, ovarian cancer, pancreatic cancer, gastrointestinal cancer, and CNS cancer.

In another embodiment, there is provided a method for healing wounds, comprising administering to a subject a therapeutically effective amount of a compound of the structural formulae herein.

In another embodiment, there is provided a method for treating a condition, comprising administering to a subject a therapeutically effective amount of a compound of the structural formulae herein, wherein the condition to be treated includes, for example, actinic keratosis, cystic fibrosis, and/or acne.

In another embodiment, there is provided a method for treating a condition comprising administering to a subject a therapeutically effective amount of a compound of the structural formulae herein, wherein the condition to be treated includes, for example, autoimmune disorder, inflammatory disorder, and/or auto-inflammatory disorder.

In another embodiment, there is provided a method that comprises administering a combination of a compound of the structural formulae herein, and at least one additional pharmaceutically active compound.

In another embodiment, there is provided a use of a compound of the structural formulae herein for manufacture of a medicament for treatment of a disease condition in a subject.

In another embodiment, there is provided a method for preparing a compound of the structural formulae herein.

In another embodiment, there is provided an intermediate useful in making a compound of the structural formulae herein.

In another embodiment, there is provided a method of enhancing cancer-treating efficacy by activating both NO and COX-2-inihibitor anti-tumor mechanisms in a subject, by administering a therapeutically effective amount of a compound of the structural formulae herein.

In another embodiment, there is provided a method of treating a subject suffering from a disease condition caused by COX-2 over-expression, including but not limited to cancer, by administering a therapeutically effective amount of a compound of the structural formulae herein.

In another embodiment, there is provided a method of improving CV safety in a subject, by administering a therapeutically effective amount of a compound of the structural formulae herein.

In another embodiment, there is provided a method of treating a subject suffering from a disease condition, including but not limited to cancer, by administering a high dose of a compound of the structural formulae herein.

In another embodiment, there is provided a method of gastro-protection in a subject, comprising administering a therapeutically effective amount of a compound of the structural formulae herein.

In another embodiment, there is provided a method of releasing NO in a subject, comprising administering a therapeutically effective amount of a compound of the structural formulae herein.

In another embodiment, there is provided a method of gastro-protection in a subject, comprising administering a therapeutically effective amount of a compound of the structural formulae herein, which releases NO in the subject, preferably by sustained release.

In another embodiment, there is provided a method of gastro-protection in a subject, comprising administering a therapeutically effective amount of a compound of the structural formulae herein, which releases NO in the subject, preferably by sustained release, wherein the NO release is likely caused by an enzymatic mechanism acting on the nitrooxy moiety of the compound of the structural formulae herein.

In another embodiment, there is provided a method of gastro-protection in a subject, comprising administering a therapeutically effective amount of a compound of the structural formulae herein, which releases NO in the subject, preferably by sustained release, wherein the NO release is likely caused by a non-enzymatic mechanism acting on the nitrooxy moiety of the compound of the structural formulae herein.

In another embodiment, there is provided a method of treating a subject suffering from a disease condition, including but not limited to cancer, comprising administering a therapeutically effective amount of a compound of the structural formulae herein, without causing substantial adverse, cardiovascular events.

In another embodiment, there is provided a method of treating a subject suffering from a disease condition, including but not limited to cancer, comprising administering a therapeutically effective amount of a compound of the structural formulae herein, without causing substantial changes in blood pressure, while maintaining gastric-sparing properties.

It will be recognized that the compounds of this invention can exist in radiolabeled form, i.e., the compounds may contain one or more atoms containing an atomic mass or mass number different from the atomic mass or mass number usually found in nature (e.g., an isotope). Alternatively, a plurality of molecules of a single structure may include at least one atom that occurs in an isotopic ratio that is different from the isotopic ratio found in nature. Radioisotopes of hydrogen, carbon, phosphorous, fluorine, chlorine and iodine include $^2H$, $^3H$, $^{11}C$, $^{13}C$, $^{14}C$, $^{15}N$, $^{35}S$, $^{18}F$, $^{36}Cl$, $^{125}I$, $^{124}I$ and $^{131}I$ respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectabilityCompounds that contain isotopes $^{11}C$, $^{13}N$, $^{15}O$, $^{124}I$ and $^{18}F$ are well suited for positron emission tomography. Radiolabeled compounds of the structural formulae herein and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

C. Definitions

The terms "substituent", "radical", "group", "moiety", and "fragment" may be used interchangeably.

If a substituent is described as being "optionally substituted," the substituent may be either (1) not substituted or (2) substituted on a substitutable position. If a substitutable position is not substituted, the default substituent is H.

Singular forms "a", and "an" may include plural reference unless the context clearly dictates otherwise.

The number of carbon atoms in a substituent can be indicated by the prefix "$C_{A-B}$" where A is the minimum and B is the maximum number of carbon atoms in the substituent.

The term "hydrido" denotes a single —H atom (H) and may be used interchangeably with the symbol "H". Hydrido may be attached, for example, to an oxygen atom to form a "hydroxy" radical (i.e., —OH) or two hydrido radicals may be attached to a carbon atom to form a "methylene" (—CH$_2$—) radical.

The terms "hydroxyl" and "hydroxy" may be used interchangeably.

The term "ester" denotes

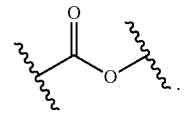 [SMILES: *OC(*)=O]

The term "O-linked ester" denotes an ester that is linked to the parent scaffold through the covalent O in the ester.

The term "halo" refers to fluoro (—F), chloro (—Cl), bromo (—Br), or iodo (—I).

The term "alkyl" denotes a linear or branched acyclic alkyl radical containing from 1 to about 15 carbon atoms and less than or about equal to the natural abundance of deuterium. In some embodiments, alkyl is a $C_{1-10}$alkyl, $C_{1-7}$alkyl, $C_{1-6}$alkyl or $C_{1-5}$alkyl radical. Examples of alkyl include, but are not limited to, methyl, ethyl, propyl, isopropyl, butyl, isobutyl, tert-butyl, sec-butyl, pentan-3-yl (i.e., 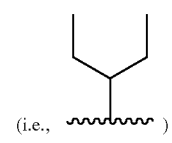 [SMILES: *C(CC)CC] )

and the like.

The term "alkylcarbonyl" denotes an alkyl radical attached to carbonyl.

The term "hydroxyalkyl" embraces a radical wherein any one or more of an alkyl carbon is substituted with a hydroxyl radical as defined above, for example, monohydroxyalkyl, dihydroxyalkyl, and trihydroxyalkyl. More specific examples of hydroxyalkyl include hydroxymethyl, hydroxyethyl, and hydroxypropyl.

Hydroxyalkyl may be substituted with, for example, alkyl, hydroxyalkyl, hydroxyalkoxy, hydroxyalkoxyalkyl, amino, aminoalkyl, aryl, aralkyl, and heterocyclyl. Further non-limiting examples include hydroxyalkyl substituted with methyl, isobutyl, benzyl, isopropyl, benzyl, and sec-butyl.

The term "hydroxyalkoxy" denotes a hydroxy radical attached to an alkoxy radical (e.g., hydroxyl-C—O-scaffold).

The term "hydroxyalkoxyalkyl" denotes a hydroxyalkoxy radical attached to an alkyl radical. Non-limiting examples include hydroxyethyl-O-ethyl and hydroxylmethyl-O-ethyl.

Hydroxyalkoxyalkyl may, for example, be substituted with alkyl, hydroxyalkyl, hydroxyalkoxy, hydroxyalkoxyalkyl, amino, aminoalkyl, aryl, aralkyl, and heterocyclyl. Further non-limiting examples include hydroxyalkoxyalkyl substituted with methyl, isobutyl, benzyl, isopropyl, and sec-butyl. More specific non-limiting examples of substituted hydroxyalkoxyalkyl include hydroxyethyl-O-ethyl substituted with methyl, isobutyl, benzyl, isopropyl, and sec-butyl.

The term "haloalkyl" embraces an alkyl radical wherein any one or more of the alkyl carbon atoms is substituted with halo as defined above. For example, monohaloalkyl, dihaloalkyl, and trihaloalkyl. A monohaloalkyl radical, for one example, may have either a bromo, chloro or a fluoro atom within the radical. A dihalo radical may have two of the same halo radicals or a combination of different halo radicals. A trihaloalkyl radical may have three of the same halo radicals or a combination of different halo radicals. Non-limiting examples of haloalkyl include fluoromethyl, difluoromethyl, trifluoromethyl, chloromethyl, dichloromethyl, trichloromethyl, trifluoroethyl, pentafluoroethyl, heptafluoropropyl, difluorochloromethyl, dichlorofluoromethyl, difluoroethyl, difluoropropyl, dichloroethyl, dichloropropyl, iodomethyl, diiodomethyl, and triiodomethyl.

The term "alkylene" denotes a divalent linear or branched saturated carbon chain containing from 2 to about 15 carbon atoms. The terms "alkylene", and "alkylenyl" may be used interchangeably. Non-limiting examples of alkylenyl radicals include methylene, ethylenyl

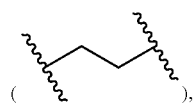 [SMILES: *CC*]

propylenyl

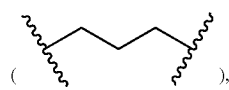

butylenyl

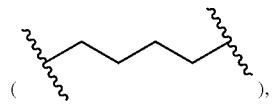 [SMILES: *CCCC*]

and pentylenyl

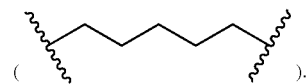 [SMILES: *CCCCC*]

One or more substitutable carbons in an alkylenyl radical may be replaced with, for example, —CH($Z^6$)—, —CH($Z^6$)—O—, —C($Z^6$)$_2$—,

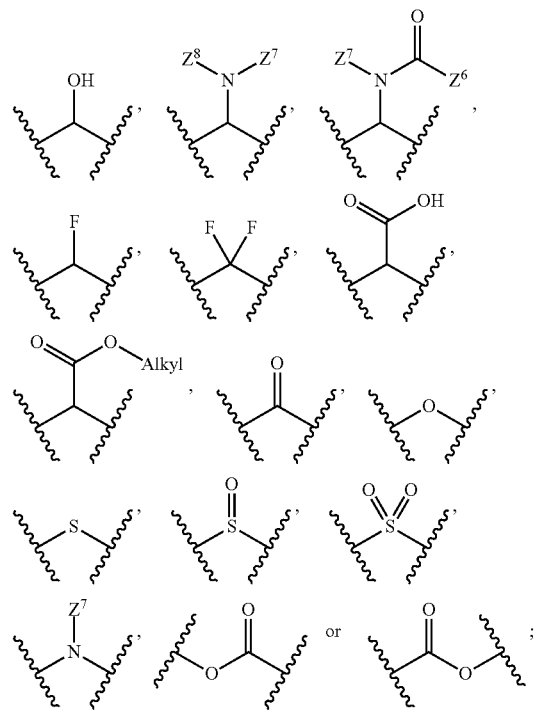

where $Z^6$, $Z^7$, and $Z^8$ may be, for example, independently selected from the group consisting of H, alkyl, hydroxy, aminoalkyl, acylamino, amido, carboxy, carboxyalkyl, hydroxyalkyl, cycloalkyl, aryl, heterocyclyl, (e.g., heteroaryl, more specifically phthalimido) aralkyl, alkyl-O—, alkyl-S—, and alkyl-NH—, or $Z^7$ may be taken together with $Z^8$ to form a cyclic ring; $Z^7$ may be, for example, H, alkyl, hydroxyalkyl, aryl, heterocyclyl, alkylcarbonyl, arylcarbonyl, heterocyclylcarbonyl, carboxyalkylcarbonyl, alkyloxycarbonylalkylcarbonyl, alkylsulfonyl, arylsulfonyl, and heteroarylsulfonyl.

Examples of substituted alkylenyl include, ethyleneoxypropylene

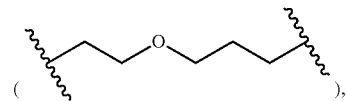 [SMILES: *CCCOCC*]

ethyleneoxycarbonylethylene

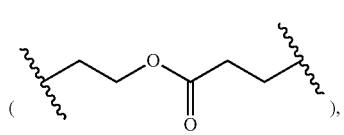 [SMILES: *CCOC(=O)CC*]

ethyleneoxy

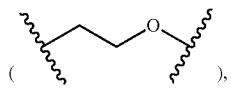

ethyleneoxymethylene

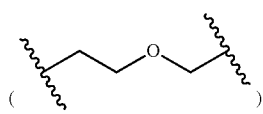 [SMILES: *CCOC*]

ethyleneoxypropylene

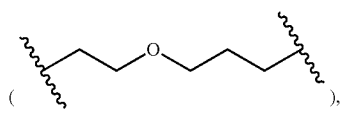 [SMILES: *CCCOCC*]

ethylcarbonyl

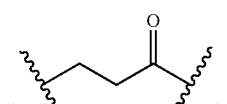

ethylenethiocarbonyl

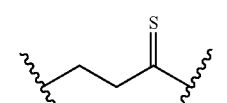

and ethylenethionyl

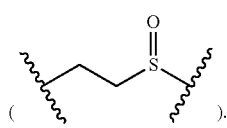

One or more adjacent substitutable carbons in an alkylenyl radical may be replaced with a

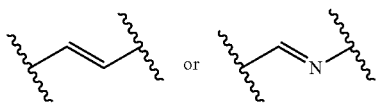

radical.

When one or more substitutable carbons in alkylenyl are substituted, and the resulting radical has multiple orientations (e.g.,

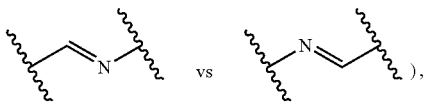

both orientations are embraced by the display of a single orientation.

The term "alkoxy" is RO— where R is alkyl as defined above. Non-limiting examples of alkoxy radicals include methoxy, ethoxy and propoxy. The terms "alkyloxy" and "alkoxy" and "alkyl-O—" may be used interchangeably.

The term "haloalkoxy" is RO— where R is halo-substituted alkyl. Non-limiting examples of haloalkoxy radicals include trifluoromethoxy and tribromomethoxy.

The term "alkoxyalkyl" refers to an alkoxy moiety substituted with an alkyl radical. Examples of alkoxyalkyl radicals include methoxymethyl, methoxyethyl, methoxypropyl and ethoxyethyl.

The term "alkoxycarbonyl" refers to an alkoxy radical substituted with carbonyl. Non-limiting examples include methoxycarbonyl and ethoxycarbonyl.

The term "alkoxycarbonylalkyl" refers to an alkoxycarbonyl radical substituted with alkyl.

The term "alkyloxycarbonylalkylcarbonyl" refers to alkoxycarbonylalkyl radical substituted with carbonyl (e.g.,

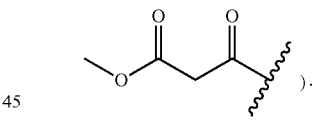

The term "alkenyl" refers to an unsaturated, acyclic hydrocarbon radical with at least one double bond. Such alkenyl radicals contain from 2 to about 15 carbon atoms.

The term "alkynyl" refers to an unsaturated, acyclic hydrocarbon radical with at least one triple bond. Such alkynyl radicals containing from 2 to about 15 carbon atoms. A non-limiting example is propargyl.

The term "cyano" denotes a carbon radical having three of four covalent bonds shared by a single nitrogen atom.

The term "silyl" denotes a

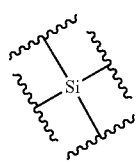 [SMILES: *[Si](*)(*)*]

radical.

The term "alkylsilyl" denotes an alkyl substituted silyl radical.

The term "carbonyl" denotes a carbon radical having two of four covalent bonds shared with a single oxygen atom.

The term "alkylcarbonyl" denotes an alkyl radical attached to a carbonyl radical.

The term "haloalkylcarbonyl" denotes a haloalkyl radical attached to a carbonyl radical.

The term "carbonylalkyl" denotes a carbonyl radical attached to an alkyl radical.

The term "carbonylalkylcarbonyl" denotes a carbonylalkyl radical attached to a carbonyl radical.

The term "carbonyloxy" denotes an oxygen radical having one of two covalent bonds shared with a carbonyl radical.

The term "alkylcarbonyloxy" denotes an alkyl radical attached to a carbonyloxy radical.

The term "alkylcarbonyloxyalkyl" denotes an alkylcarbonyloxy radical attached to an alkyl radical.

The term "alkylcarbonyloxyalkylcarbonyl" denotes an alkylcarbonyloxyalkyl radical attached to an carbonyl radical.

The term "thiocarbonyl" denotes a carbon radical having two of four covalent bonds shared with a single sulfur atom, i.e.,

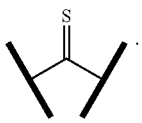

The term "ureido" denotes

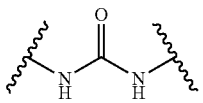 [SMILES: *NC(=O)N*]

and may be used interchangeably with carbamido.

The term "acyl", is

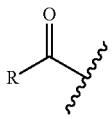

where R may be, for example, H, alkyl, nitrooxyalkylenyl, aryl and aralkyl. More specific examples of acyl include formyl, acetyl, benzoyl, nitrooxymethylcarbonyl and nitrooxyethylcarbonyl.

The term "acylamino" is

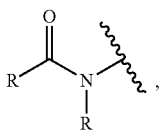

where R may be, for example, H, alkyl, nitrooxyalkylenyl, aryl and aralkyl. A more specific example of acylamino is acetylamino.

The term "carboxy" embraces a hydroxy radical attached to one of two unshared bonds in a carbonyl radical.

The term "carboxyamino" embraces a carboxy radical attached to an amino radical.

The term "carboxyaminoalkylenyl" embraces a carboxyamino radical attached to an alkylenyl radical.

The term "carboxy ester" embraces a carboxy radical attached to a parent scaffold through an ester.

The term "carboxyalkylenyl" embraces a carboxy radical attached to an alkylenyl radical (e.g.,

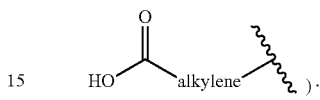

Non-limiting examples of carboxyalkylenyl include carboxymethylene and carboxyethylenyl. The terms "carboxyalkylenyl" and "hydroxycarbonylalkylenyl" may be used interchangeably.

The term "carboxyalkylcarbonyl" denotes a carboxyalkyl radical attached to a carbonyl radical.

The term "thiocarboxy" embraces a hydroxyl radical, as defined above, attached to one of two unshared bonds in a thiocarbonyl radical.

The term "thiocarboxyalkylenyl" embraces a thiocarboxy radical, as defined above, attached to an alkylenyl radical. Non-limiting examples include thiocarboxymethylene and thiocarboxyethylenyl.

The term "amido" embraces an amino radical attached to a parent molecular scaffold through carbonyl (e.g.,

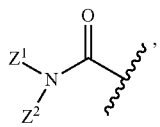

where $Z^1$ and $Z^2$ may be, H, alkyl, or aralkyl, or $Z^1$ may be taken together with $Z^2$ to form heterocyclyl, wherein at least one heteroatom is an amido nitrogen). The terms "amido" and "carboxamido" may be used interchangeably. Examples of amido radicals include monoalkylaminocarbonyl, dialkylaminocarbonyl. More specific examples of amido radicals include N-methylamino carbonyl and N,N-dimethylaminocarbonyl.

The term "carbamate" is

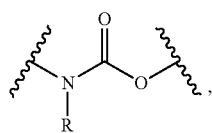

where R may be, for example, H, alkyl or acyl.

The term "cyclic ring" embraces any aromatic or non-aromatic cyclized carbon radical (e.g., aryl and cycloalkyl respectively) which may contain one or more ring heteroatoms (e.g., heteroaryl and heterocyclyl).

The term "cycloalkyl" embraces any monocyclic, bicyclic or tricyclic cyclized carbon radical of 3 to about 15 carbon atoms that is fully saturated. Cycloalkyl may be attached to an aryl, cycloalkyl or a heterocyclyl radical in a fused or pendant manner.

Cycloalkyl may be substituted with alkyl, alkoxy, carboxyalkyl, hydroxyalkyl, amino, acylamino, amido, alkylamino, nitrooxyalkylenyl, nitrooxy, carbonyl, acyl, aralkyl, aryl, heterocyclyl or cycloalkyl.

The term "cycloalkenyl" embraces any monocyclic, bicyclic, or tricyclic cyclized carbon radical, fused or pendant, of 3 to about 15 carbon atoms that is partially saturated, containing one or more double bonds, but is not aromatic.

Cycloalkenyl may be substituted with alkyl, alkoxy, carboxyalkylenyl, hydroxyalkyl, amino, acylamino, amido, alkylamino, nitrooxyalkylenyl, nitrooxy, carbonyl, acyl, aralkyl, aryl, heterocyclyl, cycloalkenyl, or cycloalkyl.

The term "aryl" refers to any monocyclic, bicyclic or tricyclic cyclized carbon radical, wherein at least one ring is aromatic. An aromatic radical may be attached to a non-aromatic cycloalkyl or heterocyclyl radical in a fused or pendant manner. Examples of aryl radicals include, but are not limited to, phenyl and naphthyl.

The term "arylcarbonyl" denotes an aryl radical attached to a carbonyl radical. The terms "aroyl" and "arylcarbonyl" may be used interchangeably. Examples of arylcarbonyl include benzoyl and toluoyl.

The term "haloarylcarbonyl" denotes a halo radical attached to a carbonyl radical.

The term "aralkyl" embraces aryl attached to an alkyl radical and may be used interchangeably with arylalkyl. Examples of aralkyl include benzyl, diphenylmethyl, triphenylmethyl, phenylethyl and diphenylethyl. The terms "benzyl" and "phenylmethyl" may be used interchangeably.

The term "heterocyclyl" refers to any monocyclic, bicyclic or tricyclic ring system having from 5 to about 15 ring members selected from carbon, nitrogen, sulfur and oxygen, wherein at least one ring member is a heteroatom. Heterocyclyl embraces a fully saturated, partially saturated and fully unsaturated radical (e.g., heteroaryl). Heterocyclyl may be fused or attached in a pendant manner to another heterocyclyl, aryl or cycloalkyl radical.

Heterocyclyl embraces combinations of different heteroatoms within the same cyclized ring system. When nitrogen is a ring member, heterocyclyl may be attached to the parent molecular scaffold through a ring nitrogen. Non-limiting examples of fully saturated five and six-membered heterocyclyl include: pyrrolidinyl, imidazolidinyl, piperidinyl, piperazinyl, tetrahydrofuranyl, morpholinyl and thiazolidinyl. Examples of partially saturated heterocyclyl include dihydrothiophenyl (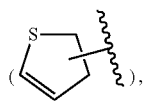), dihydropyranyl, dihydrofuranyl and dihydrothiazolyl.

Heterocyclyl may be substituted, for example, with alkyl, alkoxy, carboxyalkyl, hydroxyalkyl, amino, acylamino, amido, alkylamino, nitrooxyalkylenyl, nitrooxy, carbonyl, acyl, aralkyl, aryl, heterocyclyl or cycloalkyl. Non-limiting examples include, five-membered heterocyclyl substituted with hydroxyalkyl, alkoxyalkyl, acyl, carbonyl or alkylaminocarbonyl. More specifically, pyrrolidinyl may be substituted with hydroxyalkyl, alkoxyalkyl, acyl, carbonyl or alkylaminocarbonyl. Substituted and un-substituted 5-membered heterocyclyl may be fused or attached in a pendant manner to an additional heterocyclyl, aryl or cycloalkyl radical. For example, pyrrolidinyl-2,5-dione may be fused to phenyl giving isoindolinyl, 1,3-dione (also termed "phthalimido").

The term "heterocycloalkyl" embraces a heterocyclyl radical attached to the parent molecular scaffold through an alkyl radical (e.g., heterocyclyl-alkyl-scaffold).

The term "alkylheterocyclylcarbonyl" embraces an alkyl substituted heterocylyl radical attached to the parent molecular scaffold through a carbonyl radical (e.g., alkyl-heterocyclyl-carbonyl-scaffold).

Six-membered heterocyclyl may be substituted with, for example, hydroxyalkyl, alkoxyalkyl, acyl, carbonyl or alkylaminocarbonyl. More specifically, piperidinyl, piperazinyl and morpholinyl may be substituted with hydroxyalkyl, alkoxyalkyl, acyl, carbonyl or alkylaminocarbonyl. Substituted and un-substituted 6-membered heterocyclyl may be fused or attached in a pendant manner to an additional heterocyclyl, aryl or cycloalkyl radical.

The term "heteroaryl" refers to an aromatic heterocyclyl radical. Heteroaryl may be fused or attached in a pendant manner to another heterocyclyl, aryl or cycloalkyl radical. Heteroaryl embraces combinations of different heteroatoms within the same cyclized radical. When nitrogen is a ring member, heteroaryl may be attached to the parent molecular scaffold through a ring nitrogen. Non-limiting examples of heteroaryl include pyridyl, thienyl, furanyl, pyrimidyl, imidazolyl, pyrazolyl, thiazolyl, thiadiazolyl, isothiazolyl, oxazolyl, isoxazoyl, pyrrolyl, pyridazinyl, pyrazinyl, quinolinyl, isoquinolinyl, benzofuranyl, benzothienyl, indolyl, benzothiazolyl, benzooxazolyl, benzimidazolyl, isoindolyl, benzotriazolyl (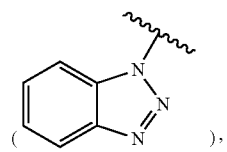 [SMILES: *n1nnc2ccccc21]), purinyl and thianaphthenyl. The term "heteroaryl" is also understood to include the N-oxide derivative of any nitrogen containing heteroaryl.

The term "heteroaryloxy" embraces a heteroaryl radical attached through an oxygen atom to the parent molecular scaffold (e.g., heteroaryl-O-scaffold).

The term "heteroarylcarbonyl" embraces a heteroaryl radical attached to a molecular scaffold through a carbonyl radical (e.g., heteroaryl-carbonyl-scaffold).

The term "haloheteroarylcarbonyl" embraces a halo-substituted heteroaryl radical attached to a molecular scaffold through a carbonyl radical (e.g., haloheteroaryl-carbonyl-scaffold).

The term "alkylamino" embraces an alkyl radical attached to a molecular scaffold through an amino radical (e.g., alkyl-NH-scaffold). Specific non-limiting examples of alkylamino include N,N-dimethylamino-scaffold and N-methylamino-scaffold.

The term "aminoalkyl" embraces an amino radical attached to a molecular scaffold through an alkyl radical (e.g., $NH_2$-alkyl-scaffold).

The term "aminoaryl" embraces an amino substituted aryl radical.

The term "aminoarylcarbonyl" embraces an aminoaryl radical attached to a molecular scaffold through a carbonyl radical (e.g., $NH_2$-aryl-carbonyl-scaffold).

The term "aminocarbonyl" embraces an amino radical attached to a carbonyl radical.

The term "arylaminocarbonyl" embraces an aryl radical attached to a molecular scaffold through an aminocarbonyl radical.

The term "aralkoxy" embraces an arylalkyl radical attached through an oxygen atom to the parent molecular scaffold. The terms "arylalkoxy" and "aralkoxy" may be used interchangeably.

The term "aralkoxycarbonyl" embraces an aralkoxy radical attached to a carbonyl radical.

The term "heteroaralkoxycarbonyl" embraces a heteroaralkoxy radical attached to a molecular scaffold through a carbonyl radical.

The term "heteroaralkylcarbonyl" embraces a heteroaralkyl radical attached to a molecular scaffold through a carbonyl radical.

The term "aryloxy" is RO—, where R is aryl.

The term "arylthio" is RS—, where R is aryl.

The term "alkylthio" is RS—, where R is alkyl (e.g., alkyl-S-scaffold).

The term "haloalkylthio" is RS—, where R is halo-substituted alkyl (e.g., haloalkyl-S-scaffold).

The term "thiolalkyl" is HSR—, where R is alkyl (e.g., HS-alkyl-scaffold).

The term "aryloxyalkyl" embraces an aryloxy radical attached to an alkyl radical.

The term "sulfonyl" is —SO$_2$—.

The term "alkylsulfonyl" embraces an alkyl radical attached to a sulfonyl radical, where alkyl is defined as above.

The term "arylsulfonyl" embraces an aryl radical attached to a sulfonyl radical.

The term "heteroarylsulfonyl" embraces a heteroaryl radical attached to a sulfonyl radical.

The term "alkylsulfonylalkyl", embraces an alkylsulfonyl radical attached to an alkyl radical, where alkyl is defined as above.

The term "haloalkylsulfonyl" embraces a haloalkyl radical attached to a sulfonyl radical, where haloalkyl is defined as above.

The term "pentafluorosulfanyl" denotes a sulfur moiety substituted with five fluoro radicals (i.e., —SF$_5$).

The term "sulfonamide" denotes sulfonyl attached to an amino radical. For example: NH$_2$SO$_2$— and —NHSO$_2$—. Sulfonamide may be used interchangeably with sulfamyl, sulfonamido and aminosulfonyl.

The term "nitrooxy" denotes

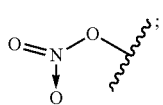 [SMILES: *O[N+](=O)[O-]]

The term "nitrooxyalkylenyl" embraces a nitrooxy radical attached to an alkylenyl radical (e.g.,

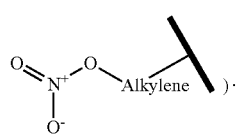).

Structural display of

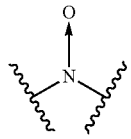

is equivalent to

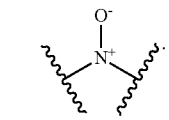

For example,

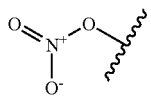

is equivalent to

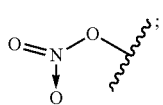 [SMILES: *O[N+](=O)[O-]];

and

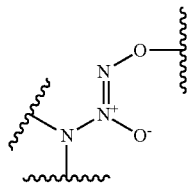 [SMILES: *O/N=[N+](\[O-])N(*)*]

is equivalent to

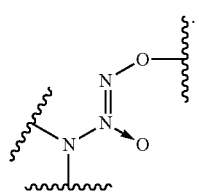 [SMILES: *O/N=[N+](\[O-])N(*)*]

The term "alkylenyloxyalkylenyl" is

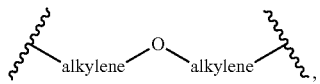

where alkylenyl is defined as above.

The term "alkylenyloxycarbonyl" is

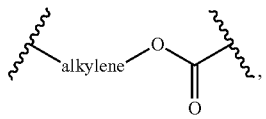

where alkylenyl is defined as above.

The term "succinyl" denotes

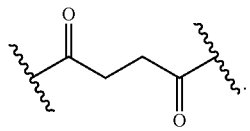 [SMILES: *C(=O)CCC(*)=O]

The term "imine" denotes a compound containing the structure >C=N—.

The term "coxib" is any member of a class of nonsteroidal anti-inflammatory drugs that causes fewer gastrointestinal side effects by selective inhibition of prostaglandin formation. The terms "coxib" and "selective COX-2 inhibitor" may be used interchangeably.

The term "pharmaceutically-acceptable" means suitable for use in pharmaceutical preparations, generally considered as safe for such use, officially approved by a regulatory agency of a national or state government for such use, or being listed in the U. S. Pharmacopoeia or other generally recognized pharmacopoeia for use in animals and more particularly in humans.

The term "pharmaceutically-acceptable salt" refers to a salt which may enhance desired pharmacological activity or may enhance stability of a compound. Examples of pharmaceutically-acceptable salts include acid addition salts formed with inorganic or organic acids, metal salts, and amine salts. Examples of acid addition salts formed with inorganic acids include salts with hydrochloric acid, hydrobromic acid, hydriodic acid, sulfuric acid, nitric acid, and phosphoric acid. Examples of acid addition salts formed with organic acids include acetic acid, propionic acid, hexanoic acid, heptanoic acid, cyclopentanepropionic acid, glycolic acid, pyruvic acid, lactic acid, citric acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo[2.2.2]oct-2-ene1-carboxylic acid, glucoheptonic acid, 4,4'-methylenebis(3-hydroxy-2-naphthoic) acid, 3-phenylpropionic acid, trimethylacetic acid, tertiary butylacetic acid, lauryl sulfuric acid, gluconic acid, glutamic acid, hydroxynaphthoic acids, salicylic acid, stearic acid, and muconic acid. Examples of metal salts include salts with sodium, potassium, calcium, magnesium, aluminum, iron, barium, bismuth, lithium, and zinc ions. Examples of amine salts include salts with ammonia, arecoline, arginine, benethamine, benzathamine, betaine, chloroprocaine, choline, clemizole, cytosine, deanol, diethanolamine, diethylamine, diethylamine, diethylaminoethanol, epolamine, ethanolamine, ethylenediamine, guanine, imidazole, lysine, meglumine, morpholineethanol, niacinamide, piperazine, procaine, pyridoxine, tert-butlamine (erbumine), thiamine, thymine, trolamine, tromethamine, and uracil.

The term "therapeutically-effective amount" refers to an amount of a compound that, when administered to a subject for treating a disease, is sufficient to effect treatment for the disease. "Therapeutically effective amount" can vary depending on the compound, the disease and its severity, the age, the weight, etc. of the subject to be treated.

A compound of the present invention can exist in tautomeric, geometric or stereoisomeric forms. An ester, metabolite, oxime, prodrug, onium, hydrate, solvate and N-oxide of a compound of Formula I are also embraced by the invention. The present invention contemplates all such compounds, including cis- and trans-geometric isomers, R- and S-enantiomers, diastereomers, d-isomers, l-isomers, mixtures of isomers and racemates thereof, as falling within the scope of the invention.

The term "solvate" denotes a molecular or ionic complex of molecules or ions of solvent with those of a compound of the present invention. The term "solvate" embraces the term "hydrate".

The term "hydrate" denotes a compound of the present invention containing water combined in the molecular form.

Some of the compounds described contain one or more stereocenters and are meant to include R, S and mixtures of R and S forms for each stereocenter present.

The term "NO-releasing" means releasing, liberating or generating nitric oxide (NO).

The term "patient" refers to both humans and non-human animals afflicted with any of the conditions described. Non-human animals could be companion animals such as, but not limited to, canine and feline species.

The terms "patient" and "subject" are meant to be interchangeable.

The term "subject" refers to suitable subjects for the methods described herein, which include mammalian subjects. Mammals according to the present invention include, but are not limited to, human, canine, feline, bovine, caprine, equine, ovine, porcine, rodents, lagomorphs, primates, and the like and encompass mammals in utero. Subjects may be of either gender and at any stage of development.

The term "chromene" refers to a compound with a 6-carbon aromatic ring fused to a six-membered heterocyclic pyran ring of the structure:

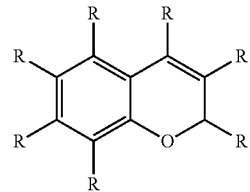

The term "chromene" is intended to embrace compounds with substitution by any substituent at any point on the structure above (denoted by "R" groups). The term "chromene" can also refer to a compound which contains a radical of the chromene structure above. The term "benzopyran" is intended to be interchangeable with the term "chromene".

The term "conjugate" refers to a compound formed by the covalent joining of two or more chemical moieties or entities.

List of Suitable Protecting Groups and Abbreviations

Acetyl (Ac)
Acylals

Benzoyl (Bz)
Benzyl (Bn, Bnl)
Benzyl esters
Carbamate
Carbobenzyloxy (Cbz)
Dimethoxytrityl, [bis-(4-methoxyphenyl)phenylmethyl] (DMT)
Dithianes
Ethoxyethyl ethers (EE)
Methoxymethyl ether (MOM)
Methoxytrityl [(4-methoxyphenyl)diphenylmethyl], (MMT)
Methyl Ethers
Methyl (Me)
Methyl esters
Methylthiomethyl ether
Orthoesters
Oxazoline
Pivaloyl (Piv)
Phthalimido
p-Methoxybenzyl carbonyl (Moz or MeOZ)
p-Methoxybenzyl (PMB)
Propargyl alcohols
Silyl groups (e.g., trimethylsilyl (TMS), tert-butyldimethylsilyl (TBDMS), tri-isopropylsilyloxymethyl (TOM) and triisopropylsilyl (TIPS))
Silyl esters
tert-Butyl esters
tert-Butyloxycarbonyl (BOC or tBOC)
Tetrahydropyranyl (THP)
Tosyl (Ts or Tos)
Trimethylsilylethoxymethyl (SEM)
Trityl (triphenylmethyl, Tr)
β-Methoxyethoxymethyl ether (MEM)
(4-nitrophenyl)sulfonyl or (4-nitrophenyl)(dioxido)-lambda (6)-sulfanyl) (Nosyl)
2-cyanoethyl
2-nitrophenylsulfenyl (Nps)
3,4-Dimethoxybenzyl (DMPM)
9-Fluorenylmethyloxycarbonyl (FMOC)

List of Abbreviations

ACN acetonitrile
BLQ below level of quantification
DCC dicyclohexylcarbodiimide
DCI dicyclohexylcarbodiimide
DCM dichloromethane or methylenechloride
DIPEA diisopropylethylamine
DMAP 4-dimethylaminopyridine or N,N-dimethylaminopyridine
DME 1,2-dimethoxyethane
DMF N,N-dimethylformamide
DMSO dimethylsulfoxide
eq. equivalents
EtOAC ethyl acetate
EtOH ethanol
Fmoc fluorenylmethyloxycarbonyl chloride
HPLC high performance liquid chromatography
h hour
$K_2CO_3$ potassium carbonate
LC/MS liquid chromatography mass spectrometry
LC/MS/MS liquid chromatography tandem mass spectrometry
MeOH methanol
$MgSO_4$ magnesium sulfate
min. minute(s)
mL milliliter
mmol millimole
$Na_2S_2O_3$ sodium thiosulfate
$Na_2SO_4$ sodium sulfate
NaH sodium hydride
$NaHCO_3$ sodium bicarbonate
NaI sodium iodide
$NaIO_4$ sodium periodate
$NaOCH_3$ sodium methoxide
NBS N-bromosuccinimide
NIS N-iodosuccinimide
NMR nuclear magnetic resonance
NO nitric oxide
psi pounds per square inch
PyBOP benzotriazole-1-yl-oxy-tris-(dimethylamino)-phosphonium hexafluorophosphate
$RuCl_3$ ruthenium trichloride hydrate
TEA triethylamine
TFA trifluoroacetic acid
THF tetrahydrofuran
TLC thin layer chromatography
TSA p-toluenesulfonic acid D. General Synthetic Schemes Compounds of the present invention can be prepared using methods illustrated in general synthetic schemes and experimental procedures detailed below. These general synthetic schemes and experimental procedures are presented for purposes of illustration and are not intended to be limiting. Starting materials used to prepare compounds of the present invention are commercially available or can be prepared using routine methods known in the art.

Chromene Acids and Acid Chlorides:

In step 1, chromene acids are made by reaction of salicylic aldehydes (made from corresponding phenols) with ethyl 4,4,4-trifluorocrotonate (Scheme 1) according to procedures described in literature (i.e., U.S. Pat. No. 6,034,256) for when $Z$=$CF_3$, or with ethyl 4,4,5,5,5-pentafluorobut-2-enoate (CAS# [37759-78-7]) for when $Z$=$CF_2CF_3$. Alternatively, chiral chromene acids, where $Z$=$CF_3$, are made by reaction of salicylic aldehydes with 4,4,4-trifluorocrotonaldehyde and chiral catalyst followed by oxidation (Scheme 2) according to procedures described in *ACS Med. Chem. Lett.* 2014, 5, 1162-1166. Chiral chromene acids, where $Z$=$CF_2CF_3$, are made by an analogous approach using 4,4,5,5,5-pentafluoropent-2-enal, which is made from 4,4,5,5,5-pentafluoropent-2-en-1-ol using the same procedure to make 4,4,4-trifluorocrotonaldehyde (INT-07) outlined below.

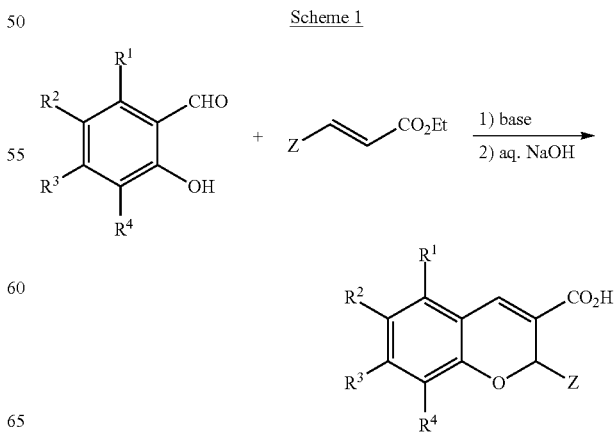

Scheme 1

Scheme 2-Step 1

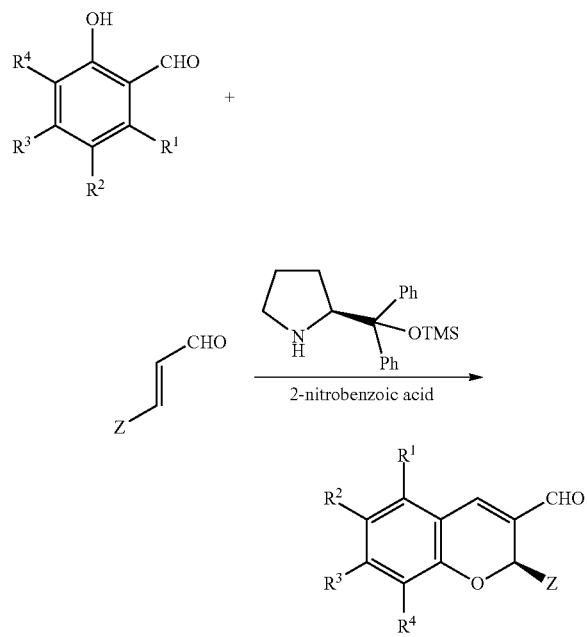

Scheme 2-Step 2

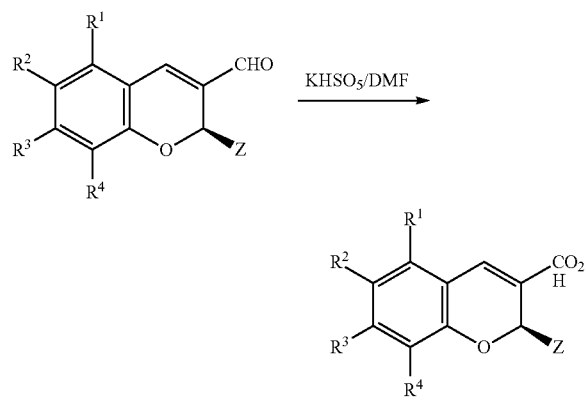

Z is CF$_3$ or CF$_2$CF$_3$;

R$^1$ is H or methyl;

R$^2$ is selected from the group consisting of Cl, Br, methyl, trifluoromethoxy, and pentafluorosulfanyl;

R$^3$ is selected from the group consisting of H, methyl, and tert-butyl; and

R$^4$ is selected from the group consisting of H, Cl, methyl, and ethyl.

Chromene acids are converted to acid chlorides using standard methods (e.g., thionyl chloride or oxalyl chloride; see Scheme 3 below).

Chromene Amides and Esters (Procedure A):

Amines or alcohols functionalized with nitrate esters (e.g. 1,3-dinitroglycerol, isosorbide mononitrate, etc.) are reacted directly with chromene acid chlorides (Scheme 3) using catalytic amount of N,N-dimethylaminopyridine and tertiary amine base (e.g., triethylamine, diisopropylethylamine, etc.) in inert solvent (e.g., dichloromethane, tetrahydrofuran, etc.).

Scheme 3

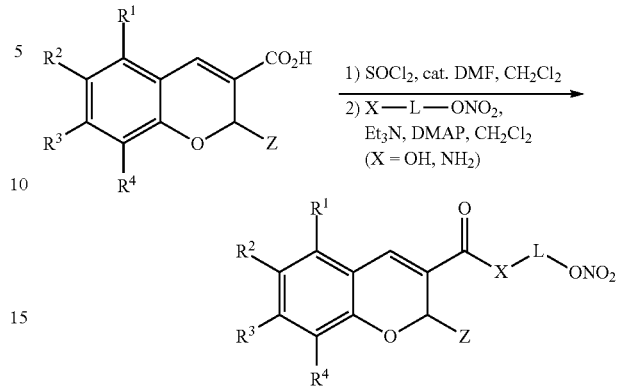

Z is CF$_3$ or CF$_2$CF$_3$;

R$^1$ is H or methyl;

R$^2$ is selected from the group consisting of Cl, Br, methyl, trifluoromethoxy, and pentafluorosulfanyl;

R$^3$ is selected from the group consisting of H, methyl, and tert-butyl;

R$^4$ is selected from the group consisting of H, Cl, methyl, and ethyl;

X is selected from the group consisting of O, NH,

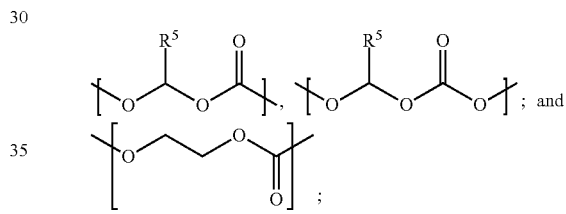; and

-L- is C$_1$-C$_8$ alkylenyl, wherein at least one —CH$_2$— radical is optionally replaced with a radical independently selected from the group consisting of CH(R$^6$) and C(R$^6$)$_2$, or -L- is selected from the group consisting of CH$_2$CH$_2$OCH$_2$CH$_2$, CH$_2$CH$_2$SCH$_2$CH$_2$, CH$_2$CH$_2$S—SCH$_2$CH$_2$, CH$_2$CH$_2$N(R$^7$)CH$_2$CH$_2$, CH$_2$N(R$^7$)CH$_2$CH$_2$, CH$_2$CH$_2$N(R$^7$)CH$_2$, CH$_2$OCH$_2$CH$_2$, CH$_2$SCH$_2$CH$_2$, and

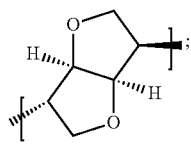;

R$^5$ is H or methyl;

R$^6$ is selected from the group consisting of methyl, and nitrooxy C$_{1-3}$ alkylenyl, with the proviso that when —X— is O or NH and -L- is C$_{1-6}$ alkylenyl, at least one —CH$_2$— radical must be replaced with a radical independently selected from the group consisting of CH(R$^6$) and C(R$^6$)$_2$; and R$^7$ is methyl or acyl.

Chromene Amides (Procedure B):

In some cases, it is more efficient to generate the alcohol-functionalized amides first and then convert the alcohol to the nitrate ester (Scheme 4). In step 1, bifunctional amino alcohols are reacted directly with chromene acid chlorides using catalytic amount of N,N-dimethylaminopyridine and tertiary amine base (e.g., triethylamine, diisopropylethylamine, etc.) in inert solvent (e.g., dichloromethane, tetrahydrofuran, etc.) to provide amide alcohols. In step 2, the alcohol is converted to the nitrate ester directly using fuming nitric acid in acetic acid and acetic anhydride as described in U.S. Pat. No. 2,975,208, or by a two-step process converting the alcohol to the bromide using carbon tetrabromide and triphenylphosphine in dichloromethane followed by treatment with silver nitrate in acetonitrile.

2-(2-aminoethoxy)ethanol, bis(2-hydroxyethyl)ether, 2,2'-thiodiethanol, 2-hydroxyethyl disulfide, etc.) are reacted neat or in inert solvent (e.g., dichloromethane, chloroform, etc.) using acid catalysis (e.g., toluenesulfonic acid, sulfuric acid, methanesulfonic acid, etc.). In step 2, the alcohol is converted to the nitrate ester directly using fuming nitric acid in acetic acid and acetic anhydride as described in U.S. Pat. No. 2,975,208, or by a two-step process converting the alcohol to the bromide using carbon tetrabromide and triphenylphosphine in dichloromethane followed by treatment with silver nitrate in acetonitrile.

Scheme 4

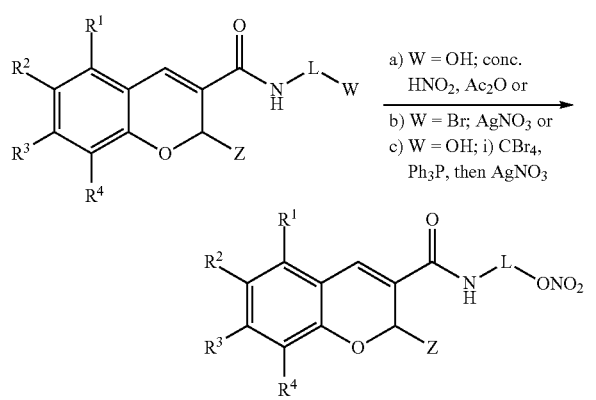

Scheme 5

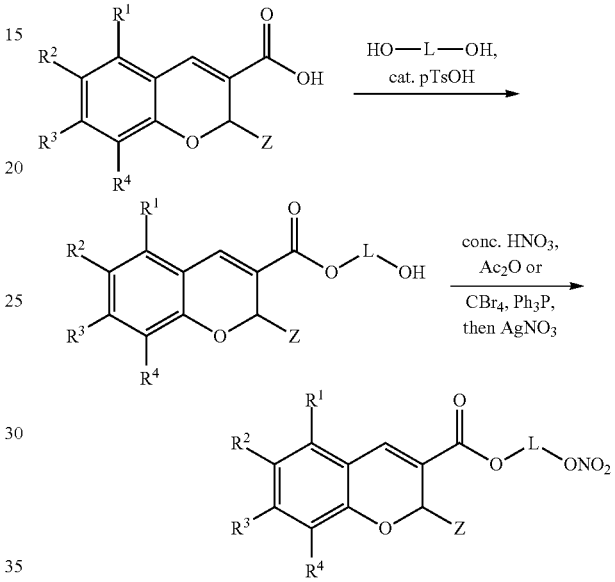

$Z$ is $CF_3$ or $CF_2CF_3$;
$R^1$ is H or methyl;
$R^2$ is selected from the group consisting of Cl, Br, methyl, trifluoromethoxy, and pentafluorosulfanyl;
$R^3$ is selected from the group consisting of H, methyl, and tert-butyl;
$R^4$ is selected from the group consisting of H, Cl, methyl, and ethyl;
-L- is $C_1$-$C_8$ alkylenyl, wherein at least one —$CH_2$— radical is optionally replaced with a radical independently selected from the group consisting of $CH(R^6)$ and $C(R^6)_2$, or
-L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)CH_2CH_2$, $CH_2N(R^7)CH_2CH_2$, $CH_2CH_2N(R^7)CH_2$, $CH_2OCH_2CH_2$, $CH_2SCH_2CH_2$, and

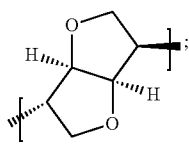

$R^5$ is H or methyl;
$R^6$ is selected from the group consisting of methyl, and nitrooxy $C_{1-3}$ alkylenyl, with the proviso that when —X— is O or NH and -L- is $C_{1-6}$ alkylenyl, at least one —$CH_2$— radical must be replaced with a radical independently selected from the group consisting of $CH(R^6)$ and $C(R^6)_2$; and
$R^7$ is methyl or acyl.

Chromene Esters (Procedure C):
In some cases, it is more efficient to generate the alcohol functionalized esters first and then convert the alcohol to the nitrate ester (Scheme 5). In step 1, chromene acids and diols (e.g., ethylene glycol, 1,3-propanediol, 1,4-propanediol, $Z$ is $CF_3$ or $CF_2CF_3$;
$R^1$ is H or methyl;
$R^2$ is selected from the group consisting of Cl, Br, methyl, trifluoromethoxy, and pentafluorosulfanyl;
$R^3$ is selected from the group consisting of H, methyl, and tert-butyl;
$R^4$ is selected from the group consisting of H, Cl, methyl, and ethyl;
-L- is $C_1$-$C_8$ alkylenyl, wherein at least one —$CH_2$— radical is optionally replaced with a radical independently selected from the group consisting of $CH(R^6)$ and $C(R^6)_2$, or
-L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)CH_2CH_2$, $CH_2N(R^7)CH_2CH_2$, $CH_2CH_2N(R^7)CH_2$, $CH_2OCH_2CH_2$, $CH_2SCH_2CH_2$, and

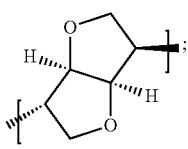

$R^5$ is H or methyl;
$R^6$ is selected from the group consisting of methyl, and nitrooxy $C_{1-3}$ alkylenyl, with the proviso that when —X— is O or NH and -L- is $C_{1-6}$ alkylenyl, at least one —$CH_2$— radical must be replaced with a radical independently selected from the group consisting of $CH(R^6)$ and $C(R^6)_2$; and
$R^7$ is methyl or acyl.

Chromene Esters (Procedure D):

In some case, it is more efficient to generate the halo-functionalized esters first and then convert the halogen to the nitrate ester (Scheme 6). In step 1, chromene acid chlorides and halo alcohols (e.g., 1,3-dibromo-2-propanol) are reacted in inert solvent (e.g., dichloromethane, tetrahydrofuran, etc.) using catalytic amount of N,N-dimethylaminopyridine and tertiary amine base (e.g., triethylamine, diisopropylethylamine, etc.). In step 2, the alcohol is converted to the nitrate ester directly with silver nitrate in acetonitrile.

Scheme 6

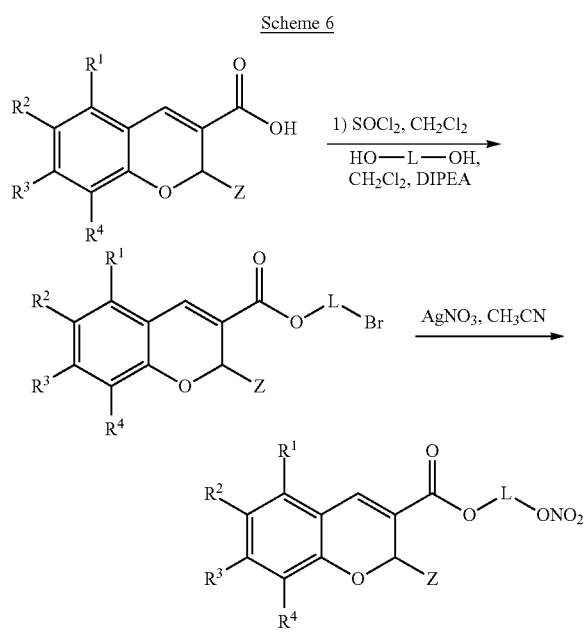

Z is $CF_3$ or $CF_2CF_3$;
$R^1$ is H or methyl;
$R^2$ is selected from the group consisting of Cl, Br, methyl, trifluoromethoxy, and pentafluorosulfanyl;
$R^3$ is selected from the group consisting of H, methyl, and tert-butyl;
$R^4$ is selected from the group consisting of H, Cl, methyl, and ethyl;
-L- is $C_1$-$C_8$ alkylenyl, wherein at least one —$CH_2$— radical is optionally replaced with a radical independently selected from the group consisting of $CH(R^6)$ and $C(R^6)_2$, or
-L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)CH_2CH_2$, $CH_2N(R^7)CH_2CH_2$, $CH_2CH_2N(R^7)CH_2$, $CH_2OCH_2CH_2$, $CH_2SCH_2CH_2$, and

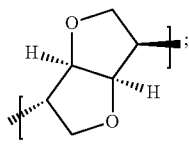

$R^5$ is H or methyl;
$R^6$ is selected from the group consisting of methyl, and nitrooxy $C_{1-3}$ alkylenyl, with the proviso that when —X— is O or NH and -L- is $C_{1-6}$ alkylenyl, at least one —$CH_2$— radical must be replaced with a radical independently selected from the group consisting of $CH(R^6)$ and $C(R^6)_2$; and
$R^7$ is methyl or acyl.

Haloalkyl Chromene Esters:

Chromene acids are converted to haloalkyl esters (Scheme 7) by standard methods as described in *Syn. Comm.*, 1984, 14(9), 857-864 using reagents such as chloromethyl chlorosulfate and chloroethyl chlorosulfate.

Scheme 7

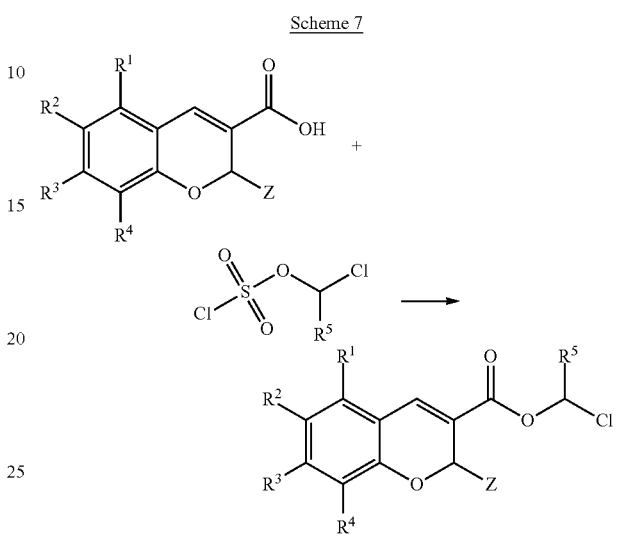

Z is $CF_3$ or $CF_2CF_3$;
$R^1$ is H or methyl;
$R^2$ is selected from the group consisting of Cl, Br, methyl, trifluoromethoxy, and pentafluorosulfanyl;
$R^3$ is selected from the group consisting of H, methyl, and tert-butyl;
$R^4$ is selected from the group consisting of H, Cl, methyl, and ethyl; and
$R^5$ is H or methyl.

Chromene Alkyl Diester Nitrate Esters:

Many carboxylic acid nitrate esters are known in the literature (Table 11) and are reacted directly with haloalkyl chromene esters (Scheme 8) using a tertiary amine base (e.g., triethylamine, diisopropylethylamine, etc.) in polar solvent (e.g., DMSO, DMF, NMP, etc.).

Scheme 8

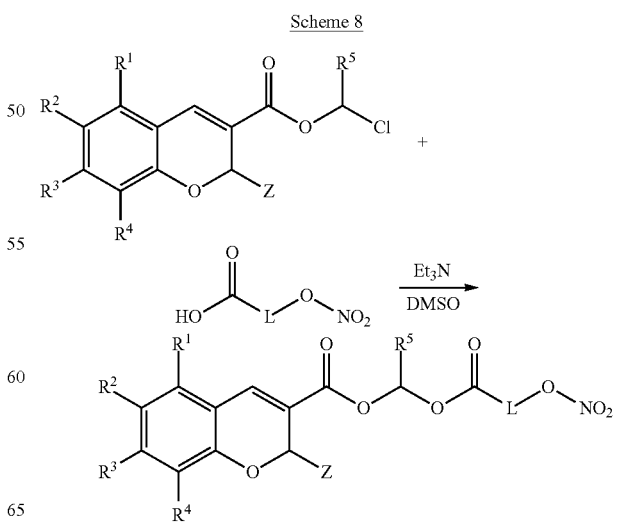

Z is $CF_3$ or $CF_2CF_3$;
$R^1$ is H or methyl;
$R^2$ is selected from the group consisting of Cl, Br, methyl, trifluoromethoxy, and pentafluorosulfanyl;
$R^3$ is selected from the group consisting of H, methyl, and tert-butyl;
$R^4$ is selected from the group consisting of H, Cl, methyl, and ethyl;
-L- is $C_1$-$C_8$ alkylenyl, wherein at least one —$CH_2$— radical is optionally replaced with a radical independently selected from the group consisting of $CH(R^6)$ and $C(R^6)_2$, or
-L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)CH_2CH_2$, $CH_2N(R^7)CH_2CH_2$, $CH_2CH_2N(R^7)CH_2$, $CH_2OCH_2CH_2$, $CH_2SCH_2CH_2$, and

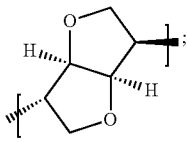

$R^5$ is H or methyl;
$R^6$ is selected from the group consisting of methyl, and nitrooxy $C_{1-3}$ alkylenyl, with the proviso that when —X— is O or NH and -L- is $C_{1-6}$ alkylenyl, at least one —$CH_2$— radical must be replaced with a radical independently selected from the group consisting of $CH(R^6)$ and $C(R^6)_2$; and
$R^7$ is methyl or acyl.

Chromene Alkyl Carbonate Nitrate Esters:

In step 1, alcohol fuctionalized nitrate esters (Table 14) are converted to haloalkyl carbonate nitrate esters by reaction with chloroalkyl chloroformates using a tertiary amine base (e.g., triethylamine, diisopropylethylamine, etc.) in inert solvent (e.g., dichloromethane, tetrahydrofuran, etc.). In steps 2, chromene acids are reacted with haloalkyl carbonate nitrate esters (Scheme 9) using a tertiary amine base (e.g., triethylamine, diisopropylethylamine, etc.) in polar solvent (e.g., DMSO, DMF, NMP, etc.).

Scheme 9

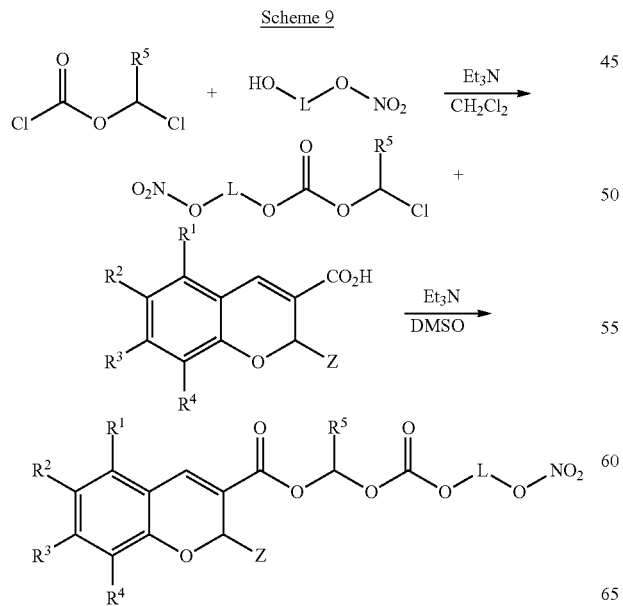

Z is $CF_3$ or $CF_2CF_3$;
$R^1$ is H or methyl;
$R^2$ is selected from the group consisting of Cl, Br, methyl, trifluoromethoxy, and pentafluorosulfanyl;
$R^3$ is selected from the group consisting of H, methyl, and tert-butyl;
$R^4$ is selected from the group consisting of H, Cl, methyl, and ethyl;
-L- is $C_1$-$C_8$ alkylenyl, wherein at least one —$CH_2$— radical is optionally replaced with a radical independently selected from the group consisting of $CH(R^6)$ and $C(R^6)_2$, or
-L- is selected from the group consisting of $CH_2CH_2OCH_2CH_2$, $CH_2CH_2SCH_2CH_2$, $CH_2CH_2S$—$SCH_2CH_2$, $CH_2CH_2N(R^7)CH_2CH_2$, $CH_2N(R^7)CH_2CH_2$, $CH_2CH_2N(R^7)CH_2$, $CH_2OCH_2CH_2$, $CH_2SCH_2CH_2$, and

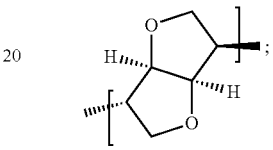

$R^5$ is H or methyl;
$R^6$ is selected from the group consisting of methyl, and nitrooxy $C_{1-3}$ alkylenyl, with the proviso that when —X— is O or NH and -L- is $C_{1-6}$ alkylenyl, at least one —$CH_2$— radical must be replaced with a radical independently selected from the group consisting of $CH(R^6)$ and $C(R^6)_2$; and
$R^7$ is methyl or acyl.

Chromene Acid 6,8-Dichloro-2-(trifluoromethyl)-2H-chromene-3-carboxylic acid (CA-01a)

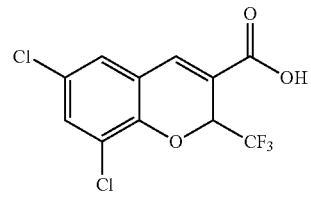 [SMILES: O=C(O)C1=Cc2cc(Cl)cc(Cl)c2OC1C(F)(F)F]

Step 1: 3,5-Dichloro-2-hydroxybenzaldehyde (INT-01)

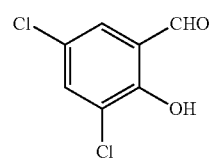 [SMILES: O=Cc1cc(Cl)cc(Cl)c1O]

Chromene acids are made starting from phenols via salicylic aldehydes. 2,4-Dichlorophenol (10.0 g, 61.3 mmol) and hexamethylenetetramine (17.2 g, 122.6 mmol) were dissolved in 80 mL methanesulfonic acid and heated at 100° C. for 1.5 h. The reaction was diluted with ethyl acetate and the organic layer was washed with water, followed by saturated sodium bicarbonate, dried over magnesium sulfate, and evaporated. The product 3,5-dichloro-2-hydroxybenzaldehyde (INT-01) was purified by chromatography using ethyl acetate/hexane gradient to give a yellow oil (7.5 g, 64% yield). $^1$H NMR (400 MHz, CDCl$_3$) δ 11.39 (s, 1H), 7.64 (s, 1H), 7.52 (s, 1H). LC t$_r$=3.95 min (C-18 column, 5 to 95% acetonitrile/water over 6 min at 1.7 mL/min with detection 254 nm, at 23° C.).

Step 2: Ethyl 6,8-dichloro-2-(trifluoromethyl)-2H-chromene-3-carboxylate (INT-02)

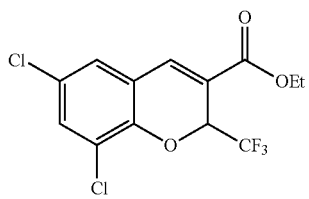 [SMILES: CCOC(=O)C1=Cc2cc(Cl)cc(Cl)c2OC1C(F)(F)F]

3,5-Dichloro-2-hydroxybenzaldehyde (INT-01) (7.5 g, 39.3 mmol) was dissolved in 15 mL of dimethylsulfoxide. Ethyl 4,4,4-trifluorocrotonate (9.38 mL, 62.8 mmol) and triethylamine (11.0 mL, 78.6 mmol) were added, and heated to 85° C. for 3 days. The reaction was cooled, diluted with water, and extracted with ethyl acetate. The organic layer was washed with 3N hydrochloric acid solution, saturated sodium bicarbonate solution and brine, dried over magnesium sulfate, and evaporated to give a tan solid INT-02 (12.5 g, 93% yield). $^1$H NMR (400 MHz, CDCl$_3$) δ 7.66 (s, 1H), 7.40 (d, J=2.4 Hz, 1H), 7.16 (d, 0.1=2.4 Hz, 1H), 5.84 (q, J=6.6 Hz, 1H), 4.43-4.40 (m, 2H), 1.38 (t, J=7.1 Hz, 3H). LC t$_r$=5.20 min (C-18 column, 5 to 95% acetonitrile/water over 6 min at 1.7 mL/min with detection 254 nm, at 23° C.). ES(pos)MS m/z 341 (M+H calcd for C$_{13}$H$_9$Cl$_2$F$_3$O$_3$ requires 341).

Step 3: 6,8-Dichloro-2-(trifluoromethyl)-2H-chromene-3-carboxylic acid (CA-01a)

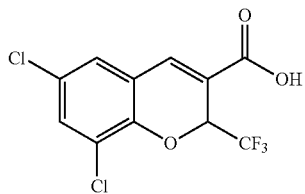

INT-02 (12.5 g, 36.6 mmol) was dissolved in 15 mL methanol and 1.5 mL water. Solid sodium hydroxide (4.47 g, 111.8 mmol) was added, and the reaction was stirred at room temperature overnight. The reaction was acidified with 1N hydrochloric acid solution and the resulting precipitate was filtered, washed with water and hexane, and dried to a tan solid CA-01a (10.2 g, 89% yield). $^1$H NMR (400 MHz, CDCl$_3$) δ 7.66 (s, 1H), 7.40 (d, J=2.4 Hz, 1H), 7.16 (d, J=2.4 Hz, 1H), 5.84 (q, J=6.6 Hz, 1H), 4.43-4.40 (m, 2H), 1.38 (t, J=7.1 Hz, 3H). LC t$_r$=4.33 min (C-18 column, 5 to 95% acetonitrile/water over 6 min at 1.7 mL/min with detection 254 nm, at 23° C.). ES(pos)MS m/z 313 (M+H calcd for C$_{11}$H$_5$Cl$_2$F$_3$O$_3$ requires 313).

(S)-7-(tert-Butyl)-6-chloro-2-(trifluoromethyl)-2H-chromene-3-carboxylic acid (CA-11)

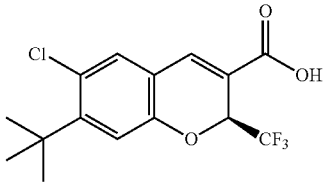 [SMILES: CC(C)(C)c1cc2c(cc1Cl)C=C(C(=O)O)[C@@H](C(F)(F)F)O2]

Step 1: 3-tert-Butyl-4-chlorophenol (INT-03)

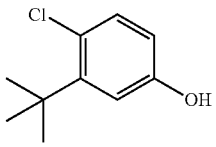

3-tert-Butyl phenol (50.0 g, 333 mmol) and ferric chloride (162.6 mg, 1.0 mmol) were heated to 60° C. in dichloromethane. Sulfuryl chloride (35.0 mL, 433 mmol) was added drop-wise and the mixture was heated at 60° C. overnight. The reaction was evaporated and dissolved in ethyl acetate. The organic layer was washed with water and brine, dried over magnesium sulfate and evaporated. The crude product INT-03 (68.4 g, 111% yield) was taken directly into the next step. $^1$H NMR (400 MHz, CDCl$_3$) δ 7.21 (d, J=8.5 Hz, 1H), 6.93 (d, J=3.0 Hz, 1H), 6.63 (dd, J=8.5, 3.0 Hz, 1H), 4.79 (s, 1H), 1.48 (s, 9H). LC t$_r$=4.18 min (C-18 column, 5 to 95% acetonitrile/water over 6 min at 1.3 mL/min with detection 254 nm, at 23° C.).

Step 2: 4-tert-Butyl-5-chloro-2-hydroxybenzaldehyde (INT-04)

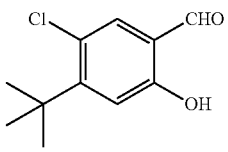

INT-03 (68.4 g, 370.4 mmol) was dissolved in methanesulfonic acid (200 mL) and the reaction was cooled to 0° C. Hexamethylene tetraamine (103.9 g, 740.8 mmol) was added, followed by methane sulfonic acid (200 mL) added portion-wise, keeping the exothermic reaction below 100° C. The reaction was then stirred at 100° C. overnight then cooled to room temperature and poured into cold water (3 L). The product was extracted with ethyl acetate and the organic layer was washed with water, saturated sodium bicarbonate and brine, dried over magnesium sulfate and evaporated to afford INT-04 as a dark oil (58.8 g, 75% yield). $^1$H NMR (400 MHz, CDCl$_3$) δ 9.84 (s, 1H), 7.53 (s, 1H), 7.12 (s, 1H), 1.51 (s, 9H). LC t$_r$=4.66 min (C-18 column, 5 to 95% acetonitrile/water over 6 min at 1.3 mL/min with detection 254 nm, at 23° C.). ES(pos)MS m/z 213 (M+H calcd for $C_{11}H_{13}ClO_2$ requires 213).

Step 3: Ethyl 7-(tert-butyl)-6-chloro-2-(trifluoromethyl)-2H-chromene-3-carboxylate (INT-05)

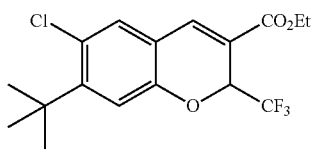 [SMILES: CCOC(=O)C1=Cc2cc(Cl)c(C(C)(C)C)cc2OC1C(F)(F)F]

INT-04 (58.8 g, 276 mmol), ethyl 4,4,4-trifluorocrotonate (45.4 mL, 304 mmol) and potassium carbonate (49.6 g, 359 mmol) were heated in DMSO (175 mL) to 85° C. After 3 h, the reaction was diluted with water and extracted with ethyl acetate. The organic layer was washed with water and brine, dried over magnesium sulfate and evaporated to afford INT-05 as a dark oil (62.8 g, 63% yield). $^1$H NMR (400 MHz, CDCl$_3$) δ 7.65 (s, 1H), 7.22 (s, 1H), 7.06 (s, 1H), 5.71 (q, J=6.8 Hz, 1H), 4.39-4.30 (m, 2H), 1.49 (s, 9H), 1.38 (t, J=7.1 Hz, 3H). LC t$_r$=5.76 min (C-18 column, 5 to 95% acetonitrile/water over 6 min at 1.3 mL/min with detection 254 nm, at 23° C.). ES(pos)MS m/z 363 (M+H calcd for $C_{17}H_{18}ClF_3O_3$ requires 363).

Step 4: 7-(tert-Butyl)-6-chloro-2-(trifluoromethyl)-2H-chromene-3-carboxylic acid (CA-11a)

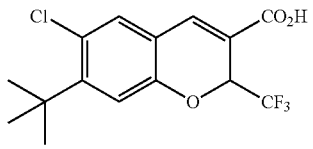 [SMILES: CC(C)(C)c1cc2c(cc1Cl)C=C(C(=O)O)C(C(F)(F)F)O2]

INT-05 (62.8 g, 173 mmol) was dissolved in methanol (1.25 L) and sodium hydroxide (22.7 g, 568 mmol) in water (125 mL) was added. The reaction was stirred at room temperature overnight. The methanol was evaporated and the resulting aqueous layer was washed with diethyl ether, acidified with 3N aqueous hydrochloric acid, then extracted with ethyl acetate. The organic layer was dried over magnesium sulfate and evaporated to a dark orange, oily solid. The solid was broken up and washed with a minimal amount of methylene chloride to remove the colored impurities to afford CA-11a as an off-white solid (34.5 g, 59% yield). $^1$H NMR (400 MHz, CDCl$_3$) δ 7.85 (s, 1H), 7.60 (s, 1H), 7.05 (s, 1H), 5.95 (q, J=7.3 Hz, 1H), 1.43 (s, 9H). LC t$_r$=4.87 min (C-18 column, 5 to 95% acetonitrile/water over 6 min at 1.3 mL/min with detection 254 nm, at 23° C.). ES(pos)MS m/z 335 (M+H calcd for $C_{15}H_{14}ClF_3O_3$ requires 335).

Step 5: (S)-7-(tert-Butyl)-6-chloro-2-(trifluoromethyl)-2H-chromene-3-carboxylic acid (CA-11)

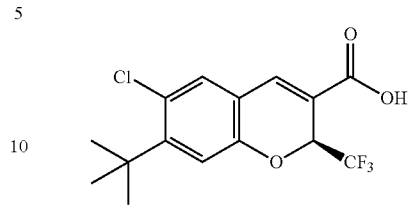

Preparative enantiomer separation was conducted on a Thar 350 preparative SFC using a ChiralPak AD column (10μ, 300×50 mmI.D.; Mobile phase A: $CO_2$ and Mobile phase B: Isopropanol; Gradient: B 25%; Flow rate: 200 mL/min; Back pressure: 100 bar; Column temperature: 38° C.; Wavelength: 220 nm). Samples were dissolved in methanol at ~45 mg/mL and injected in 3-mL portions. Compound CA-11a (20.0 g) underwent chiral chromatography to yield each enantiomer. The initial peak off the column is the (R)-isomer (8.44 g; Chiral HPLC: AD (n-hexane/i-PrOH 9:1, λ=254 nm), t$_r$=4.28 min, 93.8% ee), and the second peak off the column is the (S)-isomer CA-11 (8.16 g; Chiral HPLC: AD (n-hexane/i-PrOH 9:1, λ=254 nm), t$_r$=5.87 min, 90.4% ee).

(S)-6-Pentafluorosulfanyl-2-(trifluoromethyl)-2H-chromene-3-carboxylic acid (CA-08)

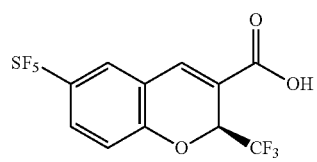

Step 1. 2-Hydroxy-5-(pentafluorosulfanyl)benzaldehyde (INT-06)

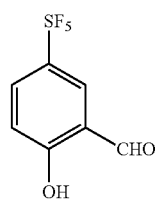

Pentafluorosulfanyl phenol (10.0 mmol) and hexamethylenetetramine (20.0 mmol) are dissolved in methanesulfonic acid (15 mL) and heated to 100° C. for 1.5 h. The reaction is diluted with ethyl acetate and the organic layer is washed with water, saturated sodium bicarbonate, dried over magnesium sulfate, and evaporated. The product is purified by silica gel column chromatography using ethyl acetate/hexane gradient to give INT-06.

Step 2: 4,4,4-Trifluorobut-2-enal (INT-07)

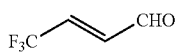

4,4,4-Trifluorobut-2-en-1-ol (3.28 g, 26.0 mmol) was dissolved in dichloromethane (80 mL). Pyridinium chlorochromate (5.61 g, 26.0 mmol) was added and the reaction was stirred at room temperature overnight. The dark red reaction mixture was filtered through Celite and decolorizing carbon. The dark brown/green filtrate containing about 25 mmol of INT-07 in ~80 mL of dichloromethane (0.31 M) was used directly in the next step.

Step 3: (S)-6-(Pentafluorosulfanyl)-2-(trifluoromethyl)-2H-chromene-3-carbaldehyde (INT-08)

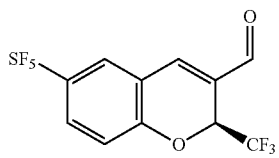

To a solution of 4,4,4-trifluorobut-2-enal (INT-07; trifluorocrotonaldehyde) in dichloromethane (~0.31 M, ~20 mmol, 66 mL) is added INT-06 (10.0 mmol), (S)-(−)-α,α-diphenyl-2-pyrrolidine methanol trimethylsilyl ether (2.0 mmol) and 2-nitrobenzoic acid (2.0 mmol). The reaction is stirred at room temperature overnight, concentrated, and purified by silica gel column chromatography (0-15% ethyl acetate-hexane gradient) to afford (INT-08).

Step 4: (S)-6-pentafluorosulfanyl-2-(trifluoromethyl)-2H-chromene-3-carboxylic acid (CA-08)

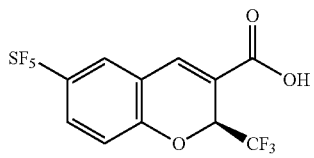

INT-08 (5.0 mmol) is dissolved in DMF (20 mL) and OXONE® (monopersulfate) (7.10 mmol) is added. The reaction is stirred at room temperature for 48 h, diluted with water, and extracted with ethyl acetate. The ethyl acetate layer is dried over anhydrous magnesium sulfate and concentrated in vacuo. The crude product is purified by silica gel column chromatography to yield (CA-08).

(S)-6-Pentafluorosulfanyl-8-methyl-2-(trifluoromethyl)-2H-chromene-3-carboxylic acid (CA-09)

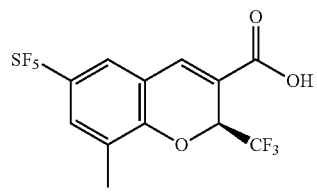

Step 1: 2-Methyl-4-(pentafluorosulfanyl)phenol (INT-09)

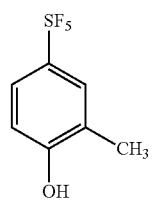

INT-06 (20 mmol) is dissolved in tetrahydrofuran (40 mL) and cooled to 0° C. To the mixture is added water (16 mL) followed by sodium borohydride (20 mmol) and the reaction is warmed to room temperature and stirred for 48 h. The reaction is diluted with 1N aqueous hydrochloric acid to adjust the pH to 6 and extracted with diethyl ether. The organic layer is washed with brine, dried over magnesium sulfate and evaporated. The crude product is purified by silica gel column chromatography (ethyl acetate/hexane gradient) to obtain INT-09.

Step 2: 2-Hydroxy-3-methyl-5-(pentafluorosulfanyl) benzaldehyde (INT-10)

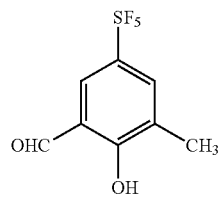

INT-09 (10.0 mmol) and hexamethylenetetramine (20.0 mmol) are dissolved in methanesulfonic acid (15 mL) and heated to 100° C. for 1.5 h. The reaction is diluted with ethyl acetate and the organic layer is washed with water, saturated sodium bicarbonate, dried over magnesium sulfate, and evaporated. The product is purified by silica gel column chromatography using ethyl acetate/hexane gradient to give INT-10.

Steps 4 & 5: (S)-6-Pentafluorosulfanyl-8-methyl-2-(trifluoromethyl)-2H-chromene-3-carboxylic acid (CA-09)

Using a similar procedure to make CA-08, INT-10 is reacted with INT-07 to give the corresponding chromene aldehyde and subsequent oxidation with OXONE® provides CA-09.

(S)-6-Pentafluorosulfanyl-8-ethyl-2-(trifluoromethyl)-2H-chromene-3-carboxylic acid (CA-10)

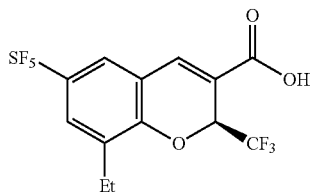

Step 1: 2-(1-Hydroxyethyl)-4-(pentafluorosulfanyl)phenol (INT-11)

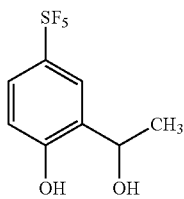

INT-06 (20 mmol) is dissolved in tetrahydrofuran (40 mL) and the mixture is cooled to 0° C. Methylmagnesium bromide (3.0 M; 20 mmol) in diethyl ether is added drop-wise to the cold solution. The reaction is monitored by TLC and upon completion, the mixture is poured into water and extracted with ethyl acetate. The organic layer is washed with saturated sodium bicarbonate, dried over magnesium sulfate, and evaporated. The product is purified by silica gel column chromatography using ethyl acetate/hexane gradient to give INT-11.

Step 2: 2-Ethyl-4-(pentafluorosulfanyl)phenol (INT-12)

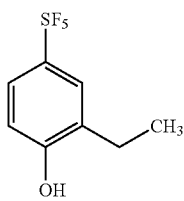

INT-11 (15 mmol) is dissolve in tetrahydrofuran (30 mL) and cooled to 0° C. To the mixture is added water (12 mL) followed by sodium borohydride (15 mmol) and the reaction is warmed to room temperature and stirred for 48 h. The reaction is diluted with 1N aqueous hydrochloric acid to adjust the pH to 6 and extracted with diethyl ether. The organic layer is washed with brine, dried over magnesium sulfate and evaporated. The crude product is purified by silica gel column chromatography (ethyl acetate/hexane gradient) to obtain INT-12.

Step 3: 3-Ethyl-2-hydroxy-5-(pentafluorosulfanyl)benz aldehyde (INT-13)

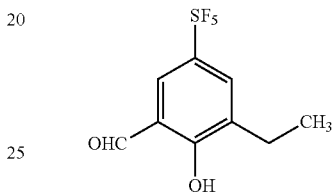

INT-12 (10.0 mmol) and hexamethylenetetramine (20.0 mmol) are dissolved in methanesulfonic acid (15 mL) and heated to 100° C. for 1.5 h. The reaction is diluted with ethyl acetate and the organic layer is washed with water, saturated sodium bicarbonate, dried over magnesium sulfate, and evaporated. The product is purified by silica gel column chromatography using ethyl acetate/hexane gradient to give INT-13.

Steps 4 & 5: (S)-6-Pentafluorosulfanyl-8-ethyl-2-(trifluoromethyl)-2H-chromene-3-carboxylic acid (CA-10)

Using a similar procedure to make CA-08, INT-13 is reacted with INT-07 to give the corresponding chromene aldehyde and subsequent oxidation with OXONE® provides CA-10.

Using a similar procedure to make CA-01a and CA-11 additional chromene acids (Table 1) are made using procedures described in U.S. Pat. No. 6,034,256.

TABLE 1

Chromene acids.

| Chromene Acid | Structure | Name |
|---|---|---|
| CA-01a | ![structure] | 6,8-dichloro-2-(trifluoromethyl)-2H-chromene-3-carboxylic acid |

TABLE 1-continued

Chromene acids.

| Chromene Acid | Structure | Name |
|---|---|---|
| CA-01 | 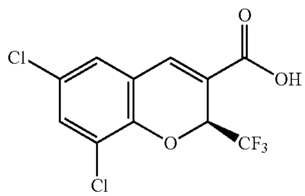 [SMILES: O=C(O)C1=Cc2cc(Cl)cc(Cl)c2O[C@@H]1C(F)(F)F] | (S)-6,8-dichloro-2-(trifluoromethyl)-2H-chromene-3-carboxylic acid |
| CA-02 | 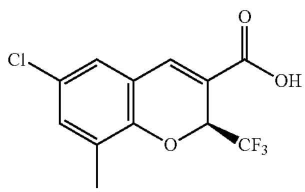 [SMILES: Cc1cc(Cl)cc2c1O[C@H](C(F)(F)F)C(C(=O)O)=C2] | (S)-6-chloro-8-methyl-2-(trifluoromethyl)-2H-chromene-3-carboxylic acid |
| CA-03 | 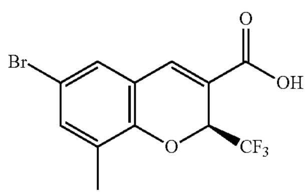 | (S)-6-bromo-8-methyl-2-(trifluoromethyl)-2H-chromene-3-carboxylic acid |
| CA-04 | 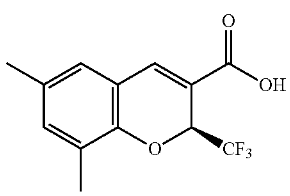 [SMILES: Cc1cc(C)c2c(c1)C=C(C(=O)O)[C@@H](C(F)(F)F)O2] | (S)-6,8-dimethyl-2-(trifluoromethyl)-2H-chromene-3-carboxylic acid |
| CA-05 | 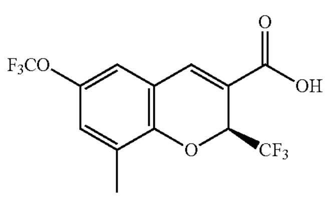 [SMILES: Cc1cc(OC(F)(F)F)cc2c1O[C@H](C(F)(F)F)C(C(=O)O)=C2] | (S)-8-methyl-6-(trifluoromethoxy)-2-(trifluoromethyl)-2H-chromene-3-carboxylic acid |
| CA-06 | 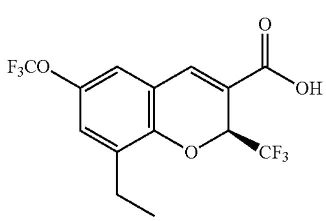 [SMILES: CCc1cc(OC(F)(F)F)cc2c1O[C@H](C(F)(F)F)C(C(=O)O)=C2] | (S)-8-ethyl-6-(trifluoromethoxy)-2-(trifluoromethyl)-2H-chromene-3-carboxylic acid |
| CA-07 | 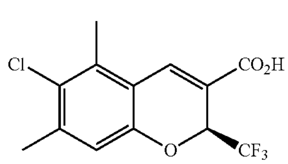 [SMILES: Cc1cc2c(c(C)c1Cl)C=C(C(=O)O)[C@@H](C(F)(F)F)O2] | (S)-6-chloro-5,7-dimethyl-2-(trifluoromethyl)-2H-chromene-3-carboxylic acid |
| CA-08 | 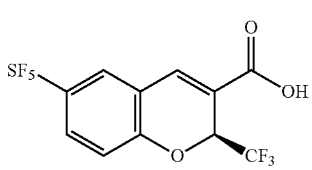 | (S)-6-pentafluorosulfanyl-2-(trifluoromethyl)-2H-chromene-3-carboxylic acid |

TABLE 1-continued

Chromene acids.

| Chromene Acid | Structure | Name |
|---|---|---|
| CA-09 | 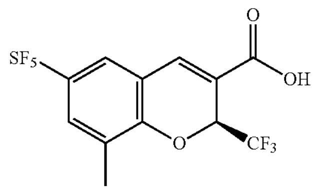 | (S)-6-pentafluorosulfanyl-8-methyl-2-(trifluoromethyl)-2H-chromene-3-carboxylic acid |
| CA-10 | 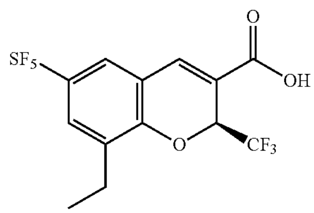 | (S)-6-pentafluorosulfanyl-8-ethyl-2-(trifluoromethyl)-2H-chromene-3-carboxylic acid |
| CA-11a | 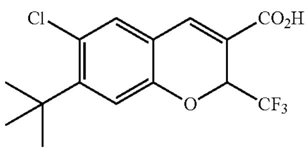 [SMILES: CC(C)(C)c1cc2c(cc1Cl)C=C(C(=O)O)C(C(F)(F)F)O2] | 7-(tert-butyl)-6-chloro-2-(trifluoromethyl)-2H-chromene-3-carboxylic acid |
| CA-11 | 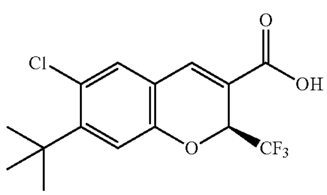 [SMILES: CC(C)(C)c1cc2c(cc1Cl)C=C(C(=O)O)[C@@H](C(F)(F)F)O2] | (S)-7-(tert-butyl)-6-chloro-2-(trifluoromethyl)-2H-chromene-3-carboxylic acid |

Chromene Acid Chlorides 6,8-Dichloro-2-(trifluoromethyl)-2H-chromene-3-carbonyl chloride (C-01)

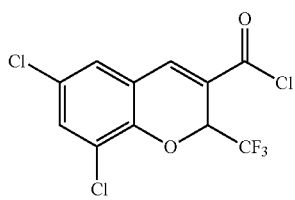 [SMILES: O=C(Cl)C1=Cc2cc(Cl)cc(Cl)c2OC1C(F)(F)F]

CA-01a (500 mg, 1.6 mmol) was dissolved in dichloromethane (5 mL). Thionyl chloride (290 µL, 4.0 mmol) and 1 drop DMF was added, and the reaction was stirred as a suspension overnight. The reaction was diluted with ethyl acetate, and the organic layer was washed with saturated sodium bicarbonate solution and brine, dried over magnesium sulfate, and evaporated. The resulting oil, C-01a was used without further purification in the next step (506 mg, 95% yield).

7-(tert-Butyl)-6-chloro-2-(trifluoromethyl)-2H-chromene-3-carbonyl chloride (C-11a)

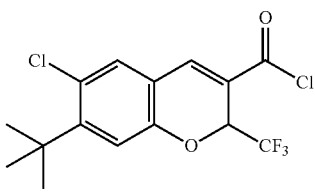 [SMILES: CC(C)(C)c1cc2c(cc1Cl)C=C(C(=O)Cl)C(C(F)(F)F)O2]

CA-11a (3.5 g, 10.46 mmol) was dissolved in dichloromethane (30 mL) and DMF (1 mL). Thionyl chloride (1.9 mL, 26.2 mmol) was added drop-wise and stirred at room temperature overnight. After 1 h, the reaction was evaporated and diluted with ethyl acetate. The organic layer was washed with saturated sodium bicarbonate and brine, dried over magnesium sulfate and evaporated. C-11a (2.48 g, 67% yield) was isolated as a light yellow solid. $^1$H NMR (400 MHz, CDCl$_3$) δ 8.02 (s, 1H), 7.35 (s, 1H), 7.12 (s, 1H), 5.71 (q, J=6.7 Hz, 1H), 1.50 (s, 9H). LC $t_r$=5.46 min (C-18 column, 5 to 95% acetonitrile/water over 6 min at 1.7 mL/min with detection 254 nm, at 23° C.).

(S)-7-(tert-Butyl)-6-chloro-2-(trifluoromethyl)-2H-chromene-3-carbonyl chloride (C-11)

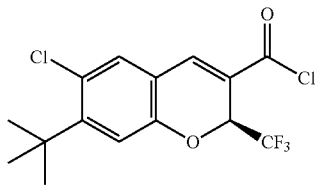 [SMILES: CC(C)(C)c1cc2c(cc1Cl)C=C(C(=O)Cl)[C@@H](C(F)(F)F)O2]

CA-11 (500 mg, 1.49 mmol) was dissolved in dichloromethane (4 mL) and DMF (1 mL). Thionyl chloride (271 µl, 3.73 mmol) was added drop-wise and the reaction stirred at room temperature. After 1 h, the reaction was evaporated and diluted with ethyl acetate. The organic layer was washed with saturated sodium bicarbonate and brine, dried over magnesium sulfate and evaporated. The resulting semi-solid C-11 (513 mg, 97% yield) was used as-is in the next step.

Using a similar procedure to make C-01a, C-11a, and C-11 additional acid chlorides (Table 2) are made by replacing CA-01a with other suitable chromene acids listed in Table 1 as well as others known in the literature.

TABLE 2

Chromene acid chlorides.

| Chromene | Structure | Name |
|---|---|---|
| C-01a | | 6,8-dichloro-2-(trifluoromethyl)-2H-chromene-3-carbonyl chloride |
| C-01 | | (S)-6,8-dichloro-2-(trifluoromethyl)-2H-chromene-3-carbonyl chloride |
| C-02 | | (S)-6-chloro-8-methyl-2-(trifluoromethyl)-2H-chromene-3-carbonyl chloride |
| C-03 | | (S)-6-bromo-8-methyl-2-(trifluoromethyl)-2H-chromene-3-carbonyl chloride |
| C-04 | 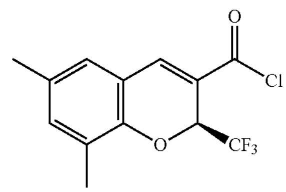 [SMILES: Cc1cc(C)c2c(c1)C=C(C(=O)Cl)[C@@H](C(F)(F)F)O2] | (S)-6,8-dimethyl-2-(trifluoromethyl)-2H-chromene-3-carbonyl chloride |
| C-05 | 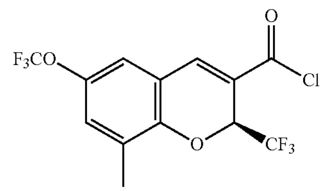 [SMILES: Cc1cc(OC(F)(F)F)cc2c1O[C@H](C(F)(F)F)C(C(=O)Cl)=C2] | (S)-8-methyl-6-(trifluoromethoxy)-2-(trifluoromethyl)-2H-chromene-3-carbonyl chloride |
| C-06 | 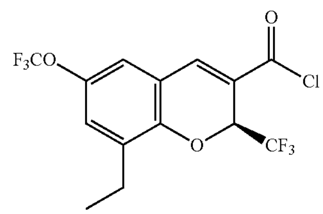 [SMILES: CCc1cc(OC(F)(F)F)cc2c1O[C@H](C(F)(F)F)C(C(=O)Cl)=C2] | (S)-8-ethyl-6-(trifluoromethoxy)-2-(trifluoromethyl)-2H-chromene-3-carbonyl chloride |
| C-07 | 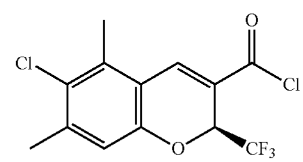 | (S)-6-chloro-5,7-dimethyl-2-(trifluoromethyl)-2H-chromene-3-carbonyl chloride |
| C-08 | 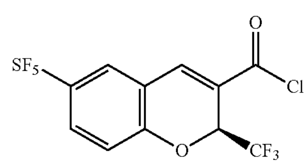 | (S)-6-pentafluorosulfanyl-2-(trifluoromethyl)-2H-chromene-3-carbonyl chloride |
| C-09 | 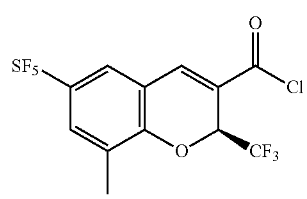 | (S)-6-pentafluorosulfanyl-8-methyl-2-(trifluoromethyl)-2H-chromene-3-carbonyl chloride |
| C-10 | 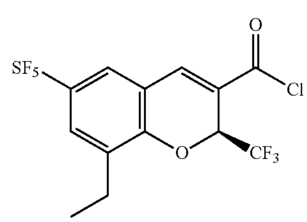 | (S)-6-pentafluorosulfanyl-8-ethyl-2-(trifluoromethyl)-2H-chromene-3-carbonyl chloride |
| C-11a | 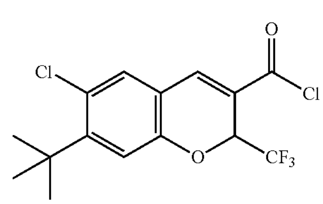 [SMILES: CC(C)(C)c1cc2c(cc1Cl)C=C(C(=O)Cl)C(C(F)(F)F)O2] | 7-(tert-butyl)-6-chloro-2-(trifluoromethyl)-2H-chromene-3-carbonyl chloride |

TABLE 2-continued

Chromene acid chlorides.

| Chromene | Structure | Name |
|---|---|---|
| C-11 | (structure shown) | (S)-7-(tert-butyl)-6-chloro-2-(trifluoromethyl)-2H-chromene-3-carbonyl chloride |

Chromene Amide Nitrate Esters

Example 1a: 2-(2-(6,8-Dichloro-2-(trifluoromethyl)-2H-chromene-3-carboxamido) ethoxy)ethyl nitrate

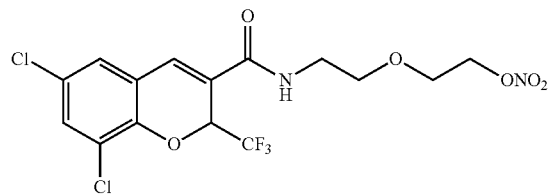

Step 1: C-01a (0.5 mmol), 2-(2-aminoethoxy)ethanol (0.5 mmol), catalytic amount of N,N-dimethylaminopyridine and diisopropylethylamine (0.6 mmol) are stirred in 2.5 mL of dichloromethane overnight. The reaction is diluted with ethyl acetate, and the organic layer is washed with saturated sodium bicarbonate solution and brine, dried over magnesium sulfate, and evaporated. The material is purified by chromatography using ethyl acetate/hexane gradient to afford alcohol INT-14.

Step 2: To a solution of INT-14 (0.4 mmol) in dichloromethane (1.0 mL) is added triphenylphosphine (0.4 mmol) and carbon tetrabromide (0.4 mmol) at room temperature. After stirring for 3 h, the reaction is poured into water (50 mL), extracted with ethyl acetate (2×50 mL), and washed with saturated brine solution (50 mL). The combined organic layers are dried over magnesium sulfate, filtered, and concentrated under reduced pressure. The residue is purified by silica gel column chromatography using ethyl acetate/hexane gradient to provide bromide INT-15.

Step 3: Nitrate Ester Formation (see also Kornblum, N, et. al., *J. Am. Chem. Soc.* 1966, 88, 1707-1711): INT-15 (0.25 mmol) is dissolved in acetonitrile (ACN, 1.0 mL) and silver nitrate (AgNO$_3$) is added (0.30 mmol). The reaction is heated at 65° C. for 24 h, cooled and silver halide precipitate is removed by filtration. The filtrate is evaporated and the residue is purified by silica gel column chromatography using ethyl acetate/hexane gradient to provide Example 1a.

Using a similar procedure to make Example 1a additional analogues (Table 3) are made by replacing C-01a with other chromene acid chlorides from Table 2.

TABLE 3

Examples of chromene amide nitrate esters.

| Chromene | Ex. | Name |
|---|---|---|
| C-01a | 1a | 2-(2-(6,8-dichloro-2-(trifluoromethyl)-2H-chromene-3-carboxamido)ethoxy)ethyl nitrate |
| C-01 | 1 | (S)-2-(2-(6,8-dichloro-2-(trifluoromethyl)-2H-chromene-3-carboxamido)ethoxy)ethyl nitrate |
| C-02 | 2 | (S)-2-(2-(6-chloro-8-methyl-2-(trifluoromethyl)-2H-chromene-3-carboxamido)ethoxy)ethyl nitrate |
| C-03 | 3 | (S)-2-(2-(6-bromo-8-methyl-2-(trifluoromethyl)-2H-chromene-3-carboxamido)ethoxy)ethyl nitrate |
| C-04 | 4 | (S)-2-(2-(6,8-dimethyl-2-(trifluoromethyl)-2H-chromene-3-carboxamido)ethoxy)ethyl nitrate |
| C-05 | 5 | (S)-2-(2-(8-methyl-6-(trifluoromethoxy)-2-(trifluoromethyl)-2H-chromene-3-carboxamido)ethoxy)ethyl nitrate |
| C-06 | 6 | (S)-2-(2-(8-ethyl-6-(trifluoromethoxy)-2-(trifluoromethyl)-2H-chromene-3-carboxamido)ethoxy)ethyl nitrate |
| C-07 | 7 | (S)-2-(2-(6-chloro-5,7-dimethyl-2-(trifluoromethyl)-2H-chromene-3-carboxamido)ethoxy)ethyl nitrate |
| C-08 | 8 | (S)-2-(2-(6-(pentaflurosulfanyl)-2-(trifluoromethyl)-2H-chromene-3-carboxamido)ethoxy)ethyl nitrate |
| C-09 | 9 | (S)-2-(2-(6-(pentaflurosulfanyl)-8-methyl-2-(trifluoromethyl)-2H-chromene-3-carboxamido)ethoxy)ethyl nitrate |
| C-10 | 10 | (S)-2-(2-(6-(pentaflurosulfanyl)-8-ethyl-2-(trifluoromethyl)-2H-chromene-3-carboxamido)ethoxy)ethyl nitrate |
| C-11 | 11 | (S)-2-(2-(7-(tert-butyl)-6-chloro-2-(trifluoromethyl)-2H-chromene-3-carboxamido)ethoxy)ethyl nitrate |

Chromene 2-Dinitroglycerine Ester Nitrate Esters

Example 12a: 1,3-bis(Nitrooxy)propan-2-yl 6,8-dichloro-2-(trifluoromethyl)-2H-chromene-3-carboxylate

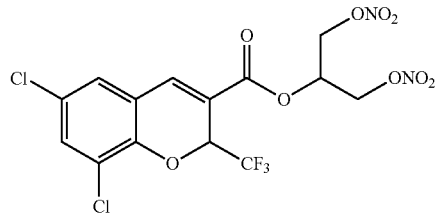

C-01a (0.5 mmol), 1,3-dinitroglycerol (0.5 mmol), (prepared according to Lange, K., et. al., *J. Bioorg. Med. Chem. Lett.* 2009, 19, 3141-3144) catalytic amount of N,N-dimethylaminopyridine and diisopropylethylamine (0.6 mmol) are stirred in 2.5 mL of dichloromethane overnight. The reaction is diluted with ethyl acetate, and the organic layer is washed with saturated sodium bicarbonate solution and brine, dried over magnesium sulfate, and evaporated. The material is purified by chromatography using ethyl acetate/hexane gradient to afford Example 12a.

Example 22a: 1,3-bis(Nitrooxy)propan-2-yl 7-(tert-butyl)-6-chloro-2-(trifluoromethyl)-2H-chromene-3-carboxylate

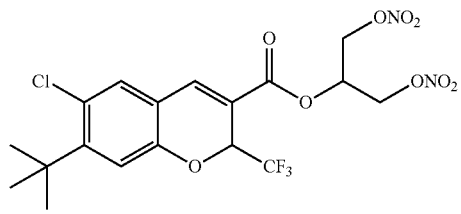

Step 1: 1,3-Dibromopropan-2-yl 7-(tert-butyl)-6-chloro-2-(trifluoromethyl)-2H-chromene-3-carboxylate (INT-16)

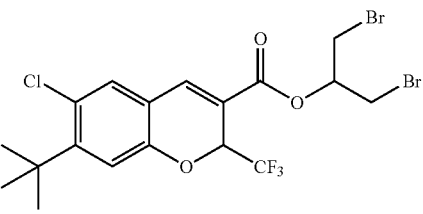 [SMILES: CC(C)(C)c1cc2c(cc1Cl)C=C(C(=O)OC(CBr)CBr)C(C(F)(F)F)O2]

C-11a (925 mg, 2.62 mmol) was dissolved in dichloromethane (10 mL). 1,3-Dibromo-2-propanol (294 µL, 2.88 mmol) and diisopropylethylamine (684 µL, 3.93 mmol) were added and the mixture was stirred at room temperature overnight. The reaction was diluted with ethyl acetate, washed with water and brine, dried over magnesium sulfate and evaporated. The product was purified by silica gel column chromatography using an ethyl acetate/hexane gradient to afford INT-16 (890 mg, 64% yield). $^1$H NMR (400 MHz, CDCl$_3$) δ 7.73 (s, 1H), 7.27 (s, 1H), 7.09 (s, 1H), 5.71 (q, J=6.8 Hz, 1H), 5.35-5.30 (m, 1H), 3.76-3.67 (m, 4H), 1.49 (s, 9H). LC t$_r$=5.87 min (C-18 column, 5 to 95% acetonitrile/water over 6 min at 1.3 mL/min with detection 254 nm, at 23° C.). ES(pos)MS m/z 535 (M+H calcd for C$_{18}$H$_{18}$Br$_2$ClF$_3$O$_3$ requires 535).

Step 2: 1,3-bis(Nitrooxy)propan-2-yl 7-(tert-butyl)-6-chloro-2-(trifluoromethyl)-2H-chromene-3-carboxylate INT-16 (890 mg, 1.66 mmol) was dissolved in acetonitrile (5 mL). Silver nitrate (892 mg, 5.25 mmol) was added and the reaction was heated to 70° C. for 4 days. The reaction was cooled, filtered, and the filtrate was evaporated. The residue was purified by silica gel column chromatography using an ethyl acetate/hexane gradient to afford Example 22a as a foam (157.3 mg, 19% yield). $^1$H NMR (400 MHz, CDCl$_3$) δ 7.70 (s, 1H), 7.26 (s, 1H), 7.09 (s, 1H), 5.67 (q, J=6.7 Hz, 1H), 5.60-5.55 (m, 1H), 4.84 (ddd, J=15.7, 10.7, 4.0 Hz, 2H), 4.71 (dd, J=12.6, 5.8 Hz, 2H), 1.49 (s, 9H). LC t$_r$=5.45 min (C-18 column, 5 to 95% acetonitrile/water over 6 min at 1.3 mL/min with detection 254 nm, at 23° C.). ES(pos)MS m/z 499 (M+H calcd for C$_{18}$H$_{18}$ClF$_3$N$_2$O$_9$ requires 499).

Using either procedure to make Example 12a or 22a additional analogues (Table 4) are made by replacing C-01 with other chromene acid chlorides from Table 2.

TABLE 4

Examples of chromene 1,3-dinitroglycerine ester nitrate esters.

| Chromene | Ex. | Name | Structure |
|---|---|---|---|
| C-01a | 12a | 1,3-bis(nitrooxy)propan-2-yl 6,8-dichloro-2-(trifluoromethyl)-2H-chromene-3-carboxylate | 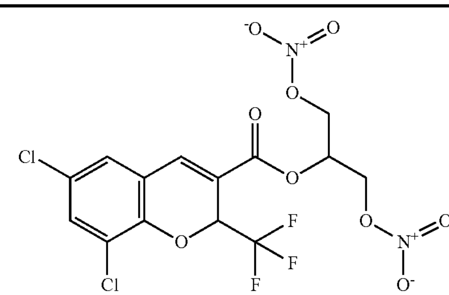 |

TABLE 4-continued

Examples of chromene 1,3-dinitroglycerine ester nitrate esters.

| Chromene | Ex. | Name | Structure |
|---|---|---|---|
| C-01 | 12 | (S)-1,3-bis(nitrooxy)propan-2-yl 6,8-dichloro-2-(trifluoromethyl)-2H-chromene-3-carboxylate | 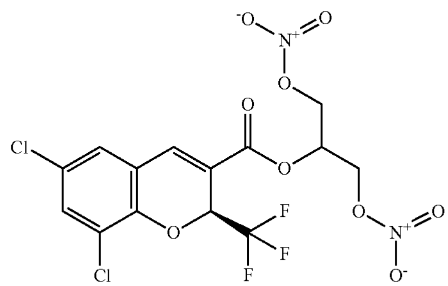 |
| C-02 | 13 | (S)-1,3-bis(nitrooxy)propan-2-yl 6-chloro-8-methyl-2-(trifluoromethyl)-2H-chromene-3-carboxylate | 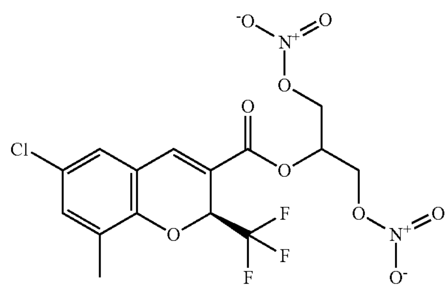 |
| C-03 | 14 | (S)-1,3-bis(nitrooxy)propan-2-yl 6-bromo-8-methyl-2-(trifluoromethyl)-2H-chromene-3-carboxylate | 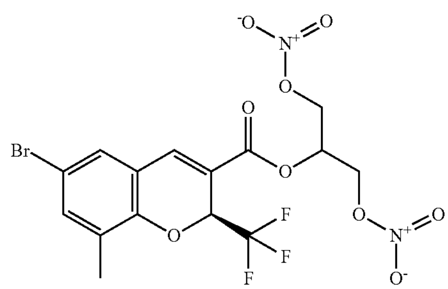 |
| C-04 | 15 | (S)-1,3-bis(nitrooxy)propan-2-yl 6,8-dimethyl-2-(trifluoromethyl)-2H-chromene-3-carboxylate | 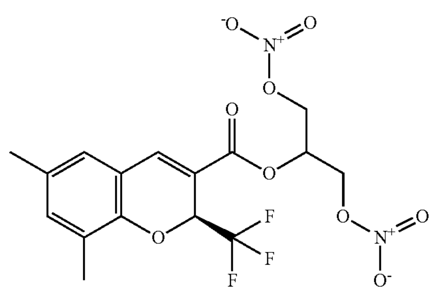 |
| C-05 | 16 | (S)-1,3-bis(nitrooxy)propan-2-yl 8-methyl-6-(trifluoromethoxy)-2-(trifluoromethyl)-2H-chromene-3-carboxylate | 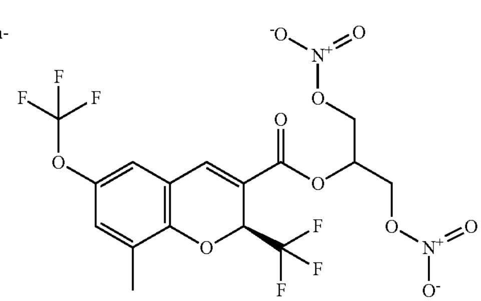 |

TABLE 4-continued

Examples of chromene 1,3-dinitroglycerine ester nitrate esters.

| Chromene | Ex. | Name | Structure |
|---|---|---|---|
| C-06 | 17 | (S)-1,3-bis(nitrooxy)propan-2-yl 8-ethyl-6-(trifluoromethoxy)-2-(trifluoromethyl)-2H-chromene-3-carboxylate | 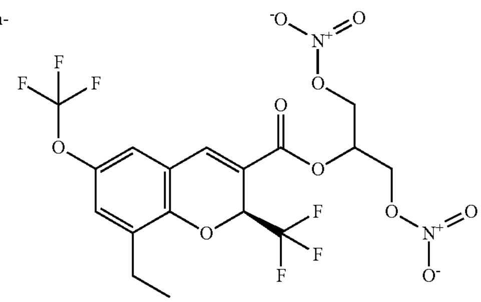 |
| C-07 | 18 | (S)-1,3-bis(nitrooxy)propan-2-yl 6-chloro-5,7-dimethyl-2-(trifluoromethyl)-2H-chromene-3-carboxylate | 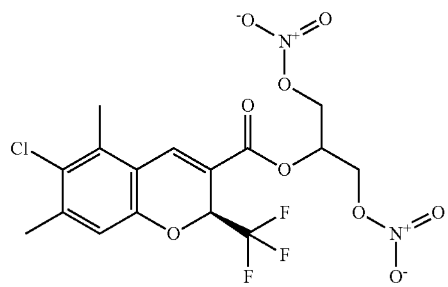 |
| C-08 | 19 | (S)-1,3-bis(nitrooxy)propan-2-yl 6-(pentafluorosulfanyl)-2-(trifluoromethyl)-2H-chromene-3-carboxylate | 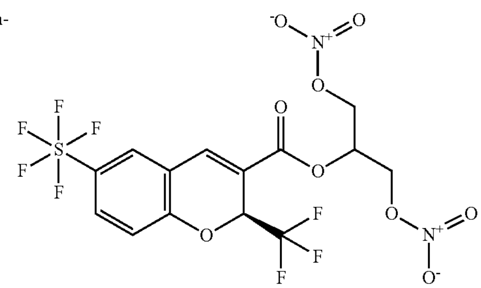 |
| C-09 | 20 | (S)-1,3-bis(nitrooxy)propan-2-yl 6-(pentafluorosulfanyl)-8-methyl-2-(trifluoromethyl)-2H-chromene-3-carboxylate | 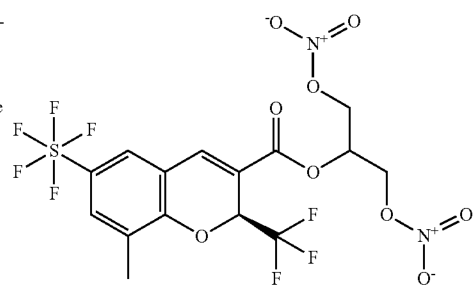 |
| C-10 | 21 | (S)-1,3-bis(nitrooxy)propan-2-yl 6-(pentafluorosulfanyl)-8-ethyl-2-(trifluoromethyl)-2H-chromene-3-carboxylate | 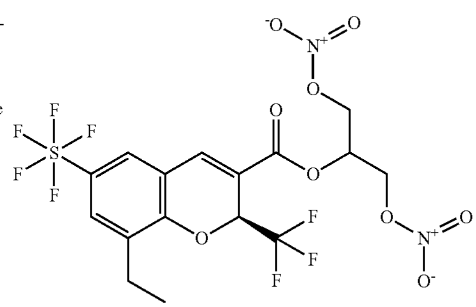 |

TABLE 4-continued

Examples of chromene 1,3-dinitroglycerine ester nitrate esters.

| Chromene | Ex. | Name | Structure |
| --- | --- | --- | --- |
| C-11a | 22a | 1,3-bis(nitrooxy)propan-2-yl 7-(tert-butyl)-6-chloro-2-(trifluoromethyl)-2H-chromene-3-carboxylate | 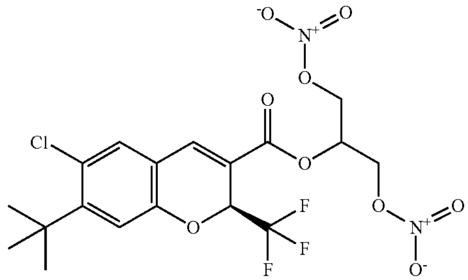 |
| C-11 | 22 | (S)-1,3-bis (nitrooxy)propan-2-yl 7-(tert-butyl)-6-chloro-2-(trifluoromethyl)-2H-chromene-3-carboxylate | 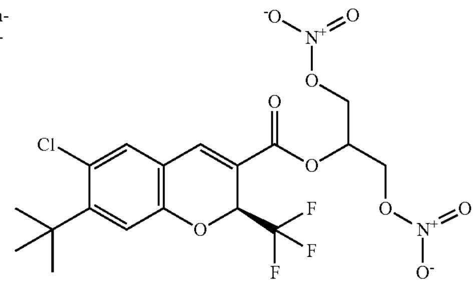 |

Chromene Isosorbide Ester Nitrate Esters

Example 33a: (3S,3aR,6R,6aS)-6-(nitrooxy)hexahydrofuro[3,2-b]furan-3-yl 7-(tert-butyl)-6-chloro-2-(trifluoromethyl)-2H-chromene-3-carboxylate

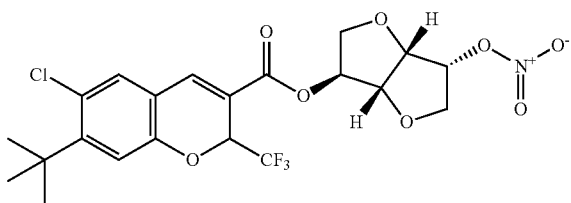 [SMILES: CC(C)(C)c1cc2c(cc1Cl)C=C(C(=O)O[C@H]1CO[C@H]3[C@@H]1OC[C@H]3O[N+](=O)[O-])C(C(F)(F)F)O2]

C-11a (500 mg, 1.42 mmol) was dissolved in dichloromethane (4 mL). Isosorbide mononitrate (298 mg, 1.56 mmol) and diisopropylethylamine (371 μL, 2.13 mmol) were added and the reaction was stirred at room temperature overnight. The mixture was diluted with ethyl acetate and washed with sodium bicarbonate and brine, dried over magnesium sulfate and evaporated. The residue was purified by silica gel column chromatography using an ethyl acetate/hexane gradient (0-30%) to afford Example 33a as a foam (495, 69% yield). $^1$H NMR (400 MHz, CDCl$_3$) δ 7.67 (d, J=13.2 Hz, 1H), 7.23 (d, J=1.9 Hz, 1H), 7.08 (s, 1H), 5.70-5.64 (m, 1H), 5.44-5.39 (m, 2H), 5.10-5.04 (m, 1H), 4.57 (dd, J=21.9, 5.3 Hz, 1H), 4.17-4.07 (m, 3H), 3.98-3.93 (m, 1H), 1.49 (s, 9H). LC t$_r$=5.42 min (C-18 column, 5 to 95% acetonitrile/water over 6 min at 1.3 mL/min with detection 254 nm, at 23° C.). ES(pos)MS m/z 508 (M+H calcd for C$_{21}$H$_{21}$ClF$_3$NO$_8$ requires 508).

Example 33: (S)-(3S,3aR,6R,6aS)-6-(nitrooxy)hexahydrofuro[3,2-b]furan-3-yl 7-(tert-butyl)-6-chloro-2-(trifluoromethyl)-2H-chromene-3-carboxylate

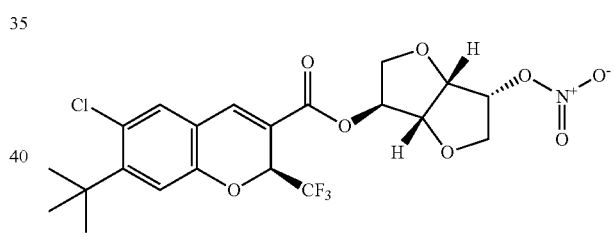

C-11 (513 mg, 1.45 mmol) was dissolved in dichloromethane (5 mL). Isosorbide mononitrate (305 mg, 1.60 mmol) and diisopropylethylamine (379 μL, 2.18 mmol) were added and the reaction was stirred at room temperature overnight. The mixture was diluted with ethyl acetate and washed with sodium bicarbonate and brine, dried over magnesium sulfate and evaporated. The residue was purified by silica gel column chromatography using an ethyl acetate/hexane gradient (0-30%) to afford Example 33 as a foam (491 mg, 67% yield). $^1$H NMR (400 MHz, CDCl$_3$) δ 7.66 (s, 1H), 7.22 (s, 1H), 7.08 (s, 1H), 5.68 (q, J=6.8 Hz, 1H), 5.43-5.40 (m, 2H), 5.09 (t, J=5.2 Hz, 1H), 4.60 (d, J=4.9 Hz, 1H), 4.16-4.08 (m, 3H), 3.96 (dd, J=11.4, 5.6 Hz, 1H), 1.49 (s, 9H). $^{19}$F NMR (400 MHz, CDCl$_3$) δ −78.5 (d, J=6.7 Hz, 3F). $^{13}$C NMR (400 MHz, CDCl$_3$) δ 162.7, 152.8, 151.7, 136.7, 131.8, 127.1, 117.4, 115.9, 115.7, 86.5, 81.6, 81.2, 78.3, 73.4, CF$_3$ (70.8, 70.5, 69.4), 36.7, 29.3. LC t$_r$=5.70 min (C-18 column, 5 to 95% acetonitrile/water over 6 min at 1.3 mL/min with detection 254 nm, at 23° C.). ES(pos)MS m/z 508 (M+H calcd for $C_{21}H_{21}ClF_3NO_8$ requires 508). Chiral HPLC: AD (n-hexane/i-PrOH 9:1, λ=254 nm), $t_r$=17.99 min, 100% ee.

Using a similar procedure to make 33a, and 33 additional analogues (Table 5) are made by replacing C-11a with other chromene acid chlorides from Table 2.

TABLE 5

Examples of chromene isosorbide ester nitrate esters.

| Chromene | Ex. | Name | Structure |
|---|---|---|---|
| C-01 | 23 | (S)-(3S,3aR,6R,6aS)-6-(nitrooxy)hexahydrofuro[3,2-b]furan-3-yl 6,8-dichloro-2-(trifluoromethyl)-2H-chromene-3-carboxylate | 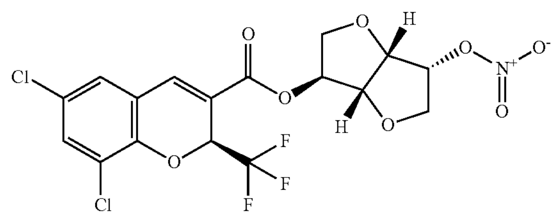 [SMILES: O=C(O[C@H]1CO[C@H]2[C@@H]1OC[C@H]2O[N+](=O)[O-])C1=Cc2cc(Cl)cc(Cl)c2O[C@@H]1C(F)(F)F] |
| C-02 | 24 | (S)-(3S,3aR,6R,6aS)-6-(nitrooxy)hexahydrofuro[3,2-b]furan-3-yl 6-chloro-8-methyl-2-(trifluoromethyl)-2H-chromene-3-carboxylate | 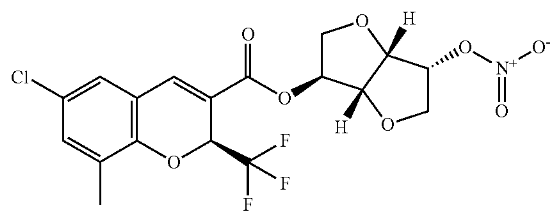 [SMILES: Cc1cc(Cl)cc2c1O[C@H](C(F)(F)F)C(C(=O)O[C@H]1CO[C@H]3[C@@H]1OC[C@H]3O[N+](=O)[O-])=C2] |
| C-03 | 25 | (S)-(3S,3aR,6R,6aS)-6-(nitrooxy)hexahydrofuro[3,2-b]furan-3-yl 6-bromo-8-methyl-2-(trifluoromethyl)-2H-chromene-3-carboxylate | 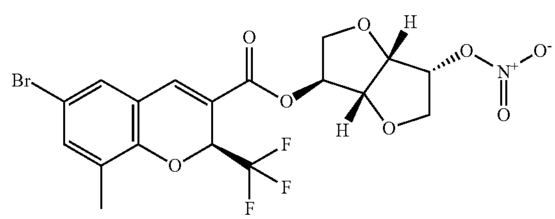 |
| C-04 | 26 | (3S,3aR,6R,6aS)-6-(nitrooxy)hexahydrofuro[3,2-b]furan-3-yl 6,8-dimethyl-2-(trifluoromethyl)-2H-chromene-3-carboxylate | 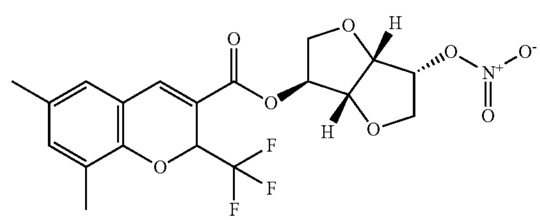 [SMILES: Cc1cc(C)c2c(c1)C=C(C(=O)O[C@H]1CO[C@H]3[C@@H]1OC[C@H]3O[N+](=O)[O-])C(C(F)(F)F)O2] |
| C-05 | 27 | (S)-(3S,3aR,6R,6aS)-6-(nitrooxy)hexahydrofuro[3,2-b]furan-3-yl 8-methyl-6-(trifluoromethoxy)-2-(trifluoromethyl)-2H-chromene-3-carboxylate | 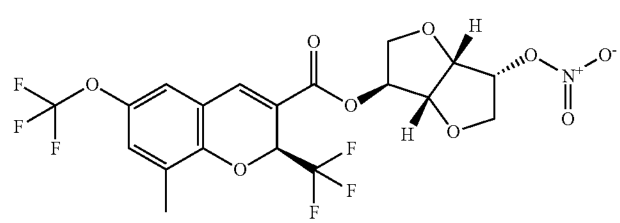 [SMILES: Cc1cc(OC(F)(F)F)cc2c1O[C@H](C(F)(F)F)C(C(=O)O[C@H]1CO[C@H]3[C@@H]1OC[C@H]3O[N+](=O)[O-])=C2] |
| C-06 | 28 | (S)-(3S,3aR,6R,6aS)-6-(nitrooxy)hexahydrofuro[3,2-b]furan-3-yl 8-ethyl-6-(trifluoromethoxy)-2-(trifluoromethyl)-2H-chromene-3-carboxylate | 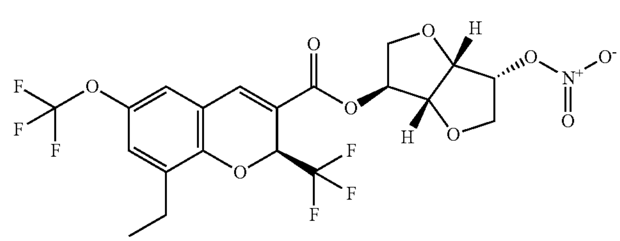 [SMILES: CCc1cc(OC(F)(F)F)cc2c1O[C@H](C(F)(F)F)C(C(=O)O[C@H]1CO[C@H]3[C@@H]1OC[C@H]3O[N+](=O)[O-])=C2] |

TABLE 5-continued

Examples of chromene isosorbide ester nitrate esters.

| Chromene | Ex. | Name | Structure |
|---|---|---|---|
| C-07 | 29 | (S)-(3S,3aR,6R,6aS)-6-(nitrooxy)hexahydrofuro[3,2-b]furan-3-yl 6-chloro-5,7-dimethyl-2-(trifluoromethyl)-2H-chromene-3-carboxylate | 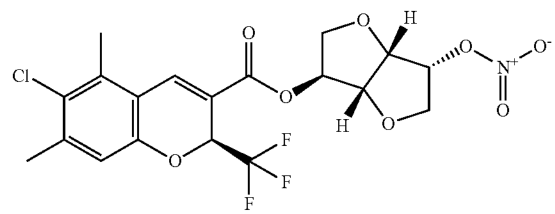 [SMILES: Cc1cc2c(c(C)c1Cl)C=C(C(=O)O[C@H]1CO[C@H]3[C@@H]1OC[C@H]3O[N+](=O)[O-])[C@@H](C(F)(F)F)O2] |
| C-08 | 30 | (S)-(3S,3aR,6R,6aS)-6-(nitrooxy)hexahydrofuro[3,2-b]furan-3-yl 6-pentafluorosulfanyl-2-(trifluoromethyl)-2H-chromene-3-carboxylate | 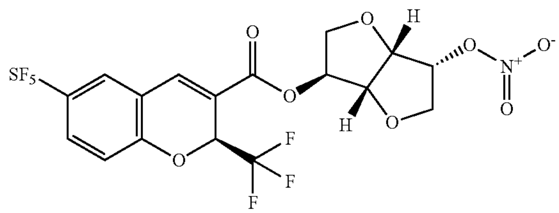 |
| C-09 | 31 | (S)-(3S,3aR,6R,6aS)-6-(nitrooxy)hexahydrofuro[3,2-b]furan-3-yl 6-(pentafluorosulfanyl)-8-methyl-2-(trifluoromethyl)-2H-chromene-3-carboxylate | 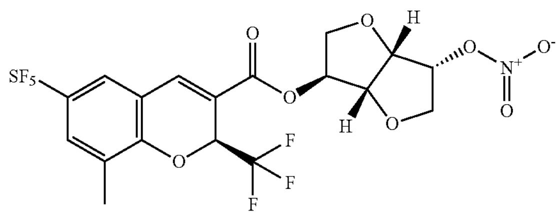 |
| C-10 | 32 | (S)-(3S,3aR,6R,6aS)-6-(nitrooxy)hexahydrofuro[3,2-b]furan-3-yl 6-(pentafluorosulfanyl)-8-ethyl-2-(trifluoromethyl)-2H-chromene-3-carboxylate | 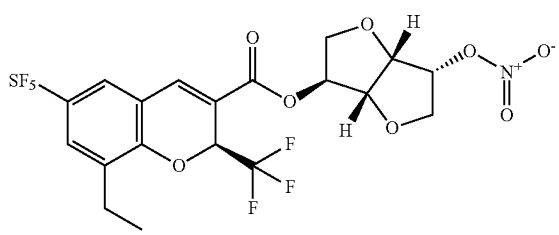 |
| C-11a | 33a | (3S,3aR,6R,6aS)-6-(nitrooxy)hexahydrofuro[3,2-b]furan-3-yl 7-(tert-butyl)-6-chloro-2-(trifluoromethyl)-2H-chromene-3-carboxylate | 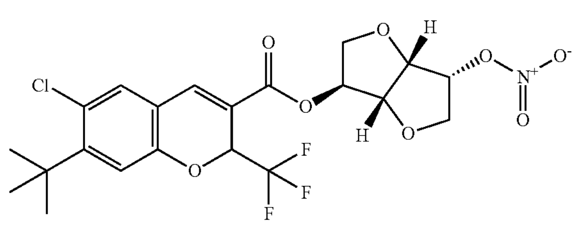 [SMILES: CC(C)(C)c1cc2c(cc1Cl)C=C(C(=O)O[C@H]1CO[C@H]3[C@@H]1OC[C@H]3O[N+](=O)[O-])C(C(F)(F)F)O2] |
| C-11 | 33 | (S)-(3S,3aR,6R,6aS)-6-(nitrooxy)hexahydrofuro[3,2-b]furan-3-yl 7-(tert-butyl)-6-chloro-2-(trifluoromethyl)-2H-chromene-3-carboxylate | 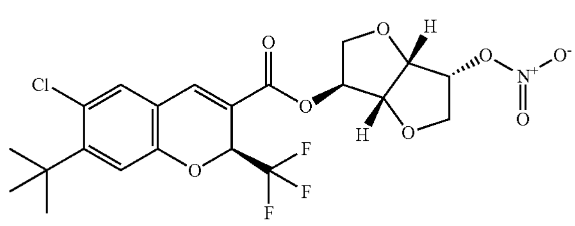 [SMILES: CC(C)(C)c1cc2c(cc1Cl)C=C(C(=O)O[C@H]1CO[C@H]3[C@@H]1OC[C@H]3O[N+](=O)[O-])[C@@H](C(F)(F)F)O2] |

Chromene Diethylene Glycol Ester Nitrate Esters

Example 34a: 2-(Nitrooxy)ethoxy)ethyl 6,8-dichloro-2-(trifluoromethyl)-2H-chromene-3-carboxylate

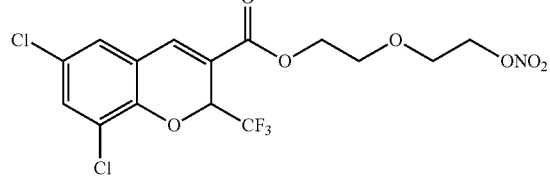

C-01a (0.5 mmol), 2-(2-hydroxyethoxy)ethyl nitrate (1.0 mmol), (prepared according to WO 2011/101245), catalytic amount of N,N-dimethylaminopyridine and diisopropylethylamine (0.6 mmol) are stirred in 2.5 mL of dichloromethane overnight. The reaction is diluted with ethyl acetate, and the organic layer is washed with saturated sodium bicarbonate solution and brine, dried over magnesium sulfate, and evaporated. The material is purified by chromatography using ethyl acetate/hexane gradient to afford Example 34a.

Using a similar procedure to make Example 34a additional analogues (Table 6) are made by replacing C-01a with other chromene acid chlorides from Table 2.

Chromene Diethylene Thioglycol Ester Nitrate Esters

Example 45a: 2-((2-(Nitrooxy)ethyl)thio)ethyl 6,8-dichloro-2-(trifluoromethyl)-2H-chromene-3-carboxylate

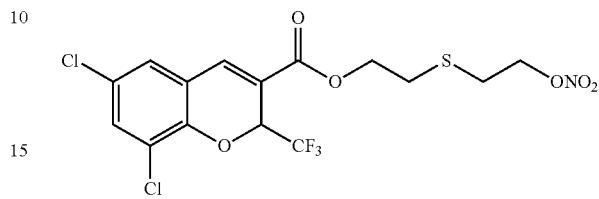

Step 1: C-01a (0.5 mmol), 2,2'-thiodiethanol (1.0 mmol), catalytic amount of N,N-dimethylaminopyridine and diisopropylethylamine (0.6 mmol) are stirred in 2.5 mL of dichloromethane overnight. The reaction is diluted with ethyl acetate, and the organic layer is washed with saturated sodium bicarbonate solution and brine, dried over magnesium sulfate, and evaporated. The material is purified by chromatography using ethyl acetate/hexane gradient to afford alcohol INT-17.

Step 2: To a solution of INT-17 (0.4 mmol) in dichloromethane (1.0 mL) is added triphenylphosphine (0.4 mmol) and carbon tetrabromide (0.4 mmol) at room temperature. After stirring for 3 h, the reaction is poured into water (50 mL), extracted with ethyl acetate (2×50 mL), and washed with saturated brine solution (50 mL). The combined organic layers are dried over magnesium sulfate, filtered, and concentrated under reduced pressure. The residue is purified by silica gel column chromatography using ethyl acetate/hexane gradient to provide bromide INT-18.

Step 3: INT-18 (0.25 mmol) is dissolved in acetonitrile (1.0 mL) and silver nitrate (0.30 mmol) is added (0.30 mmol). The reaction is heated at 65° C. for 24 h, cooled, and

TABLE 6

Examples of chromene diethylene glycol ester nitrate esters.

| Chromene | Ex. | Name |
|---|---|---|
| C-01a | 34a | 2-(2-(nitrooxy)ethoxy)ethyl 6,8-dichloro-2-(trifluoromethyl)-2H-chromene-3-carboxylate |
| C-01 | 34 | (S)-2-(2-(nitrooxy)ethoxy)ethyl 6,8-dichloro-2-(trifluoromethyl)-2H-chromene-3-carboxylate |
| C-02 | 35 | (S)-2-(2-(nitrooxy)ethoxy)ethyl 6-chloro-8-methyl-2-(trifluoromethyl)-2H-chromene-3-carboxylate |
| C-03 | 36 | (S)-2-(2-(nitrooxy)ethoxy)ethyl 6-bromo-8-methyl-2-(trifluoromethyl)-2H-chromene-3-carboxylate |
| C-04 | 37 | (S)-2-(2-(nitrooxy)ethoxy)ethyl 6,8-dimethyl-2-(trifluoromethyl)-2H-chromene-3-carboxylate |
| C-05 | 38 | (S)-2-(2-(nitrooxy)ethoxy)ethyl 8-methyl-6-(trifluoromethoxy)-2-(trifluoromethyl)-2H-chromene-3-carboxylate |
| C-06 | 39 | (S)-2-(2-(nitrooxy)ethoxy)ethyl 8-ethyl-6-(trifluoromethoxy)-2-(trifluoromethyl)-2H-chromene-3-carboxylate |
| C-07 | 40 | (S)-2-(2-(nitrooxy)ethoxy)ethyl 6-chloro-5,7-dimethyl-2-(trifluoromethyl)-2H-chromene-3-carboxylate |
| C-08 | 41 | (S)-2-(2-(nitrooxy)ethoxy)ethyl 6-(pentafluorosulfanyl)-2-(trifluoromethyl)-2H-chromene-3-carboxylate |
| C-09 | 42 | (S)-2-(2-(nitrooxy)ethoxy)ethyl 8-methyl-6-(pentafluorosulfanyl)-2-(trifluoromethyl)-2H-chromene-3-carboxylate |
| C-10 | 43 | (S)-2-(2-(nitrooxy)ethoxy)ethyl 8-ethyl-6-(pentafluorosulfanyl)-2-(trifluoromethyl)-2H-chromene-3-carboxylate |
| C-11 | 44 | (S)-2-(2-(nitrooxy)ethoxy)ethyl 7-(tert-butyl)-6-chloro-2-(trifluoromethyl)-2H-chromene-3-carboxylate | silver halide precipitate is removed by filtration. The filtrate is evaporated and the residue is purified by silica gel column chromatography using ethyl acetate/hexane gradient to provide Example 45a.

Using a similar procedure to make Example 45a additional analogues (Table 7) are made by replacing C-01a with other chromene acid chlorides from Table 2.

magnesium sulfate, and evaporated. The material is purified by chromatography using methanol-dichloromethane gradient to afford alcohol INT-19.

Step 2: C-01 (0.5 mmol), INT-19 (1.0 mmol), catalytic amount of N,N-dimethylaminopyridine and diisopropylethylamine (0.6 mmol) are stirred in 2.5 mL of dichloromethane overnight. The reaction is diluted with ethyl acetate, and the

TABLE 7

Examples of chromene diethylene thioglycol ester nitrate esters.

| Chromene | Ex. | Name |
|---|---|---|
| C-01a | 45a | 2-((2-(nitrooxy)ethyl)thio)ethyl 6,8-dichloro-2-(trifluoromethyl)-2H-chromene-3-carboxylate |
| C-01 | 45 | (S)-2-((2-(nitrooxy)ethyl)thio)ethyl 6,8-dichloro-2-(trifluoromethyl)-2H-chromene-3-carboxylate |
| C-02 | 46 | (S)-2-((2-(nitrooxy)ethyl)thio)ethyl 6-chloro-8-methyl-2-(trifluoromethyl)-2H-chromene-3-carboxylate |
| C-03 | 47 | (S)-2-((2-(nitrooxy)ethyl)thio)ethyl 6-bromo-8-methyl-2-(trifluoromethyl)-2H-chromene-3-carboxylate |
| C-04 | 48 | (S)-2-((2-(nitrooxy)ethyl)thio)ethyl 6,8-dimethyl-2-(trifluoromethyl)-2H-chromene-3-carboxylate |
| C-05 | 49 | (S)-2-((2-(nitrooxy)ethyl)thio)ethyl 8-methyl-6-(trifluoromethoxy)-2-(trifluoromethyl)-2H-chromene-3-carboxylate |
| C-06 | 50 | (S)-2-((2-(nitrooxy)ethyl)thio)ethyl 8-ethyl-6-(trifluoromethoxy)-2-(trifluoromethyl)-2H-chromene-3-carboxylate |
| C-07 | 51 | (S)-2-((2-(nitrooxy)ethyl)thio)ethyl 6-chloro-5,7-dimethyl-2-(trifluoromethyl)-2H-chromene-3-carboxylate |
| C-08 | 52 | (S)-2-((2-(nitrooxy)ethyl)thio)ethyl 6-(pentafluorosulfanyl)-2-(trifluoromethyl)-2H-chromene-3-carboxylate |
| C-09 | 53 | (S)-2-((2-(nitrooxy)ethyl)thio)ethyl 6-(pentafluorosulfanyl)-8-methyl-2-(trifluoromethyl)-2H-chromene-3-carboxylate |
| C-10 | 54 | (S)-2-((2-(nitrooxy)ethyl)thio)ethyl 6-(pentafluorosulfanyl)-8-ethyl-2-(trifluoromethyl)-2H-chromene-3-carboxylate |
| C-11 | 55 | (S)-2-((2-(nitrooxy)ethyl)thio)ethyl 7-(tert-butyl)-6-chloro-2-(trifluoromethyl)-2H-chromene-3-carboxylate |

Chromene Diethylene Acetamide Ester Nitrate Esters

Example 56a: 2-(N-(2-(Nitrooxy)ethyl)acetamido)ethyl 6,8-dichloro-2-(trifluoromethyl)-2H-chromene-3-carboxylate

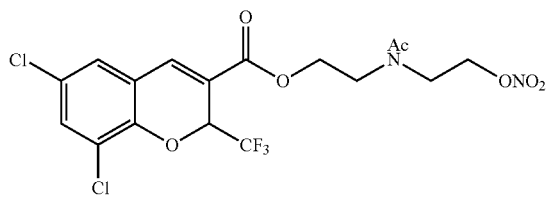

Step 1: Diethanol amine (5.0 mmol) and diisopropylethylamine (5.0 mmol) are dissolved in dichloromethane (10 mL), and acetyl chloride (4.5 mmol) is added dropwise at 0° C. and the mixture is stirred for 2 h. The reaction is diluted with ethyl acetate, and the organic layer is washed with saturated sodium bicarbonate solution and brine, dried over magnesium sulfate, and evaporated. The material is purified by chromatography using ethyl acetate/hexane gradient to afford alcohol INT-20.

Step 3: To a solution of INT-20 (0.4 mmol) in dichloromethane (1.0 mL) is added triphenylphosphine (0.4 mmol) and carbon tetrabromide (0.4 mmol) at room temperature. After stirring for 3 h, the reaction is poured into water (50 mL), extracted with ethyl acetate (2×50 mL), and washed with saturated brine solution (50 mL). The combined organic layers are dried over magnesium sulfate, filtered, and concentrated under reduced pressure. The residue is purified by silica gel column chromatography using ethyl acetate/hexane gradient to provide bromide INT-21.

Step 4: INT-21 (0.25 mmol) is dissolved in acetonitrile (1.0 mL) and silver nitrate (0.30 mmol) is added. The reaction is heated at 65° C. for 24 h, cooled, and silver halide precipitate is removed by filtration. The filtrate is evaporated and the residue is purified by silica gel column chromatography using ethyl acetate/hexane gradient to provide Example 56a.

Using a similar procedure to make Example 56a additional analogues (Table 8) are made by replacing C-01a with other chromene acid chlorides from Table 2.

TABLE 8

Examples of chromene diethylene acetamide ester nitrate esters

| Chromene | Ex. | Name |
|---|---|---|
| C-01a | 56a | 2-(N-(2-(nitrooxy)ethyl)acetamido)ethyl 6,8-dichloro-2-(trifluoromethyl)-2H-chromene-3-carboxylate |

TABLE 8-continued

Examples of chromene diethylene acetamide ester nitrate esters

| Chromene | Ex. | Name |
|---|---|---|
| C-01 | 56 | (S)-2-(N-(2-(nitrooxy)ethyl)acetamido)ethyl 6,8-dichloro-2-(trifluoromethyl)-2H-chromene-3-carboxylate |
| C-02 | 57 | (S)-2-(N-(2-(nitrooxy)ethyl)acetamido)ethyl 6-chloro-8-methyl-2-(trifluoromethyl)-2H-chromene-3-carboxylate |
| C-03 | 58 | (S)-2-(N-(2-(nitrooxy)ethyl)acetamido)ethyl 6-bromo-8-methyl-2-(trifluoromethyl)-2H-chromene-3-carboxylate |
| C-04 | 59 | (S)-2-(N-(2-(nitrooxy)ethyl)acetamido)ethyl 6,8-dimethyl-2-(trifluoromethyl)-2H-chromene-3-carboxylate |
| C-05 | 60 | (S)-2-(N-(2-(nitrooxy)ethyl)acetamido)ethyl 8-methyl-6-(trifluoromethoxy)-2-(trifluoromethyl)-2H-chromene-3-carboxylate |
| C-06 | 61 | (S)-2-(N-(2-(nitrooxy)ethyl)acetamido)ethyl 8-ethyl-6-(trifluoromethoxy)-2-(trifluoromethyl)-2H-chromene-3-carboxylate |
| C-07 | 62 | (S)-2-(N-(2-(nitrooxy)ethyl)acetamido)ethyl 6-chloro-5,7-dimethyl-2-(trifluoromethyl)-2H-chromene-3-carboxylate |
| C-08 | 63 | (S)-2-(N-(2-(nitrooxy)ethyl)acetamido)ethyl 6-(pentafluorosulfanyl)-2-(trifluoromethyl)-2H-chromene-3-carboxylate |
| C-09 | 64 | (S)-2-(N-(2-(nitrooxy)ethyl)acetamido)ethyl 6-(pentafluorosulfanyl)-8-methyl-2-(trifluoromethyl)-2H-chromene-3-carboxylate |
| C-10 | 65 | (S)-2-(N-(2-(nitrooxy)ethyl)acetamido)ethyl 6-(pentafluorosulfanyl)-8-ethyl-2-(trifluoromethyl)-2H-chromene-3-carboxylate |
| C-11 | 66 | (S)-2-(N-(2-(nitrooxy)ethyl)acetamido)ethyl 7-(tert-butyl)-6-chloro-2-(trifluoromethyl)-2H-chromene-3-carboxylate |

Chromene Diethylene N-Methylamino Ester Nitrate Esters

Example 67a: 2-(Methyl(2-(nitrooxy)ethyl)amino)ethyl 6,8-dichloro-2-(trifluoromethyl)-2H-chromene-3-carboxylate

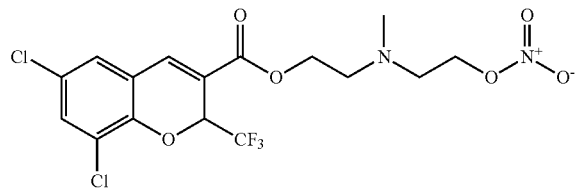 [SMILES: CN(CCOC(=O)C1=Cc2cc(Cl)cc(Cl)c2OC1C(F)(F)F)CCO[N+](=O)[O-]]

Step 1: 2-(Methylamino)ethanol (1.0 mmol) is nitrated using fuming nitric acid in dichloromethane followed by the addition of acetic anhydride. The resulting 2-(methylamino)ethyl nitrate salt is dissolved in 7 M aqueous sodium hydroxide and alkylated using bromoethanol to provide 2-((2-hydroxyethyl)(methyl)amino)ethyl nitrate.

Step 2: C-01a (0.5 mmol), 2-((2-hydroxyethyl)(methyl)amino)ethyl nitrate (0.51 mmol), catalytic amount of N,N-dimethylaminopyridine and diisopropylethylamine (0.6 mmol) are stirred in 2.5 mL of dichloromethane overnight. The reaction is diluted with ethyl acetate, and the organic layer is washed with saturated sodium bicarbonate solution and brine, dried over magnesium sulfate, and evaporated to provide Example 67a.

Using a similar procedure additional analogues (Table 9) are made by replacing C-01a with other chromene acid chlorides from Table 2.

TABLE 9

Examples of chromene diethylene N-methylamino ester nitrate esters.

| Chromene | Ex. | Name |
|---|---|---|
| C-01a | 67a | 2-(methyl(2-(nitrooxy)ethyl)amino)ethyl 6,8-dichloro-2-(trifluoromethyl)-2H-chromene-3-carboxylate |
| C-01 | 67 | (S)-2-(methyl(2-(nitrooxy)ethyl)amino)ethyl 6,8-dichloro-2-(trifluoromethyl)-2H-chromene-3-carboxylate |
| C-02 | 68 | (S)-2-(methyl(2-(nitrooxy)ethyl)amino)ethyl 6-chloro-8-methyl-2-(trifluoromethyl)-2H-chromene-3-carboxylate |
| C-03 | 69 | (S)-2-(methyl(2-(nitrooxy)ethyl)amino)ethyl 6-bromo-8-methyl-2-(trifluoromethyl)-2H-chromene-3-carboxylate |
| C-04 | 70 | (S)-2-(methyl(2-(nitrooxy)ethyl)amino)ethyl 6,8-dimethyl-2-(trifluoromethyl)-2H-chromene-3-carboxylate |
| C-05 | 71 | (S)-2-(methyl(2-(nitrooxy)ethyl)amino)ethyl 8-methyl-6-(trifluoromethoxy)-2-(trifluoromethyl)-2H-chromene-3-carboxylate |
| C-06 | 72 | (S)-2-(methyl(2-(nitrooxy)ethyl)amino)ethyl 8-ethyl-6-(trifluoromethoxy)-2-(trifluoromethyl)-2H-chromene-3-carboxylate |
| C-07 | 73 | (S)-2-(methyl(2-(nitrooxy)ethyl)amino)ethyl 6-chloro-5,7-dimethyl-2-(trifluoromethyl)-2H-chromene-3-carboxylate |
| C-08 | 74 | (S)-2-(methyl(2-(nitrooxy)ethyl)amino)ethyl 6-(pentafluorosulfanyl)-2-(trifluoromethyl)-2H-chromene-3-carboxylate |
| C-09 | 75 | (S)-2-(methyl(2-(nitrooxy)ethyl)amino)ethyl 6-(pentafluorosulfanyl)-8-methyl-2-(trifluoromethyl)-2H-chromene-3-carboxylate |

TABLE 9-continued

Examples of chromene diethylene N-methylamino ester nitrate esters.

| Chromene | Ex. | Name |
|---|---|---|
| C-10 | 76 | (S)-2-(methyl(2-(nitrooxy)ethyl)amino)ethyl 6-(pentafluorosulfanyl)-8-ethyl-2-(trifluoromethyl)-2H-chromene-3-carboxylate |
| C-11 | 77 | (S)-2-(methyl(2-(nitrooxy)ethyl)amino)ethyl 7-(tert-butyl)-6-chloro-2-(trifluoromethyl)-2H-chromene-3-carboxylate |

Chromene Ethyldisulfide Ester Nitrate Esters

Example 78a: 2-((2-(Nitrooxy)ethyl)disulfanyl)ethyl 6,8-dichloro-2-(trifluoromethyl)-2H-chromene-3-carboxylate

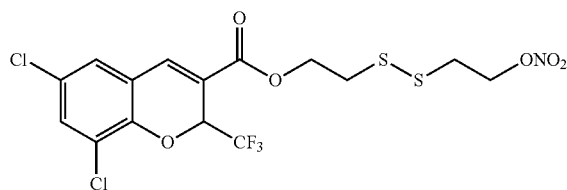

Step 1: C-01a (0.5 mmol), 2-hydroxyethyl disulfide (1.0 mmol), catalytic amount of N,N-dimethylaminopyridine and diisopropylethylamine (0.6 mmol) are stirred in 2.5 mL of dichloromethane overnight. The reaction is diluted with ethyl acetate, and the organic layer is washed with saturated sodium bicarbonate solution and brine, dried over magnesium sulfate, and evaporated. The material is purified by chromatography using ethyl acetate/hexane gradient to afford alcohol INT-22.

Step 2: To a solution of INT-22 (0.4 mmol) in dichloromethane (1.0 mL) is added triphenylphosphine (0.4 mmol) and carbon tetrabromide (0.4 mmol) at room temperature. After stirring for 3 h, the reaction is poured into water (50 mL), extracted with ethyl acetate (2×50 mL), and washed with saturated brine solution (50 mL). The combined organic layers are dried over magnesium sulfate, filtered, and concentrated under reduced pressure. The residue is purified by silica gel column chromatography using ethyl acetate/hexane gradient to provide bromide INT-23.

Step 3: INT-23 (0.25 mmol) is dissolved in acetonitrile (1.0 mL) and silver nitrate (0.30 mmol) is added (0.30 mmol). The reaction is heated at 65° C. for 24 h, cooled, and silver halide precipitate is removed by filtration. The filtrate is evaporated and the residue is purified by silica gel column chromatography using ethyl acetate/hexane gradient to provide Example 78a.

Using a similar procedure to make Example 78a additional analogues (Table 10) are made by replacing C-01a with other chromene acid chlorides from Table 2.

TABLE 10

Examples of chromene ethyl disulfide ester nitrate esters.

| Chromene | Ex. | Name |
|---|---|---|
| C-01a | 78a | 2-((2-(nitrooxy)ethyl)disulfanyl)ethyl 6,8-dichloro-2-(trifluoromethyl)-2H-chromene-3-carboxylate |
| C-01 | 78 | (S)-2-((2-(nitrooxy)ethyl)disulfanyl)ethyl 6,8-dichloro-2-(trifluoromethyl)-2H-chromene-3-carboxylate |
| C-02 | 79 | (S)-2-((2-(nitrooxy)ethyl)disulfanyl)ethyl 6-chloro-8-methyl-2-(trifluoromethyl)-2H-chromene-3-carboxylate |
| C-03 | 80 | (S)-2-((2-(nitrooxy)ethyl)disulfanyl)ethyl 6-bromo-8-methyl-2-(trifluoromethyl)-2H-chromene-3-carboxylate |
| C-04 | 81 | (S)-2-((2-(nitrooxy)ethyl)disulfanyl)ethyl 6,8-dimethyl-2-(trifluoromethyl)-2H-chromene-3-carboxylate |
| C-05 | 82 | (S)-2-((2-(nitrooxy)ethyl)disulfanyl)ethyl 8-methyl-6-(trifluoromethoxy)-2-(trifluoromethyl)-2H-chromene-3-carboxylate |
| C-06 | 83 | (S)-2-((2-(nitrooxy)ethyl)disulfanyl)ethyl 8-ethyl-6-(trifluoromethoxy)-2-(trifluoromethyl)-2H-chromene-3-carboxylate |
| C-07 | 84 | (S)-2-((2-(nitrooxy)ethyl)disulfanyl)ethyl 6-chloro-5,7-dimethyl-2-(trifluoromethyl)-2H-chromene-3-carboxylate |
| C-08 | 85 | (S)-2-((2-(nitrooxy)ethyl)disulfanyl)ethyl 6-(pentafluorosulfanyl)-2-(trifluoromethyl)-2H-chromene-3-carboxylate |
| C-09 | 86 | (S)-2-((2-(nitrooxy)ethyl)disulfanyl)ethyl 6-(pentafluorosulfanyl)-8-methyl-2-(trifluoromethyl)-2H-chromene-3-carboxylate |
| C-10 | 87 | (S)-2-((2-(nitrooxy)ethyl)disulfanyl)ethyl 6-(pentafluorosulfanyl)-8-ethyl-2-(trifluoromethyl)-2H-chromene-3-carboxylate |
| C-11 | 88 | (S)-2-((2-(nitrooxy)ethyl)disulfanyl)ethyl 7-(tert-butyl)-6-chloro-2-(trifluoromethyl)-2H-chromene-3-carboxylate |

Nitrooxy Carboxlyic Acids

Methods to make nitrooxy carboxylic acids are known in the literature and representative synthetic procedures are cited in Table 11.

TABLE 11

Nitrooxy carboxylic acids.

| Nitrooxy Acids | Structure | Name | Literature Preparation |
|---|---|---|---|
| NA-01 | 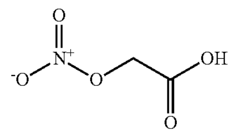 | 2-(nitrooxy)acetic acid | Wang, X.; et al. Synthesis and biological evaluation of nitric oxide releasing derivatives of 6-amino-3-n-butylphthalide as potential antiplatelet agents. *Bioorg. Med. Chem. Lett.* 2013, 23, 1985-1988 |
| NA-02 | 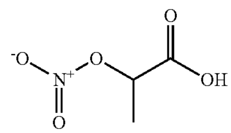 | 2-(nitrooxy)propanoic acid | Jpn. Kokai Tokkyo Koho 1990, JP 02091054 and Platz, R.; et al. 1976, DE 1618150 |
| NA-03 | 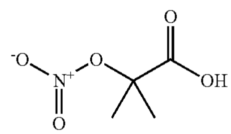 | 2-methyl-2-(nitrooxy)propanoic acid | Endres, S.; et al. NO-Donors, part 3: nitrooxyacylated thiosalicylates and salicylates-synthesis and biological activities. *Eur. J. Med. Chem.* 1999, 34, 895-901 |
| NA-04 | 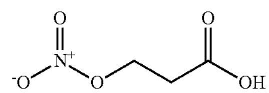 | 3-(nitrooxy)propanoic acid | Wang, X.; et al. Synthesis and biological evaluation of nitric oxide releasing derivatives of 6-amino-3-n-butylphthalide as potential antiplatelet agents. *Bioorg. Med. Chem. Lett.* 2013, 23, 1985-1988. |
| NA-05 | 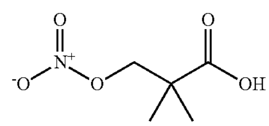 | 2,2-dimethyl-3-(nitrooxy)propanoic acid | Koenig, A.; et al.. NO donors. Part 16: Investigations on structure-activity relationships of organic mononitrates reveal 2-nitrooxyethylammoniumnitrate as a high potent vasodilator. *Bioorg. Med. Chem. Lett.* 2007, 17, 5881-5885 |
| NA-06 | 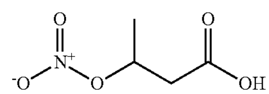 | 3-(nitrooxy)butanoic acid | Krow, G. R. 2004. The Baeyer-Villiger Oxidation of Ketones and Aldehydes. Organic Reactions. 251-798 |
| NA-07 | 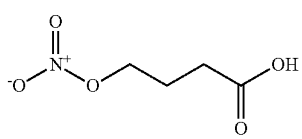 | 4-(nitrooxy)butanoic acid | Anzini, M.; et al. Novel Analgesic/Anti-Inflammatory Agents: 1,5-Diarylpyrrole Nitrooxyalkyl Ethers and Related Compounds as Cyclooxygenase-2 Inhibiting Nitric Oxide Donors. *J. Med. Chem.* 2013, 56, 3191-3206 |
| NA-08 | 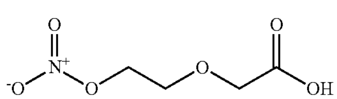 | 2-(2-(nitrooxy)ethoxy)acetic acid | Almirante, N.; et al Nitric oxide releasing compounds for the treatment of neuropathic pain. PCT Int. Appl. 2011, WO 2011101245 |
| NA-09 | 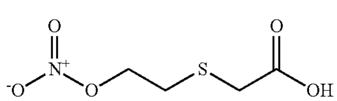 | 2-((2-(nitrooxy)ethyl)thio)acetic acid | Myers, G. S.; et al. U.S. Pat. No. 2,975,208 |
| NA-10 | 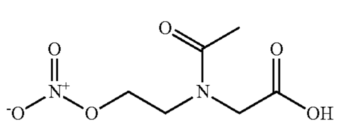 | 2-(N-(2-(nitrooxy)ethyl)acetamido)acetic acid | Myers, G. S.; et al. U.S. Pat. No. 2,975,208 |
| NA-11 | 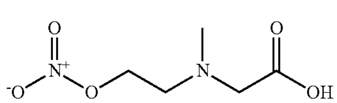 | 2-(methyl(2-(nitrooxy)ethyl)amino)acetic acid | Decker, M.; et al. Synthesis and vasorelaxant properties of hybrid molecules out of NO-donors and the â-receptor blocking drug propranolol *Bioorg. Med. Chem.* |

TABLE 11-continued

Nitrooxy carboxylic acids.

| Nitrooxy Acids | Structure | Name | Literature Preparation |
|---|---|---|---|
| | | | Lett. 2004, 14, 4995-4997. J. F. Gilmer et al. Evaluation of nitrate-substituted pseudocholine esters of aspirin as potential nitro-aspirins. Bioorg. Med. Chem. Lett. 2007, 17, 3217-3220. |

2-(Methyl(2-(nitrooxy)ethyl)amino)acetic acid (NA-11)

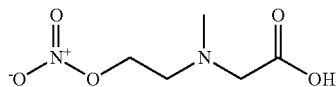

Nitration of 2-((2-hydroxyethyl)(methyl)amino)acetic acid, without protection of the carboxylic acid, is done using fuming nitric acid in acetic acid and acetic anhydride as described in U.S. Pat. No. 2,975,208 to afford NA-11. Alternatively, treatment of ethyl 2-((2-hydroxyethyl)(methyl)amino)acetate under the conditions mentioned above provides ethyl 2-(methyl(2-(nitrooxy)ethyl)amino)acetate and saponification affords the desired acid NA-11. This protocol is adapted from Decker, M., et. al., Bioorg. Med. Chem. Lett. 2004, 14, 4995-4997. For another reliable method see; J. F. Gilmer et. al., Bioorg. Med. Chem. Lett. 2007, 17, 3217-3220.

Chromene Haloalkyl Esters

Chloromethyl 6,8-dichloro-2-(trifluoromethyl)-2H-chromene-3-carboxylate (C-12a)

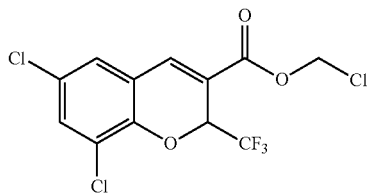 [SMILES: O=C(OCCl)C1=Cc2cc(Cl)cc(Cl)c2OC1C(F)(F)F]

Chromene acids are converted to chloromethyl esters as described in Syn. Comm., 1984, 14(9), 857-864. Carboxylic acid CA-01a (200 mg, 0.64 mmol), tetrabutylammonium hydrogensulfate (22 mg, 0.06 mmol) and sodium bicarbonate (204 mg, 2.43 mmol) were dissolved 1:1 dichloromethane-water mixture (1.2 mL). Chloromethyl chlorosulfate (75 µL, 0.74 mmol) in 150 µL of dichloromethane was added drop-wise, and stirred at room temperature overnight. The reaction was diluted with ethyl acetate, and the organic layer was washed with saturated sodium bicarbonate solution and brine, dried over magnesium sulfate, and evaporated to give C-12a (197 mg, 85% yield). $^1$H NMR (400 MHz, CDCl$_3$) δ 7.77 (s, 1H), 7.44 (d, J=2.5 Hz, 1H), 7.19 (dd, J=2.5, 0.3 Hz, 1H), 5.91 (abq, J=36.4, 6.2 Hz, 2H), 5.84 (q, J=6.6 Hz, 1H). LC t$_r$=5.04 min (C-18 column, 5 to 95% acetonitrile/water over 6 min at 1.7 mL/min with detection 254 nm, at 23° C.).

Iodomethyl 6,8-dichloro-2-(trifluoromethyl)-2H-chromene-3-carboxylate (C-13a)

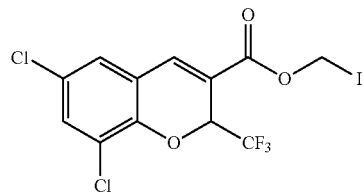 [SMILES: O=C(OCI)C1=Cc2cc(Cl)cc(Cl)c2OC1C(F)(F)F]

C-12a (530 mg, 1.69 mmol) and sodium iodide (381 mg, 2.54 mmol) were heated to 60° C. in 1.5 mL of acetonitrile for 5 h, then stirred at room temperature for 48 h. The reaction was diluted with ethyl acetate. The organic layer was washed with 0.2 M sodium thiosulfate solution and brine, dried over magnesium sulfate, and evaporated to give C-13a as a light yellow oil (505 mg, 66% yield). $^1$H NMR (400 MHz, CDCl$_3$) δ 7.72 (s, 1H), 7.44 (d, J=2.4 Hz, 1H), 7.19 (d, J=2.4 Hz, 1H), 6.11 (abq, J=32.7, 5.0 Hz, 2H), 5.82 (q, J=6.6 Hz, 1H). LC t$_r$=5.21 min (C-18 column, 5 to 95% acetonitrile/water over 6 min at 1.7 mL/min with detection 254 nm, at 23° C.).

1-Chloroethyl 6,8-dichloro-2-(trifluoromethyl)-2H-chromene-3-carboxylate (C-14a)

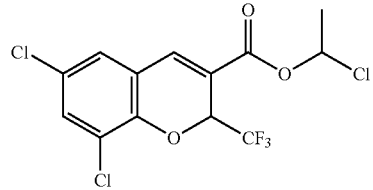 [SMILES: CC(Cl)OC(=O)C1=Cc2cc(Cl)cc(Cl)c2OC1C(F)(F)F]

Carboxylic acid CA-01a (0.50 mmol), tetrabutylammonium hydrogensulfate (0.05 mmol) and sodium bicarbonate (2.0 mmol) are dissolved 1:1 dichloromethane-water mixture (1.0 mL). 1-Chloroethyl chlorosulfate (0.60 mmol, prepared as described in U.S. Pat. No. 2,860,123 A) in 150 µL of dichloromethane is added drop-wise, and stirred at room temperature overnight. The reaction is diluted with ethyl acetate, and the organic layer is washed with saturated sodium bicarbonate solution and brine, dried over magnesium sulfate, and evaporated to afford C-14a.

Using similar procedures to make C-12a through C-14a additional haloalkyl chromene esters (Table 12) are made by replacing CA-01a with other suitable chromene acids listed in Table 1 and known in the literature.

TABLE 12

Haloalkyl chromene esters.

| Chromene Acid | Chromene | Structure | Name |
|---|---|---|---|
| CA-01a | C-12a | | chloromethyl 6,8-dichloro-2-(trifluoromethyl)-2H-chromene-3-carboxylate |
| CA-01a | C-13a | | iodomethyl 6,8-dichloro-2-(trifluoromethyl)-2H-chromene-3-carboxylate |
| CA-01a | C-14a | | 1-chloroethyl 6,8-dichloro-2-(trifluoromethyl)-2H-chromene-3-carboxylate |
| CA-01 | C-12 | | (S)-chloromethyl 6,8-dichloro-2-(trifluoromethyl)-2H-chromene-3-carboxylate |
| CA-01 | C-13 | | (S)-iodomethyl 6,8-dichloro-2-(trifluoromethyl)-2H-chromene-3-carboxylate |
| CA-01 | C-14 | | (2S)-1-chloroethyl 6,8-dichloro-2-(trifluoromethyl)-2H-chromene-3-carboxylate |
| CA-02 | C-15 | 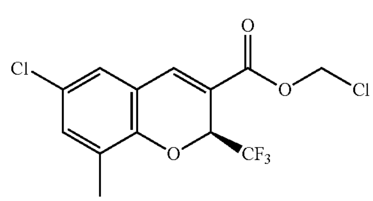 [SMILES: Cc1cc(Cl)cc2c1O[C@H](C(F)(F)F)C(C(=O)OCCl)=C2] | (S)-chloromethyl 6-chloro-8-methyl-2-(trifluoromethyl)-2H-chromene-3-carboxylate |

TABLE 12-continued

Haloalkyl chromene esters.

| Chromene Acid | Chromene | Structure | Name |
|---|---|---|---|
| CA-02 | C-16 | | (S)-iodomethyl 6-chloro-8-methyl-2-(trifluoromethyl)-2H-chromene-3-carboxylate |
| CA-02 | C-17 | | (2S)-1-chloroethyl 6-chloro-8-methyl-2-(trifluoromethyl)-2H-chromene-3-carboxylate |
| CA-03 | C-18 | | (S)-chloromethyl 6-bromo-8-methyl-2-(trifluoromethyl)-2H-chromene-3-carboxylate |
| CA-03 | C-19 | | (S)-iodomethyl 6-bromo-8-methyl-2-(trifluoromethyl)-2H-chromene-3-carboxylate |
| CA-03 | C-20 | | (2S)-1-chloroethyl 6-bromo-8-methyl-2-(trifluoromethyl)-2H-chromene-3-carboxylate |
| CA-04 | C-21 | | (S)-chloromethyl 6,8-dimethyl-2-(trifluoromethyl)-2H-chromene-3-carboxylate |
| CA-04 | C-22 | | (S)-iodomethyl 6,8-dimethyl-2-(trifluoromethyl)-2H-chromene-3-carboxylate |

TABLE 12-continued

Haloalkyl chromene esters.

| Chromene Acid | Chromene | Structure | Name |
|---|---|---|---|
| CA-04 | C-23 | 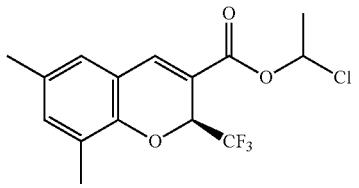 [SMILES: Cc1cc(C)c2c(c1)C=C(C(=O)OC(C)Cl)[C@@H](C(F)(F)F)O2] | (2S)-1-chloroethyl 6,8-dimethyl-2-(trifluoromethyl)-2H-chromene-3-carboxylate |
| CA-05 | C-24 | 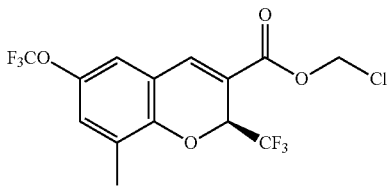 [SMILES: Cc1cc(OC(F)(F)F)cc2c1O[C@H](C(F)(F)F)C(C(=O)OCCl)=C2] | (S)-chloromethyl 8-methyl-6-(trifluoromethoxy)-2-(trifluoromethyl)-2H-chromene-3-carboxylate |
| CA-05 | C-25 | 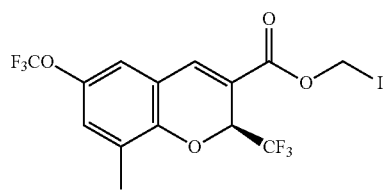 [SMILES: Cc1cc(OC(F)(F)F)cc2c1O[C@H](C(F)(F)F)C(C(=O)OCI)=C2] | (S)-iodomethyl 8-methyl-6-(trifluoromethoxy)-2-(trifluoromethyl)-2H-chromene-3-carboxylate |
| CA-05 | C-26 | 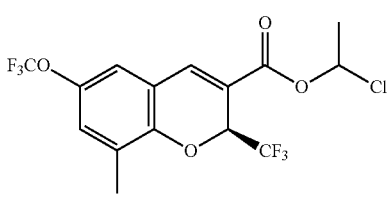 [SMILES: Cc1cc(OC(F)(F)F)cc2c1O[C@H](C(F)(F)F)C(C(=O)OC(C)Cl)=C2] | (2S)-1-chloroethyl 8-methyl-6-(trifluoromethoxy)-2-(trifluoromethyl)-2H-chromene-3-carboxylate |
| CA-06 | C-27 | 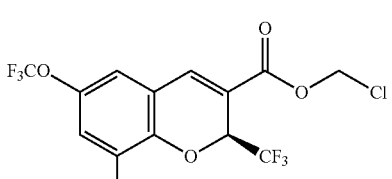 | (S)-chloromethyl 8-ethyl-6-(trifluoromethoxy)-2-(trifluoromethyl)-2H-chromene-3-carboxylate |
| CA-06 | C-28 | 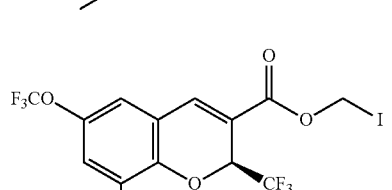 | (S)-iodomethyl 8-ethyl-6-(trifluoromethoxy)-2-(trifluoromethyl)-2H-chromene-3-carboxylate |
| CA-06 | C-29 | 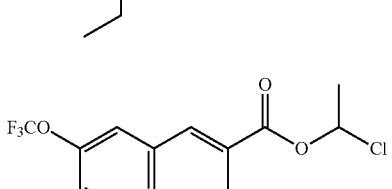 | (2S)-1-chloroethyl 8-ethyl-6-(trifluoromethoxy)-2-(trifluoromethyl)-2H-chromene-3-carboxylate |

TABLE 12-continued

Haloalkyl chromene esters.

| Chromene Acid | Chromene | Structure | Name |
|---|---|---|---|
| CA-07 | C-30 | | (S)-chloromethyl 6-chloro-5,7-dimethyl-2-(trifluoromethyl)-2H-chromene-3-carboxylate |
| CA-07 | C-31 | | (S)-iodomethyl 6-chloro-5,7-dimethyl-2-(trifluoromethyl)-2H-chromene-3-carboxylate |
| CA-07 | C-32 | | (2S)-1-chloroethyl 6-chloro-5,7-dimethyl-2-(trifluoromethyl)-2H-chromene-3-carboxylate |
| CA-08 | C-33 | | (S)-chloromethyl 6-pentafluorosulfanyl-2-(trifluoromethyl)-2H-chromene-3-carboxylate |
| CA-08 | C-34 | | (S)-iodomethyl 6-pentafluorosulfanyl-2-(trifluoromethyl)-2H-chromene-3-carboxylate |
| CA-08 | C-35 | | (2S)-1-chloroethyl 6-pentafluorosulfanyl-2-(trifluoromethyl)-2H-chromene-3-carboxylate |
| CA-09 | C-36 | | (S)-chloromethyl 6-pentafluorosulfanyl-8-methyl-2-(trifluoromethyl)-2H-chromene-3-carboxylate |
| CA-09 | C-37 | | (S)-iodomethyl 6-pentafluorosulfanyl-8-methyl-2-(trifluoromethyl)-2H-chromene-3-carboxylate |

TABLE 12-continued

Haloalkyl chromene esters.

| Chromene Acid | Chromene | Structure | Name |
|---|---|---|---|
| CA-09 | C-38 | 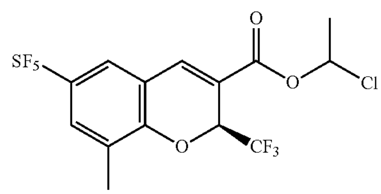 | (2S)-1-chloroethyl 6-pentafluorosulfanyl-8-methyl-2-(trifluoromethyl)-2H-chromene-3-carboxylate |
| CA-10 | C-39 | | (S)-chloromethyl 6-pentafluorosulfanyl-8-ethyl-2-(trifluoromethyl)-2H-chromene-3-carboxylate |
| CA-10 | C-40 | | (S)-iodomethyl 6-pentafluorosulfanyl-8-ethyl-2-(trifluoromethyl)-2H-chromene-3-carboxylate |
| CA-10 | C-41 | | (2S)-1-chloroethyl 6-pentafluorosulfanyl-8-ethyl-2-(trifluoromethyl)-2H-chromene-3-carboxylate |
| CA-11 | C-42 | | (S)-chloromethyl 7-(tert-butyl)-6-chloro-2-(trifluoromethyl)-2H-chromene-3-carboxylate |
| CA-11 | C-43 | | (S)-iodomethyl 7-(tert-butyl)-6-chloro-2-(trifluoromethyl)-2H-chromene-3-carboxylate |
| CA-11 | C-44 | | (2S)-1-chloroethyl 7-(tert-butyl)-6-chloro-2-(trifluoromethyl)-2H-chromene-3-carboxylate |

Chromene Alkyl Diester Nitrate Esters

Example 89a: (2-(Nitrooxy)acetoxy)methyl 6,8-dichloro-2-(trifluoromethyl)-2H-chromene-3-carboxylate

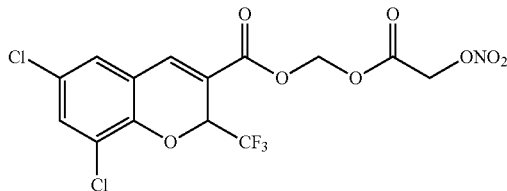

2-(Nitrooxy)acetic acid (NA-01) (1.0 mmol), C-12a (1.0 mmol) and triethylamine (1.25 mmol) are dissolved in 3 mL dimethyl sulfoxide, and stirred at room temperature for 48 h. The reaction is diluted with ethyl acetate. The organic layer is washed with saturated sodium bicarbonate solution and brine, dried over magnesium sulfate, and evaporated. Purification by chromatography using an ethyl acetate/hexane gradient affords Example 89a.

Using a similar procedure to make Example 89a additional analogues (Table 13) are made by replacing C-12a with other chromene haloalkyl esters from Table 12 and other nitrooxy acids from Table 11.

TABLE 13

Examples of chromene methylene diester nitrate esters.

| Chromene | Nitrate Acid | Ex. | Name |
|---|---|---|---|
| C-12a | NA-01 | 89a | (2-(nitrooxy)acetoxy)methyl 6,8-dichloro-2-(trifluoromethyl)-2H-chromene-3-carboxylate |
| C-12 | NA-01 | 89 | (S)-(2-(nitrooxy)acetoxy)methyl 6,8-dichloro-2-(trifluoromethyl)-2H-chromene-3-carboxylate |
| C-14 | NA-01 | 90 | (S)-(2-(nitrooxy)acetoxy)ethyl 6,8-dichloro-2-(trifluoromethyl)-2H-chromene-3-carboxylate |
| C-15 | NA-01 | 91 | (S)-(2-(nitrooxy)acetoxy)methyl 6-chloro-8-methyl-2-(trifluoromethyl)-2H-chromene-3-carboxylate |
| C-17 | NA-01 | 92 | (S)-(2-(nitrooxy)acetoxy)ethyl 6-chloro-8-methyl-2-(trifluoromethyl)-2H-chromene-3-carboxylate |
| C-18 | NA-01 | 93 | (S)-(2-(nitrooxy)acetoxy)methyl 6-bromo-8-methyl-2-(trifluoromethyl)-2H-chromene-3-carboxylate |
| C-20 | NA-01 | 94 | (S)-(2-(nitrooxy)acetoxy)ethyl 6-bromo-8-methyl-2-(trifluoromethyl)-2H-chromene-3-carboxylate |
| C-21 | NA-01 | 95 | (S)-(2-(nitrooxy)acetoxy)methyl 6,8-dimethyl-2-(trifluoromethyl)-2H-chromene-3-carboxylate |
| C-23 | NA-01 | 96 | (2S)-1-(2-(nitrooxy)acetoxy)ethyl 6,8-dimethyl-2-(trifluoromethyl)-2H-chromene-3-carboxylate |
| C-24 | NA-01 | 97 | (S)-(2-(nitrooxy)acetoxy)methyl 8-methyl-6-(trifluoromethoxy)-2-(trifluoromethyl)-2H-chromene-3-carboxylate |
| C-26 | NA-01 | 98 | (S)-(2-(nitrooxy)acetoxy)ethyl 8-methyl-6-(trifluoromethoxy)-2-(trifluoromethyl)-2H-chromene-3-carboxylate |
| C-27 | NA-01 | 99 | (S)-(2-(nitrooxy)acetoxy)methyl 8-ethyl-6-(trifluoromethoxy)-2-(trifluoromethyl)-2H-chromene-3-carboxylate |
| C-29 | NA-01 | 100 | (S)-(2-(nitrooxy)acetoxy)ethyl 8-ethyl-6-(trifluoromethoxy)-2-(trifluoromethyl)-2H-chromene-3-carboxylate |
| C-30 | NA-01 | 101 | (S)-(2-(nitrooxy)acetoxy)methyl 6-chloro-5,7-dimethyl-2-(trifluoromethyl)-2H-chromene-3-carboxylate |
| C-32 | NA-01 | 102 | (S)-(2-(nitrooxy)acetoxy)ethyl 6-chloro-5,7-dimethyl-2-(trifluoromethyl)-2H-chromene-3-carboxylate |
| C-33 | NA-01 | 103 | (S)-(2-(nitrooxy)acetoxy)methyl 6-pentafluorosulfanyl-2-(trifluoromethyl)-2H-chromene-3-carboxylate |
| C-35 | NA-01 | 104 | (S)-(2-(nitrooxy)acetoxy)ethyl 6-pentafluorosulfanyl-2-(trifluoromethyl)-2H-chromene-3-carboxylate |
| C-36 | NA-01 | 105 | (S)-(2-(nitrooxy)acetoxy)methyl 6-pentafluorosulfanyl-8-methyl-2-(trifluoromethyl)-2H-chromene-3-carboxylate |
| C-38 | NA-01 | 106 | (S)-(2-(nitrooxy)acetoxy)ethyl 6-pentafluorosulfanyl-8-methyl-2-(trifluoromethyl)-2H-chromene-3-carboxylate |
| C-39 | NA-01 | 107 | (S)-(2-(nitrooxy)acetoxy)methyl 6-pentafluorosulfanyl-8-ethyl-2-(trifluoromethyl)-2H-chromene-3-carboxylate |
| C-41 | NA-01 | 108 | (S)-(2-(nitrooxy)acetoxy)ethyl 6-pentafluorosulfanyl-8-ethyl-2-(trifluoromethyl)-2H-chromene-3-carboxylate |
| C-42 | NA-01 | 109 | (S)-(2-(nitrooxy)acetoxy)methyl 7-(tert-butyl)-6-chloro-2-(trifluoromethyl)-2H-chromene-3-carboxylate |
| C-44 | NA-01 | 110 | (S)-(2-(nitrooxy)acetoxy)ethyl 7-(tert-butyl)-6-chloro-2-(trifluoromethyl)-2H-chromene-3-carboxylate |
| C-12 | NA-04 | 111 | (S)-((3-(nitrooxy)propanoyl)oxy)methyl 6,8-dichloro-2-(trifluoromethyl)-2H-chromene-3-carboxylate |
| C-14 | NA-04 | 112 | (S)-((3-(nitrooxy)propanoyl)oxy)ethyl 6,8-dichloro-2-(trifluoromethyl)-2H-chromene-3-carboxylate |
| C-15 | NA-04 | 113 | (S)-((3-(nitrooxy)propanoyl)oxy)methyl 6-chloro-8-methyl-2-(trifluoromethyl)-2H-chromene-3-carboxylate |
| C-17 | NA-04 | 114 | (S)-((3-(nitrooxy)propanoyl)oxy)ethyl 6-chloro-8-methyl-2-(trifluoromethyl)-2H-chromene-3-carboxylate |
| C-18 | NA-04 | 115 | (S)-((3-(nitrooxy)propanoyl)oxy)methyl 6-bromo-8-methyl-2-(trifluoromethyl)-2H-chromene-3-carboxylate |

TABLE 13-continued

Examples of chromene methylene diester nitrate esters.

| Chromene | Nitrate Acid | Ex. | Name |
|---|---|---|---|
| C-20 | NA-04 | 116 | (S)-((3-(nitrooxy)propanoyl)oxy)ethyl 6-bromo-8-methyl-2-(trifluoromethyl)-2H-chromene-3-carboxylate |
| C-21 | NA-04 | 117 | (S)-((3-(nitrooxy)propanoyl)oxy)methyl 6,8-dimethyl-2-(trifluoromethyl)-2H-chromene-3-carboxylate |
| C-23 | NA-04 | 118 | (2S)-1-((3-(nitrooxy)propanoyl)oxy)ethyl 6,8-dimethyl-2-(trifluoromethyl)-2H-chromene-3-carboxylate |
| C-24 | NA-04 | 119 | (S)-((3-(nitrooxy)propanoyl)oxy)methyl 8-methyl-6-(trifluoromethoxy)-2-(trifluoromethyl)-2H-chromene-3-carboxylate |
| C-26 | NA-04 | 120 | (S)-((3-(nitrooxy)propanoyl)oxy)ethyl 8-methyl-6-(trifluoromethoxy)-2-(trifluoromethyl)-2H-chromene-3-carboxylate |
| C-27 | NA-04 | 121 | (S)-((3-(nitrooxy)propanoyl)oxy)methyl 8-ethyl-6-(trifluoromethoxy)-2-(trifluoromethyl)-2H-chromene-3-carboxylate |
| C-29 | NA-04 | 122 | (S)-((3-(nitrooxy)propanoyl)oxy)ethyl 8-ethyl-6-(trifluoromethoxy)-2-(trifluoromethyl)-2H-chromene-3-carboxylate |
| C-30 | NA-04 | 123 | (S)-((3-(nitrooxy)propanoyl)oxy)methyl 6-chloro-5,7-dimethyl-2-(trifluoromethyl)-2H-chromene-3-carboxylate |
| C-32 | NA-04 | 124 | (S)-((3-(nitrooxy)propanoyl)oxy)ethyl 6-chloro-5,7-dimethyl-2-(trifluoromethyl)-2H-chromene-3-carboxylate |
| C-33 | NA-04 | 125 | (S)-((3-(nitrooxy)propanoyl)oxy)methyl 6-pentafluorosulfanyl-2-(trifluoromethyl)-2H-chromene-3-carboxylate |
| C-35 | NA-04 | 126 | (S)-((3-(nitrooxy)propanoyl)oxy)ethyl 6-pentafluorosulfanyl-2-(trifluoromethyl)-2H-chromene-3-carboxylate |
| C-36 | NA-04 | 127 | (S)-((3-(nitrooxy)propanoyl)oxy)methyl 6-pentafluorosulfanyl-8-methyl-2-(trifluoromethyl)-2H-chromene-3-carboxylate |
| C-38 | NA-04 | 128 | (S)-((3-(nitrooxy)propanoyl)oxy)ethyl 6-pentafluorosulfanyl-8-methyl-2-(trifluoromethyl)-2H-chromene-3-carboxylate |
| C-39 | NA-04 | 129 | (S)-((3-(nitrooxy)propanoyl)oxy)methyl 6-pentafluorosulfanyl-8-ethyl-2-(trifluoromethyl)-2H-chromene-3-carboxylate |
| C-41 | NA-04 | 130 | (S)-((3-(nitrooxy)propanoyl)oxy)ethyl 6-pentafluorosulfanyl-8-ethyl-2-(trifluoromethyl)-2H-chromene-3-carboxylate |
| C-42 | NA-04 | 131 | (S)-((3-(nitrooxy)propanoyl)oxy)methyl 7-(tert-butyl)-6-chloro-2-(trifluoromethyl)-2H-chromene-3-carboxylate |
| C-44 | NA-04 | 132 | (S)-((3-(nitrooxy)propanoyl)oxy)ethyl 7-(tert-butyl)-6-chloro-2-(trifluoromethyl)-2H-chromene-3-carboxylate |
| C-12 | NA-07 | 133 | (S)-((4-(nitrooxy)butanoyl)oxy)methyl 6,8-dichloro-2-(trifluoromethyl)-2H-chromene-3-carboxylate |
| C-14 | NA-07 | 134 | (S)-((4-(nitrooxy)butanoyl)oxy)ethyl 6,8-dichloro-2-(trifluoromethyl)-2H-chromene-3-carboxylate |
| C-15 | NA-07 | 135 | (S)-((4-(nitrooxy)butanoyl)oxy)methyl 6-chloro-8-methyl-2-(trifluoromethyl)-2H-chromene-3-carboxylate |
| C-17 | NA-07 | 136 | (S)-((4-(nitrooxy)butanoyl)oxy)ethyl 6-chloro-8-methyl-2-(trifluoromethyl)-2H-chromene-3-carboxylate |
| C-18 | NA-07 | 137 | (S)-((4-(nitrooxy)butanoyl)oxy)methyl 6-bromo-8-methyl-2-(trifluoromethyl)-2H-chromene-3-carboxylate |
| C-20 | NA-07 | 138 | (S)-((4-(nitrooxy)butanoyl)oxy)ethyl 6-bromo-8-methyl-2-(trifluoromethyl)-2H-chromene-3-carboxylate |
| C-21 | NA-07 | 139 | (S)-((4-(nitrooxy)butanoyl)oxy)methyl 6,8-dimethyl-2-(trifluoromethyl)-2H-chromene-3-carboxylate |
| C-23 | NA-07 | 140 | (2S)-1-((4-(nitrooxy)butanoyl)oxy)ethyl 6,8-dimethyl-2-(trifluoromethyl)-2H-chromene-3-carboxylate |
| C-24 | NA-07 | 141 | (S)-((4-(nitrooxy)butanoyl)oxy)methyl 8-methyl-6-(trifluoromethoxy)-2-(trifluoromethyl)-2H-chromene-3-carboxylate |
| C-26 | NA-07 | 142 | (S)-((4-(nitrooxy)butanoyl)oxy)ethyl 8-methyl-6-(trifluoromethoxy)-2-(trifluoromethyl)-2H-chromene-3-carboxylate |
| C-27 | NA-07 | 143 | (S)-((4-(nitrooxy)butanoyl)oxy)methyl 8-ethyl-6-(trifluoromethoxy)-2-(trifluoromethyl)-2H-chromene-3-carboxylate |
| C-29 | NA-07 | 144 | (S)-((4-(nitrooxy)butanoyl)oxy)ethyl 8-ethyl-6-(trifluoromethoxy)-2-(trifluoromethyl)-2H-chromene-3-carboxylate |
| C-30 | NA-07 | 145 | (S)-((4-(nitrooxy)butanoyl)oxy)methyl 6-chloro-5,7-dimethyl-2-(trifluoromethyl)-2H-chromene-3-carboxylate |
| C-32 | NA-07 | 146 | (S)-((4-(nitrooxy)butanoyl)oxy)ethyl 6-chloro-5,7-dimethyl-2-(trifluoromethyl)-2H-chromene-3-carboxylate |
| C-33 | NA-07 | 147 | (S)-((4-(nitrooxy)butanoyl)oxy)methyl 6-pentafluorosulfanyl-2-(trifluoromethyl)-2H-chromene-3-carboxylate |
| C-35 | NA-07 | 148 | (S)-((4-(nitrooxy)butanoyl)oxy)ethyl 6-pentafluorosulfanyl-2-(trifluoromethyl)-2H-chromene-3-carboxylate |

TABLE 13-continued

Examples of chromene methylene diester nitrate esters.

| Chromene | Nitrate Acid | Ex. | Name |
|---|---|---|---|
| C-36 | NA-07 | 149 | (S)-((4-(nitrooxy)butanoyl)oxy)methyl 6-pentafluorosulfanyl-8-methyl-2-(trifluoromethyl)-2H-chromene-3-carboxylate |
| C-38 | NA-07 | 150 | (S)-((4-(nitrooxy)butanoyl)oxy)ethyl 6-pentafluorosulfanyl-8-methyl-2-(trifluoromethyl)-2H-chromene-3-carboxylate |
| C-39 | NA-07 | 151 | (S)-((4-(nitrooxy)butanoyl)oxy)methyl 6-pentafluorosulfanyl-8-ethyl-2-(trifluoromethyl)-2H-chromene-3-carboxylate |
| C-41 | NA-07 | 152 | (S)-((4-(nitrooxy)butanoyl)oxy)ethyl 6-pentafluorosulfanyl-8-ethyl-2-(trifluoromethyl)-2H-chromene-3-carboxylate |
| C-42 | NA-07 | 153 | (S)-((4-(nitrooxy)butanoyl)oxy)methyl 7-(tert-butyl)-6-chloro-2-(trifluoromethyl)-2H-chromene-3-carboxylate |
| C-44 | NA-07 | 154 | (S)-((4-(nitrooxy)butanoyl)oxy)ethyl 7-(tert-butyl)-6-chloro-2-(trifluoromethyl)-2H-chromene-3-carboxylate |
| C-42 | NA-02 | 155 | (2S)-((2-(nitrooxy)propanoyl)oxy)methyl 7-(tert-butyl)-6-chloro-2-(trifluoromethyl)-2H-chromene-3-carboxylate |
| C-42 | NA-03 | 156 | (S)-((2-methyl-2-(nitrooxy)propanoyl)oxy)methyl 7-(tert-butyl)-6-chloro-2-(trifluoromethyl)-2H-chromene-3-carboxylate |
| C-42 | NA-05 | 157 | (2S)-((2,2-dimethyl-3-(nitrooxy)propanoyl)oxy)methyl 7-(tert-butyl)-6-chloro-2-(trifluoromethyl)-2H-chromene-3-carboxylate |
| C-42 | NA-06 | 158 | (2S)-((3-(nitrooxy)butanoyl)oxy)methyl 7-(tert-butyl)-6-chloro-2-(trifluoromethyl)-2H-chromene-3-carboxylate |
| C-42 | NA-08 | 159 | (S)-(2-(2-(nitrooxy)ethoxy)acetoxy)methyl 7-(tert-butyl)-6-chloro-2-(trifluoromethyl)-2H-chromene-3-carboxylate |
| C-42 | NA-09 | 160 | (S)-(2-((2-(nitrooxy)ethyl)thio)acetoxy)methyl 7-(tert-butyl)-6-chloro-2-(trifluoromethyl)-2H-chromene-3-carboxylate |
| C-42 | NA-10 | 161 | (S)-(2-(N-(2-(nitrooxy)ethyl)acetamido)acetoxy)methyl 7-(tert-butyl)-6-chloro-2-(trifluoromethyl)-2H-chromene-3-carboxylate |
| C-42 | NA-11 | 162 | (S)-(2-(methyl(2-(nitrooxy)ethyl)amino)acetoxy)methyl 7-(tert-butyl)-6-chloro-2-(trifluoromethyl)-2H-chromene-3-carboxylate |

Nitrooxy Alcohols

Methods to make nitrooxy alcohol are known in the literature and representative synthesis procedures are cited in Table 14.

TABLE 14

Nitrooxy alcohols.

| Nitrooxy Alcohols | Structure | Name | Literature Preparation |
|---|---|---|---|
| NAA-01 | HO-CH$_2$CH$_2$-O-NO$_2$ | 2-hydroxyethyl nitrate<br>CAS Registry Number: 16051-48-2 | Kawashima, Y.; et al. Synthesis and pharmacological evaluation of (nitrooxy)alkyl apovincaminate. *J. Med. Chem.* 1993, 36, 815-19. |
| NAA-02 | HO-CH$_2$-CH(CH$_3$)-O-NO$_2$ | 1-hydroxypropan-2-yl nitrate<br>CAS Registry Number: 20266-74-4 | Kobayashi, T.; et al. Novel 2-amino-1,4-dihydropyridine calcium antagonists. I. Synthesis and antihypertensive effects of 2-amino-1,4-dihydropyridine derivatives having nitroxyalkoxycarbonyl groups at 3- and/or 5-position. *Chem. Pharm. Bull.* 1995, 43, 788-796. |
| NAA-03 | CH$_3$-CH(OH)-CH$_2$-O-NO$_2$ | 2-hydroxypropyl nitrate<br>CAS Registry Number: 20266-65-3 | Das, B.; et al. Efficient regio- and stereoselective conversions of oxiranes and aziridines into β-(nitrooxy)-substituted alcohols and amines by using bismuth nitrate. *Helv. Chim. Acta* 2007, 90, 110-113. |
| NAA-04 | HO-CH$_2$CH$_2$CH$_2$-O-NO$_2$ | 3-hydroxypropyl nitrate<br>CAS Registry Number: 100502-66-7 | Rolando, B.; et al. Synthesis physicochemical profile and PAMPA study of new NO-donor edaravone co-drugs. *Bioorg. Med. Chem.* 2012, 20, 841-850. |

TABLE 14-continued

Nitrooxy alcohols.

| Nitrooxy Alcohols | Structure | Name | Literature Preparation |
|---|---|---|---|
| NAA-05 | HO–C(CH₃)₂–CH₂–O–NO₂ | 3-hydroxy-2,2-dimethylpropyl nitrate CAS Registry Number: 849138-74-5 | Ziakas, G. N.; et al. Nitric oxide releasing derivatives of tolfenamic acid with anti-inflammatory activity and safe gastrointestinal profile. *Bioorg. Med. Chem.* 2005, 13, 6485-6492. |
| NAA-06 | CH₃CH(OH)CH₂CH₂–O–NO₂ | 3-hydroxybutyl nitrate CAS Registry Number: 141299-18-5 | Castedo, L.; et al. New one-pot synthesis of alkyl nitrates from alcohols. *Syn. Comm.* 1992, 22, 677-681. |
| NAA-07 | HOCH₂CH₂CH(CH₃)–O–NO₂ | 4-hydroxybutan-2-yl nitrate CAS Registry Number: 256430-15-6 | Treves, K.; et al. Rate Coefficients for the Reactions of Cl Atoms with a Series of C3-C6 Hydroxyalkyl Nitrates at 296 ± 2K. *J. Phys. Chem.* A 2002, 106, 5902-5907. |
| NAA-08 | HO–(CH₂)₄–O–NO₂ | 4-hydroxybutyl nitrate CAS Registry Number: 22911-39-3 | Almirante, N.; et al. Nitric oxide releasing compounds and their preparation and use for the treatment of neuropathic pain. PCT Int. Appl. (2011), WO 2011101245. |
| NAA-09 | HO–CH₂CH₂–O–CH₂CH₂–O–NO₂ | 2-(2-hydroxyethoxy)ethyl nitrate CAS Registry Number: 20633-16-3 | Almirante, N.; et al. Nitric oxide releasing compounds and their preparation and use for the treatment of neuropathic pain. PCT Int. Appl. (2011), WO 2011101245. |
| NAA-10 | HO–CH₂CH₂–S–CH₂CH₂–O–NO₂ | 2-((2-hydroxyethyl)thio)ethyl nitrate | Supuran, C.; et al. Preparation of nitrate esters of (hetero)arylsulfonamide carbonic anhydrase inhibitors as agents for treating eye disorders and cancer. PCT Int. Appl. (2008), WO 2008071421 |
| NAA-11 | HO–CH₂CH₂–N(CH₃)–CH₂CH₂–O–NO₂ | 2-((2-hydroxyethyl)(methyl)amino)ethyl nitrate CAS Registry Number: 941702-79-0 | Gilmer, J. F.; et al. Evaluation of nitrate-substituted pseudocholine esters of aspirin as potential nitro-aspirins. *Bioorg. Med. Chem. Lett.* 2007, 17, 3217-3220. |
| NAA-12 | O₂NO–CH₂–CH(OH)–CH₂–ONO₂ | 1,3-dinitroglycerol or 2-hydroxypropane-1,3-diyl dinitrate CAS Registry Number: 623-87-0 | Lange, K.; Koenig, A.; Roegler, C.; Seeling, A.; Lehmann, J. *Bioorg. Med. Chem. Lett.* 2009, 19, 3141-3144. |

2-((2-Hydroxyethyl)thio)ethyl nitrate (NAA-10)

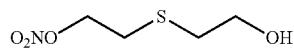

Commercially available 2-((2-chloroethyl)thio)ethyl acetate is converted to the corresponding iodide by treatment with potassium iodide in acetone. 2-((2-Iodoethyl)thio)ethyl acetate is immediately treated with silver nitrate in acetonitrile in the dark to give 2-((2-(nitrooxy)ethyl)thio)ethyl acetate. 2-((2-(Nitrooxy)ethyl)thio)ethyl acetate is saponified with aqueous sodium hydroxide to provide 2-((2-hydroxyethyl)thio)ethyl nitrate.

Nitrooxy Chloroalkyl Carbonates

Chloromethyl (2-(nitrooxy)ethyl) carbonate (NC-01)

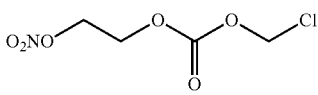

Nitrooxy alcohol NAA-01 (0.50 mmol) and triethylamine (0.60 mmol) are dissolved in dichloromethane (1.0 mL). Chloromethyl chloroformate (0.60 mmol) is added dropwise, and the mixture is stirred at room temperature for 2 h.

The reaction is diluted with ethyl acetate, and the organic layer is washed with 0.1 N hydrochloric acid solution and brine, dried over magnesium sulfate, and evaporated to afford NC-01. The residue is used without further purification.

Using a similar procedure to make NC-01 additional chloromethyl carbonates (Table 15) are made by replacing NAA-01 with other nitrooxy alcohols from Table 14, and a chloroformates such as chloromethyl chloroformate and 1-chloroethyl chloroformate.

TABLE 15

Nitrooxy chloroalkyl carbonates.

| Alcohol | Chloroformate | Carbonates | Name |
| --- | --- | --- | --- |
| NAA-01 | chloromethyl chloroformate | NC-01 | chloromethyl (2-(nitrooxy)ethyl) carbonate |
| NAA-02 | chloromethyl chloroformate | NC-02 | chloromethyl (2-(nitrooxy)propyl) carbonate |
| NAA-03 | chloromethyl chloroformate | NC-03 | chloromethyl (1-(nitrooxy)propan-2-yl) carbonate |
| NAA-04 | chloromethyl chloroformate | NC-04 | chloromethyl (3-(nitrooxy)propyl) carbonate |
| NAA-05 | chloromethyl chloroformate | NC-05 | chloromethyl (2,2-dimethyl-3-(nitrooxy)propyl) carbonate |
| NAA-06 | chloromethyl chloroformate | NC-06 | chloromethyl (4-(nitrooxy)butan-2-yl) carbonate |
| NAA-07 | chloromethyl chloroformate | NC-07 | chloromethyl (3-(nitrooxy)butyl) carbonate |
| NAA-08 | chloromethyl chloroformate | NC-08 | chloromethyl (4-(nitrooxy)butyl) carbonate |
| NAA-09 | chloromethyl chloroformate | NC-09 | chloromethyl (2-(2-(nitrooxy)ethoxy)ethyl) carbonate |
| NAA-10 | chloromethyl chloroformate | NC-10 | chloromethyl (2-((2-(nitrooxy)ethyl)thio)ethyl) carbonate |
| NAA-11 | chloromethyl chloroformate | NC-11 | chloromethyl (2-(methyl(2-(nitrooxy)ethyl)amino)ethyl) carbonate |
| NAA-01 | 1-chloroethyl chloroformate | NC-12 | 1-chloroethyl (2-(nitrooxy)ethyl) carbonate |
| NAA-02 | 1-chloroethyl chloroformate | NC-13 | 1-chloroethyl (2-(nitrooxy)propyl) carbonate |
| NAA-03 | 1-chloroethyl chloroformate | NC-14 | 1-chloroethyl (1-(nitrooxy)propan-2-yl) carbonate |
| NAA-04 | 1-chloroethyl chloroformate | NC-15 | 1-chloroethyl (3-(nitrooxy)propyl) carbonate |
| NAA-05 | 1-chloroethyl chloroformate | NC-16 | 1-chloroethyl (2,2-dimethyl-3-(nitrooxy)propyl) carbonate |
| NAA-06 | 1-chloroethyl chloroformate | NC-17 | 1-chloroethyl (4-(nitrooxy)butan-2-yl) carbonate |
| NAA-07 | 1-chloroethyl chloroformate | NC-18 | 1-chloroethyl (3-(nitrooxy)butyl) carbonate |
| NAA-08 | 1-chloroethyl chloroformate | NC-19 | 1-chloroethyl (4-(nitrooxy)butyl) carbonate |
| NAA-09 | 1-chloroethyl chloroformate | NC-20 | 1-chloroethyl (2-(2-(nitrooxy)ethoxy)ethyl) carbonate |
| NAA-10 | 1-chloroethyl chloroformate | NC-21 | 1-chloroethyl (2-((2-(nitrooxy)ethyl)thio)ethyl) carbonate |
| NAA-11 | 1-chloroethyl chloroformate | NC-22 | 1-chloroethyl (2-(methyl(2-(nitrooxy)ethyl)amino)ethyl) carbonate |
| NAA-12 | chloromethyl chloroformate | NC-23 | 1,3-bis(nitrooxy)propan-2-yl (chloromethyl) carbonate |
| NAA-12 | 1-chloroethyl chloroformate | NC-24 | 1,3-bis(nitrooxy)propan-2-yl (1-chloroethyl) carbonate |

Chromene Alkyl Carbonate Nitrate Esters

Example 163: (S)-(((2-(nitrooxy)ethoxy)carbonyl)oxy)methyl 6,8-dichloro-2-(trifluoromethyl)-2H-chromene-3-carboxylate

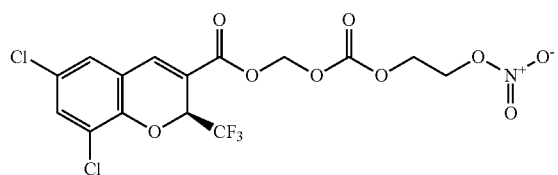 [SMILES: O=C(OCCO[N+](=O)[O-])OCOC(=O)C1=Cc2cc(Cl)cc(Cl)c2O[C@@H]1C(F)(F)F]

Chloromethyl carbonate NC-01 (1.0 mmol), chromene acid CA-01 (1.0 mmol) and triethylamine (1.25 mmol) are dissolved in 3 mL dimethyl sulfoxide, and stirred at room temperature for 48 h. The reaction is diluted with ethyl acetate. The organic layer is washed with saturated sodium bicarbonate solution and brine, dried over magnesium sulfate, and evaporated. Purification by chromatography using an ethyl acetate/hexane gradient affords Example 163.

Using a similar procedure to make Example 163 additional analogues (Table 16) are made by replacing NC-01 with other chloroalkyl carbonates from Table 15, and by replacing CA-01 with other suitable chromene acids listed in Table 1 and known in the literature.

TABLE 16

Examples of chromene methylene diester nitrate esters.

| Chromene Acid | Nitrooxy Chloroformates | Ex. | Name |
|---|---|---|---|
| CA-01 | NC-01 | 163 | (S)-(((2-(nitrooxy)ethoxy)carbonyl)oxy)methyl 6,8-dichloro-2-(trifluoromethyl)-2H-chromene-3-carboxylate |
| CA-01 | NC-02 | 164 | (2S)-(((2-(nitrooxy)propoxy)carbonyl)oxy)methyl 6,8-dichloro-2-(trifluoromethyl)-2H-chromene-3-carboxylate |
| CA-01 | NC-03 | 165 | (2S)-((((1-(nitrooxy)propan-2-yl)oxy)carbonyl)oxy)methyl 6,8-dichloro-2-(trifluoromethyl)-2H-chromene-3-carboxylate |
| CA-01 | NC-04 | 166 | (S)-(((3-(nitrooxy)propoxy)carbonyl)oxy)methyl 6,8-dichloro-2-(trifluoromethyl)-2H-chromene-3-carboxylate |
| CA-01 | NC-05 | 167 | (S)-(((2,2-dimethyl-3-(nitrooxy)propoxy)carbonyl)oxy)methyl 6,8-dichloro-2-(trifluoromethyl)-2H-chromene-3-carboxylate |
| CA-01 | NC-06 | 168 | (2S)-((((4-(nitrooxy)butan-2-yl)oxy)carbonyl)oxy)methyl 6,8-dichloro-2-(trifluoromethyl)-2H-chromene-3-carboxylate |
| CA-01 | NC-07 | 169 | (2S)-(((3-(nitrooxy)butoxy)carbonyl)oxy)methyl 6,8-dichloro-2-(trifluoromethyl)-2H-chromene-3-carboxylate |
| CA-01 | NC-08 | 170 | (S)-(((4-(nitrooxy)butoxy)carbonyl)oxy)methyl 6,8-dichloro-2-(trifluoromethyl)-2H-chromene-3-carboxylate |
| CA-01 | NC-09 | 171 | (S)-(((2-(2-(nitrooxy)ethoxy)ethoxy)carbonyl)oxy)methyl 6,8-dichloro-2-(trifluoromethyl)-2H-chromene-3-carboxylate |
| CA-01 | NC-10 | 172 | (S)-(((2-((2-(nitrooxy)ethyl)thio)ethoxy)carbonyl)oxy)methyl 6,8-dichloro-2-(trifluoromethyl)-2H-chromene-3-carboxylate |
| CA-01 | NC-11 | 173 | (S)-(((2-(methyl(2-(nitrooxy)ethyl)amino)ethoxy)carbonyl)oxy)methyl 6,8-dichloro-2-(trifluoromethyl)-2H-chromene-3-carboxylate |
| CA-01 | NC-12 | 174 | (2S)-1-(((2-(nitrooxy)ethoxy)carbonyl)oxy)ethyl 6,8-dichloro-2-(trifluoromethyl)-2H-chromene-3-carboxylate |
| CA-01 | NC-13 | 175 | (2S)-1-(((2-(nitrooxy)propoxy)carbonyl)oxy)ethyl 6,8-dichloro-2-(trifluoromethyl)-2H-chromene-3-carboxylate |
| CA-01 | NC-14 | 176 | (2S)-1-((((1-(nitrooxy)propan-2-yl)oxy)carbonyl)oxy)ethyl 6,8-dichloro-2-(trifluoromethyl)-2H-chromene-3-carboxylate |
| CA-01 | NC-15 | 177 | (2S)-1-(((3-(nitrooxy)propoxy)carbonyl)oxy)ethyl 6,8-dichloro-2-(trifluoromethyl)-2H-chromene-3-carboxylate |
| CA-01 | NC-16 | 178 | (2S)-1-(((2,2-dimethyl-3-(nitrooxy)propoxy)carbonyl)oxy)ethyl 6,8-dichloro-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-01 | NC-17 | 179 | (2S)-1-((((4-(nitrooxy)butan-2-yl)oxy)carbonyl)oxy)ethyl 6,8-dichloro-2-(trifluoromethyl)-2H-chromene-3-carboxylate |
| CA-01 | NC-18 | 180 | (2S)-1-(((3-(nitrooxy)butoxy)carbonyl)oxy)ethyl 6,8-dichloro-2-(trifluoromethyl)-2H-chromene-3-carboxylate |
| CA-01 | NC-19 | 181 | (2S)-1-(((4-(nitrooxy)butoxy)carbonyl)oxy)ethyl 6,8-dichloro-2-(trifluoromethyl)-2H-chromene-3-carboxylate |
| CA-01 | NC-20 | 182 | (2S)-1-(((2-(2-(nitrooxy)ethoxy)ethoxy)carbonyl)oxy)ethyl 6,8-dichloro-2-(trifluoromethyl)-2H-chromene-3-carboxylate |
| CA-01 | NC-21 | 183 | (2S)-1-(((2-((2-(nitrooxy)ethyl)thio)ethoxy)carbonyl)oxy)ethyl 6,8-dichloro-2-(trifluoromethyl)-2H-chromene-3-carboxylate |
| CA-01 | NC-22 | 184 | (2S)-1-(((2-(methyl((nitrooxy)methyl)amino)ethoxy)carbonyl)oxy)ethyl 6,8-dichloro-2-(trifluoromethyl)-2H-chromene-3-carboxylate |
| CA-02 | NC-01 | 185 | (S)-(((2-(nitrooxy)ethoxy)carbonyl)oxy)methyl 6-chloro-8-methyl-2-(trifluoromethyl)-2H-chromene-3-carboxylate |
| CA-02 | NC-02 | 186 | (2S)-(((2-(nitrooxy)propoxy)carbonyl)oxy)methyl 6-chloro-8-methyl-2-(trifluoromethyl)-2H-chromene-3-carboxylate |
| CA-02 | NC-03 | 187 | (2S)-((((1-(nitrooxy)propan-2-yl)oxy)carbonyl)oxy)methyl 6-chloro-8-methyl-2-(trifluoromethyl)-2H-chromene-3-carboxylate |
| CA-02 | NC-04 | 188 | (S)-(((3-(nitrooxy)propoxy)carbonyl)oxy)methyl 6-chloro-8-methyl-2-(trifluoromethyl)-2H-chromene-3-carboxylate |
| CA-02 | NC-05 | 189 | (S)-(((2,2-dimethyl-3-(nitrooxy)propoxy)carbonyl)oxy)methyl 6-chloro-8-methyl-2-(trifluoromethyl)-2H-chromene-3-carboxylate |
| CA-02 | NC-06 | 190 | (2S)-((((4-(nitrooxy)butan-2-yl)oxy)carbonyl)oxy)methyl 6-chloro-8-methyl-2-(trifluoromethyl)-2H-chromene-3-carboxylate |
| CA-02 | NC-07 | 191 | (2S)-(((3-(nitrooxy)butoxy)carbonyl)oxy)methyl 6-chloro-8-methyl-2-(trifluoromethyl)-2H-chromene-3-carboxylate |
| CA-02 | NC-08 | 192 | (S)-(((4-(nitrooxy)butoxy)carbonyl)oxy)methyl 6-chloro-8-methyl-2-(trifluoromethyl)-2H-chromene-3-carboxylate |
| CA-02 | NC-09 | 193 | (S)-(((2-(2-(nitrooxy)ethoxy)ethoxy)carbonyl)oxy)methyl 6-chloro-8-methyl-2-(trifluoromethyl)-2H-chromene-3-carboxylate |
| CA-02 | NC-10 | 194 | (S)-(((2-((2-(nitrooxy)ethyl)thio)ethoxy)carbonyl)oxy)methyl 6-chloro-8-methyl-2-(trifluoromethyl)-2H-chromene-3-carboxylate |
| CA-02 | NC-11 | 195 | (S)-(((2-(methyl(2-(nitrooxy)ethyl)amino)ethoxy)carbonyl)oxy)methyl 6-chloro-8-methyl-2-(trifluoromethyl)-2H-chromene-3-carboxylate |
| CA-02 | NC-12 | 196 | (2S)-1-(((2-(nitrooxy)ethoxy)carbonyl)oxy)ethyl 6-chloro-8-methyl-2-(trifluoromethyl)-2H-chromene-3-carboxylate |
| CA-02 | NC-13 | 197 | (2S)-1-(((2-(nitrooxy)propoxy)carbonyl)oxy)ethyl 6-chloro-8-methyl-2-(trifluoromethyl)-2H-chromene-3-carboxylate |
| CA-02 | NC-14 | 198 | (2S)-1-((((1-(nitrooxy)propan-2-yl)oxy)carbonyl)oxy)ethyl 6-chloro-8-methyl-2-(trifluoromethyl)-2H-chromene-3-carboxylate |
| CA-02 | NC-15 | 199 | (2S)-1-(((3-(nitrooxy)propoxy)carbonyl)oxy)ethyl 6-chloro-8-methyl-2-(trifluoromethyl)-2H-chromene-3-carboxylate |
| CA-02 | NC-16 | 200 | (2S)-1-(((2,2-dimethyl-3-(nitrooxy)propoxy)carbonyl)oxy)ethyl 6-chloro-8-methyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-02 | NC-17 | 201 | (2S)-1-((((4-(nitrooxy)butan-2-yl)oxy)carbonyl)oxy)ethyl 6-chloro-8-methyl-2-(trifluoromethyl)-2H-chromene-3-carboxylate |
| CA-02 | NC-18 | 202 | (2S)-1-(((3-(nitrooxy)butoxy)carbonyl)oxy)ethyl 6-chloro-8-methyl-2-(trifluoromethyl)-2H-chromene-3-carboxylate |
| CA-02 | NC-19 | 203 | (2S)-1-(((4-(nitrooxy)butoxy)carbonyl)oxy)ethyl 6-chloro-8-methyl-2-(trifluoromethyl)-2H-chromene-3-carboxylate |
| CA-02 | NC-20 | 204 | (2S)-1-(((2-(2-(nitrooxy)ethoxy)ethoxy)carbonyl)oxy)ethyl 6-chloro-8-methyl-2-(trifluoromethyl)-2H-chromene-3-carboxylate |
| CA-02 | NC-21 | 205 | (2S)-1-(((2-((2-(nitrooxy)ethyl)thio)ethoxy)carbonyl)oxy)ethyl 6-chloro-8-methyl-2-(trifluoromethyl)-2H-chromene-3-carboxylate |
| CA-02 | NC-22 | 206 | (2S)-1-(((2-(methyl(2-(nitrooxy)ethyl)amino)ethoxy)carbonyl)oxy)ethyl 6-chloro-8-methyl-2-(trifluoromethyl)-2H-chromene-3-carboxylate |
| CA-03 | NC-01 | 207 | (S)-(((2-(nitrooxy)ethoxy)carbonyl)oxy)methyl 6-bromo-8-methyl-2-(trifluoromethyl)-2H-chromene-3-carboxylate |
| CA-03 | NC-02 | 208 | (2S)-(((2-(nitrooxy)propoxy)carbonyl)oxy)methyl 6-bromo-8-methyl-2-(trifluoromethyl)-2H-chromene-3-carboxylate |
| CA-03 | NC-03 | 209 | (2S)-((((1-(nitrooxy)propan-2-yl)oxy)carbonyl)oxy)methyl 6-bromo-8-methyl-2-(trifluoromethyl)-2H-chromene-3-carboxylate |
| CA-03 | NC-04 | 210 | (S)-(((3-(nitrooxy)propoxy)carbonyl)oxy)methyl 6-bromo-8-methyl-2-(trifluoromethyl)-2H-chromene-3-carboxylate |
| CA-03 | NC-05 | 211 | (S)-(((2,2-dimethyl-3-(nitrooxy)propoxy)carbonyl)oxy)methyl 6-bromo-8-methyl-2-(trifluoromethyl)-2H-chromene-3-carboxylate |
| CA-03 | NC-06 | 212 | (2S)-((((4-(nitrooxy)butan-2-yl)oxy)carbonyl)oxy)methyl 6-bromo-8-methyl-2-(trifluoromethyl)-2H-chromene-3-carboxylate |
| CA-03 | NC-07 | 213 | (2S)-(((3-(nitrooxy)butoxy)carbonyl)oxy)methyl 6-bromo-8-methyl-2-(trifluoromethyl)-2H-chromene-3-carboxylate |
| CA-03 | NC-08 | 214 | (S)-(((4-(nitrooxy)butoxy)carbonyl)oxy)methyl 6-bromo-8-methyl-2-(trifluoromethyl)-2H-chromene-3-carboxylate |
| CA-03 | NC-09 | 215 | (S)-(((2-(2-(nitrooxy)ethoxy)ethoxy)carbonyl)oxy)methyl 6-bromo-8-methyl-2-(trifluoromethyl)-2H-chromene-3-carboxylate |
| CA-03 | NC-10 | 216 | (S)-(((2-((2-(nitrooxy)ethyl)thio)ethoxy)carbonyl)oxy)methyl 6-bromo-8-methyl-2-(trifluoromethyl)-2H-chromene-3-carboxylate |
| CA-03 | NC-11 | 217 | (S)-(((2-(methyl(2-(nitrooxy)ethyl)amino)ethoxy)carbonyl)oxy)methyl 6-bromo-8-methyl-2-(trifluoromethyl)-2H-chromene-3-carboxylate |
| CA-03 | NC-12 | 218 | (2S)-1-(((2-(nitrooxy)ethoxy)carbonyl)oxy)ethyl 6-bromo-8-methyl-2-(trifluoromethyl)-2H-chromene-3-carboxylate |
| CA-03 | NC-13 | 219 | (2S)-1-(((2-(nitrooxy)propoxy)carbonyl)oxy)ethyl 6-bromo-8-methyl-2-(trifluoromethyl)-2H-chromene-3-carboxylate |
| CA-03 | NC-14 | 220 | (2S)-1-((((1-(nitrooxy)propan-2-yl)oxy)carbonyl)oxy)ethyl 6-bromo-8-methyl-2-(trifluoromethyl)-2H-chromene-3-carboxylate |
| CA-03 | NC-15 | 221 | (2S)-1-(((3-(nitrooxy)propoxy)carbonyl)oxy)ethyl 6-bromo-8-methyl-2-(trifluoromethyl)-2H-chromene-3-carboxylate |
| CA-03 | NC-16 | 222 | (2S)-1-(((2,2-dimethyl-3-(nitrooxy)propoxy)carbonyl)oxy)ethyl 6-bromo-8-methyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-03 | NC-17 | 223 | (2S)-1-((((4-(nitrooxy)butan-2-yl)oxy)carbonyl)oxy)ethyl 6-bromo-8-methyl-2-(trifluoromethyl)-2H-chromene-3-carboxylate |
| CA-03 | NC-18 | 224 | (2S)-1-(((3-(nitrooxy)butoxy)carbonyl)oxy)ethyl 6-bromo-8-methyl-2-(trifluoromethyl)-2H-chromene-3-carboxylate |
| CA-03 | NC-19 | 225 | (2S)-1-(((4-(nitrooxy)butoxy)carbonyl)oxy)ethyl 6-bromo-8-methyl-2-(trifluoromethyl)-2H-chromene-3-carboxylate |
| CA-03 | NC-20 | 226 | (2S)-1-(((2-(2-(nitrooxy)ethoxy)ethoxy)carbonyl)oxy)ethyl 6-bromo-8-methyl-2-(trifluoromethyl)-2H-chromene-3-carboxylate |
| CA-03 | NC-21 | 227 | (2S)-1-(((2-((2-(nitrooxy)ethyl)thio)ethoxy)carbonyl)oxy)ethyl 6-bromo-8-methyl-2-(trifluoromethyl)-2H-chromene-3-carboxylate |
| CA-03 | NC-22 | 228 | (2S)-1-(((2-(methyl(2-(nitrooxy)ethyl)amino)ethoxy)carbonyl)oxy)ethyl 6-bromo-8-methyl-2-(trifluoromethyl)-2H-chromene-3-carboxylate |
| CA-04 | NC-01 | 229 | (S)-(((2-(nitrooxy)ethoxy)carbonyl)oxy)methyl 6,8-dimethyl-2-(trifluoromethyl)-2H-chromene-3-carboxylate |
| CA-04 | NC-02 | 230 | (2S)-(((2-(nitrooxy)propoxy)carbonyl)oxy)methyl 6,8-dimethyl-2-(trifluoromethyl)-2H-chromene-3-carboxylate |
| CA-04 | NC-03 | 231 | (2S)-((((1-(nitrooxy)propan-2-yl)oxy)carbonyl)oxy)methyl 6,8-dimethyl-2-(trifluoromethyl)-2H-chromene-3-carboxylate |
| CA-04 | NC-04 | 232 | (S)-(((3-(nitrooxy)propoxy)carbonyl)oxy)methyl 6,8-dimethyl-2-(trifluoromethyl)-2H-chromene-3-carboxylate |
| CA-04 | NC-05 | 233 | (S)-(((2,2-dimethyl-3-(nitrooxy)propoxy)carbonyl)oxy)methyl 6,8-dimethyl-2-(trifluoromethyl)-2H-chromene-3-carboxylate |
| CA-04 | NC-06 | 234 | (2S)-((((4-(nitrooxy)butan-2-yl)oxy)carbonyl)oxy)methyl 6,8-dimethyl-2-(trifluoromethyl)-2H-chromene-3-carboxylate |
| CA-04 | NC-07 | 235 | (2S)-(((3-(nitrooxy)butoxy)carbonyl)oxy)methyl 6,8-dimethyl-2-(trifluoromethyl)-2H-chromene-3-carboxylate |
| CA-04 | NC-08 | 236 | (S)-(((4-(nitrooxy)butoxy)carbonyl)oxy)methyl 6,8-dimethyl-2-(trifluoromethyl)-2H-chromene-3-carboxylate |
| CA-04 | NC-09 | 237 | (S)-(((2-(2-(nitrooxy)ethoxy)ethoxy)carbonyl)oxy)methyl 6,8-dimethyl-2-(trifluoromethyl)-2H-chromene-3-carboxylate |
| CA-04 | NC-10 | 238 | (S)-(((2-((2-(nitrooxy)ethyl)thio)ethoxy)carbonyl)oxy)methyl 6,8-dimethyl-2-(trifluoromethyl)-2H-chromene-3-carboxylate |
| CA-04 | NC-11 | 239 | (S)-(((2-(methyl(2-(nitrooxy)ethyl)amino)ethoxy)carbonyl)oxy)methyl 6,8-dimethyl-2-(trifluoromethyl)-2H-chromene-3-carboxylate |
| CA-04 | NC-12 | 240 | (2S)-1-(((2-(nitrooxy)ethoxy)carbonyl)oxy)ethyl 6,8-dimethyl-2-(trifluoromethyl)-2H-chromene-3-carboxylate |
| CA-04 | NC-13 | 241 | (2S)-1-(((2-(nitrooxy)propoxy)carbonyl)oxy)ethyl 6,8-dimethyl-2-(trifluoromethyl)-2H-chromene-3-carboxylate |
| CA-04 | NC-14 | 242 | (2S)-1-((((1-(nitrooxy)propan-2-yl)oxy)carbonyl)oxy)ethyl 6,8-dimethyl-2-(trifluoromethyl)-2H-chromene-3-carboxylate |
| CA-04 | NC-15 | 243 | (2S)-1-(((3-(nitrooxy)propoxy)carbonyl)oxy)ethyl 6,8-dimethyl-2-(trifluoromethyl)-2H-chromene-3-carboxylate |
| CA-04 | NC-16 | 244 | (2S)-1-(((2,2-dimethyl-3-(nitrooxy)propoxy)carbonyl)oxy)ethyl 6,8-dimethyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-04 | NC-17 | 245 | (2S)-1-((((4-(nitrooxy)butan-2-yl)oxy)carbonyl)oxy)ethyl 6,8-dimethyl-2-(trifluoromethyl)-2H-chromene-3-carboxylate |
| CA-04 | NC-18 | 246 | (2S)-1-(((3-(nitrooxy)butoxy)carbonyl)oxy)ethyl 6,8-dimethyl-2-(trifluoromethyl)-2H-chromene-3-carboxylate |
| CA-04 | NC-19 | 247 | (2S)-1-(((4-(nitrooxy)butoxy)carbonyl)oxy)ethyl 6,8-dimethyl-2-(trifluoromethyl)-2H-chromene-3-carboxylate |
| CA-04 | NC-20 | 248 | (2S)-1-(((2-(2-(nitrooxy)ethoxy)ethoxy)carbonyl)oxy)ethyl 6,8-dimethyl-2-(trifluoromethyl)-2H-chromene-3-carboxylate |
| CA-04 | NC-21 | 249 | (2S)-1-(((2-((2-(nitrooxy)ethyl)thio)ethoxy)carbonyl)oxy)ethyl 6,8-dimethyl-2-(trifluoromethyl)-2H-chromene-3-carboxylate |
| CA-04 | NC-22 | 250 | (2S)-1-(((2-(methyl(2-(nitrooxy)ethyl)amino)ethoxy)carbonyl)oxy)ethyl 6,8-dimethyl-2-(trifluoromethyl)-2H-chromene-3-carboxylate |
| CA-05 | NC-01 | 251 | (S)-(((2-(nitrooxy)ethoxy)carbonyl)oxy)methyl 6-trifluoromethoxy-8-methyl-2-(trifluoromethyl)-2H-chromene-3-carboxylate |
| CA-05 | NC-02 | 252 | (2S)-(((2-(nitrooxy)propoxy)carbonyl)oxy)methyl 6-trifluoromethoxy-8-methyl-2-(trifluoromethyl)-2H-chromene-3-carboxylate |
| CA-05 | NC-03 | 253 | (2S)-((((1-(nitrooxy)propan-2-yl)oxy)carbonyl)oxy)methyl 6-trifluoromethoxy-8-methyl-2-(trifluoromethyl)-2H-chromene-3-carboxylate |
| CA-05 | NC-04 | 254 | (S)-(((3-(nitrooxy)propoxy)carbonyl)oxy)methyl 6-trifluoromethoxy-8-methyl-2-(trifluoromethyl)-2H-chromene-3-carboxylate |
| CA-05 | NC-05 | 255 | (S)-(((2,2-dimethyl-3-(nitrooxy)propoxy)carbonyl)oxy)methyl 6-trifluoromethoxy-8-methyl-2-(trifluoromethyl)-2H-chromene-3-carboxylate |
| CA-05 | NC-06 | 256 | (2S)-((((4-(nitrooxy)butan-2-yl)oxy)carbonyl)oxy)methyl 6-trifluoromethoxy-8-methyl-2-(trifluoromethyl)-2H-chromene-3-carboxylate |
| CA-05 | NC-07 | 257 | (2S)-(((3-(nitrooxy)butoxy)carbonyl)oxy)methyl 6-trifluoromethoxy-8-methyl-2-(trifluoromethyl)-2H-chromene-3-carboxylate |
| CA-05 | NC-08 | 258 | (S)-(((4-(nitrooxy)butoxy)carbonyl)oxy)methyl 6-trifluoromethoxy-8-methyl-2-(trifluoromethyl)-2H-chromene-3-carboxylate |
| CA-05 | NC-09 | 259 | (S)-(((2-(2-(nitrooxy)ethoxy)ethoxy)carbonyl)oxy)methyl 8-methyl-6-(trifluoromethoxy)-2-(trifluoromethyl)-2H-chromene-3-carboxylate |
| CA-05 | NC-10 | 260 | (S)-(((2-((2-(nitrooxy)ethyl)thio)ethoxy)carbonyl)oxy)methyl 8-methyl-6-(trifluoromethoxy)-2-(trifluoromethyl)-2H-chromene-3-carboxylate |
| CA-05 | NC-11 | 261 | (S)-(((2-(methyl(2-(nitrooxy)ethyl)amino)ethoxy)carbonyl)oxy)methyl 8-methyl-6-(trifluoromethoxy)-2-(trifluoromethyl)-2H-chromene-3-carboxylate |
| CA-05 | NC-12 | 262 | (2S)-1-(((2-(nitrooxy)ethoxy)carbonyl)oxy)ethyl 6-trifluoromethoxy-8-methyl-2-(trifluoromethyl)-2H-chromene-3-carboxylate |
| CA-05 | NC-13 | 263 | (2S)-1-(((2-(nitrooxy)propoxy)carbonyl)oxy)ethyl 6-trifluoromethoxy-8-methyl-2-(trifluoromethyl)-2H-chromene-3-carboxylate |
| CA-05 | NC-14 | 264 | (2S)-1-((((1-(nitrooxy)propan-2-yl)oxy)carbonyl)oxy)ethyl 6-trifluoromethoxy-8-methyl-2-(trifluoromethyl)-2H-chromene-3-carboxylate |
| CA-05 | NC-15 | 265 | (2S)-1-(((3-(nitrooxy)propoxy)carbonyl)oxy)ethyl 6-trifluoromethoxy-8-methyl-2-(trifluoromethyl)-2H-chromene-3-carboxylate |
| CA-05 | NC-16 | 266 | (2S)-1-(((2,2-dimethyl-3-(nitrooxy)propoxy)carbonyl)oxy)ethyl 6- |

TABLE 16-continued

Examples of chromene methylene diester nitrate esters.

| Chromene Acid | Nitrooxy Chloroformates | Ex. | Name |
|---|---|---|---|
| CA-05 | NC-17 | 267 | trifluoromethoxy-8-methyl-2-(trifluoromethyl)-2H-chromene-3-carboxylate<br>(2S)-1-((((4-(nitrooxy)butan-2-yl)oxy)carbonyl)oxy)ethyl 6-trifluoromethoxy-8-methyl-2-(trifluoromethyl)-2H-chromene-3-carboxylate |
| CA-05 | NC-18 | 268 | (2S)-1-(((3-(nitrooxy)butoxy)carbonyl)oxy)ethyl 6-trifluoromethoxy-8-methyl-2-(trifluoromethyl)-2H-chromene-3-carboxylate |
| CA-05 | NC-19 | 269 | (2S)-1-(((4-(nitrooxy)butoxy)carbonyl)oxy)ethyl 6-trifluoromethoxy-8-methyl-2-(trifluoromethyl)-2H-chromene-3-carboxylate |
| CA-05 | NC-20 | 270 | (2S)-1-(((2-(2-(nitrooxy)ethoxy)ethoxy)carbonyl)oxy)ethyl 8-methyl-6-(trifluoromethoxy)-2-(trifluoromethyl)-2H-chromene-3-carboxylate |
| CA-05 | NC-21 | 271 | (2S)-1-(((2-((2-(nitrooxy)ethyl)thio)ethoxy)carbonyl)oxy)ethyl 8-methyl-6-(trifluoromethoxy)-2-(trifluoromethyl)-2H-chromene-3-carboxylate |
| CA-05 | NC-22 | 272 | (2S)-1-(((2-(methyl(2-(nitrooxy)ethyl)amino)ethoxy)carbonyl)oxy)ethyl 8-methyl-6-(trifluoromethoxy)-2-(trifluoromethyl)-2H-chromene-3-carboxylate |
| CA-06 | NC-01 | 273 | (S)-(((2-(nitrooxy)ethoxy)carbonyl)oxy)methyl 6-trifluoromethoxy-8-ethyl-2-(trifluoromethyl)-2H-chromene-3-carboxylate |
| CA-06 | NC-02 | 274 | (2S)-(((2-(nitrooxy)propoxy)carbonyl)oxy)methyl 6-trifluoromethoxy-8-ethyl-2-(trifluoromethyl)-2H-chromene-3-carboxylate |
| CA-06 | NC-03 | 275 | (2S)-((((1-(nitrooxy)propan-2-yl)oxy)carbonyl)oxy)methyl 6-trifluoromethoxy-8-ethyl-2-(trifluoromethyl)-2H-chromene-3-carboxylate |
| CA-06 | NC-04 | 276 | (S)-(((3-(nitrooxy)propoxy)carbonyl)oxy)methyl 6-trifluoromethoxy-8-ethyl-2-(trifluoromethyl)-2H-chromene-3-carboxylate |
| CA-06 | NC-05 | 277 | (S)-(((2,2-dimethyl-3-(nitrooxy)propoxy)carbonyl)oxy)methyl 6-trifluoromethoxy-8-ethyl-2-(trifluoromethyl)-2H-chromene-3-carboxylate |
| CA-06 | NC-06 | 278 | (2S)-((((4-(nitrooxy)butan-2-yl)oxy)carbonyl)oxy)methyl 6-trifluoromethoxy-8-ethyl-2-(trifluoromethyl)-2H-chromene-3-carboxylate |
| CA-06 | NC-07 | 279 | (2S)-(((3-(nitrooxy)butoxy)carbonyl)oxy)methyl 6-trifluoromethoxy-8-ethyl-2-(trifluoromethyl)-2H-chromene-3-carboxylate |
| CA-06 | NC-08 | 280 | (S)-(((4-(nitrooxy)butoxy)carbonyl)oxy)methyl 6-trifluoromethoxy-8-ethyl-2-(trifluoromethyl)-2H-chromene-3-carboxylate |
| CA-06 | NC-09 | 281 | (S)-(((2-(2-(nitrooxy)ethoxy)ethoxy)carbonyl)oxy)methyl 8-ethyl-6-(trifluoromethoxy)-2-(trifluoromethyl)-2H-chromene-3-carboxylate |
| CA-06 | NC-10 | 282 | (S)-(((2-((2-(nitrooxy)ethyl)thio)ethoxy)carbonyl)oxy)methyl 8-ethyl-6-(trifluoromethoxy)-2-(trifluoromethyl)-2H-chromene-3-carboxylate |
| CA-06 | NC-11 | 283 | (S)-(((2-(methyl(2-(nitrooxy)ethyl)amino)ethoxy)carbonyl)oxy)methyl 8-ethyl-6-(trifluoromethoxy)-2-(trifluoromethyl)-2H-chromene-3-carboxylate |
| CA-06 | NC-12 | 284 | (2S)-1-(((2-(nitrooxy)ethoxy)carbonyl)oxy)ethyl 6-trifluoromethoxy-8-ethyl-2-(trifluoromethyl)-2H-chromene-3-carboxylate |
| CA-06 | NC-13 | 285 | (2S)-1-(((2-(nitrooxy)propoxy)carbonyl)oxy)ethyl 6-trifluoromethoxy-8-ethyl-2-(trifluoromethyl)-2H-chromene-3-carboxylate |
| CA-06 | NC-14 | 286 | (2S)-1-((((1-(nitrooxy)propan-2-yl)oxy)carbonyl)oxy)ethyl 6-trifluoromethoxy-8-ethyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-06 | NC-15 | 287 | (2S)-1-(((3-(nitrooxy)propoxy)carbonyl)oxy)ethyl 6-trifluoromethoxy-8-ethyl-2-(trifluoromethyl)-2H-chromene-3-carboxylate |
| CA-06 | NC-16 | 288 | (2S)-1-(((2,2-dimethyl-3-(nitrooxy)propoxy)carbonyl)oxy)ethyl 6-trifluoromethoxy-8-ethyl-2-(trifluoromethyl)-2H-chromene-3-carboxylate |
| CA-06 | NC-17 | 289 | (2S)-1-((((4-(nitrooxy)butan-2-yl)oxy)carbonyl)oxy)ethyl 6-trifluoromethoxy-8-ethyl-2-(trifluoromethyl)-2H-chromene-3-carboxylate |
| CA-06 | NC-18 | 290 | (2S)-1-(((3-(nitrooxy)butoxy)carbonyl)oxy)ethyl 6-trifluoromethoxy-8-ethyl-2-(trifluoromethyl)-2H-chromene-3-carboxylate |
| CA-06 | NC-19 | 291 | (2S)-1-(((4-(nitrooxy)butoxy)carbonyl)oxy)ethyl 6-trifluoromethoxy-8-ethyl-2-(trifluoromethyl)-2H-chromene-3-carboxylate |
| CA-06 | NC-20 | 292 | (2S)-1-(((2-(2-(nitrooxy)ethoxy)ethoxy)carbonyl)oxy)ethyl 8-ethyl-6-(trifluoromethoxy)-2-(trifluoromethyl)-2H-chromene-3-carboxylate |
| CA-06 | NC-21 | 293 | (2S)-1-(((2-((2-(nitrooxy)ethyl)thio)ethoxy)carbonyl)oxy)ethyl 8-ethyl-6-(trifluoromethoxy)-2-(trifluoromethyl)-2H-chromene-3-carboxylate |
| CA-06 | NC-22 | 294 | (2S)-1-(((2-(methyl(2-(nitrooxy)ethyl)amino)ethoxy)carbonyl)oxy)ethyl 8-ethyl-6-(trifluoromethoxy)-2-(trifluoromethyl)-2H-chromene-3-carboxylate |
| CA-07 | NC-01 | 295 | (S)-(((2-(nitrooxy)ethoxy)carbonyl)oxy)methyl 6-chloro-5,7-dimethyl-2-(trifluoromethyl)-2H-chromene-3-carboxylate |
| CA-07 | NC-02 | 296 | (2S)-(((2-(nitrooxy)propoxy)carbonyl)oxy)methyl 6-chloro-5,7-dimethyl-2-(trifluoromethyl)-2H-chromene-3-carboxylate |
| CA-07 | NC-03 | 297 | (2S)-((((1-(nitrooxy)propan-2-yl)oxy)carbonyl)oxy)methyl 6-chloro-5,7-dimethyl-2-(trifluoromethyl)-2H-chromene-3-carboxylate |
| CA-07 | NC-04 | 298 | (S)-(((3-(nitrooxy)propoxy)carbonyl)oxy)methyl 6-chloro-5,7-dimethyl-2-(trifluoromethyl)-2H-chromene-3-carboxylate |
| CA-07 | NC-05 | 299 | (S)-(((2,2-dimethyl-3-(nitrooxy)propoxy)carbonyl)oxy)methyl 6-chloro-5,7-dimethyl-2-(trifluoromethyl)-2H-chromene-3-carboxylate |
| CA-07 | NC-06 | 300 | (2S)-((((4-(nitrooxy)butan-2-yl)oxy)carbonyl)oxy)methyl 6-chloro-5,7-dimethyl-2-(trifluoromethyl)-2H-chromene-3-carboxylate |
| CA-07 | NC-07 | 301 | (2S)-(((3-(nitrooxy)butoxy)carbonyl)oxy)methyl 6-chloro-5,7-dimethyl-2-(trifluoromethyl)-2H-chromene-3-carboxylate |
| CA-07 | NC-08 | 302 | (S)-(((4-(nitrooxy)butoxy)carbonyl)oxy)methyl 6-chloro-5,7-dimethyl-2-(trifluoromethyl)-2H-chromene-3-carboxylate |
| CA-07 | NC-09 | 303 | (S)-(((2-(2-(nitrooxy)ethoxy)ethoxy)carbonyl)oxy)methyl 6-chloro-5,7-dimethyl-2-(trifluoromethyl)-2H-chromene-3-carboxylate |
| CA-07 | NC-10 | 304 | (S)-(((2-((2-(nitrooxy)ethyl)thio)ethoxy)carbonyl)oxy)methyl 6-chloro-5,7-dimethyl-2-(trifluoromethyl)-2H-chromene-3-carboxylate |
| CA-07 | NC-11 | 305 | (S)-(((2-(methyl(2-(nitrooxy)ethyl)amino)ethoxy)carbonyl)oxy)methyl 6-chloro-5,7-dimethyl-2-(trifluoromethyl)-2H-chromene-3-carboxylate |
| CA-07 | NC-12 | 306 | (2S)-1-(((2-(nitrooxy)ethoxy)carbonyl)oxy)ethyl 6-chloro-5,7-dimethyl-2-(trifluoromethyl)-2H-chromene-3-carboxylate |
| CA-07 | NC-13 | 307 | (2S)-1-(((2-(nitrooxy)propoxy)carbonyl)oxy)ethyl 6-chloro-5,7-dimethyl-2-(trifluoromethyl)-2H-chromene-3-carboxylate |
| CA-07 | NC-14 | 308 | (2S)-1-((((1-(nitrooxy)propan-2-yl)oxy)carbonyl)oxy)ethyl 6-chloro-5,7-dimethyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-07 | NC-15 | 309 | (2S)-1-(((3-(nitrooxy)propoxy)carbonyl)oxy)ethyl 6-chloro-5,7-dimethyl-2-(trifluoromethyl)-2H-chromene-3-carboxylate |
| CA-07 | NC-16 | 310 | (2S)-1-(((2,2-dimethyl-3-(nitrooxy)propoxy)carbonyl)oxy)ethyl 6-chloro-5,7-dimethyl-2-(trifluoromethyl)-2H-chromene-3-carboxylate |
| CA-07 | NC-17 | 311 | (2S)-1-((((4-(nitrooxy)butan-2-yl)oxy)carbonyl)oxy)ethyl 6-chloro-5,7-dimethyl-2-(trifluoromethyl)-2H-chromene-3-carboxylate |
| CA-07 | NC-18 | 312 | (2S)-1-(((3-(nitrooxy)butoxy)carbonyl)oxy)ethyl 6-chloro-5,7-dimethyl-2-(trifluoromethyl)-2H-chromene-3-carboxylate |
| CA-07 | NC-19 | 313 | (2S)-1-(((4-(nitrooxy)butoxy)carbonyl)oxy)ethyl 6-chloro-5,7-dimethyl-2-(trifluoromethyl)-2H-chromene-3-carboxylate |
| CA-07 | NC-20 | 314 | (2S)-1-(((2-(2-(nitrooxy)ethoxy)ethoxy)carbonyl)oxy)ethyl 6-chloro-5,7-dimethyl-2-(trifluoromethyl)-2H-chromene-3-carboxylate |
| CA-07 | NC-21 | 315 | (2S)-1-(((2-((2-(nitrooxy)ethyl)thio)ethoxy)carbonyl)oxy)ethyl 6-chloro-5,7-dimethyl-2-(trifluoromethyl)-2H-chromene-3-carboxylate |
| CA-07 | NC-22 | 316 | (2S)-1-(((2-(methyl(2-(nitrooxy)ethyl)amino)ethoxy)carbonyl)oxy)ethyl 6-chloro-5,7-dimethyl-2-(trifluoromethyl)-2H-chromene-3-carboxylate |
| CA-08 | NC-01 | 317 | (S)-(((2-(nitrooxy)ethoxy)carbonyl)oxy)methyl 6-pentafluorosulfanyl-2-(trifluoromethyl)-2H-chromene-3-carboxylate |
| CA-08 | NC-02 | 318 | (2S)-(((2-(nitrooxy)propoxy)carbonyl)oxy)methyl 6-pentafluorosulfanyl-2-(trifluoromethyl)-2H-chromene-3-carboxylate |
| CA-08 | NC-03 | 319 | (2S)-((((1-(nitrooxy)propan-2-yl)oxy)carbonyl)oxy)methyl 6-pentafluorosulfanyl-2-(trifluoromethyl)-2H-chromene-3-carboxylate |
| CA-08 | NC-04 | 320 | (S)-(((3-(nitrooxy)propoxy)carbonyl)oxy)methyl 6-pentafluorosulfanyl-2-(trifluoromethyl)-2H-chromene-3-carboxylate |
| CA-08 | NC-05 | 321 | (S)-(((2,2-dimethyl-3-(nitrooxy)propoxy)carbonyl)oxy)methyl 6-pentafluorosulfanyl-2-(trifluoromethyl)-2H-chromene-3-carboxylate |
| CA-08 | NC-06 | 322 | (2S)-((((4-(nitrooxy)butan-2-yl)oxy)carbonyl)oxy)methyl 6-pentafluorosulfanyl-2-(trifluoromethyl)-2H-chromene-3-carboxylate |
| CA-08 | NC-07 | 323 | (2S)-(((3-(nitrooxy)butoxy)carbonyl)oxy)methyl 6-pentafluorosulfanyl-2-(trifluoromethyl)-2H-chromene-3-carboxylate |
| CA-08 | NC-08 | 324 | (S)-(((4-(nitrooxy)butoxy)carbonyl)oxy)methyl 6-pentafluorosulfanyl-2-(trifluoromethyl)-2H-chromene-3-carboxylate |
| CA-08 | NC-09 | 325 | (S)-(((2-(2-(nitrooxy)ethoxy)ethoxy)carbonyl)oxy)methyl 6-pentafluorosulfanyl-2-(trifluoromethyl)-2H-chromene-3-carboxylate |
| CA-08 | NC-10 | 326 | (S)-(((2-((2-(nitrooxy)ethyl)thio)ethoxy)carbonyl)oxy)methyl 6-pentafluorosulfanyl-2-(trifluoromethyl)-2H-chromene-3-carboxylate |
| CA-08 | NC-11 | 327 | (S)-(((2-(methyl(2-(nitrooxy)ethyl)amino)ethoxy)carbonyl)oxy)methyl 6-pentafluorosulfanyl-2-(trifluoromethyl)-2H-chromene-3-carboxylate |
| CA-08 | NC-12 | 328 | (2S)-1-(((2-(nitrooxy)ethoxy)carbonyl)oxy)ethyl 6-pentafluorosulfanyl-2-(trifluoromethyl)-2H-chromene-3-carboxylate |
| CA-08 | NC-13 | 329 | (2S)-1-(((2-(nitrooxy)propoxy)carbonyl)oxy)ethyl 6-pentafluorosulfanyl-2-(trifluoromethyl)-2H-chromene-3-carboxylate |
| CA-08 | NC-14 | 330 | (2S)-1-((((1-(nitrooxy)propan-2-yl)oxy)carbonyl)oxy)ethyl 6-pentafluorosulfanyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-08 | NC-15 | 331 | (2S)-1-(((3-(nitrooxy)propoxy)carbonyl)oxy)ethyl 6-pentafluorosulfanyl-2-(trifluoromethyl)-2H-chromene-3-carboxylate |
| CA-08 | NC-16 | 332 | (2S)-1-(((2,2-dimethyl-3-(nitrooxy)propoxy)carbonyl)oxy)ethyl 6-pentafluorosulfanyl-2-(trifluoromethyl)-2H-chromene-3-carboxylate |
| CA-08 | NC-17 | 333 | (2S)-1-((((4-(nitrooxy)butan-2-yl)oxy)carbonyl)oxy)ethyl 6-pentafluorosulfanyl-2-(trifluoromethyl)-2H-chromene-3-carboxylate |
| CA-08 | NC-18 | 334 | (2S)-1-(((3-(nitrooxy)butoxy)carbonyl)oxy)ethyl 6-pentafluorosulfanyl-2-(trifluoromethyl)-2H-chromene-3-carboxylate |
| CA-08 | NC-19 | 335 | (2S)-1-(((4-(nitrooxy)butoxy)carbonyl)oxy)ethyl 6-pentafluorosulfanyl-2-(trifluoromethyl)-2H-chromene-3-carboxylate |
| CA-08 | NC-20 | 336 | (2S)-1-(((2-(2-(nitrooxy)ethoxy)ethoxy)carbonyl)oxy)ethyl 6-pentafluorosulfanyl-2-(trifluoromethyl)-2H-chromene-3-carboxylate |
| CA-08 | NC-21 | 337 | (2S)-1-(((2-((2-(nitrooxy)ethyl)thio)ethoxy)carbonyl)oxy)ethyl 6-pentafluorosulfanyl-2-(trifluoromethyl)-2H-chromene-3-carboxylate |
| CA-08 | NC-22 | 338 | (2S)-1-(((2-(methyl(2-(nitrooxy)ethyl)amino)ethoxy)carbonyl)oxy)ethyl 6-pentafluorosulfanyl-2-(trifluoromethyl)-2H-chromene-3-carboxylate |
| CA-09 | NC-01 | 339 | (S)-(((2-(nitrooxy)ethoxy)carbonyl)oxy)methyl 6-pentafluorosulfanyl-8-methyl-2-(trifluoromethyl)-2H-chromene-3-carboxylate |
| CA-09 | NC-02 | 340 | (2S)-(((2-(nitrooxy)propoxy)carbonyl)oxy)methyl 6-pentafluorosulfanyl-8-methyl-2-(trifluoromethyl)-2H-chromene-3-carboxylate |
| CA-09 | NC-03 | 341 | (2S)-((((1-(nitrooxy)propan-2-yl)oxy)carbonyl)oxy)methyl 6-pentafluorosulfanyl-8-methyl-2-(trifluoromethyl)-2H-chromene-3-carboxylate |
| CA-09 | NC-04 | 342 | (S)-(((3-(nitrooxy)propoxy)carbonyl)oxy)methyl 6-pentafluorosulfanyl-8-methyl-2-(trifluoromethyl)-2H-chromene-3-carboxylate |
| CA-09 | NC-05 | 343 | (S)-(((2,2-dimethyl-3-(nitrooxy)propoxy)carbonyl)oxy)methyl 6-pentafluorosulfanyl-8-methyl-2-(trifluoromethyl)-2H-chromene-3-carboxylate |
| CA-09 | NC-06 | 344 | (2S)-((((4-(nitrooxy)butan-2-yl)oxy)carbonyl)oxy)methyl 6-pentafluorosulfanyl-8-methyl-2-(trifluoromethyl)-2H-chromene-3-carboxylate |
| CA-09 | NC-07 | 345 | (2S)-(((3-(nitrooxy)butoxy)carbonyl)oxy)methyl 6-pentafluorosulfanyl-8-methyl-2-(trifluoromethyl)-2H-chromene-3-carboxylate |
| CA-09 | NC-08 | 346 | (S)-(((4-(nitrooxy)butoxy)carbonyl)oxy)methyl 6-pentafluorosulfanyl-8-methyl-2-(trifluoromethyl)-2H-chromene-3-carboxylate |
| CA-09 | NC-09 | 347 | (S)-(((2-(2-(nitrooxy)ethoxy)ethoxy)carbonyl)oxy)methyl 6-pentafluorosulfanyl-8-methyl-2-(trifluoromethyl)-2H-chromene-3-carboxylate |
| CA-09 | NC-10 | 348 | (S)-(((2-((2-(nitrooxy)ethyl)thio)ethoxy)carbonyl)oxy)methyl 6-pentafluorosulfanyl-8-methyl-2-(trifluoromethyl)-2H-chromene-3-carboxylate |
| CA-09 | NC-11 | 349 | (S)-(((2-(methyl(2-(nitrooxy)ethyl)amino)ethoxy)carbonyl)oxy)methyl 6-pentafluorosulfanyl-8-methyl-2-(trifluoromethyl)-2H-chromene-3-carboxylate |
| CA-09 | NC-12 | 350 | (2S)-1-(((2-(nitrooxy)ethoxy)carbonyl)oxy)ethyl 6-pentafluorosulfanyl-8-methyl-2-(trifluoromethyl)-2H-chromene-3-carboxylate |
| CA-09 | NC-13 | 351 | (2S)-1-(((2-(nitrooxy)propoxy)carbonyl)oxy)ethyl 6-pentafluorosulfanyl-8-methyl-2-(trifluoromethyl)-2H-chromene-3-carboxylate |
| CA-09 | NC-14 | 352 | (2S)-1-((((1-(nitrooxy)propan-2-yl)oxy)carbonyl)oxy)ethyl 6-pentafluorosulfanyl-8- |

TABLE 16-continued

Examples of chromene methylene diester nitrate esters.

| Chromene Acid | Nitrooxy Chloroformates | Ex. | Name |
|---|---|---|---|
| | | | methyl-2-(trifluoromethyl)-2H-chromene-3-carboxylate |
| CA-09 | NC-15 | 353 | (2S)-1-(((3-(nitrooxy)propoxy)carbonyl)oxy)ethyl 6-pentafluorosulfanyl-8-methyl-2-(trifluoromethyl)-2H-chromene-3-carboxylate |
| CA-09 | NC-16 | 354 | (2S)-1-(((2,2-dimethyl-3-(nitrooxy)propoxy)carbonyl)oxy)ethyl 6-pentafluorosulfanyl-8-methyl-2-(trifluoromethyl)-2H-chromene-3-carboxylate |
| CA-09 | NC-17 | 355 | (2S)-1-((((4-(nitrooxy)butan-2-yl)oxy)carbonyl)oxy)ethyl 6-pentafluorosulfanyl-8-methyl-2-(trifluoromethyl)-2H-chromene-3-carboxylate |
| CA-09 | NC-18 | 356 | (2S)-1-(((3-(nitrooxy)butoxy)carbonyl)oxy)ethyl 6-pentafluorosulfanyl-8-methyl-2-(trifluoromethyl)-2H-chromene-3-carboxylate |
| CA-09 | NC-19 | 357 | (2S)-1-(((4-(nitrooxy)butoxy)carbonyl)oxy)ethyl 6-pentafluorosulfanyl-8-methyl-2-(trifluoromethyl)-2H-chromene-3-carboxylate |
| CA-09 | NC-20 | 358 | (2S)-1-(((2-(2-(nitrooxy)ethoxy)ethoxy)carbonyl)oxy)ethyl 6-pentafluorosulfanyl-8-methyl-2-(trifluoromethyl)-2H-chromene-3-carboxylate |
| CA-09 | NC-21 | 359 | (2S)-1-(((2-((2-(nitrooxy)ethyl)thio)ethoxy)carbonyl)oxy)ethyl 6-pentafluorosulfanyl-8-methyl-2-(trifluoromethyl)-2H-chromene-3-carboxylate |
| CA-09 | NC-22 | 360 | (2S)-1-(((2-(methyl(2-(nitrooxy)ethyl)amino)ethoxy)carbonyl)oxy)ethyl 6-pentafluorosulfanyl-8-methyl-2-(trifluoromethyl)-2H-chromene-3-carboxylate |
| CA-10 | NC-01 | 361 | (S)-(((2-(nitrooxy)ethoxy)carbonyl)oxy)methyl 6-pentafluorosulfanyl-8-ethyl-2-(trifluoromethyl)-2H-chromene-3-carboxylate |
| CA-10 | NC-02 | 362 | (2S)-(((2-(nitrooxy)propoxy)carbonyl)oxy)methyl 6-pentafluorosulfanyl-8-ethyl-2-(trifluoromethyl)-2H-chromene-3-carboxylate |
| CA-10 | NC-03 | 363 | (2S)-((((1-(nitrooxy)propan-2-yl)oxy)carbonyl)oxy)methyl 6-pentafluorosulfanyl-8-ethyl-2-(trifluoromethyl)-2H-chromene-3-carboxylate |
| CA-10 | NC-04 | 364 | (S)-(((3-(nitrooxy)propoxy)carbonyl)oxy)methyl 6-pentafluorosulfanyl-8-ethyl-2-(trifluoromethyl)-2H-chromene-3-carboxylate |
| CA-10 | NC-05 | 365 | (S)-(((2,2-dimethyl-3-(nitrooxy)propoxy)carbonyl)oxy)methyl 6-pentafluorosulfanyl-8-ethyl-2-(trifluoromethyl)-2H-chromene-3-carboxylate |
| CA-10 | NC-06 | 366 | (2S)-((((4-(nitrooxy)butan-2-yl)oxy)carbonyl)oxy)methyl 6-pentafluorosulfanyl-8-ethyl-2-(trifluoromethyl)-2H-chromene-3-carboxylate |
| CA-10 | NC-07 | 367 | (2S)-(((3-(nitrooxy)butoxy)carbonyl)oxy)methyl 6-pentafluorosulfanyl-8-ethyl-2-(trifluoromethyl)-2H-chromene-3-carboxylate |
| CA-10 | NC-08 | 368 | (S)-(((4-(nitrooxy)butoxy)carbonyl)oxy)methyl 6-pentafluorosulfanyl-8-ethyl-2-(trifluoromethyl)-2H-chromene-3-carboxylate |
| CA-10 | NC-09 | 369 | (S)-(((2-(2-(nitrooxy)ethoxy)ethoxy)carbonyl)oxy)methyl 6-pentafluorosulfanyl-8-ethyl-2-(trifluoromethyl)-2H-chromene-3-carboxylate |
| CA-10 | NC-10 | 370 | (S)-(((2-((2-(nitrooxy)ethyl)thio)ethoxy)carbonyl)oxy)methyl 6-pentafluorosulfanyl-8-ethyl-2-(trifluoromethyl)-2H-chromene-3-carboxylate |
| CA-10 | NC-11 | 371 | (S)-(((2-(methyl(2-(nitrooxy)ethyl)amino)ethoxy)carbonyl)oxy)methyl 6-pentafluorosulfanyl-8-ethyl-2-(trifluoromethyl)-2H-chromene-3-carboxylate |
| CA-10 | NC-12 | 372 | (2S)-1-(((2-(nitrooxy)ethoxy)carbonyl)oxy)ethyl 6-pentafluorosulfanyl-8-ethyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-10 | NC-13 | 373 | (2S)-1-(((2-(nitrooxy)propoxy)carbonyl)oxy)ethyl 6-pentafluorosulfanyl-8-ethyl-2-(trifluoromethyl)-2H-chromene-3-carboxylate |
| CA-10 | NC-14 | 374 | (2S)-1-((((1-(nitrooxy)propan-2-yl)oxy)carbonyl)oxy)ethyl 6-pentafluorosulfanyl-8-ethyl-2-(trifluoromethyl)-2H-chromene-3-carboxylate |
| CA-10 | NC-15 | 375 | (2S)-1-(((3-(nitrooxy)propoxy)carbonyl)oxy)ethyl 6-pentafluorosulfanyl-8-ethyl-2-(trifluoromethyl)-2H-chromene-3-carboxylate |
| CA-10 | NC-16 | 376 | (2S)-1-(((2,2-dimethyl-3-(nitrooxy)propoxy)carbonyl)oxy)ethyl 6-pentafluorosulfanyl-8-ethyl-2-(trifluoromethyl)-2H-chromene-3-carboxylate |
| CA-10 | NC-17 | 377 | (2S)-1-((((4-(nitrooxy)butan-2-yl)oxy)carbonyl)oxy)ethyl 6-pentafluorosulfanyl-8-ethyl-2-(trifluoromethyl)-2H-chromene-3-carboxylate |
| CA-10 | NC-18 | 378 | (2S)-1-(((3-(nitrooxy)butoxy)carbonyl)oxy)ethyl 6-pentafluorosulfanyl-8-ethyl-2-(trifluoromethyl)-2H-chromene-3-carboxylate |
| CA-10 | NC-19 | 379 | (2S)-1-(((4-(nitrooxy)butoxy)carbonyl)oxy)ethyl 6-pentafluorosulfanyl-8-ethyl-2-(trifluoromethyl)-2H-chromene-3-carboxylate |
| CA-10 | NC-20 | 380 | (2S)-1-(((2-(2-(nitrooxy)ethoxy)ethoxy)carbonyl)oxy)ethyl 6-pentafluorosulfanyl-8-ethyl-2-(trifluoromethyl)-2H-chromene-3-carboxylate |
| CA-10 | NC-21 | 381 | (2S)-1-(((2-((2-(nitrooxy)ethyl)thio)ethoxy)carbonyl)oxy)ethyl 6-pentafluorosulfanyl-8-ethyl-2-(trifluoromethyl)-2H-chromene-3-carboxylate |
| CA-10 | NC-22 | 382 | (2S)-1-(((2-(methyl(2-(nitrooxy)ethyl)amino)ethoxy)carbonyl)oxy)ethyl 6-pentafluorosulfanyl-8-ethyl-2-(trifluoromethyl)-2H-chromene-3-carboxylate |
| CA-11 | NC-01 | 383 | (S)-(((2-(nitrooxy)ethoxy)carbonyl)oxy)methyl 6-chloro-7-tert-butyl-2-(trifluoromethyl)-2H-chromene-3-carboxylate |
| CA-11 | NC-02 | 384 | (2S)-(((2-(nitrooxy)propoxy)carbonyl)oxy)methyl 6-chloro-7-tert-butyl-2-(trifluoromethyl)-2H-chromene-3-carboxylate |
| CA-11 | NC-03 | 385 | (2S)-((((1-(nitrooxy)propan-2-yl)oxy)carbonyl)oxy)methyl 6-chloro-7-tert-butyl-2-(trifluoromethyl)-2H-chromene-3-carboxylate |
| CA-11 | NC-04 | 386 | (S)-(((3-(nitrooxy)propoxy)carbonyl)oxy)methyl 6-chloro-7-tert-butyl-2-(trifluoromethyl)-2H-chromene-3-carboxylate |
| CA-11 | NC-05 | 387 | (S)-(((2,2-dimethyl-3-(nitrooxy)propoxy)carbonyl)oxy)methyl 6-chloro-7-tert-butyl-2-(trifluoromethyl)-2H-chromene-3-carboxylate |
| CA-11 | NC-06 | 388 | (2S)-((((4-(nitrooxy)butan-2-yl)oxy)carbonyl)oxy)methyl 6-chloro-7-tert-butyl-2-(trifluoromethyl)-2H-chromene-3-carboxylate |
| CA-11 | NC-07 | 389 | (2S)-(((3-(nitrooxy)butoxy)carbonyl)oxy)methyl 6-chloro-7-tert-butyl-2-(trifluoromethyl)-2H-chromene-3-carboxylate |
| CA-11 | NC-08 | 390 | (S)-(((4-(nitrooxy)butoxy)carbonyl)oxy)methyl 6-chloro-7-tert-butyl-2-(trifluoromethyl)-2H-chromene-3-carboxylate |
| CA-11 | NC-09 | 391 | (S)-(((2-(2-(nitrooxy)ethoxy)ethoxy)carbonyl)oxy)methyl 6-chloro-7-tert-butyl-2-(trifluoromethyl)-2H-chromene-3-carboxylate |
| CA-11 | NC-10 | 392 | (S)-(((2-((2-(nitrooxy)ethyl)thio)ethoxy)carbonyl)oxy)methyl 6-chloro-7-tert-butyl-2-(trifluoromethyl)-2H-chromene-3-carboxylate |
| CA-11 | NC-11 | 393 | (S)-(((2-(methyl(2-(nitrooxy)ethyl)amino)ethoxy)carbonyl)oxy)methyl 6-chloro-7-tert-butyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-11 | NC-12 | 394 | (2S)-1-(((2-(nitrooxy)ethoxy)carbonyl)oxy)ethyl 6-chloro-7-tert-butyl-2-(trifluoromethyl)-2H-chromene-3-carboxylate |
| CA-11 | NC-13 | 395 | (2S)-1-(((2-(nitrooxy)propoxy)carbonyl)oxy)ethyl 6-chloro-7-tert-butyl-2-(trifluoromethyl)-2H-chromene-3-carboxylate |
| CA-11 | NC-14 | 396 | (2S)-1-((((1-(nitrooxy)propan-2-yl)oxy)carbonyl)oxy)ethyl 6-chloro-7-tert-butyl-2-(trifluoromethyl)-2H-chromene-3-carboxylate |
| CA-11 | NC-15 | 397 | (2S)-1-(((3-(nitrooxy)propoxy)carbonyl)oxy)ethyl 6-chloro-7-tert-butyl-2-(trifluoromethyl)-2H-chromene-3-carboxylate |
| CA-11 | NC-16 | 398 | (2S)-1-(((2,2-dimethyl-3-(nitrooxy)propoxy)carbonyl)oxy)ethyl 6-chloro-7-tert-butyl-2-(trifluoromethyl)-2H-chromene-3-carboxylate |
| CA-11 | NC-17 | 399 | (2S)-1-((((4-(nitrooxy)butan-2-yl)oxy)carbonyl)oxy)ethyl 6-chloro-7-tert-butyl-2-(trifluoromethyl)-2H-chromene-3-carboxylate |
| CA-11 | NC-18 | 400 | (2S)-1-(((3-(nitrooxy)butoxy)carbonyl)oxy)ethyl 6-chloro-7-tert-butyl-2-(trifluoromethyl)-2H-chromene-3-carboxylate |
| CA-11 | NC-19 | 401 | (2S)-1-(((4-(nitrooxy)butoxy)carbonyl)oxy)ethyl 6-chloro-7-tert-butyl-2-(trifluoromethyl)-2H-chromene-3-carboxylate |
| CA-11 | NC-20 | 402 | (2S)-1-(((2-(2-(nitrooxy)ethoxy)ethoxy)carbonyl)oxy)ethyl 6-chloro-7-tert-butyl-2-(trifluoromethyl)-2H-chromene-3-carboxylate |
| CA-11 | NC-21 | 403 | (2S)-1-(((2-((2-(nitrooxy)ethyl)thio)ethoxy)carbonyl)oxy)ethyl 6-chloro-7-tert-butyl-2-(trifluoromethyl)-2H-chromene-3-carboxylate |
| CA-11 | NC-22 | 404 | (2S)-1-(((2-(methyl(2-(nitrooxy)ethyl)amino)ethoxy)carbonyl)oxy)ethyl 6-chloro-7-tert-butyl-2-(trifluoromethyl)-2H-chromene-3-carboxylate |
| CA-03 | NC-23 | 405 | (S)-((((1,3-bis(nitrooxy)propan-2-yl)oxy)carbonyl)oxy)methyl 6-bromo-8-methyl-2-(trifluoromethyl)-2H-chromene-3-carboxylate |
| CA-03 | NC-24 | 406 | (2S)-1-((((1,3-bis(nitrooxy)propan-2-yl)oxy)carbonyl)oxy)ethyl 6-bromo-8-methyl-2-(trifluoromethyl)-2H-chromene-3-carboxylate |
| CA-02 | NC-23 | 407 | (S)-((((1,3-bis(nitrooxy)propan-2-yl)oxy)carbonyl)oxy)methyl 6-chloro-8-methyl-2-(trifluoromethyl)-2H-chromene-3-carboxylate |
| CA-02 | NC-24 | 408 | (2S)-1-((((1,3-bis(nitrooxy)propan-2-yl)oxy)carbonyl)oxy)ethyl 6-chloro-8-methyl-2-(trifluoromethyl)-2H-chromene-3-carboxylate |
| CA-05 | NC-23 | 409 | (S)-((((1,3-bis(nitrooxy)propan-2-yl)oxy)carbonyl)oxy)methyl 8-methyl-6-(trifluoromethoxy)-2-(trifluoromethyl)-2H-chromene-3-carboxylate |
| CA-05 | NC-24 | 410 | (2S)-1-((((1,3-bis(nitrooxy)propan-2-yl)oxy)carbonyl)oxy)ethyl 8-methyl-6-(trifluoromethoxy)-2-(trifluoromethyl)-2H-chromene-3-carboxylate |
| CA-06 | NC-23 | 411 | (S)-((((1,3-bis(nitrooxy)propan-2-yl)oxy)carbonyl)oxy)methyl 8-ethyl-6-(trifluoromethoxy)-2-(trifluoromethyl)-2H-chromene-3-carboxylate |
| CA-06 | NC-24 | 412 | (2S)-((((1,3-bis(nitrooxy)propan-2-yl)oxy)carbonyl)oxy)ethyl 8-ethyl-6-(trifluoromethoxy)-2-(trifluoromethyl)-2H-chromene-3-carboxylate |
| CA-04 | NC-23 | 413 | (S)-((((1,3-bis(nitrooxy)propan-2-yl)oxy)carbonyl)oxy)methyl 6,8-dimethyl-2-(trifluoromethyl)-2H-chromene-3-carboxylate |
| CA-04 | NC-24 | 414 | (2S)-1-((((1,3-bis(nitrooxy)propan-2-yl)oxy)carbonyl)oxy)ethyl 6,8-dimethyl-2-(trifluoromethyl)-2H-chromene-3-carboxylate |
| CA-07 | NC-23 | 415 | (S)-((((1,3-bis(nitrooxy)propan-2-yl)oxy)carbonyl)oxy)methyl 6-chloro-5,7-dimethyl-2-(trifluoromethyl)-2H-chromene-3-carboxylate |

TABLE 16-continued

Examples of chromene methylene diester nitrate esters.

| Chromene Acid | Nitrooxy Chloroformates | Ex. | Name |
|---|---|---|---|
| CA-07 | NC-24 | 416 | (2S)-1-((((1,3-bis(nitrooxy)propan-2-yl)oxy)carbonyl)oxy)ethyl 6-chloro-5,7-dimethyl-2-(trifluoromethyl)-2H-chromene-3-carboxylate |
| CA-11 | NC-23 | 417 | (S)-((((1,3-bis(nitrooxy)propan-2-yl)oxy)carbonyl)oxy)methyl 7-(tert-butyl)-6-chloro-2-(trifluoromethyl)-2H-chromene-3-carboxylate |
| CA-11 | NC-24 | 418 | (2S)-1-((((1,3-bis(nitrooxy)propan-2-yl)oxy)carbonyl)oxy)ethyl 7-(tert-butyl)-6-chloro-2-(trifluoromethyl)-2H-chromene-3-carboxylate |
| CA-09 | NC-23 | 419 | (S)-((((1,3-bis(nitrooxy)propan-2-yl)oxy)carbonyl)oxy)methyl 6-pentafluorosulfanyl-8-methyl-2-(trifluoromethyl)-2H-chromene-3-carboxylate |
| CA-09 | NC-24 | 420 | (2S)-1-((((1,3-bis(nitrooxy)propan-2-yl)oxy)carbonyl)oxy)ethyl 6-pentafluorosulfanyl-8-methyl-2-(trifluoromethyl)-2H-chromene-3-carboxylate |
| CA-10 | NC-23 | 421 | (S)-((((1,3-bis(nitrooxy)propan-2-yl)oxy)carbonyl)oxy)methyl 6-pentafluorosulfanyl-8-ethyl-2-(trifluoromethyl)-2H-chromene-3-carboxylate |
| CA-10 | NC-24 | 422 | (2S)-1-((((1,3-bis(nitrooxy)propan-2-yl)oxy)carbonyl)oxy)ethyl 6-pentafluorosulfanyl-8-ethyl-2-(trifluoromethyl)-2H-chromene-3-carboxylate |
| CA-08 | NC-23 | 423 | (S)-((((1,3-bis(nitrooxy)propan-2-yl)oxy)carbonyl)oxy)methyl 6-pentafluorosulfanyl-2-(trifluoromethyl)-2H-chromene-3-carboxylate |
| CA-08 | NC-24 | 424 | (2S)-1-((((1,3-bis(nitrooxy)propan-2-yl)oxy)carbonyl)oxy)ethyl 6-pentafluorosulfanyl-2-(trifluoromethyl)-2H-chromene-3-carboxylate |

E. Method of Treatment

A compound of the structural formulae herein is meant to include a pharmaceutically acceptable salt, or solvate of a compound or salt, of the structural formulae herein.

The present invention further provides methods for treating a disease condition in a subject having or susceptible to having such a disease condition, by administering to the subject a therapeutically-effective amount of one or more compounds as described by the structural formulae herein. In one embodiment, the treatment is preventative treatment. In another embodiment, the treatment is palliative treatment. In another embodiment, the treatment is restorative treatment, for example, treatments for wound healing, acne, and inflammation. In another embodiment, the subject is a mammal. In yet another embodiment, the subject is a human.

1. Conditions

The conditions that can be treated in accordance with the present invention include, but are not limited to, autoimmune disorders, chronic inflammatory disorders, acute inflammatory disorders, auto-inflammatory disorders, pain, cancer, neoplasia, lung cancer, colorectal cancer, and the like.

In one embodiment, methods described herein are used to treat, prevent, or ameliorate a disease condition comprising administering to a subject in need thereof a therapeutically effective amount of a compound of the structural formulae herein, wherein the condition is selected from the group consisting of cancer pain, Barrett's esophagus, Lynch syndrome, non-small cell lung cancer, head and neck cancer, skin cancer, liver cancer, metastatic colorectal cancer (and FAP), renal cell cancer, glioblastoma, squamous cell cancer, bladder cancer, breast cancer, biliary tract cancer, cervical cancer, prostate cancer, small cell lung cancer, ovarian cancer, pancreatic cancer, gastrointestinal cancer, and CNS cancer.

In another embodiment, methods described herein are used to treat, prevent, or ameliorate a disease condition comprising administering to a subject in need thereof a therapeutically effective amount of a compound of the structural formulae herein, wherein the condition is selected from the group consisting of cancer, actinic keratosis, cystic fibrosis, and acne.

In yet another embodiment, methods described herein are used for healing wounds by administering to a subject in need thereof a therapeutically effective amount of a compound of the structural formulae herein.

In one embodiment, methods described herein are used to treat, prevent, or ameliorate a disease condition comprising administering to a subject in need thereof a therapeutically effective amount of a compound of the structural formulae herein, wherein the condition is selected from the group consisting of colorectal cancer, non-small cell lung cancer, and head and neck cancer.

In some embodiments the methods described herein are used for administering to a patient in need thereof, a therapeutically effective amount of a compound of the structural formulae herein, to treat, prevent, or ameliorate a disease condition or disorder arising from dysregulated enzymes, and/or dysregulated inflammatory mediator production, stability, secretion, and posttranslational processing. Examples of inflammatory mediators that may be dysregulated include nitric oxide, prostaglandins, and leukotrienes. Examples of enzymes which may be dysregulated include cyclooxygenase and nitric oxide synthase.

In some embodiments, the methods described herein are used for administering to a patient in need thereof a therapeutically effective amount of a compound of the structural formulae herein, to treat, prevent, or ameliorate a disease condition or disorder that is, arises from, or is related to an autoimmune disorder, chronic, and/or acute inflammatory disorder, and/or auto-inflammatory disorder. Examples of disorders include, but are not limited to arthritis, rheumatoid arthritis, osteoarthritis, juvenile arthritis, psoriatic arthritis.

In some embodiments, the methods described herein can be used for administering to a patient in need thereof a therapeutically effective amount of a compound of the structural formulae herein, to treat, prevent, or ameliorate neoplasia and the symptoms thereof. Examples of these conditions include but are not limited to the following:

acral lentiginous melanoma
actinic keratoses
adenocarcinoma
adenoid cycstic carcinoma
adenomas
adenosarcoma
adenosquamous carcinoma
astrocytic tumors
bartholin gland carcinoma
basal cell carcinoma
bladder cancer
breast cancer
biliary tract cancer
bronchial gland carcinomas
capillary
carcinoids
carcinoma
carcinosarcoma
cavernous
cervical cancer
cholangiocarcinoma
chondosarcoma
choroid plexus
papilloma/carcinoma
clear cell carcinoma
CNS cancer
cystadenoma
endodermal sinus tumor
endometrial hyperplasia
endometrial stromal sarcoma
endometrioid adenocarcinoma
ependymal
epitheloid
Ewing's sarcoma
familial adenomatous polyposis (FAP)
fibrolamellar carcinoma
focal nodular hyperplasia
gastrinoma
gastrointestinal cancer
germ cell tumors
glioblastoma
glucagonoma
hemangiblastomas
hemangioendothelioma
hemangiomas
hepatic adenoma
hepatic adenomatosis
hepatocellular carcinoma
insulinoma
intaepithelial neoplasia
interepithelial squamous cell neoplasia
invasive squamous cell carcinoma
large cell carcinoma
leiomyosarcoma
lentigo maligna melanomas
liver cancer
malignant melanoma
malignant mesothelial tumors -continued medulloblastoma
medulloepithelioma
melanoma
meningeal
mesothelial
metastatic carcinoma
metastatic colorectal cancer
mucoepidermoid carcinoma
neuroblastoma
neuroepithelial
adenocarcinoma nodular melanoma
non-small cell lung cancer
oat cell carcinoma
oligodendroglial
osteosarcoma
ovarian cancer
pancreatic cancer
papillary serous adenocarcinoma
pineal cell
pituitary tumors
plasmacytoma
prostate cancer
pseudosarcoma
pulmonary blastoma
renal cell carcinoma
retinoblastoma
rhabdomyosarcoma
sarcoma
serous carcinoma
skin cancer
small cell carcinoma
small cell lung cancer
soft tissue carcinomas
somatostatin-secreting tumor
squamous carcinoma
squamous cell carcinoma
submesothelial
superficial spreading melanoma
undifferentiatied carcinoma
uveal melanoma
verrucous carcinoma
vipoma
well differentiated carcinoma
Wilm's tumor In one embodiment, the methods described herein can be used for administering to a patient in need thereof a therapeutically effective amount of a compound of the structural formulae herein, to treat, prevent, or ameliorate metastatic colorectal cancer.

In an additional embodiment, the methods described herein can be used for administering to a patient in need thereof a therapeutically effective amount of a compound of the structural formulae herein, to treat, prevent, or ameliorate a disease condition characterized by or related to COX-2 over-expression, including but not limited to cancer, an autoimmune disorder such as rheumatoid arthritis, and other disorders characterized by pain and/or inflammation.

COX-2 over-expression is found in a variety of medical conditions. Examples of conditions characterized by COX-2 over-expression given herein are not intended to be limiting and are solely for illustrative purposes. The journal article *Transgenic mouse for conditional, tissue-specific Cox-2 over expression* (Kamei et al. Genesis. 2006 April; 44(4):177-82.) states that COX-2 over-expression is found in, for example, cardiovascular conditions, acute and chronic inflammatory responses, neurodegenerative diseases, and cancer. Exemplary and non-limiting cardiovascular conditions include septicemia (Cuenca et al., Infiltration of Inflammatory Cells Plays an Important Role in Matrix Metalloproteinase Expression and Activation in the Heart during Sepsis. 2006; Am J Pathol. 169(5): 1567-1576.), aortic aneurysms (King et al., Selective Cyclooxygenase-2 Inhibition with Celecoxib Decreases Angiotensin II-Induced Abdominal Aortic Aneurysm Formation in Mice. November 2006; Arterioscler Thromb Vasc Biol. 26: 1137-1143.), and mycardial infarction (LaPointe et al., Inhibition of cyclooxygenase-2 improves cardiac function after myocardial infarction in the mouse. 2004; Am J Physiol Heart Circ Physiol. 286: H1416-H1424,). Exemplary and non-limiting acute and chronic inflammatory responses include injury-related inflammation and Rhematoid Arthritis respectively. Exemplary and non-limiting neurodegenerative diseases include Parkinson's disease (Teismann, Peter. COX-2 in the neurodegenerative process of Parkinson's disease. November 2012; 38(6): 395-397.) and Alzheimer's disease (Rogers, Joseph. Neuroinflammatory Mechanisms in Alzheimer's Disease: Basic and Clinical Research. Springer Science and Business Media, January 2001, 203-204). Exemplary and non-limiting cancers include non-small cell lung cancer and colorectal cancer.

In another embodiment, patients with high baseline COX-2 activity are more likely to improve upon administration of a therapeutically effective amount of a compound of the structural formulae herein. Baseline levels of COX-2 activity can be determined by urinary PGE-M content.

The term patient refers to both humans and non-human animals with the abovementioned conditions. Non-human animals could be companion animals such as, but not limited to, canine and feline species. The terms "patient" and "subject" are meant to be interchangeable.

2. Subjects

Suitable subjects for the methods described herein include mammalian subjects. Mammals according to the present invention include, but are not limited to, human, canine, feline, bovine, caprine, equine, ovine, porcine, rodents, lagomorphs, primates, and the like and encompass mammals in utero. Subjects may be of either gender and at any stage of development.

3. Administration and Dosing

A compound of the present invention may be administered in the form of a prodrug in a therapeutically effective amount.

A compound of the present invention can be administered by any suitable route in the form of a pharmaceutical composition adapted to such a route and in a dose effective for the treatment intended. Therapeutically effective doses of a compound of the present invention required to prevent or arrest the progress of, to treat or ameliorate the medical condition, or to alleviate symptoms thereof, such as pain or inflammation, are readily ascertained by one of ordinary skill in the art using preclinical and clinical approaches familiar to the medicinal arts.

For convenience a compound of the present invention can be administered in a unit dosage form. If desired, multiple doses per day of the unit dosage form can be used to increase the total daily dose. The unit dosage form, for example, may be a tablet or capsule containing about 0.01, about 0.05, about 0.1, about 0.5, about 1, about 5, about 10, about 15, about 20, about 25, about 30, about 35, about 40, about 45, about 50, about 55, about 60, about 65, about 70, about 75, about 80, about 85, about 90, about 95, about 100, about 125, about 150, about 175, about 200, about 250, or about 500 mg of a compound of the present invention. In one embodiment, the unit dosage form contains from about 0.01 mg to about 500 mg of a compound of the present invention. In another embodiment, the unit dosage form contains from about 0.02 to about 400 mg of a compound of the present invention. In another embodiment, the unit dosage form contains from about 0.05 mg to about 250 mg of a compound of the present invention. In another embodiment, the unit dosage form contains from about 0.1 mg to about 200 mg of a compound of the present invention. In another embodiment, the unit dosage form contains from about 0.5 mg to about 150 mg of a compound of the present invention. In another embodiment, the unit dosage form contains from about 1.0 mg to about 100 mg of a compound of the present invention.

The dosage regimen required for therapeutic effect for compounds of the present invention and/or compositions containing compounds of the present invention is based on a variety of factors, including the type, age, weight, sex, and medical condition of the patient, the severity of the condition, the route of administration, and the activity of the particular compound employed. Thus, the dosage regimen may vary based on patient to patient variability of individual factors, including but not limited to those listed here. Dosage levels from about 0.001 mg to about 100 mg of a compound of the present invention per kilogram of body weight per day are useful in the treatment of the above-indicated conditions. In one embodiment, the total daily dose of a compound of the present invention (administered in single or divided doses) is typically from about 0.001 mg/kg to about 20 mg/kg (i.e., mg compound/kg body weight). In another embodiment, the total daily dose of a compound of the present invention is from about 0.005 mg/kg to about 10 mg/kg. In another embodiment, the total daily dose is from about 0.005 mg/kg to about 5 mg/kg. In another embodiment, the total daily dose is from about 0.01 mg/kg to about 1 mg/kg. In another embodiment, the total daily dose is from about 0.8 mg/kg to about 15 mg/kg. In another embodiment, the total daily dose is from about 0.2 mg/kg to about 4 mg/kg. These dosages are based on an average human subject having a weight of about 65 kg to about 75 kg. A physician will readily be able to determine doses for subjects whose weight falls outside of this range, such as infants or children. The administration of a compound of the present invention can be repeated a plurality of times in a day (typically no greater than 4 times) to achieve the desired daily dose.

The present invention further comprises use of a compound of the present invention as a medicament (such as a unit dosage tablet or unit dosage capsule).

In another embodiment, the present invention comprises the use of a compound of the present invention for the manufacture of a medicament (such as a unit dosage tablet or unit dosage capsule) to treat one or more of the conditions previously identified in the above sections discussing methods of treatment. In one embodiment, the condition is cancer. In another embodiment the condition is an inflammatory condition.

F. Pharmaceutical Compositions

For treatment of the conditions referred to above, a compound or several compounds described herein can be administered as follows, these representations are not meant to be limiting:

1. Oral Administration

A compound or several compounds of the present invention may be administered orally, including by swallowing, so that the compound enters the gastrointestinal tract, or absorbed into the blood stream directly from the mouth (e.g., buccal or sublingual administration).

Suitable compositions for oral administration include, but are not limited to, solid formulations such as tablets, lozenges, pills, cachets, and hard and soft capsules, which can contain liquids, gels, or powders.

Compositions for oral administration may be formulated as immediate or modified release, including delayed or sustained release, optionally with enteric coating.

Liquid formulations can include, but are not limited to, solutions, syrups, and suspensions, which can be used in soft or hard capsules. Such formulations may include a pharmaceutically acceptable carrier, for example, water, ethanol, polyethylene glycol, cellulose, or an oil or oils. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, methyl cellulose, sodium or calcium carboxymethyl cellulose, croscarmellose sodium, polyvinylpyrrolidone, hydroxypropyl cellulose, starch, and the like.

Suitable lubricants, for use in a tablet, may be present in amounts from about 0.1% to about 5% by weight and include, but are not limited to, calcium, zinc or magnesium stearate, sodium stearyl fumarate, and the like.

Suitable binders, for use in a tablet, include, but are not limited to, gelatin, polyethylene glycol, sugars, gums, starch, hydroxypropyl cellulose, and the like. Suitable diluents, for use in a tablet, include, but are not limited to, mannitol, xylitol, lactose, dextrose, sucrose, sorbitol, and starch.

Suitable surface active agents and glidants, for use in a tablet, may be present in amounts from about 0.1% to about 3% by weight and include, but are not limited to, polysorbate 80, sodium dodecyl sulfate, talc, and silicon dioxide.

In another embodiment, a pharmaceutical composition comprises a therapeutically effective amount of a compound of the structural formulae herein or a pharmaceutically acceptable salt thereof, and a pharmaceutically acceptable carrier.

2. Parenteral Administration

Compounds of the present invention may be administered directly into the blood stream, muscle, or internal organs. Suitable means for parenteral administration include, but are not limited to, intravenous, intra-muscular, subcutaneous intraarterial, intraperitoneal, intrathecal, intracranial, and the like. Suitable devices for parenteral administration include, but are not limited to, injectors (including needle and needle-free injectors) and infusion methods.

Compositions for parenteral administration may be formulated as immediate or modified release, including delayed or sustained release.

Most parenteral formulations are aqueous solutions containing excipients, including, but not limited to, salts, buffering agents, and carbohydrates.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

3. Topical Administration

Compounds of the present invention may be administered topically to the skin or transdermally. Formulations for this topical administration can include, but are not limited to, lotions, solutions, creams, gels, hydrogels, ointments, foams, implants, patches, and the like. Pharmaceutically acceptable carriers for topical administration formulations can include, but are not limited to, water, alcohol, mineral oil, glycerin, polyethylene glycol, and the like. Topical administration can also be performed by electroporation, iontophoresis, phonophoresis, and the like.

Compositions for topical administration may be formulated as immediate or modified release, including delayed or sustained release.

4. Rectal Administration

Suppositories for rectal administration of a compound of the present invention can be prepared by mixing the active agent with a suitable non-irritating excipient including, but not limited to, cocoa butter, synthetic mono-, di-, or triglycerides, fatty acids, or polyethylene glycols which are solid at ordinary temperatures but liquid at the rectal temperature, and which will therefore melt in the rectum and release the drug.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art, and are described in standard textbooks. Formulation of drugs is discussed in, for example, Hoover, John E., Remington's Pharmaceutical Sciences, Mack Publishing Co., Easton, Pa., 1975; Liberman, et al., Eds., Pharmaceutical Dosage Forms, Marcel Decker, New York, N.Y., 1980; and Kibbe, et al., Eds., Handbook of Pharmaceutical Excipients ($3^{rd}$ Ed.), American Pharmaceutical Association, Washington, 1999.

G. Combinations and Combination Therapy

A compound of the present invention can be used, alone or in combination with other pharmaceutically active compounds, to treat conditions such as those previously described above. A compound or several compounds of the present invention and other pharmaceutically active compound(s) can be administered simultaneously (either in the same dosage form or in separate dosage forms) or sequentially. Accordingly, in one embodiment, the present invention comprises methods for treating a condition by administering to the subject a therapeutically-effective amount of one or more compounds of the present invention, and one or more additional pharmaceutically active compounds.

In another embodiment, there is provided a pharmaceutical composition comprising one or more compounds of the present invention, one or more additional pharmaceutically active compounds, and a pharmaceutically acceptable carrier.

In another embodiment, the one or more additional pharmaceutically active compounds is selected from the group consisting of anti-inflammatory drugs, cytostatic drugs, cytotoxic drugs, anti-proliferative agents, and angiogenesis inhibitors.

In another embodiment, the one or more additional pharmaceutically active compounds is selected from the group consisting of anti-cancer drugs and anti-inflammatory drugs.

NO-releasing chromene conjugates described herein are also optionally used in combination with other therapeutic reagents that are selected for their therapeutic value for the condition to be treated. In general, the compounds described herein, and in embodiments where combinational therapy is employed, other agents, do not have to be administered in the same pharmaceutical composition and, because of different physical and chemical characteristics, are optionally administered by different routes. The initial administration is generally made according to established protocols and then, based upon the observed effects, the dosage, modes of administration, and times of administration subsequently modified. In certain instances, it is appropriate to administer an NO-releasing chromene conjugate, as described herein, in combination with another therapeutic agent or NO-releasing chromene conjugate. By way of example only, the therapeutic effectiveness of an NO-releasing chromene conjugate is enhanced by administration of another therapeutic agent (which also includes a therapeutic regimen) that also has therapeutic benefit. Regardless of the disease, disorder or condition being treated, the overall benefit experienced by the patient is either simply additive of the two therapeutic agents or the patient experiences an enhanced benefit.

Therapeutically effective dosages vary when the drugs are used in treatment combinations. Methods for experimentally determining therapeutically effective dosages of drugs and other agents for use in combination treatment regimens are documented methodologies. Combination treatment further includes periodic treatments that start and stop at various times to assist with the clinical management of the patient. In any case, the multiple therapeutic agents (one of which is an NO-releasing chromene conjugate as described herein) are administered in any order, or even simultaneously. If simultaneously, the multiple therapeutic agents are optionally provided in a single, unified form, or in multiple forms (by way of example only, either as a single pill or as two separate pills).

In some embodiments, one of the therapeutic agents is given in multiple doses, or both are given as multiple doses. If not simultaneous, the timing between the multiple doses optionally varies from more than zero weeks to less than twelve weeks.

In addition, the combination methods, compositions, and formulations are not to be limited to the use of only two agents, the use of multiple therapeutic combinations are also envisioned. It is understood that the dosage regimen to treat, prevent, or ameliorate the condition(s) for which relief is sought, is optionally modified in accordance with a variety of factors. These factors include, but are not limited to, the disorder from which the subject suffers, as well as the age, weight, sex, diet, and medical condition of the subject. Thus, the dosage regimen actually employed varies widely, in some embodiments, and therefore deviates from the dosage regimens set forth herein.

The pharmaceutical agents which make up the combination therapy disclosed herein are optionally a combined dosage form or in separate dosage forms intended for substantially simultaneous administration. The pharmaceutical agents that make up the combination therapy are optionally also administered sequentially, with either agent being administered by a regimen calling for two-step administration. The two-step administration regimen optionally calls for sequential administration of the active agents or spaced-apart administration of the separate active agents. The time period between the multiple administration steps ranges from a few minutes to several hours, depending upon the properties of each pharmaceutical agent, including, but not limited to, potency, solubility, bioavailability, plasma half-life, and kinetic profile of the pharmaceutical agent.

In another embodiment, an NO-releasing chromene conjugate is optionally used in combination with procedures that provide additional benefit to the patient. An NO-releasing chromene conjugate and any additional therapies are optionally administered before, during or after the occurrence of a disease or condition, and the timing of administering the composition containing an NO-releasing chromene prodrug varies in some embodiments. Thus, for example, an NO-releasing chromene conjugate is used as a prophylactic, and is administered continuously to subjects with a propensity to develop conditions or diseases in order to prevent the occurrence of the disease or condition. An NO-releasing chromene conjugate is optionally administered to a subject during or as soon as possible after the onset of the symptoms. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that in some embodiments of the invention various alternatives to the embodiments described herein are employed in practicing the invention.

A NO-releasing chromene conjugate can be used in combination with anti-cancer drugs, including but not limited to the following classes: alkylating agents, anti-metabolites, plant alkaloids and terpenoids, topoisomerase inhibitors, cytotoxic antibiotics, angiogenesis inhibitors, and tyrosine kinase inhibitors.

For use in cancer and neoplastic diseases, an NO-releasing chromene conjugate may be optimally used together with one or more of the following non-limiting examples of anti-cancer agents. As a first example, alkylating agents include but are not limited to cisplatin (PLATIN), carboplatin (PARAPLATIN), streptozocin (ZANOSAR), busulfan (MYLERAN), and cyclophosphamide (ENDOXAN). As a second example, anti-metabolites include but are not limited to mercaptopurine (PURINETHOL), thioguanine, pentostatin (NIPENT), cytosine arabinoside (ARA-C), and methotrexate (RHEUMATREX). As a third example, plant alkaloids and terpenoids include but are not limited to vincristine (ONCOVIN), vinblastine, and paclitaxel (TAXOL). As a fourth example, topoisomerase inhibitors include but are not limited to irinotecan (CAMPTOSAR), topotecan (HYCAMTIN), and etoposide (EPOSIN). As a fifth example, cytotoxic antibiotics include but are not limited to actinomycin D (COSMEGEN), doxorubicin (ADRIAMYCIN), bleomycin (BLENOXANE), and mitomycin (MITOSOL). As a sixth example, angiogenesis inhibitors include but are not limited to sunitinib (SUTENT) and bevacizumab (AVASTIN). As a seventh example, tyrosine kinase inhibitors include but are not limited to imatinib (GLEEVEC), erlotinib (TARCEVA), lapatininb (TYKERB), and axitinib (INLYTA). As an eighth example, EGFR inhibitors include but are not limited to the monoclonal antibody cetuximab (ERBITUX). As a ninth example, agents that target HER2 include but are not limited to the monoclonal antibodies pertuzumab (PERJETA) and trastuzumab (HERCEPTIN) which have strong co-expression links to COX-2 in prostrate and breast cancer.

Where a subject is suffering from or at risk of suffering from an inflammatory condition, an NO-releasing chromene conjugate described herein is optionally used together with one or more agents or methods for treating an inflammatory condition in any combination. Therapeutic agents/treatments for treating an autoimmune and/or inflammatory condition include, but are not limited to any of the following examples. As a first example, corticosteroids include but are not limited to cortisone, dexamethasone, and methylprednisolone. As a second example, nonsteroidal anti-inflammatory drugs (NSAIDs) include but are not limited to ibuprofen, naproxen, acetaminophen, aspirin, fenoprofen (NALFON), flurbiprofen (ANSAID), ketoprofen, oxaprozin (DAYPRO), diclofenac sodium (VOLTAREN), diclofenac potassium (CATAFLAM), etodolac (LODINE), indomethacin (INDOCIN), ketorolac (TORADOL), sulindac (CLINORIL), tolmetin (TOLECTIN), meclofenamate (MECLOMEN), mefenamic acid (PONS TEL), nabumetone (RELAFEN), and piroxicam (FELDENE). As a third example, immunosuppressants include but are not limited to methotrexate (RHEUMATREX), leflunomide (ARAVA), azathioprine (IMURAN), cyclosporine (NEORAL, SANDIMMUNE), tacrolimus, and cyclophosphamide (CYTOXAN). As a fourth example, CD20 blockers include but are not limited to rituximab (RITUXAN). As a fifth example, Tumor Necrosis Factor (TNF) blockers include but are not limited to etanercept (ENBREL), infliximab (REMICADE), and adalimumab (HUMIRA). As a sixth example, interleukin-1 receptor antagonists include but are not limited to anakinra (KINERET). As a seventh example, interleukin-6 inhibitors include but are not limited to tocilizumab (ACTEMRA). As an eighth example, interleukin-17 inhibitors include but are not limited to AIN457. As a ninth example, Janus kinase inhibitors include but are not limited to tasocitinib. As a tenth example, syk inhibitors include but are not limited to fostamatinib.

H. Kits

The present invention further comprises kits that are suitable for use in performing the methods of treatment or prevention described above. In one embodiment, the kit contains a first dosage form comprising one or more of the compounds of the present invention, and a container for the dosage, in quantities sufficient to carry out the methods of the present invention.

I. Biological Assays

Compound Metabolism in Plasma & Microsomal Stability

The present invention includes compounds that are enzymatically activated in vivo to produce chromenes. Compounds are analyzed, after incubation in plasma or S9 liver microsomes fractions, for the rate of disappearance of the compound species and appearance of chromene and/or intermediate compounds.

Compounds (1 μM) are incubated, in triplicate, in plasma or S9 liver microsomes fractions (rat or human) at 37° C., reactions are quenched by acetonitrile, and samples are analyzed by LC/MS/MS (T=0, 10, 20, 30, 45, and 60 min). Standard reverse phase HPLC and API 4000 triple quadrupole mass spectrometry are used for analysis. Elimination rate constant, in vitro half-life, and intrinsic clearance are calculated from results.

Measurement of Nitric Oxide Release In Vivo

The compounds of the present invention contain NO-releasing moieties, which release NO in vivo. Pharmacokinetics (PK) of nitric oxide release is measured by administering a single oral (PO) gavage dose to Sprague Dawley rats. For each test compound, 2-6 Sprague Dawley (CD® IGS) male rats are used. Animals are fasted before the study and fed only after the 8-hour blood draw. Animals are weighed and dosed individually by body weight on the day of treatment. Compounds are administered orally (PO) in 2% DMSO/0.5% methylcellulose/0.1% Tween 20 in water or 2% DMSO/25% HP-β-CD (hydroxypropyl-beta-cyclodextrin) in water at 30-100 mg/kg using 10 mL/kg volume per animal. Compounds are formulated by making a 150 mg/mL DMSO compound stock and adding to warm vehicle at 35-40° C. to make a clear solution or fine suspension. Animals found in severe distress, or a moribund condition, are euthanized. Peripheral blood collections are done primarily through venipuncture of the tail or saphenous veins or by jugular catheter at various times (e.g. pre-dose, 15 min, 30 min, 1 h, 2 h, 4 h, 8 h, and 24 h). Whole blood samples are collected in $K_2$EDTA microtainer (Fisher #02-669-38), processed to plasma by centrifugation, and the plasma is frozen at −80° C.

Thawed plasma samples (30 μL) are dilute with into PBS (70 μL) along with control rat plasma. Samples are spun at 2000×g for 10 min and then 80 μL of 30% PBS-diluted plasma samples are transferred into the appropriate well of a 96-well plate. Sodium nitrate is used in standard curve wells at 100, 33.3, 11.1, 3.7, 1.23, and 0.41 μM. To each well is added 10 μL of the nitrate reductase solution and 10 μL of the enzyme co-factors solution to convert nitrate to nitrite (Cayman Chemical #780001 Nitrate/Nitrite Colorimetric Assay Kit). The plate is incubated at room temperature for 2 h and then 50 μL of Griess Reagent A is added to each well, and mixed. After 5 min., 50 μL of Griess Reagent B is added to each well, and mixed. The plate is incubated for 10 min at room temperature, and the absorbance is measured at 540 nm with a microplate reader. A standard curve is generated from the reference standard wells and nitrate/nitrite (NOx) levels are determined (μM) and standard deviations (+/− S.D.) for each blood draw and plotted against time of blood draw.

TABLE 18

Nitric oxide release in vivo after oral administration in rats.

| Time of Blood Sampling | Ex. 22a* | Ex. 33a* | Ex. 33** |
|---|---|---|---|
| Dose (mpk) | 62.6 | 66.0 | 33.0 |
| Pre-Dose NOx (μM) | 15.4 (+/−2.8) | 14.8 (+/−1.9) | 10.5 (+/−3.0) |
| 30 min NOx (μM) | 20.5 (+/−5.9) | 21.4 (+/−7.1) | 10.5 (+/−3.7) |
| 1 hour NOx (μM) | 28.0 (+/−0.4) | 24.2 (+/−4.6) | 12.3 (+/−3.9) |

TABLE 17

Maximal % release of chromene acid after 60 min of incubation in rat or human S9 liver microsome fractions or fresh plasma relative to total possible (+/−S.D.).

| Ex. # | Rat S9 | Human S9 | Rat Plasma | Human Plasma |
|---|---|---|---|---|
| 22a | 18.5% (+/−1.0%) | 11.7% (+/−1.1%) | N.D. | 1.5% (+/−0.3%) |
| 33a | 42.1% (+/−1.2%) | 31.8% (+/−1.5%) | N.D. | 0.4% (+/−0.1%) |
| 33 | 55.5% (+/−2.2%) | 64.9% (+/−3.0%) | 59.9% (+/−2.4%) | <1% (BLQ) |

TABLE 18-continued

Nitric oxide release in vivo after oral administration in rats.

| Time of Blood Sampling | Ex. 22a* | Ex. 33a* | Ex. 33** |
|---|---|---|---|
| 2 hour NOx (μM) | 36.9 (+/−0.4) | 28.6 (+/−7.5) | 16.6 (+/−6.0) |
| 3 hour NOx (μM) | 43.1 (+/−1.6) | 34.8 (+/−8.0) | 20.8 (+/−8.4) |
| 4 hour NOx (μM) | 36.0 (+/−7.2) | 23.4 (+/−3.4) | 23.0 (+/−9.8) |
| 8 hour NOx (μM) | 11.9 (+/−3.0) | 16.3 (+/−9.4) | 23.4 (+/−8.5) |
| 24 hour NOx (μM) | 15.4 (+/−2.8) | 14.8 (+/−1.9) | 17.9 (+/−2.7) |

*Average of two rats
**Average of three rats

Rat Air-Pouch Model for Acute Inflammation

A study of chromene release is assessed by measurement of PGE2 levels, which are indicative of inflammatory response. Compounds of the present invention lower the inflammatory response by selective COX-2 inhibition, decreasing PGE-2 levels in patients.

Animals: Sprague-Dawley rats (Charles River Laboratories, R #3234, PO #738990, male, 160-180 g) are received, individually examined, and housed in cages of five rats each. The rats are ear notched for identification purposes.

Compounds and dosing solutions: The vehicle is prepared by dissolving 40 g (2-hydroxypropyl)-β-cyclodextrin (HP-β-CD, Sigma, Cat. 332593, lot MKBJ5858V) in 160 mL sterile saline for injection, USP (Hospira, lot 26-801-FW) making a 25% solution which is filter sterilized (0.2 μm, Nalgene, Cat. 151-4020, lot 1095610). A 1% carrageenan solution is prepared by dissolving 0.6 g λ-carrageenan (Fluka, Cat. 22049, lot 1318338) in hot 60 mL sterile saline for injection, USP. This solution is stored at 4-8° C. Test compounds are dissolved in DMSO (Fisher Scientific, Cat. D128-500, lot 874999) to make 75 mM stocks. 0.25 mL of compound DMSO stocks are mixed with 12.5 mL of HP-β-CD solution at 50° C. (maximum DMSO concentration is 2% of the final volume of vehicle,). Final concentration of all test compounds is 1.5 mM and compounds are dosed within 2 h of preparation at 0.01 mmol/kg (12 nmol of test compound per rat).

Day 0—Air pouch initiation: The rats are anesthetized in a biological cabinet, the nape of the neck is cleansed with 70% isopropanol (Butler Schein Animal Health, Cat. 002498, lot 29EMS07104547) followed by 1% povidone-iodine solution (Ricca Chemical Co., Cat. 3955-16, lot 2205469). Twenty mL of sterile (0.22 μm, Millipore, Cat. SLGP033RS, lot R2KA55925, exp August 2015) air is injected subcutaneously (SC) using a 23 G×1½ inch needle fixed to a 20 mL syringe. The rats are returned to routine housing.

Day 3—Air pouch maintenance: The rats are anesthetized in a biological cabinet, the nape of the neck is cleansed with 70% isopropanol followed by 1% povidone-iodine solution. Ten mL of sterile air is injected SC using a 23 G×1½ inch needle fixed to a 20 mL syringe. The rats are returned to routine housing in clean cages.

Day 6—Compound administration and carrageenan insult: At commencement of the study, each rat is weighed and sorted into treatment groups of 5 rats/group based upon average weight. Each rat is dosed orally via gavage at 6.809 mL/kg (1.6 mL/235 g) with their respective test material/vehicle. Two hours after test material/vehicle administration, the rats are injected with 1.0 mL of the room temperature 1% carrageenan saline solution into the air pouch. Four hours after carrageenan injection, the rats are anesthetized, and 5 mL of the exudate buffer is injected into the air pouch. The pouch is gently massaged, the exudate immediately removed, and exudate volume recorded. The exudate is collected in a serum separator tube on an ice bath. The exudates are centrifuged (refrigerated) and an aliquot of the supernatant is stored in a labeled Eppendorf tube at −80° C.

Termination of Study: Animals are euthanized via $CO_2$ asphyxiation at the completion of the in-life portion of this study and carcasses are disposed of according to standard protocols.

Data analysis: The exudate samples are thawed to room temperature and assayed by ELISA for PGE2 (R&D Systems, Cat. KGE004B, lot 307711). Statistical significance of treatments on mean exudate volumes are determined by comparison of means for treatment groups with vehicle group. Mean cytokine concentrations and standard deviations are determined for each group. Statistical significance of treatments on cytokine concentrations are determined for each compound group compared to vehicle group. Statistical significance (p-value) is calculated vs control groups by Student's t-Test. Percent PGE2 produced relative to control is calculated using the following equations:

% PGE2 Production=(100/Mean Vehicle Control)* (Mean Test)

S.D. % PGE2 Production=(100/Mean Vehicle Control Value)*(S.D.)

TABLE 19

In vivo percent inhibition of PGE2 production relative to control.

| Example | % Inhibition of PGE2 production relative to control (+/−S.D.) |
|---|---|
| 22a | 75.4 (+/−9.1) |
| 33a | 76.7 (+/−7.8) |
| 33 | 91.8 (+/−4.9) |

Evaluation of COX-1 & COX-2 Activity In Vitro

The present invention includes compounds that are chromene conjugates, therefore they are evaluated for selective COX-1 or COX-2 inhibition. Assays for COX-1 and COX-2 activity in vitro are described in U.S. Pat. No. 5,760,068.

Preparation of Recombinant COX-1 and COX-2:

1. A fragment containing the coding region of either human or murine COX-1 or COX-2 is cloned into a BamH1 site of a baculovirus transfer vector to generate transfer vectors for COX-I and COX-II.
2. Recombinant baculoviruses are isolated by transfecting baculovirus transfer vector DNA into SF9 insect cells.
3. Recombinant viruses are purified and high titer stocks of virus are prepared.
4. SF9 insect cells are infected with the recombinant baculovirus stock. After 72 h the cells are centrifuged and the cell pellet homogenized. The homogenate is centrifuged and the supernatant is assayed for COX activity.

Assay for COX-1 and COX-2 Activity:

1. COX activity is assayed as PGE2 formed/μg protein/time using an ELISA to detect the prostaglandin formed.
2. Insect cell membranes containing the appropriate COX enzyme are incubated in buffer containing arachidonic acid.

3. Compounds are pre-incubated with the enzyme for 10-20 min prior to the addition of arachidonic acid.
4. Reaction between the arachidonic acid and the enzyme is stopped after ten minutes and the PGE2 formed is measured by standard ELISA technology.

Assessment of Anti-Proliferative Activity

Compounds of the present invention are intended to inhibit growth of tumors in patients. Anti-tumor growth potential of test compounds are evaluated in vitro using various human tumor cells, available from the American Type Culture Collection (ATCC), such as A549 lung tumor cells, DU145 prostate tumor cells, HT29 colon cancer cells, MIA PaCa-2 pancreatic cancer cells, MCF-7 (ER$^+$) breast tumor cells, and BEAS-2B cells (immortalized normal lung epithelial cells) as control (Clin. Cancer Res. 6, 2006-2011 (2000)). Test compound effect on cell proliferation is determined using the MTT based cell proliferation assay. MTT based cell proliferation assays are described in U.S. Pat. No. 8,143,237.

MTT [3-(4,5-dimethylthiazol-2-yl)-2,5-diphenyltetrazolium bromide] incorporation based cell proliferation assay is performed using the MTT cell proliferation assay kit (Roche Applied Sciences, Germany). The assay is carried out according to the instruction provided by the vendor. Briefly, equal numbers of cells are plated in 96-well flat-bottomed plates and are incubated with test compounds at various concentrations for a period of three days. Vehicle control culture wells receive an equal volume of vehicle solution. Thereafter, 0.5 mg/mL of MTT reagent is added to each well and the microplate is incubated further for 4 h at 37° C. in presence of 5% $CO_2$. Cells are then solubilized by adding solubilizing solution and allowed to incubate at 37° C. overnight. After complete solubilization of the formazan crystals, the absorbance is read at 540 nm in a microplate reader (BioRad, USA). The results (mean optical density (OD)±standard dethroughtion (SD)) obtained from quadruplicate wells are used to calculate the inhibition of cell proliferation (50% of inhibitory concentration, $IC_{50}$) of the test compounds.

Suppression of Lung Cancer Cell Migration

Compounds of the present invention are intended to have anti-lung cancer effects. Efficacy testing is done to evaluate test compound suppression of lung cancer cell migration, a model of metastasis. Methods to evaluate lung cancer cell migration are described in Mol. Med. Reports 3, 1007-1013 (2010).

Cell Culture: Human lung cancer cells A549 are obtained from American Type Culture Collection (ATCC, Manassas, Va.). Cells are incubated in RPMI-1640 medium supplemented with 10% fetal bovine serum (FBS) and penicillin/streptomycin (GibcoBRL, Grand Island, N.Y., USA).

Monolayer Wound Healing Assay

Compounds of the present invention are intended to have wound-healing properties. Cell proliferation in confluent A549 monolayers is blocked by a 30 minute pre-incubation in the presence of mitomycin C (3 μg/mL). Test compounds, in cell culture buffer, are added to confluent monolayers 30 min before wound induction. A549 monolayers are subsequently scratched with a pipette tip. Wound areas are evaluated with phase contrast microscopy on an inverted microscope. Images of the same areas are obtained at intervals from zero to 96 h. Cell migration rate through wound healing is evaluated from the images using Paint.Net v. 3.10 software. Cell migration is expressed as the fold change in the migration area, relative to untreated control cells at the same time period.

Compound Formulations for Intravenous (IV), Oral Gavage (PO), or Intraperitoneal (IP) Administration Compounds are formulated for administration using 25% hydroxypropyl-β-cyclodextrin-PBS buffer (HP-β-CD-PBS) at 1 mg/mL. HBCD-PBS is the preferred formulation media for compound administration. Additional formulation vehicles may also be used, including 2% Tween 80 in saline and 20% polyethylene glycol (PEG-300) in 0.9% sodium chloride in water.

Determination of Maximum Tolerated Dose (MTD) of Test Compounds in Rats

In order to estimate the doses of test compounds for use in efficacy testing in animal models of cancer, the dosage at which adverse events occur is determined. Methods to determine MTD in rats are described in Mol. Cancer Ther. 5, 1530-1538 (2006).

In order to determine doses for efficacy studies, the maximum tolerated dose (MTD) is determined. Male F344 rats are fed various concentrations of test compounds for six weeks. MTD is determined based on the highest dose that causes a 10% loss in body weight without mortality or signs of toxicity. Body weights are recorded twice weekly. Animals are examined daily for signs of toxicity. At termination, animals are euthanized, and organs dissected and examined.

Compound Metabolism (PK) in Rats

The pharmacokinetics (PK) of compounds is tested by single dose IV administration to Sprague Dawley rats.

For each test compound, three (3) Sprague Dawley (CD® IGS) male rats are used. Animals are weighed and dosed individually by body weight on the day of treatment. Compounds are administered intravenously (IV), through surgically placed jugular catheters, at 10 mg/kg using 10 mL/kg volume per animal. Animals found in severe distress or a moribund condition are euthanized. Peripheral blood collections are done primarily through venipuncture of the tail or saphenous veins at various times (T=15 min, 30 min, 1 h, 2 h, 4 h, 8 h, and 24 h). Whole blood samples are collected in an EDTA microtainer, processed to plasma by centrifugation and the plasma frozen at −80° C. Bioanalysis is done using LC/MS/MS methods using standard reverse phase HPLC and API 4000 triple quadrupole mass spectrometry. The amount of compound present is used to calculate PK parameters $C_{max}$, $T_{max}$, and AUC.

Compound Effects on Blood Pressure

COX-2 inhibitors have been shown to have adverse effects on blood pressure in vivo, the effect of the present compounds is evaluated for blood pressure effects in spontaneously hypertensive rats (SHR).

Thirty-two male, spontaneously hypertensive rats (SHR), 12-weeks old (four groups of eight) are used in this study. Initially, mean arterial blood pressure (MAP) is measured through tail-cuff daily, throughout the study. Animals undergo 2 days of blood pressure training and 1 day of baseline blood pressure measurements. Animals are weighed and dosed individually by body weight on the day of treatment. Compounds are administered orally (PO) or by intraperitoneal (IP) injection once on Day 1 at 10 mg/kg using 10 mL/kg volume per animal. Blood pressures are monitored for 6 days post-dose. A total of 7 time points are measured: Day 0 for baseline and Days 1, 2, 3, 4, 5, and 6 of the study. Animals found in severe distress or in a moribund condition are euthanized. Celecoxib is the positive control tested in these studies.

Anti-inflammatory Efficacy: Rat Carrageenan Foot Pad Edema: The compounds of the present invention are conjugates of chromenes, therefore they are evaluated for efficacy in vivo in a model of inflammation. Methods to determine efficacy in rat carrageenan foot pad edema are described in U.S. Pat. No. 5,760,068.

Male Sprague Dawley rats are selected for equal average body weight per group. After fasting, with free access to water sixteen hours prior to test, animals are dosed orally (1 mL) with test compounds in a vehicle containing 0.5% methylcellulose and 0.025% surfactant. The control group is dosed with vehicle alone.

One hour after dosing, a subplantar injection of 0.1 mL of 1% solution of carrageenan/sterile 0.9% saline is administered in one foot, to all animals. The volume of the injected foot is measured using a displacement plethysmometer. Foot volume is measured again three hours after carrageenan injection. The three hour foot volume measurement is compared between treated and control groups; the percent inhibition of edema is calculated.

Anti-Inflammatory Efficacy—Rat Carrageenan-Induced Analgesia Test

The compounds of the present invention are conjugates of chromenes, therefore they are evaluated for efficacy in vivo in a model of inflammatory analgesia. Methods to determine efficacy in rat carrageenan-induced analgesia test are described in U.S. Pat. No. 5,760,068.

Male Sprague Dawley rats are selected for equal average body weight per group. After fasting, with free access to water sixteen hours prior to test, animals are dosed orally (1 mL) with test compounds in vehicle containing 0.5% methylcellulose and 0.025% surfactant. Control groups are dosed with vehicle alone.

One hour after dosing, a subplantar injection of 0.1 mL of 1% solution of carrageenan/sterile 0.9% saline is administered in one foot, to all animals. Three hours after carrageenan injection, rats are placed in a plexiglass container with a high intensity lamp under the floor. After twenty minutes, thermal stimulation is begun on either the injected or the uninjected foot. Foot withdrawal is determined by a photoelectric cell. The time until foot withdrawal is measured and compared between treated and control groups. The percent inhibition of the hyperalgesic foot withdrawal is calculated.

Tumor Growth Inhibition in Xenograft Mouse Model of Colon Cancer

Compounds of the present invention are intended to have anti-colon cancer effects in patients. Efficacy testing is done in animal models of cancer tumors. Methods to determine tumor growth inhibition in xenograft mouse models of colon cancer are described in *J. Drug Delivery* 2011, 1-9 (Article ID 869027) and *Invest. New Drugs* 2014, 32(6), 1105-12.

HT-29 cells are trypsinized, resuspended in sterile PBS, and pelleted by brief centrifugation at 200×g. The cell pellet is resuspended in sterile PBS and counted using a hemocytometer. Cells are resuspended in PBS to a final concentration of $5 \times 10^7$ cells/mL. Female HRLN nu/nu mice are injected subcutaneously into the high axilla region with $5 \times 10^6$ HT-29 cells in 0.1 mL of PBS. Mice are triaged into treatment groups (10 mice/group) when mean tumor burden is 100-200 mg (target 150 mg, ~10 days of logarithmic growth), at which point treatment is initiated. Mice are distributed into treatment groups such that the mean tumor burden in each group is within 10% of the overall mean. Body weights and tumor measures are recorded 3×/week, and clinical signs are recorded daily. Tumor volume is determined using digital calipers and calculated according to the equation $V=(L \times W^2)/2$, where V is the volume, L is the length, and W is the width. Mice are dosed individually by body weight once daily (QD) or twice daily (bid or Q12H× 2). Testing compounds are formulated in 1% methylcellulose/0.1% Tween-80/2% DMSO or 2% DMSO/25% hydroxypropyl-β-cyclodextrin (HP-β-CD) in water and administered via oral dosing (p.o.) at 1, 3, or 10 mpk. 5-FU (i.p. dosing; Q7D×3; 100 mpk) and celecoxib (p.o. dosing; Q12H×2; 30 mpk) are administered as positive controls and vehicle alone as the negative control. Animals with tumor burdens greater than 2 g or found in a moribund condition are euthanized, otherwise animals are euthanized, and tumors are harvested and measured after 28 days of treatment. Gross necropsy is performed on every animal leaving the study and abnormal findings are recorded. Drug efficacy is measured based on animal survival and tumor growth inhibition relative to negative control.

Tumor Growth Inhibition in Xenograft Mouse Model of NSCLC

Compounds of the present invention are intended to inhibit the growth of cancerous tumors in patients. Efficacy testing is done in animal models of cancer tumors. Methods to determine tumor growth inhibition in xenograft mouse models of NSCLC are described in *Clin. Cancer Res.* 7, 724-733 (2001) and are similar to the detail method described above for Colon Cancer.

Female HRLN nu/nu mice are injected subcutaneously with $1 \times 10^7$ MV-522 cells in 0.1 mL of phosphate-buffered saline. Treatment is initiated when tumors measure 5×5 mm. Mice are weighed and tumors measured by calipers twice weekly. Animals are euthanized, and tumors are harvested and measured after 67 days or when animal dies. Drug efficacy is measured based on animal survival and tumor growth.

Growth Inhibition of Gallbladder Adenocarcinoma in Transgenic Mice

Compounds of the present invention are intended to inhibit the growth of cancerous tumors in patients. Efficacy testing is done in animal models of cancer tumors. Gallbladder adenocarcinoma in transgenic mice is described in *Mol. Cancer Ther.* 6, 1709-1717 (2007).

Homozygous BK5.ErbB-2 transgenic mice, that overexpress rat ErbB-2 and nontransgenic littermates receive a control AIN76A diet or an experimental diet containing the test compound for one month. The transgenic mice develop adenocarcinoma of the gallbladder with a 90% incidence. Ultrasound image analysis and histologic evaluation are used to determine compound effects on gall bladder tumor reversion to a milder phenotype and inhibition of tumor progression.

Inhibition of Colon Cancer in Azomethane-Treated Rats

Compounds of the present invention are intended to have anti-colon cancer effects in patients. Efficacy testing is done in animal models of cancer tumors. Colon cancer in azomethane-treated rats is described in *Mol. Cancer Ther.* 5, 1530-1538 (2006).

Male F344 rats (Charles River Breeding Laboratories) are given test compounds blended into the diet. Efficacy of test compounds are determined following initiation of azoxymethane-induced colon cancer. Rats are randomly distributed by weight into various groups and housed in cages. Azomethane treated animals are injected subcutaneous (s.c.), twice weekly, at 15 mg/kg body weight. Vehicle-treated groups are injected with normal saline. Rats are placed on control diet or diets containing test compounds, two weeks after the second injection of azomethane or saline. Body weights are measured every two weeks until termination, 52 weeks after the last azoxymethane treatment. Organs are dissected and examined using a dissecting microscope.

Colon tumors with a diameter of >0.4 cm are fixed in 10% neutral buffered formalin for histopathologic evaluation. Test compounds are evaluated for effect on colonocyte proliferation. Proliferating cell nuclear antigen (PCNA) expression is determined by immunohistochemistry. Paraffin-embedded colons are sectioned and mounted on slides. PCNA antibody (PharMingen, San Diego, Calif.), at a 1:200 dilution, is added for 1 h. Sections are washed, then incubated with secondary anti-rabbit IgG (30 min). Following washing, avidin biotin-complex reagent (Vector Laboratories, Burlingame, Calif.) is added. Sections are washed, 3,3"-diaminobenzidine is added, and sections are counterstained with hematoxylin. Proliferation index is calculated based on the number of positive cells (brown nucleus) per crypt.

Patient Selection Using Urinary PGE-M

Compounds of the present invention inhibit COX-2 activity. Urinary PGE-M can serve as a diagnostic marker of aberrant COX-2 over-expression in patients with COX-2 dependent cancers. Accordingly, urinary PGE-M levels can be useful in patient selection, as patients with elevated PGE-M levels can be targeted for therapy with compounds of the present invention. Urinary PGE-M level is typically measured using a liquid chromatography/tandem mass spectrometric method as described in Murphey, L. J. et al.: "Quantification of major urinary metabolite of PGE2 by a liquid chromatographic/mass spectrometric assay: Determination of cyclooxygenase specific PGE2 synthesis in healthy humans and those with lung cancer" *Anal. Biochem.* 2004, 334, 266-75 and US Patent Application 2012/0016002 A1, the entire contents of which are hereby incorporated by reference. Alternatively, urinary PGE-M level is also measured using commercially available ELISA kits from vendors such as Cayman Chemical (Item Number 514531) following protocols outlined in accompanying technical documents, the entire contents of which are hereby incorporated by reference.

Urinary PGE-M LCMS Protocol: Briefly, 0.75 mL urine is acidified to pH 3 with dilute aqueous hydrochloric acid and endogenous PGE-M is then converted to O-methyloxime derivative by treatment with methyloxime hydrochloride. The methoximated PGE-M is extracted with ethyl acetate, applied to a C-18 Sep-Pak, and eluted with ethyl acetate. An [$^2$H$_6$]—O-methyloxime PGE-M internal standard is then added. Liquid chromatography is performed on a Zorbax Eclipse XDB-C18 column attached to a Thermo Finnigan Surveyor MS Pump (Thermo Finnigan, San Jose, Calif.). For endogenous PGE-M, the predominant product ion m/z 336 representing [M-OCH$_3$+H$_2$O]$^-$ and the analogous ion, m/z 339 (M-OC[$^2$H]$_3$+H$_2$O)]$^-$, for the deuterated internal standard, are monitored in the selected reaction monitoring (SRM) mode. Quantification of endogenous PGE-M utilizes the ratio of the mass chromatogram peak areas of the m/z 336 and m/z 339 ions. Urinary creatinine levels are measured using a test kit from SIGMA Company (St. Louis, Mo.). Urine samples for each case-control pair are analyzed in the same batch and adjacently to eliminate between-assay variability. Individuals having elevated PGE-M levels relative to control urine are identified and administered therapy as described herein.

All mentioned documents are incorporated by reference as if herein written. When introducing elements of the present invention or the exemplary embodiment(s) thereof, the articles "a," "an," "the", and "said" are intended to mean that there are one or more of the elements. The terms "comprising," "including", and "having" are intended to be inclusive and mean that there may be additional elements other than the listed elements. Although this invention has been described with respect to specific embodiments, the details of these embodiments are not to be construed as limitations.

What is claimed is:

1. A compound, or pharmaceutically acceptable salt or solvate of a compound or salt of Formula (VI):

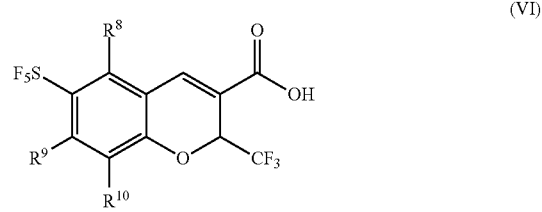

(VI)

wherein:
$R^8$ is hydrido;
$R^9$ is selected from the group consisting of hydrido, methyl, and tert-butyl; and
$R^{10}$ is selected from the group consisting of the group consisting of hydrido, Cl, methyl, and ethyl;
or an isomer thereof.

2. The compound, salt, or solvate of claim 1, wherein: $R^9$ is hydrido.

3. The compound, salt, or solvate of claim 2, wherein the compound is (S)-6-pentafluorosulfanyl-2-(trifluoromethyl)-2H-chromene-3-carboxylic acid, or a salt or solvate thereof.

4. The compound, salt, or solvate of claim 2, wherein the compound is (S)-6-pentafluorosulfanyl-8-methyl-2-(trifluoromethyl)-2H-chromene-3-carboxylic acid, or a salt or solvate thereof.

5. The compound, salt, or solvate of claim 2, wherein the compound is (S)-6-pentafluorosulfanyl-8-ethyl-2-(trifluoromethyl)-2H-chromene-3-carboxylic acid, or a salt or solvate thereof.

6. The solvate of claim 1, wherein the solvate is a hydrate.

* * * * *